(12) United States Patent
McDonagh et al.

(10) Patent No.: US 8,927,694 B2
(45) Date of Patent: Jan. 6, 2015

(54) HUMAN SERUM ALBUMIN LINKERS AND CONJUGATES THEREOF

(75) Inventors: Charlotte McDonagh, Winchester, MA (US); Michael Feldhaus, Grantham, NH (US); Alexandra Huhalov, Cambridge, MA (US)

(73) Assignee: Merrimack Pharmaceuticals, Inc., Cambridge, MA (US)

(*) Notice: Subject to any disclaimer, the term of this patent is extended or adjusted under 35 U.S.C. 154(b) by 889 days.

(21) Appl. No.: 13/130,007

(22) PCT Filed: Oct. 14, 2009

(86) PCT No.: PCT/US2009/060721
§ 371 (c)(1),
(2), (4) Date: Sep. 15, 2011

(87) PCT Pub. No.: WO2010/059315
PCT Pub. Date: May 27, 2010

(65) Prior Publication Data
US 2012/0003221 A1    Jan. 5, 2012

Related U.S. Application Data

(63) Continuation-in-part of application No. PCT/US2009/040259, filed on Apr. 10, 2009.

(60) Provisional application No. 61/115,797, filed on Nov. 18, 2008.

(51) Int. Cl.
*C07K 16/00* (2006.01)
*C07K 14/765* (2006.01)
*A61K 38/00* (2006.01)

(52) U.S. Cl.
CPC .............. *C07K 14/765* (2013.01); *A61K 38/00* (2013.01)
USPC .......................................... 530/363; 530/350

(58) Field of Classification Search
None
See application file for complete search history.

(56) References Cited

U.S. PATENT DOCUMENTS

| | | | |
|---|---|---|---|
| 4,450,103 A | 5/1984 | Konrad et al. |
| 4,588,585 A | 5/1986 | Mark et al. |
| 4,704,692 A | 11/1987 | Ladner |
| 4,737,462 A | 4/1988 | Mark et al. |
| 4,816,567 A | 3/1989 | Cabilly et al. |
| 4,946,778 A | 8/1990 | Ladner et al. |
| 4,959,314 A | 9/1990 | Mark et al. |
| 5,091,513 A | 2/1992 | Huston et al. |
| 5,132,405 A | 7/1992 | Huston et al. |
| 5,168,062 A | 12/1992 | Stinski |
| 5,258,498 A | 11/1993 | Huston et al. |
| 5,260,203 A | 11/1993 | Ladner et al. |
| 5,292,658 A | 3/1994 | Cormier et al. |
| 5,385,839 A | 1/1995 | Stinski |
| 5,455,030 A | 10/1995 | Ladner et al. |
| 5,476,786 A | 12/1995 | Huston |
| 5,482,858 A | 1/1996 | Huston et al. |
| 5,518,889 A | 5/1996 | Ladner et al. |
| 5,525,491 A | 6/1996 | Huston et al. |
| 5,530,101 A | 6/1996 | Queen et al. |
| 5,534,254 A | 7/1996 | Huston et al. |
| 5,534,621 A | 7/1996 | Ladner et al. |
| 5,612,196 A | 3/1997 | Becquart et al. |
| 5,622,701 A | 4/1997 | Berg |
| 5,631,158 A | 5/1997 | Dorai et al. |
| 5,656,730 A | 8/1997 | Lee |
| 5,658,763 A | 8/1997 | Dorai et al. |
| 5,670,356 A | 9/1997 | Sherf et al. |
| 5,730,978 A | 3/1998 | Wayner |
| 5,733,782 A | 3/1998 | Dorai et al. |
| 5,738,845 A | 4/1998 | Imakawa |
| 5,753,204 A | 5/1998 | Huston et al. |
| 5,753,627 A | 5/1998 | Albert et al. |
| 5,763,733 A | 6/1998 | Whitlow et al. |
| 5,766,883 A | 6/1998 | Ballance et al. |
| 5,767,260 A | 6/1998 | Whitlow et al. |
| 5,780,594 A | 7/1998 | Carter |
| 5,800,815 A | 9/1998 | Chestnut et al. |
| 5,821,231 A | 10/1998 | Arrhenius et al. |
| 5,837,846 A | 11/1998 | Huston et al. |
| 5,840,299 A | 11/1998 | Bendig et al. |
| 5,856,456 A | 1/1999 | Whitlow et al. |
| 5,869,448 A | 2/1999 | Arrhenius et al. |
| 5,869,620 A | 2/1999 | Whitlow et al. |

(Continued)

FOREIGN PATENT DOCUMENTS

| | | |
|---|---|---|
| AU | 612370 | 12/1988 |
| AU | 648591 | 4/1994 |
| AU | 664030 | 11/1995 |
| CA | 2100671 | 8/1992 |
| CA | 1341364 | 6/2002 |

(Continued)

OTHER PUBLICATIONS

Johnson et al, Cancer Treatment Review vol. 2 p. 1 (1975).*

(Continued)

*Primary Examiner* — Sheela J Huff
(74) *Attorney, Agent, or Firm* — Clark & Elbing LLP

(57) ABSTRACT

Disclosed is a human serum albumin (HSA) linker and HSA linker with binding, diagnostic, and therapeutic agents conjugated thereto. Also disclosed is a conjugate in which the HSA linker is covalently bonded to amino and carboxy terminal binding moieties that are first and second single-chain Fv molecules (scFvs). Exemplified conjugates are useful, e.g., in reducing tumor cell proliferation, e.g., for therapeutic therapeutic applications. Also disclosed are methods and kits for the diagnostic and therapeutic application of an HSA linker conjugate.

21 Claims, 53 Drawing Sheets

(56) References Cited

U.S. PATENT DOCUMENTS

| | | | |
|---|---|---|---|
| 5,874,540 A | 2/1999 | Hansen et al. |
| 5,876,969 A | 3/1999 | Fleer et al. |
| 5,914,110 A | 6/1999 | Holmes et al. |
| 5,917,021 A | 6/1999 | Lee |
| 5,928,904 A | 7/1999 | Holmes et al. |
| 5,936,065 A | 8/1999 | Arrhenius et al. |
| 5,977,322 A | 11/1999 | Marks et al. |
| 5,990,275 A | 11/1999 | Whitlow et al. |
| 6,025,165 A | 2/2000 | Whitlow et al. |
| 6,027,725 A | 2/2000 | Whitlow et al. |
| 6,033,665 A | 3/2000 | Yednock |
| 6,103,889 A | 8/2000 | Whitlow et al. |
| 6,121,424 A | 9/2000 | Whitlow et al. |
| 6,171,809 B1 | 1/2001 | Roelant |
| 6,191,269 B1 | 2/2001 | Pollock et al. |
| 6,197,794 B1 | 3/2001 | Head et al. |
| 6,207,804 B1 | 3/2001 | Huston et al. |
| 6,210,670 B1 | 4/2001 | Berg |
| 6,229,011 B1 | 5/2001 | Chen et al. |
| 6,265,572 B1 | 7/2001 | Chen et al. |
| 6,288,267 B1 | 9/2001 | Hull et al. |
| 6,323,322 B1 | 11/2001 | Filpula et al. |
| 6,329,372 B1 | 12/2001 | Head et al. |
| 6,331,415 B1 | 12/2001 | Cabilly et al. |
| 6,333,396 B1 | 12/2001 | Filpula et al. |
| 6,348,463 B1 | 2/2002 | Head et al. |
| 6,362,204 B1 | 3/2002 | Head et al. |
| 6,365,619 B1 | 4/2002 | Shi |
| 6,380,387 B1 | 4/2002 | Sidduri et al. |
| 6,388,084 B1 | 5/2002 | Kaplan et al. |
| 6,423,512 B1 | 7/2002 | Digan et al. |
| 6,423,728 B1 | 7/2002 | Hull et al. |
| 6,426,348 B1 | 7/2002 | Hull et al. |
| 6,445,550 B1 | 9/2002 | Ishi |
| 6,458,844 B2 | 10/2002 | Hull et al. |
| 6,479,666 B2 | 11/2002 | Hull et al. |
| 6,482,849 B1 | 11/2002 | Lobl et al. |
| 6,495,525 B1 | 12/2002 | Lee et al. |
| 6,515,110 B1 | 2/2003 | Filpula et al. |
| 6,596,752 B1 | 7/2003 | Lobl et al. |
| 6,602,503 B1 | 8/2003 | Lobb et al. |
| 6,667,331 B2 | 12/2003 | Duplantier et al. |
| 6,668,527 B2 | 12/2003 | Duplantier et al. |
| 6,677,436 B1 | 1/2004 | Sato et al. |
| 6,685,617 B1 | 2/2004 | Blinn et al. |
| 6,686,179 B2 | 2/2004 | Fleer et al. |
| 6,692,942 B2 | 2/2004 | Filpula et al. |
| 6,743,896 B2 | 6/2004 | Filpula et al. |
| 6,743,908 B2 | 6/2004 | Filpula et al. |
| 6,764,853 B2 | 7/2004 | Filpula et al. |
| 6,806,365 B2 | 10/2004 | Chen et al. |
| 6,818,216 B2 | 11/2004 | Young et al. |
| 6,835,738 B1 | 12/2004 | Brown et al. |
| 6,855,706 B2 | 2/2005 | Tanaka et al. |
| 6,872,719 B1 | 3/2005 | Brown et al. |
| 6,878,718 B2 | 4/2005 | Brand et al. |
| 6,903,128 B2 | 6/2005 | Duplantier et al. |
| 6,905,688 B2 | 6/2005 | Rosen et al. |
| 6,911,451 B1 | 6/2005 | Porter et al. |
| 6,916,933 B2 | 7/2005 | Kaplan et al. |
| 6,926,898 B2 | 8/2005 | Rosen et al. |
| 6,946,134 B1 | 9/2005 | Rosen et al. |
| 6,962,978 B2 | 11/2005 | Pepinsky et al. |
| 6,972,322 B2 | 12/2005 | Fleer et al. |
| 6,987,006 B2 | 1/2006 | Fleer et al. |
| 6,989,365 B2 | 1/2006 | Fleer et al. |
| 6,994,857 B2 | 2/2006 | Rosen et al. |
| 7,015,216 B2 | 3/2006 | Konradi et al. |
| 7,045,318 B2 | 5/2006 | Ballance |
| 7,067,313 B1 | 6/2006 | Jacquemin et al. |
| 7,105,520 B2 | 9/2006 | Suzuki et al. |
| 7,141,547 B2 | 11/2006 | Rosen et al. |
| 7,153,963 B2 | 12/2006 | Makino et al. |
| 7,160,874 B2 | 1/2007 | Tanaka et al. |
| 7,183,092 B2 | 2/2007 | Choi et al. |
| 7,189,690 B2 | 3/2007 | Rosen et al. |
| 7,193,108 B2 | 3/2007 | Chiba et al. |
| 7,238,344 B2 | 7/2007 | Pedersen et al. |
| 7,238,660 B2 | 7/2007 | Rosen et al. |
| 7,238,667 B2 | 7/2007 | Rosen et al. |
| 7,250,516 B2 | 7/2007 | Okuzumi et al. |
| 7,291,645 B2 | 11/2007 | Konradi et al. |
| 7,332,580 B2 | 2/2008 | Adams et al. |
| 7,332,585 B2 | 2/2008 | Adams et al. |
| 7,482,013 B2 | 1/2009 | Ballance et al. |
| 8,691,771 B2 * | 4/2014 | Nielsen et al. ............... 514/21.2 |
| 2002/0031508 A1 | 3/2002 | Wagner et al. |
| 2002/0107284 A1 | 8/2002 | Uckun et al. |
| 2002/0151011 A1 | 10/2002 | Fleer et al. |
| 2003/0004196 A1 | 1/2003 | Duplantier et al. |
| 2003/0018016 A1 | 1/2003 | Adams et al. |
| 2003/0022308 A1 | 1/2003 | Fleer et al. |
| 2003/0036170 A1 | 2/2003 | Fleer et al. |
| 2003/0036172 A1 | 2/2003 | Fleer et al. |
| 2003/0054554 A1 | 3/2003 | Becquart et al. |
| 2003/0054994 A1 | 3/2003 | Noteborn et al. |
| 2003/0078249 A1 | 4/2003 | Baldwin et al. |
| 2003/0082747 A1 | 5/2003 | Fleer et al. |
| 2003/0083267 A1 | 5/2003 | Adams et al. |
| 2003/0086919 A1 | 5/2003 | Rosenblum et al. |
| 2003/0100585 A1 | 5/2003 | Duplantier et al. |
| 2003/0104578 A1 | 6/2003 | Ballance |
| 2003/0119042 A1 | 6/2003 | Franco De Sarabia Rosado et al. |
| 2003/0166559 A1 | 9/2003 | Desjarlais et al. |
| 2004/0039040 A1 | 2/2004 | Takahashi et al. |
| 2004/0053907 A1 | 3/2004 | Zheng et al. |
| 2004/0087574 A1 | 5/2004 | Takahashi et al. |
| 2004/0102496 A1 | 5/2004 | Duplantier et al. |
| 2004/0132809 A1 | 7/2004 | Scott et al. |
| 2004/0175824 A1 | 9/2004 | Sun et al. |
| 2004/0224389 A1 | 11/2004 | Bellgrau et al. |
| 2004/0229858 A1 | 11/2004 | Baldwin et al. |
| 2004/0229859 A1 | 11/2004 | Albers et al. |
| 2004/0247565 A1 | 12/2004 | Liu et al. |
| 2004/0265311 A1 | 12/2004 | Wagner et al. |
| 2005/0020815 A1 | 1/2005 | Carter |
| 2005/0100991 A1 | 5/2005 | Rosen et al. |
| 2005/0186664 A1 | 8/2005 | Rosen et al. |
| 2005/0187177 A1 | 8/2005 | Godbey et al. |
| 2005/0226876 A1 | 10/2005 | Graus et al. |
| 2005/0265962 A1 | 12/2005 | Desjarlais et al. |
| 2005/0266533 A1 | 12/2005 | Ballance et al. |
| 2006/0014966 A1 | 1/2006 | Lee et al. |
| 2006/0018859 A1 | 1/2006 | Carter |
| 2006/0030553 A1 | 2/2006 | Zheng et al. |
| 2006/0099205 A1 | 5/2006 | Adams et al. |
| 2006/0166866 A1 | 7/2006 | Adams et al. |
| 2006/0166961 A1 | 7/2006 | Scott et al. |
| 2006/0211630 A1 | 9/2006 | Cossio et al. |
| 2006/0241132 A1 | 10/2006 | Ishigaki et al. |
| 2007/0031423 A1 | 2/2007 | Fanger et al. |
| 2007/0041987 A1 | 2/2007 | Carter |
| 2007/0054909 A1 | 3/2007 | Baldwin et al. |
| 2007/0066533 A1 | 3/2007 | Lee et al. |
| 2007/0086942 A1 | 4/2007 | Chang et al. |
| 2007/0232601 A1 | 10/2007 | Yoneda et al. |
| 2007/0243163 A1 | 10/2007 | Liu |
| 2007/0274950 A1 | 11/2007 | Patten et al. |
| 2008/0004206 A1 | 1/2008 | Rosen et al. |
| 2008/0113411 A1 | 5/2008 | Sheffer et al. |
| 2008/0113412 A1 | 5/2008 | Sheffer et al. |
| 2008/0124334 A1 | 5/2008 | Akita et al. |
| 2008/0125574 A1 | 5/2008 | Sheffer et al. |
| 2008/0166358 A1 | 7/2008 | Tung |
| 2008/0267962 A1 | 10/2008 | Ballance et al. |
| 2010/0280227 A1 | 11/2010 | Ambrose et al. |

FOREIGN PATENT DOCUMENTS

| | | |
|---|---|---|
| CA | 1341415 | 1/2003 |
| CN | 1074243 A | 7/1993 |
| CN | 1146664 C | 4/2004 |
| CN | 101072581 A | 11/2007 |
| CN | 101120021 A | 2/2008 |

(56) References Cited

FOREIGN PATENT DOCUMENTS

| | | |
|---|---|---|
| EP | 0318554 B2 | 6/1989 |
| EP | 0399666 | 11/1990 |
| EP | 0413622 A1 | 2/1991 |
| EP | 0281604 B1 | 3/1993 |
| EP | 0573551 B1 | 12/1993 |
| EP | 0623679 A1 | 11/1994 |
| EP | 0624195 B1 | 11/1994 |
| EP | 0870039 B1 | 10/1998 |
| EP | 1136556 A1 | 9/2001 |
| EP | 0870039 B1 | 3/2006 |
| WO | WO-98/04718 A1 | 2/1998 |
| WO | WO 01/79271 | 10/2001 |
| WO | WO-02/00914 A2 | 1/2002 |
| WO | WO 03/060071 | 7/2003 |
| WO | WO 2005/117973 | 12/2005 |
| WO | WO 2005/118642 | 12/2005 |
| WO | WO 2006/091209 | 8/2006 |
| WO | WO 2008/030558 | 3/2008 |
| WO | WO-2008/033413 A2 | 3/2008 |
| WO | WO 2008/140493 | 11/2008 |
| WO | WO 2009/126920 | 10/2009 |
| WO | WO-2010/059315 A1 | 5/2010 |
| WO | WO-2011133668 A2 | 10/2011 |

OTHER PUBLICATIONS

Anderson et al., "Perspective-FcRn Transports Albumin: Relevance to Immunology and Medicine," *Trends Immuno.* 27(7):343-348, 2006.

Bird et al., "Single-Chain Antigen-Binding Proteins," *Science* 242:423-426, 1988.

Breast cancer cell line ZR7530, National Institutes of Health: Lawrence Berkeley National Laboratory, retrieved Jul. 31, 2012 from http://icbp.lbl.gov/ccc/viewline.php?id=69.

Brennan et al., "Albumin Redhill (-1 Arg, 320 Ala→Thr): A Glycoprotein Variant of Human Serum Albumin Whose Precursor Has an Aberrant Signal Peptidase Cleavage Site," *Proc. Natl. Acad. Sci. USA* 87:26-30, 1990.

Britsch et al., "The ErbB2 and ErbB3 Receptors and Their Ligand, Neuregulin-1, Are Essential for Development of the Sympathetic Nervous System," *Genes Dev.* 12(12):1825-1836, 1998.

Carlson et al., "Alloalbuminemia in Sweden: Structural Study and Phenotypic Distribution of Nine Albumin Variants," *Proc. Natl. Acad. Sci. USA* 89:8225-8229, 1992.

Chapman et al., "Therapeutic Antibody Fragments with Prolonged in vivo Half-lives," *Nat. Biotechnol.* 17(8):780-783, 1999.

Chapman, "PEGylated Antibodies and Antibody Fragments for Improved Therapy: a Review," *Adv. Drug Deliv. Rev.* 54(4):531-545, 2002.

Chaudhury et al., "Albumin Binding to FcRn: Distinct from the FcRn-IgG Interaction," *Biochemistry* 45(17):4983-4990, 2006.

Chaudhury et al., "The Major Histocompatibility Complex-related Fc Receptor for IgG (FcRn) Binds Albumin and Prolongs Its Lifespan," *J. Exp. Med.* 197(3):315-322, 2003.

Christodoulou et al., "$^1$H NMR of Albumin in Human Blood Plasma: Drug Binding and Redox Reactions at $Cys^{34}$," *FEBS Letters* 376(1-2):1-5, 1995.

Chua et al., "Albumin Church Bay: 560Lys→Glu a New Mutation Detected by Electrospray Ionization Mass Spectrometry," *Biochem. Biophys. Acta.* 1382(2):305-310, 1998.

Dennis et al., "Albumin Binding as a General Strategy for Improving the Pharmacokinetics of Proteins," *J. Biol. Chem.* 277(38):35035-35043, 2002.

Di Fiore et al., "ErbB-2 is a Potent Oncogene When Overexpressed in NIH/3T3 Cells," *Science* 237:178-182, 1987.

Dockal et al., "The Three Recombinant Domains of Human Serum Albumin: Structural Characterization and Ligand Binding Properties," *J. Biol. Chem.* 274(41):29303-29310, 1999.

Drummon et al., "Enhanced Pharmacodynamic and Antitumor Properties of a Histone Deacetylase Inhibitor Encapsulated in Liposomes or ErbB2-targeted Immunoliposomes," *Clin. Cancer Res.* 11: 3392-3401, 2005.

Erickson et al., "ErbB3 Is Required for Normal Cerebellar and Cardiac Development: A Comparison with ErbB2-and Heregulin-Deficient Mice," *Development* 124:4999-5011, 1997.

Fang et al., "Characterization of an Anti-Human Ovarian Carcinoma x anti-Human CD3 Bispecific Single-Chain Antibody with an Albumin-Original Interlinker," *Gynecol. Oncol.* 92:135-146, 2004.

Folgiero et al., "Induction of ErbB-3 Expression by α6β4 Integrin Contributes to Tamoxifen Resistance in ERβ1-Negative Breast Carcinomas," *PLoS One* 3(2):e1592, 2008.

Galliano et al., "Mutations in Genetic Variants of Human Serum Albumin Found in Italy," *Proc. Natl. Acad. Sci. USA* 87:8721-8725, 1990.

Guy et al., "Insect Cell-Expressed $P180^{erbB3}$ Possesses an Impaired Tyrosine Kinase Activity," *Proc. Natl. Acad. Sci. USA* 91(17):8132-8136. 1994.

Horak et al., "Isolation of scFvs to In Vitro Produced Extracellular Domains of EGFR Family Members," *Cancer Biother. Radiopharm.* 20(6):603-613, 2005.

Hudziak et al., "Increased Expression of the Putative Growth Factor Receptor $p185^{HER2}$ Causes Transformation and Tumorigenesis of NIH 3T3 Cells," *Proc. Natl. Acad. Sci. USA* 84(20):7159-7163, 1987.

Huston et al., "Protein Engineering of Antibody Binding Sites: Recovery of Specific Activity in an Anti-Digoxin Single-Chain FV Analogue Produced in *Escherichia coli*," *Proc. Natl. Acad. Sci. USA* 85:5879-5883, 1988.

Hutchinson et al., "The N-Terminal Sequence of Albumin Redhill, A Variant of Human Serum Albumin," *FEBS Letters* 193:211-212, 1985.

Karacay et al., "Pretargeting for Cancer Radioimmunotherapy with Bispecific Antibodies: Role of the Bispecific Antibody's Valency for the Tumor Target Antigen," *Bioconjug. Chem.* 13(5):1054-1070, 2002.

Kirpotin, et al., "Antibody Targeting of Long-Circulating Lipidic Nanoparticles does not Increase Tumor Localization but does Increase Internalization in Animal Models," *Cancer Res.* 66:6732-6740, 2006.

Klapper et al., "The ErbB-2/HER2 Oncoprotein of Human Carcinomas May Function Solely as a Shared Coreceptor for Multiple Stroma-Derived Growth Factors," *Proc. Natl. Acad. Sci. USA* 96(9):4995-5000, 1999.

Koumakpayi et al., "Expression and Nuclear Localization of ErbB3 in Prostate Cancer," *Clin. Cancer Res.* 12(9):2730-2737, 2006.

Lemmens et al., "Role of Neuregulin-1/ErbB Signaling in Cardiovascular Physiology and Disease: Implications for Therapy of Heart Failure," *Circulation* 116(8):954-960, 2007.

Lemoine et al., "Expression of the *ERBB3* Gene Product in Breast Cancer," *Br. J. Cancer* 66(6):1116-1121, 1992.

Liu et al., "Downregulation of ErbB3 Abrogates ErbB2-Mediated Tamoxifen Resistance in Breast Cancer Cells," *Int. J. Cancer* 120(9):1874-1882, 2007.

Madison et al., "Genetic Variants of Human Serum Albumin in Italy: Point Mutants and a Carboxyl-Terminal Variant," *Proc. Natl. Acad. Sci. USA* 91:6476-6480, 1994.

McCurdy et al., "A Covalently Linked Recombinant Albumin Dimer is More Rapidly Cleared in vivo than are Wild-type and Mutant C34A Albumin," *J. Lab. Clin. Med.* 143(2):115-124, 2004.

Minchiotti et al., "Structural Characterization of Four Genetic Variants of Human Serum Albumin Associated with Alloalbuminemia in Italy," *Eur. J. Biochem.* 247:476-482, 1997.

Müller et al., "Improved Pharmacokinetics of Recombinant Bispecific Antibody Molecules by Fusion to Human Serum Albumin," *J. Biol. Chem.* 282(17): 12650-12660, 2007.

Naidu et al., "Expression of c-erbB3 Protein in Primary Breast Carcinomas," *Br. J. Cancer.* 78(10):1385-1390, 1998.

Nakaoka et al., "Gab Family Proteins are Essential for Postnatal Maintenance of Cardiac Function via Neuregulin-1/ErbB Signaling," *J. Clin. Invest.* 117(7):1771-1781, 2007.

Neve et al., "Biological Effects of Anti-ErbB2 Single Chain Antibodies Selected for Internalizing Function," *Biochem. Biophys. Res. Commun.* 280(1):274-279. 2001.

Park et al., "Anti-HER2 Immunoliposomes: Enhanced Efficacy Attributable to Targeted Delivery," *Clin. Cancer Res.* 8:1172-81, 2002.

(56) References Cited

OTHER PUBLICATIONS

Peach et al., "Structural Characterization of a Glycoprotein Variant of Human Serum Albumin: Albumin Casebrook (494 Asp →Asn)," *Biochim. Biophys. Acta.* 1097:49-54, 1991.
Robinson et al., "Molecular Clocks," *Proc. Natl. Acad. Sci. USA* 98(3):944-949, 2001.
Schier et al., "In Vitro and In Vivo Characterization of a Human Anti-c-erbB-2 Single-Chain Fv Isolated from a Filamentous Phage Antibody Library," *Immunotechnology* 1(1):73-81, 1995.
Schier et al., "Isolation of Picomolar Affinity Anti-c-erbB-2 Single-Chain Fv by Molecular Evolution of the Complementarity Determining Regions in the Center of the Antibody Binding Site," *J. Mol. Biol.* 263(4):551-567, 1996.
Smith et al., "Prolonged In Vivo Residence Times of Antibody Fragments Associated with Albumin," *Bioconjug. Chem.* 12(5):750-756, 2001.
Soltoff et al., "ErbB3 is Involved in Activation of Phosphatidylinositol 3-Kinase by Epidermal Growth Factor," *Mol. Cell Biol.* 14(6):3550-3558, 1994.
Sugio et al., "Crystal Structure of Human Serum Albumin at 2.5Å Resolution," *Protein Eng.* 12:439-446, 1999.
Tanner et al., "ErbB-3 Predicts Survival in Ovarian Cancer," *J. Clin. Oncol.* 24(26):4317-4323, 2006.
Tárnoky, "Genetic and Drug-Induced Variation in Serum Albumin," *Adv. Clin. Chem.* 21: 101-146, 1980.
Tsukada et al., "The Effect of Bispecific Monoclonal Antibody Recognizing Both Hepatomaspecific Membrane Glycoprotein and Anthracycline Drugs on the Metastatic Growth of Hepatoma AH66," *Cancer. Biochem. Biophys.* 10(3):247-256, 1989 (abstract).
Völkel et al., "Optimized Linker Sequences for the Expression of Monomeric and Dimeric Bispecific Single-chain Diabodies," *Protein Eng.* 14(10):815-823, 2001.
Wallasch et al., "Heregulin-Dependent Regulation of HER2/neu Oncogenic Signaling by Heterodimerization with HER3," *Embo J.* 14(17):4267-4275, 1995.
Ward et al., "Binding Activities of a Repertoire of Single Immunoglobulin Variable Domains Secreted from *Escherichia coli*," *Nature* 341:544-546, 1989.
Yarden et al., "Untangling the ErbB Signalling Network," *Nat. Rev. Mol. Cell Biol.* 2(2):127-137, 2001.
Yukawa et al., "Bispecific Rabbit Fab'-Bovine Serum Albumin Conjugate Use in Hemagglutination Immunoassay for Beta-Microseminoprotein," *J. Immunoassay* 18(3):215-233, 1997.
International Search Report (PCT/US2009/040259) mailed Jan. 26, 2010.
Written Opinion of the International Searching Authority (PCT/US2009/040259) mailed Jan. 26, 2010.
International Search Report (PCT/US2009/060721) mailed Apr. 13, 2010.
Written Opinion of the International Searching Authority (PCT/US2009/060721) mailed Apr. 13, 2010.
Examination Report issued by the Intellectual Property Office of New Zealand for New Zealand Patent Application No. 589086, dated Mar. 23, 2011.
International Preliminary Report on Patentability (PCT/US2009/060721) issued May 24, 2011.
Arya et al., "Rapid synthesis and introduction of a protected EDTA-like group during the solid-phase assembly of peptides," Bioconjug Chem. 2(5):323-26 (1991).
Chakrabarty et al., "Feedback upregulation of HER3 (ErbB3) expression and activity attenuates antitumor effect of P13K inhibitors," Proc Natl Acad Sci USA. 109(8):2718-23 (2012).
Clackson et al., "Making antibody fragments using phage display libraries," Nature. 352:624-28 (1991).
Doronina et al., "Development of potent monoclonal antibody auristatin conjugates for cancer therapy," Nat Biotechnol. 21(7):778-84 (2003).
Engel et al., "Establishment and characterization of three new continuous cell lines derived from human breast carcinomas," Cancer Res. 38(10):3352-64 (1978).

Engelman et al., "MET amplification leads to gefitinib resistance in lung cancer by activating ERBB3 signaling," Science. 316(5827):1039-43 (2007).
Hutcheson et al., "Heregulin beta1 drives gefitinib-resistant growth and invasion in tamoxifen-resistant MCF-7 breast cancer cells," Breast Cancer Res. 9(4):R50 1-14 (2007).
Kem et al., "Purification and characterization of the cytotoxic cerebratulus A toxins," J Biol Chem. 253(16):5752-57 (1978).
Köhler et al., "Continuous cultures of fused cells secreting antibody of predefined specificity," Nature. 256:495-497 (1975).
Langer, "New methods of drug delivery," Science. 249(4976):1527-33 (1990).
Leuschner et al., "Targeting breast and prostate cancers through their hormone receptors," Biol Reprod. 73:860-65 (2005).
Lonberg et al., "Antigen-specific human antibodies from mice comprising four distinct genetic modifications," Nature. 368(6474):856-59 (1994).
Marks et al., "By-passing immunization. Human antibodies from V-gene libraries displayed on phage," J Mol Biol. 222:581-97 (1991).
Masuda et al., "cDNA cloning and characterization of vascular apoptosis-inducing protein 1," Biochem Biophys Res Commun. 278:197-204 (2000).
McDonagh et al., "Antitumor activity of a novel bispecific antibody that targets the ErbB2/ErbB3 oncogenic unit and inhibits heregulin-induced activation of ErbB3," Mol Cancer Ther. 11(3):582-93 (2012).
Nielsen et al., "Using computational modeling to drive the development of targeted therapeutics," IDrugs. 8(10):822-26 (2005).
Press et al., "Expression of the HER-2/neu proto-oncogene in normal human adult and fetal tissues," Oncogene. 5(7):953-62 (1990).
Prigent et al., "Expression of the c-erbB-3 protein in normal human adult and fetal tissues," Oncogene. 7(7):1273-78 (1992).
Sergina et al., "Escape from HER-family tyrosnie kinase inhibitor therapy by the kinase-inactive HER3," Nature. 445(7126):437-41 (2007) (11 pages).
Sheets et al., "Efficient construction of a large nonimmune phage antibody library: the production of high-affinity human single-chain antibodies to protein antigens," Proc Natl Acad Sci USA. 95(11):6157-62 (1998).
Simon et al., "Accelerated titration designs for phase I clinical trials in oncology," J Natl Cancer Inst. 89(15):1138-47 (1997).
Takada et al., "The primary structure of the alpha$^4$ subunit of VLA-4: homology to other integrins and a possible cell-cell adhesion function," EMBO J. 8(5):1361-68 (1989).
Thorpe et al., "The preparation and cytotoxic properties of antibody-toxin conjugates," Immunol Rev. 62:119-58 (1982).
Tokunaga et al., "Deregulation of the AKT pathway in human cancer," Curr Cancer Drug Targets. 8(1):27-36 (2008).
van der Horst et al., "Anti-HER-3 MAbs inhibit HER-3-mediated signaling in breast cancer cell lines resistant to Anti-HER-2 antibodies," Int J Cancer. 115(4):519-27 (2005).
Vivanco et al., "The phosphatidylinositol 3-kinase AKT pathway in human cancer," Nat Rev Cancer. 2(7):489-501 (2002).
Zahn-Zabal et al., "Development of stable cell lines for production or regulated expression using matrix attachment regions," J Biotechnol. 87(1):29-42 (2001).
Zhang et al., "Combination of MM-111, an ErbB2/ErbB3 bispecific antibody, with endocrine therapies as a treatment strategy in models of ER+/HER2+ breast cancer," Presentation at 102nd Annual Meeting of AACR (2011) (1 page).
International Preliminary Report on Patentability and Written Opinion for International Patent Application No. PCT/US2012/026602, dated Oct. 22, 2013 (7 pages).
International Preliminary Report on Patentability and Written Opinion of the International Searching Authority for International Application No. PCT/US2011/064496, issued Jun. 25, 2013 (5 pages).
International Search Report for International Application No. PCT/US2012/026602, mailed Jun. 8, 2012 (4 pages).
International Search Report for International Application No. PCT/US2013/057714, mailed Dec. 20, 2013 (5 pages).
Japanese Office Action in Japanese Patent Application No. 2011-536365 mailed Dec. 16, 2013 (with English Translation) (6 pages).

(56) References Cited

OTHER PUBLICATIONS

Office Action for Chinese Patent Application No. 200980154509.9, mailed Nov. 18, 2013 (with English Translation) (11 pages).

Written Opinion of the International Searching Authority for International Application No. PCT/US2012/026602, mailed Jun. 8, 2012 (6 pages).

Written Opinion of the International Searching Authority for International Application No. PCT/US2013/057714, mailed Dec. 20, 2013 (8 pages).

Bai et al., "Improving the oral efficacy of recombinant granulocyte colony-stimulating factor and transferrin fusion protein by spacer optimization," *Pharm Res.* 23(9): 2116-21, 2006.

Bera et al., "A bivalent disulfide-stabilized Fv with improved antigen binding to erbB2," *J Mol Biol.* 281(3): 475-83, 1998.

Jenkins, "Modifications of therapeutic proteins: challenges and prospects," *Cytotechnology.* 53(1-3): 121-25, 2007.

Robinson et al., "Targeting ErbB2 and ErbB3 with a bispecific single-chain Fv enhances targeting selectivity and induces a therapeutic effect in vitro," *Br J Cancer.* 99(9): 1415-25, 2008.

Invitation to Respond to Written Opinion in Singapore Patent Application No. 2010074375, dated Oct. 11, 2012 (17 pages).

Communication enclosing the Extended European Search Report and Search Opinion for European Patent Application No. 09730096.6, dated Jan. 16, 2013 (9 pages).

Office Action for Chinese Patent Application No. CN200980154509.9, dated Feb. 20, 2013 (13 pages).

Office Action in Eurasian Patent Application No. 201001625, dated Jun. 28, 2013 (12 pages).

Notice of Allowance for U.S. Appl. No. 12/757,801, dated Sep. 2, 2014 (2 pages).

\* cited by examiner

US 8,927,694 B2

HUMAN SERUM ALBUMIN LINKERS AND CONJUGATES THEREOF

CROSS-REFERENCE TO RELATED APPLICATIONS

This application is a National Stage Application of PCT/US2009/060721, filed Oct. 14, 2009, which is a continuation-in-part of PCT/US2009/040259, filed Apr. 10, 2009, which claims benefit to U.S. provisional patent application 61/115,797, filed Nov. 18, 2008, each of which is hereby incorporated by reference.

FIELD OF THE INVENTION

Provided are a human serum albumin (HSA) linker conjugates and binding, diagnostic, and therapeutic conjugates thereof. In one embodiment, the HSA linker includes two amino acid substitutions. Another embodiment is a conjugate in which the HSA linker is covalently bonded to amino and carboxy terminal binding moieties that are first and second single-chain Fv molecules (scFvs). Exemplified conjugates are useful, e.g., in reducing tumor cell proliferation, e.g., for therapeutic applications. Further provided are methods for the manufacture and administration of diagnostic and therapeutic HSA linker conjugates.

BACKGROUND OF THE INVENTION

Antibody-like binding moieties (including those in intact antibodies, antibody fragments, and scFvs) are often used for therapeutic applications. Antibody fragments and scFvs generally exhibit shorter serum half lives than intact antibodies, and in some therapeutic applications increased in vivo half lives would be desireable for therapeutic agents possessing the functionality of such fragments and scFvs.

Human serum albumin (HSA) is a protein of about 66,500 kD and is comprised of 585 amino acids including at least 17 disulphide bridges. As with many of the members of the albumin family, human serum albumin plays an important role in human physiology and is located in virtually every human tissue and bodily secretion. HSA has the ability to bind and transport a wide spectrum of ligands throughout the circulatory system, including the long-chain fatty acids, which are otherwise insoluble in circulating plasma.

The serum albumins belong to a family of proteins that includes alpha-fetoprotein and human group-specific component, also known as vitamin-D binding protein. The serum albumins are the major soluble proteins of the circulatory system and contribute to many vital physiological processes. Serum albumin generally comprises about 50% of the total blood component by dry weight. The albumins and their related blood proteins also play an important role in the transport, distribution, and metabolism of many endogenous and exogenous ligands in the human body, including a variety of chemically diverse molecules, such as fatty acids, amino acids, steroids, calcium, metals such as copper and zinc, and various pharmaceutical agents. The albumin family of molecules is generally thought to facilitate transfer of many of these ligands across organ-circulatory interfaces, such as the liver, intestines, kidneys, and the brain. The albumins are thus involved in a wide range of circulatory and metabolic functions.

SUMMARY OF THE INVENTION

In a first aspect, the invention provides an HSA linker conjugate that includes a human serum albumin (HSA) linker that comprises an amino acid sequence set forth in any one of SEQ ID NOS:6-15 and first and second binding moieties selected from antibodies, single-chain Fv molecules, bispecific single chain Fv ((scFv')$_2$) molecules, domain antibodies, diabodies, triabodies, hormones, Fab fragments, F(ab')$_2$ molecules, tandem seFv (taFv) fragments, receptors (e.g., cell surface receptors), ligands, aptamers, and biologically-active fragments thereof, in which the first binding moiety is bonded to the amino terminus of the HSA linker and the second binding moiety is bonded to the carboxy terminus of the HSA linker. In one embodiment, the first binding moiety specifically binds ErbB3 and the second binding moiety specifically binds ErbB2. In other embodiments, the HSA linker comprises an amino acid sequence set forth in SEQ ID NO:1, 9, 10, 14 or 15.

In a second aspect, three or more binding moieties (e.g., 4, 5, 6, 7, 8, 9, 10, or more) can be included in the agent; these additional binding moieties can be added to the agent, e.g., in tandem (e.g., 2, 3, 4, or 5 or more in tandem) with the first or second binding moiety.

In a third aspect, the invention provides an HSA linker that comprises an amino acid sequence having at least 90% sequence identity to the sequence set forth in SEQ ID NO:1, and a serine residue at position 34 and a glutamine residue at position 503 of the amino acid sequence set forth in SEQ ID NO:1. In one embodiment, the amino acid sequence has at least 95% sequence identity to the sequence set forth in SEQ ID NO: 1. In another embodiment, the HSA linker comprises the amino acid sequence set forth in SEQ ID NO:1. In yet another embodiment, the HSA linker has the amino acid sequence set forth in SEQ ID NO: 1.

In a fourth aspect, the invention provides an HSA linker conjugate that includes an HSA linker having at least 90% amino acid sequence identity to the sequence set forth in SEQ ID NO:1 and at least a first binding moiety. In one embodiment, the HSA linker conjugate includes a first peptide connector that binds the first binding moiety to the HSA linker.

In a fifth aspect, the invention features an MSA linker conjugate that includes an HSA linker having an amino acid sequence set forth in any one of SEQ ID NOs:11-15, or a fragment or variant of any one of these sequences, and at least a first binding moiety.

In certain embodiments of either the fourth or fifth aspect of the invention, the HSA linker conjugate further includes a first peptide connector (e.g., AAS, AAQ, or AAAL (SEQ ID NO:5)) that binds the first binding moiety to the amino or carboxy terminus of the HSA linker. In an embodiment, the first connector covalently binds the first binding moiety to the HSA linker.

In certain embodiments of either the fourth or fifth aspect of the invention, the HSA linker conjugate further includes at least a second binding moiety. In an embodiment, the HSA linker conjugate further includes a second peptide connector (e.g., AAS, AAQ, or AAAL (SEQ ID NO:5)) that binds the second binding moiety to the HSA linker. In other embodiments, the second connector binds the second binding moiety to the amino or carboxy terminus of the HSA linker. In a further embodiment, the second connector covalently binds the second binding moiety to the HSA linker. In other embodiments, the HSA linker conjugate further includes three or more binding moieties which are included in tandem with the first or second binding moiety; the three or more binding moieties can further include a connector sequence that joins the three or more binding moieties to the first or second binding moiety and to each other.

In certain embodiments of either the fourth or fifth aspect of the invention, the HSA linker conjugate includes a first peptide connector that covalently binds a first binding moiety to the amino terminus of the HSA linker and a second peptide connector that covalently binds a second binding moiety to the carboxy terminus of the HSA linker. In one embodiment, the first connector has the amino acid sequence AAS or AAQ and the second connector has the amino acid sequence set forth in SEQ ID NO:5.

In certain embodiments of either the fourth or fifth aspect of the invention, the first or second binding moiety (or third or more binding moiety) is an antibody, single-chain Fv molecule, bispecific single chain Fv ((scFv')$_2$) molecule, domain antibody, diabody, triabody, hormone, Fab fragment, F(ab')$_2$ molecule, tandem scFv (taFv) fragment, receptor (e.g., cell surface receptor), ligand, aptamer, or biologically-active fragment thereof. In other embodiments, the HSA linker conjugates provided herein include combinations of these different types of binding moieties. In one embodiment, at least the first or second binding moiety is a human or humanized single-chain Fv molecule.

In an embodiment of any one of the first, second, third, fourth, or fifth aspects of the invention, one or more of the first or second binding moiety (or, if present, the third or further binding moiety) is or specifically binds to a protein selected from the group consisting of an insulin-like growth factor 1 receptor (IGF1R), IGF2R, insulin-like growth factor (IGF), mesenchymal epithelial transition factor receptor (c-met; also known as hepatocyte growth factor receptor (HGFR)), hepatocyte growth factor (HGF), epidermal growth factor receptor (EGFR), epidermal growth factor (EGF), heregulin, fibroblast growth factor receptor (FGFR), platelet-derived growth factor receptor (PDGFR), platelet-derived growth factor (PDGF), vascular endothelial growth factor receptor (VEGFR), vascular endothelial growth factor (VEGF), tumor necrosis factor receptor (TNFR), tumor necrosis factor alpha (TNF-α), TNF-β, folate receptor (FOLR), folate, transferrin receptor (TfR), mesothelin, Fc receptor, c-kit receptor, c-kit, an integrin (e.g., an α4 integrin or β-1 integrin), P-selectin, sphingosine-1-phosphate receptor-1 (S1PR), hyaluronate receptor, leukocyte function antigen-1 (LFA-1), CD4, CD11, CD18, CD20, CD25, CD27, CD52, CD70, CD80, CD85, CD95 (Fas receptor), CD106 (vascular cell adhesion molecule 1 (VCAM1), CD166 (activated leukocyte cell adhesion molecule (ALCAM)), CD178 (Fas ligand), CD253 (TNF-related apoptosis-inducing ligand (TRAIL)), ICOS ligand, CCR2, CXCR3, CCR5, CXCL12 (stromal cell-derived factor 1 (SDF-1)), interleukin 1 (IL-1), CTLA-4, MART-1, gp100, MAGE-1, ephrin (Eph) receptor, mucosal addressin cell adhesion molecule 1 (MAdCAM-1), carcinoembryonic antigen (CEA), Lewis$^Y$, MUC-1, epithelial cell adhesion molecule (EpCAM), cancer antigen 125 (CA125), prostate specific membrane antigen (PSMA), TAG-72 antigen, and fragments thereof. In a further embodiment, one or more of the first or second binding moiety (or, if present, the third or further binding moiety) is or specifically binds to erythroblastic leukemia viral oncogene homolog (ErbB) receptor (e.g., ErbB1 receptor; ErbB2 receptor; ErbB3 receptor; and ErbB4 receptor). In another embodiment, one or more of the first or second binding moiety (or, if present, the third or further binding moiety) is or specifically binds to alpha-fetoprotein (AFP) or an interferon, or a biologically-active fragment thereof. In a further embodiment, one or more of the first or second binding moiety (or, if present, the third or further binding moiety) is natalizumab, infliximab, adalimumab, rituximab, alemtuzumab, bevacizumab, daclizumab, efalizumab, golimumab, certolizumab, trastuzumab, abatacept, etanercept, pertuzumab, cetuximab, panitumumab, or anakinra.

In any one of the first, second, third, fourth, or fifth aspects of the invention, the HSA linker conjugate is conjoined to a diagnostic, a therapeutic agent, or both. In one embodiment, the diagnostic agent is a detectable label, such as a radioactive, fluorescent, or heavy metal label. In another embodiment, the therapeutic agent is a cytotoxic, cytostatic, or immunomodulatory agent. Cytotoxic agents include alkylating agents, antibiotics, antineoplastic agents, antiproliferative agents, antimetabolites, tubulin inhibitors, topoisomerase I or II inhibitors, hormonal agonists or antagonists, immunomodulators, DNA minor groove binders, and radioactive agents, or any agent capable of binding to and killing a tumor cell or inhibiting tumor cell proliferation. Antineoplastic agents include cyclophosphamide, camptothecin, homocamptothecin, colchicine, combrestatin, combrestatin, rhizoxin, dolistatin, ansamitocin p3, maytansinoid, auristatin, caleachimicin, methotrexate, 5-fluorouracil (5-FU), doxorubicin, paclitaxel, docetaxel, cisplatin, carboplatin, tamoxifen, raloxifene, letrozole, epirubicin, bevacizumab, pertuzumab, trastuzumab, and their derivatives.

In any one of the first, second, third, fourth, or fifth aspects of the invention, the HSA linker conjugate is admixed with a pharmaceutically acceptable carrier, excipient, or diluent. In one embodiment, the agent exhibits an in vivo half-life of between 6 hours and 7 days. In another embodiment, the agent exhibits an in vivo half-life greater than 8 hours.

In a sixth aspect, the invention features a method for treating a mammal having a disease or disorder by administering any one of the HSA linker conjugates described herein. In one embodiment, the disease or disorder is associated with cellular signaling through a cell surface receptor. In another embodiment, the mammal is a human. In a further embodiment, the disease or disorder is a proliferative or autoimmune disease. Proliferative diseases include such cancers as melanoma, clear cell sarcoma, head and neck cancer, bladder cancer, breast cancer, colon cancer, ovarian cancer, endometrial cancer, gastric cancer, pancreatic cancer, renal cancer, prostate cancer, salivary gland cancer, lung cancer, liver cancer, skin cancer, and brain cancer. Autoimmune diseases include multiple sclerosis, psoriasis, myasthenia gravis, uveitis, systemic lupus erythematosus, and rheumatoid arthritis. In one embodiment, the HSA linker conjugate is administered in combination with one or more therapeutic agents, such as an antineoplastic agent.

In a seventh aspect, the invention features a method for making an HSA linker conjugate by bonding at least a first binding moiety to the amino terminus and a second binding moiety to the carboxy terminus of an HSA linker having the amino acid sequence set forth in any one of SEQ ID NOS:1, 3, or 6-15, or a sequence having at least 90%, 95%, 97%, or 100% sequence identity to a sequence set forth in any one of SEQ ID NOS:1, 3, or 6-15. In one embodiment, the first or second binding moiety is covalently joined to the amino or carboxy terminus of the HSA linker. In other embodiments, a third or additional binding moiety (e.g., a fourth, fifth, sixth, seventh, eighth, ninth, or tenth binding moiety) is covalently joined in tandem with the first or second binding moiety to the amino or carboxy terminus of the HSA linker. In another embodiment, one or more of the first or second binding moiety (or, if present, the third or further binding moiety) is an antibody, single-chain Fv molecule, bispecific single chain Fv ((scFv')$_2$) molecule, domain antibody, diabody, triabody, hormone, Fab fragment, F(ab')$_2$ molecule, tandem scFv (taFv) fragment, receptor (e.g., cell surface receptor), ligand, or aptamer. In another embodiment, the first or second binding moiety (or, if present, the third or further binding moiety) is a human or humanized single-chain Fv molecule. In yet another embodiment, one or more of the first or second binding moiety (or, if present, the third or further binding moiety) is or specifically binds to insulin-like growth factor 1 receptor (IGF1R), IGF2R, insulin-like growth factor (IGF), mesenchymal epithelial transition factor receptor (c-met; also known as hepatocyte growth factor receptor (HGFR)), hepatocyte growth factor (HGF), epidermal growth factor receptor (EGFR), epidermal growth factor (EGF), heregulin, fibroblast growth factor receptor (FGFR), platelet-derived growth factor receptor (PDGFR), platelet-derived growth factor (PDGF), vascular endothelial growth factor receptor (VEGFR), vascular endothelial growth factor (VEGF), tumor necrosis factor receptor (TNFR), tumor necrosis factor alpha (TNF-α), TNF-β, folate receptor (FOLR), folate, transferrin receptor (TfR), mesothelin, Fc receptor, c-kit receptor, c-kit, an integrin (e.g., an α4 integrin or β-1 integrin), P-selectin, sphingosine-1-phosphate receptor-1 (S1PR), hyaluronate receptor, leukocyte function antigen-1 (LFA-1), CD4, CD11, CD18, CD20, CD25, CD27, CD52, CD70, CD80, CD85, CD95 (Fas receptor), CD106 (vascular cell adhesion molecule 1 (VCAM1), CD166 (activated leukocyte cell adhesion molecule (ALCAM)), CD178 (Fas ligand), CD253 (TNF-related apoptosis-inducing ligand (TRAIL)), ICOS ligand, CCR2, CXCR3, CCR5, CXCL12 (stromal cell-derived factor 1 (SDF-1)), interleukin 1 (IL-1), CTLA-4, MART-1, gp100, MAGE-1, ephrin (Eph) receptor, mucosal addressin cell adhesion molecule 1 (MAdCAM-1), carcinoembryonic antigen (CEA), Lewis$^Y$, MUC-1, epithelial cell adhesion molecule (EpCAM), cancer antigen 125 (CA125), prostate specific membrane antigen (PSMA), TAG-72 antigen, and fragments thereof. In a further embodiment, one or more of the first or second binding moiety (or, if present, the third or further binding moiety) is or specifically binds to erythroblastic leukemia viral oncogene homolog (ErbB) receptor (e.g., ErbB1 receptor; ErbB2 receptor; ErbB3 receptor; and ErbB4 receptor). In another embodiment, one or more of the first or second binding moiety (or, if present, the third or further binding moiety) is or specifically binds to alpha-fetoprotein (AFP) or an interferon, or a biologically-active fragment thereof. In a further embodiment, one or more of the first or second binding moiety (or, if present, the third or further binding moiety) is natalizumab, infliximab, adalimumab, rituximab, alemtuzumab, bevacizumab, daclizumab, efalizumab, golimumab, certolizumab, trastuzumab, abatacept, etanercept, pertuzumab, cetuximab, panitumumab, or anakinra. In another embodiment, the agent is conjoined to a diagnostic or therapeutic agent. In one embodiment, the diagnostic agent is a detectable label, such as a radioactive, bioluminescent, fluorescent, heavy metal, or epitope tag. In another embodiment, the therapeutic agent is a cytotoxic agent, cytostatic, or immunomodulatory agent. Cytotoxic agents include alkylating agents, antibiotics, antineoplastic agents, antiproliferative agents, antimetabolites, tubulin inhibitors, topoisomerase I and II inhibitors, hormonal agonists or antagonists, immunomodulators, DNA minor groove binders, and radioactive agents, or any agent capable of binding to and killing a tumor cell or inhibiting tumor cell proliferation. Antineoplastic agents include cyclophosphamide, camptothecin, homocamptothecin, colchicine, combrestatin, combrestatin, rhizoxin, dolistatin, ansamitocin p3, maytansinoid, auristatin, caleachimicin, methotrexate, 5-fluorouracil (5-FU), doxorubicin, paclitaxel, docetaxel, cisplatin, carboplatin, tamoxifen, raloxifene, letrozole, epirubicin, bevacizumab, pertuzumab, trastuzumab, and their derivatives. In a further embodiment, the agent is admixed with a pharmaceutically acceptable carrier, excipient, or diluent.

In a eighth aspect, the invention features a method for making an HSA linker by substituting one or more surface-exposed amino acid residues in the amino acid sequences set forth in any one of SEQ ID NOS:1, 3, and 6-15 with a substitute amino acid capable of chemical modification that allows conjugation of a diagnostic or therapeutic agent. In one embodiment, the substitute amino acid is cysteine and the surface exposed amino acid residues are serine or threonine. In another embodiment, the chemical modification results in a covalent bond between the substitute amino acid and the diagnostic or therapeutic agent. In a further embodiment, the surface-exposed amino acid residues is threonine at position 496, serine at position 58, threonine at position 76, threonine at position 79, threonine at position 83, threonine at position 125, threonine at position 236, serine at position 270, serine at position 273, serine at position 304, serine at position 435, threonine at position 478, threonine at position 506, or threonine at position 508.

In a ninth aspect, the invention features a method for making an HSA linker by substituting one or more of the residues in the amino acid sequences set forth in any one of SEQ ID NOS:1, 3, and 6-15 with an asparagine, serine, or threonine, thereby incorporating a glycosylation site within the HSA agent.

In a tenth aspect, the invention features a method for making an HSA linker by substituting one or more of the asparagine, serine, or threonine residues in the amino acid sequences set forth in any one of SEQ ID NOS:1, 3, and 6-15 with any amino acid other than asparagine, serine, or threonine, thereby removing a glycosylation site from the HSA agent.

In an eleventh aspect, the invention features an HSA linker that comprises a sequence that has at least 90% sequence identity to one of the amino acid sequences set forth in SEQ ID NOS:16-25. In one embodiment, the HSA linker has at least 95% sequence identity to one of the amino acid sequences set forth in SEQ ID NOS:16-25. In another embodiment, the HSA linker comprises one of the amino acid sequences set forth in SEQ ID NOS:16-25. In yet another embodiment, the HSA linker has one of the amino acid sequences set forth in SEQ ID NOS:16-25.

In a further embodiment, the HSA linker or HSA linker conjugate is conjoined to a diagnostic or therapeutic agent. Diagnostic agents include detectable labels, such as a radioactive, bioluminescent, fluorescent, or heavy metal labels, or epitope tags. Fluorescent molecules that can serve as detectable labels include green fluorescent protein (GFP), enhanced GFP (eGFP), yellow fluorescent protein (YFP), cyan fluorescent protein (CFP), red fluorescent protein (RFP), and dsRed. In one embodiment, the bioluminescent molecule is luciferase. In another embodiment, the epitope tag is c-myc, hemagglutinin, or a histidine tag. In a further embodiment, the therapeutic agent is a cytotoxic polypeptide such as cytochrome c, caspase 1-10, granzyme A or B, tumor necrosis factor-alpha (TNF-α), TNF-β, Fas, Fas ligand, Fas-associated death doman-like IL-1⊕ converting enzyme (FLICE), TRAIL/APO2L, TWEAK/APO3L, Bax, Bid, Bik, Bad, Bak, RICK, vascular apoptosis inducing proteins 1 and 2 (VAP1 and VAP2), pierisin, apoptosis-inducing protein (AIP), IL-1α propiece polypeptide, apoptin, apoptin-associated protein 1 (AAP-1), endostatin, angiostatin, and biologically-active fragments thereof. An HSA linker or HSA linker conjugate can be combined with (e.g., conjoined to or mixed with in a pharmaceutical composition) one or more therapeutic agents such as cyclophosphamide, camptothecin, homocamptothecin, colchicine, combrestatin, combrestatin, rhizoxin, dolistatin, ansamitocin p3, maytansinoid, auristatin, caleachimicin, methotrexate, 5-fluorouracil (5-FU), doxorubicin, paclitaxel, docetaxel, cisplatin, carboplatin, tamoxifen, raloxifene, letrozole, epirubicin, bevacizumab, pertuzumab, trastuzumab, and derivatives thereof.

In an embodiment of any aspect described herein, the first and second binding moieties (and, if present, one or more of the third or further binding moiety) specifically bind the same target molecule. In another embodiment of any aspect, the first and second binding moieties (and, if present, one or more of the third or further binding moiety) specifically bind different target molecules. In a further embodiment of any aspect, the first and second binding moieties (and, if present, one or more of the third or further binding moiety) specifically bind different epitopes on the same target molecule.

In a twelfth aspect, the invention features an HSA linker that comprises one or both of amino acid residues 25-44 and 494-513 of the amino acid sequence set forth in SEQ ID NO:1. In one embodiment, the HSA linker comprises amino acid residues 25-70 and 450-513 of the amino acid sequence set forth in SEQ ID NO:1. In another embodiment, the HSA linker comprises amino acid residues 15-100 and 400-520 of the amino acid sequence set forth in SEQ ID NO:1. In a further embodiment, the HSA linker comprises amino acid residues 10-200 and 300-575 of the amino acid sequence set forth in SEQ ID NO:1. In another embodiment, the HSA linker comprises amino acid residues 5-250 and 275-580 of the amino acid sequence set forth in SEQ ID NO:1.

In the twelfth aspect of the invention, the HSA linker is conjoined to at least a first binding moiety, for form an HSA linker conjugate. In one embodiment, the HSA linker conjugate includes at least a first peptide connector that binds the first binding moiety to the amino or carboxy terminus of the HSA linker. In another embodiment, the first peptide connector covalently binds the first binding moiety to the HSA linker. In a further embodiment, the HSA linker includes a second binding moiety. In one embodiment, the HSA linker includes a second peptide connector that binds the second binding moiety to the HSA linker. In other embodiments, the second connector binds the second binding moiety to the amino or carboxy terminus of the HSA linker. In a further embodiment, the second connector covalently binds the second binding moiety to the HSA linker. In other embodiments, the HSA linker includes a third, fourth, fifth, sixth, seventh, eighth, ninth, or tenth binding moiety. In other embodiments, these additional binding moieties are present in tandem with one or both of the first or second binding moiety. In yet other embodiments, a peptide connector (e.g., AAS, AAQ, or AAAL (SEQ ID NO:5)) separates one or more of these additional binding moities from each other, the first or second binding moiety, or the HSA linker.

In the twelfth aspect of the invention, the HSA linker includes a first peptide connector that covalently binds a first binding moiety to the amino terminus of the polypeptide linker and a second peptide connector that covalently binds a second binding moiety to the carboxy terminus of the HSA linker. In one embodiment, the first connector has the amino acid sequence AAS or AAQ and the second connector has the amino acid sequence set forth in SEQ ID NO:5.

In the twelfth aspect of the invention, one or more of the first or second binding moiety (or, if present, the third or further binding moiety) is an antibody, single-chain Fv molecule, bispecific single chain Fv ((scFv')$_2$) molecule, domain antibody, diabody, triabody, hormone, Fab fragment, F(ab')$_2$ molecule, tandem scFv (taFv) fragment, receptor (e.g., cell surface receptor), ligand, aptamer, or biologically-active fragment thereof. In one embodiment, one or more of the first or second binding moiety (or, if present, the third or further binding moiety) is a human or humanized single-chain Fv molecule.

In the twelfth aspect of the invention, one or more of the first or second binding moiety (or, if present, the third or further binding moiety) is or specifically binds to a protein selected from the group consisting of an insulin-like growth factor 1 receptor (IGF1R), IGF2R, insulin-like growth factor (IGF), mesenchymal epithelial transition factor receptor (c-met; also known as hepatocyte growth factor receptor (HGFR)), hepatocyte growth factor (HGF), epidermal growth factor receptor (EGFR), epidermal growth factor (EGF), heregulin, fibroblast growth factor receptor (FGFR), platelet-derived growth factor receptor (PDGFR), platelet-derived growth factor (PDGF), vascular endothelial growth factor receptor (VEGFR), vascular endothelial growth factor (VEGF), tumor necrosis factor receptor (TNFR), tumor necrosis factor alpha (TNF-α), TNF-β, folate receptor (FOLR), folate, transferrin receptor (TfR), mesothelin, Fc receptor, c-kit receptor, c-kit, an integrin (e.g., an α4 integrin or β-1 integrin), P-selectin, sphingosine-1-phosphate receptor-1 (S1PR), hyaluronate receptor, leukocyte function antigen-1 (LFA-1), CD4, CD11, CD18, CD20, CD25, CD27, CD52, CD70, CD80, CD85, CD95 (Fas receptor), CD106 (vascular cell adhesion molecule 1 (VCAM1), CD166 (activated leukocyte cell adhesion molecule (ALCAM)), CD178 (Fas ligand), CD253 (TNF-related apoptosis-inducing ligand (TRAIL)), ICOS ligand, CCR2, CXCR3, CCR5, CXCL12 (stromal cell-derived factor 1 (SDF-1)), interleukin 1 (IL-1), CTLA-4, MART-1, gp100, MAGE-1, ephrin (Eph) receptor, mucosal addressin cell adhesion molecule 1 (MAdCAM-1), carcinoembryonic antigen (CEA), Lewis$^Y$, MUC-1, epithelial cell adhesion molecule (EpCAM), cancer antigen 125 (CA125), prostate specific membrane antigen (PSMA), TAG-72 antigen, and fragments thereof. In a further embodiment, the first or second binding moiety is or specifically binds to erythroblastic leukemia viral oncogene homolog (ErbB) receptor (e.g., ErbB1 receptor; ErbB2 receptor; ErbB3 receptor; and ErbB4 receptor). In another embodiment, one or more of the first or second binding moiety (or, if present, the third or further binding moiety) is or specifically binds to alpha-fetoprotein (AFP) or an interferon, or a biologically-active fragment thereof. In a further embodiment, one or more of the first or second binding moiety (or, if present, the third or further binding moiety) is natalizumab, infliximab, adalimumab, rituximab, alemtuzumab, bevacizumab, daclizumab, efalizumab, golimumab, certolizumab, trastuzumab, abatacept, etanercept, pertuzumab, cetuximab, panitumumab, or anakinra.

In the twelfth aspect of the invention, the HSA linker is conjoined to a diagnostic agent, a therapeutic agent, or both. In one embodiment, the diagnostic agent is a detectable label, such as a radioactive, fluorescent, or heavy metal label. In another embodiment, the therapeutic agent is a cytotoxic agent, cytostatic, or immunomodulatory agent. Cytotoxic agents include alkylating agents, antibiotics, antineoplastic agents, antiproliferative agents, antimetabolites, tubulin inhibitors, topoisomerase I or II inhibitors, hormonal agonists or antagonists, immunomodulators, DNA minor groove binders, and radioactive agents, or any agent capable of binding to and killing a tumor cell or inhibiting tumor cell proliferation. Antineoplastic agents include cyclophosphamide, camptothecin, homocamptothecin, colchicine, combrestatin, combrestatin, rhizoxin, dolistatin, ansamitocin p3, maytansinoid, auristatin, caleachimicin, methotrexate, 5-fluorouracil (5-FU), doxorubicin, paclitaxel, docetaxel, cisplatin, carboplatin, tamoxifen, raloxifene, letrozole, epirubicin, bevacizumab, pertuzumab, trastuzumab, and their derivatives. In one embodiment, the conjoined HSA linker is admixed with a pharmaceutically acceptable carrier, excipient, or diluent. In another embodiment, the HSA linker exhibits an in vivo half-life of between 6 hours and 7 days. In a further embodiment, the HSA linker exhibits an in vivo half-life greater than 8 hours.

A thirteenth aspect of the invention features an agent of any of the prior aspects of the invention (one through twelve), in which the HSA linker is replaced by another polypeptide linker. For example, the polypeptide linker sequence could be a mammalian, non-human serum albumin polypeptide sequence, such as, e.g., a bovine, murine, feline, and canine serum albumin (BSA) polypeptide sequence. In other embodiments this polypeptide linker sequence is between 5 and 1,000 amino acids in length, e.g., 10, 20, 30, 40, 50, 60, 70, 80, 90, 100, 200, 300, 400, 500, 600, 700, 800, or 900 amino acids in length, or any number of amino acids within this range. In other embodiments, the polypeptide linker sequence includes a single amino acid (including, but not limited to, e.g., glycine, alanine, serine, glutamine, leucine, and valine), or combinations of amino acids.

In another embodiment, the HSA linker is replaced by an alpha-fetoprotein (AFP) polypeptide, e.g., mammalian AFP polypeptide, such as a human, murine, bovine, or canine AFP polypeptide. In an embodiment, the AFP linker corresponds to the full-length human AFP polypeptide sequence (a.a. 1-609; SEQ ID NO:58), the mature human AFP polypeptide sequence lacking amino acids 1-18 of the signal sequence (a.a., 19-609 of SEQ ID NO:58), or fragments thereof. In other embodiments, the AFP polypeptide linker contains at least 5 to 8 contiguous amino acids, preferably at least 10, 20, or 50 contiguous amino acids, more preferably at least 100 contiguous amino acids, and most preferably at least 200, 300, 400, or more contiguous amino acids of SEQ ID NO:58, or has at least 90% sequence identity (e.g., at least 95%, 97%, 99%, or more sequence identity) to a continguous polypeptide sequence of SEQ ID NO:58 having one or more of these lengths. For example, an AFP polypeptide linker sequence having 90% sequence identity to a 34-mer human AFP peptide corresponding to amino acids 446-479 of SEQ ID NO:58 (LSEDKLLACGEGAADIIIGHLCIRHEMTPVNPGV; SEQ ID NO:59) may contain up to 3 amino acids altered from the 446-479 segment of SEQ ID NO:58. One such example of sequence deviation in biologically active human AFP fragments is found in, e.g., U.S. Pat. No. 5,707,963 (incorporated by reference herein), which discloses a 34-amino acid fragment of human AFP (SEQ ID NO:59) with flexibility at two amino acid residues (amino acid 9 and 22 of SEQ ID NO:59). Other examples of AFP polypeptide linker sequences include, e.g., amino acids 19-198 of SEQ ID NO:58 (human AFP Domain I), amino acids 217-408 of SEQ ID NO:58 (human AFP Domain 11), amino acids 409-609 of SEQ ID NO:58 (human AFP Domain III), amino acids 19-408 of SEQ ID NO:58 (human AFP Domain I+II), amino acids 217-609 of SEQ ID NO:58 (human AFP Domain II+III), and amino acids 285-609 of SEQ ID NO:58 (human AFP Fragment I). In another embodiment, the human AFP polypeptide linker sequence is an 8-amino acid sequence that includes amino acids 489-496 (i.e., EMTPVNPG) of SEQ ID NO:58.

A fourteenth aspect of the invention features kits that include any of the HSA linkers, HSA linker conjugates, or any other agents described in the first, second, third, fourth, fifth, eleventh, twelfth, and thirteenth aspects discussed above. The kits further include instructions to allow a practitioner (e.g., a physician, nurse, or patient) to administer the compositions and agents contained therein. In an embodiment, the kits include multiple packages of a single- or multi-dose pharmaceutical composition containing an effective amount of an agent, e.g.,. HSA linker conjugate as described herein or an HSA linker that includes, e.g., one or more binding moieties (e.g., antibodies or antibody fragments (e.g., scFv)), diagnostic agents (e.g., radionuclide or chelating agents), and/or therapeutic agents (e.g., cytotoxic or immunomodulatory agents). Optionally, instruments or devices necessary for administering the pharmaceutical composition(s) may be included in the kits. For instance, a kit may provide one or more pre-filled syringes containing an effective amount of an HSA linker conjugate or HSA linker, or any binding, diagnostic, and/or therapeutic agent conjugated thereto. Furthermore, the kits may also include additional components such as instructions or administration schedules for a patient suffering from a disease or condition (e.g., a cancer, autoimmune disease, or cardiovascular disease) to use the pharmaceutical composition(s) containing, e.g., an HSA linker conjugate or HSA linker, or any binding, diagnostic, and/or therapeutic agent conjugated thereto.

DEFINITIONS

The term "antibody" as used interchangeably herein, includes whole antibodies or immunoglobulins and any antigen-binding fragment or single chains thereof. Antibodies, as used herein, can be mammalian (e.g., human or mouse), humanized, chimeric, recombinant, synthetically produced, or naturally isolated. In most mammals, including humans, whole antibodies have at least two heavy (H) chains and two light (I) chains connected by disulfide bonds. Each heavy chain consists of a heavy chain variable region (abbreviated herein as $V_H$) and a heavy chain constant region. The heavy chain constant region consists of three domains, $C_H1$, $C_H2$, and $C_H3$ and a hinge region between $C_H1$ and $C_H2$. Each light chain consists of a light chain variable region (abbreviated herein as $V_L$) and a light chain constant region. The light chain constant region consists of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Antibodies of the present invention include all known forms of antibodies and other protein scaffolds with antibody-like properties. For example, the antibody can be a human antibody, a humanized antibody, a bispecific antibody, a chimeric antibody, or a protein scaffold with antibody-like properties, such as fibronectin or ankyrin repeats. The antibody also can be a Fab, Fab'2, scFv, SMIP, diabody, nanobody, aptamers, or a domain antibody. The antibody can have any of the following isotypes: IgG (e.g., IgG1, IgG2, IgG3, and IgG4), IgM, IgA (e.g., IgA1, IgA2, and IgAsec), IgD, or IgE. Antibodies that can be used as binding moieties, as defined herein, in combination with an HSA linker include, but are not limited to, natalizumab, infliximab, adalimumab, rituximab, alemtuzumab, bevacizumab, daclizumab, efalizumab, golimumab, certolizumab, trastuzumab, abatacept, etanercept, pertuzumab, cetuximab, and panitumumab.

The term "antibody fragment," as used herein, refers to one or more fragments of an antibody that retain the ability to specifically bind to an antigen (e.g., ErbB2). The antigen-binding function of an antibody can be performed by fragments of a full-length antibody. Examples of binding fragments encompassed within the term "antigen-binding portion" of an antibody include but are not limited to: (i) a Fab fragment, a monovalent fragment consisting of the $V_L$, $V_H$, $C_L$, and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., Nature 341:544-546 (1989)), which consists of a $V_H$ domain; (vii) a dAb which consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., Science 242:423-426 (1988) and Huston et al., Proc. Natl. Acad. Sci. USA 85:5879-5883 (1988)). These antibody fragments are obtained using conventional techniques known to those with skill in the art, and the fragments are screened for utility in the same manner as are intact antibodies. Antibody fragments can be produced by recombinant DNA techniques, or by enzymatic or chemical cleavage of intact immunoglobulins.

By "autoimmune disease" is meant a disease in which an immune system response is generated against self epitopes or antigens. Examples of autoimmune diseases include, but are not limited to, alopecia areata, ankylosing spondylitis, antiphospholipid syndrome, autoimmune Addison's disease, autoimmune hemolytic anemia, autoimmune hepatitis, Behcet's disease, bullous pemphigoid, cardiomyopathy, celiac Sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, Grave's disease, Guillain-Barré syndrome, Hashimoto's thyroiditis, hypothyroidism, idiopathic pulmonary fibrosis, idiopathic thrombocytopenia purpura (ITP), IgA nephropathy, insulin dependent diabetes, juvenile arthritis, lichen planus, lupus, Ménière's disease, mixed connective tissue disease, multiple sclerosis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, Stiff-Man syndrome, systemic lupus erythematosus (SLE), Takayasu arteritis, temporal arteritis/giant cell arteritis, ulcerative colitis, uveitis (e.g., birdshot retinochoroidopathy uveitis and sarcoid uveitis), vasculitis, vitiligo, Wegener's granulomatosis, and myasthenia gravis.

By "binding moiety" is meant any molecule that specifically binds to a target epitope, antigen, ligand, or receptor. Binding moieties include but are not limited to antibodies (e.g., monoclonal, polyclonal, recombinant, humanized, and chimeric antibodies), antibody fragments (e.g., Fab fragments, Fab'2, scFv antibodies, SMIP, domain antibodies, diabodies, minibodies, scFv-Fc, affibodies, nanobodies, and domain antibodies), receptors, ligands, aptamers, and other molecules having a known binding partner.

By "biologically-active" is meant that a molecule, including biological molecules, such as nucleic acids, peptides, polypeptides, and proteins, exerts a physical or chemical activity on itself or other molecule. For example, a "biologically-active" molecule may possess, e.g., enzymatic activity, protein binding activity (e.g., antibody interactions), or cytotoxic activities are "biologically-active."

The term "chimeric antibody" refers to an immunoglobulin or antibody whose variable regions derive from a first species and whose constant regions derive from a second species. Chimeric antibodies can be constructed, for example, by genetic engineering, from immunoglobulin gene segments belonging to different species (e.g., from a mouse and a human).

By "connector" or "peptide connector" is meant an amino acid sequence of 2 to 20 residues in length that is covalently attached to one or both of the amino or carboxy termini of an HSA linker, or is covalently attached to one or more residues of an HSA linker (e.g., a residue between the amino and carboxy terminal residues). In preferred embodiments, the peptide connector attached to the amino terminus of an HSA linker has the amino acid sequence AAS or AAQ and the connector attached to the carboxy terminus has the amino acid sequence "AAAL" (SEQ ID NO:5).

The terms "effective amount" or "amount effective to" or "therapeutically effective amount" means an amount of an agent (e.g., an HSA linker bonded with one or more binding moieties or diagnostic or therapeutic agents with or without a connector sequence) sufficient to produce a desired result, for example, killing a cancer cell, reducing tumor cell proliferation, reducing inflammation in a diseased tissue or organ, or labeling a specific population of cells in a tissue, organ, or organism (e.g., a human).

The term "human antibody," as used herein, is intended to include antibodies, or fragments thereof, having variable regions in which both the framework and CDR regions are derived from human germline immunoglobulin sequences as described, for example, by Kabat et al., (Sequences of proteins of Immunological Interest, Fifth Edition, U.S. Department of Health and Human Services, NIH Publication No. 91-3242 (1991)). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences (i.e., a humanized antibody or antibody fragment).

The term "humanized antibody" refers to any antibody or antibody fragment that includes at least one immunoglobulin domain having a variable region that includes a variable framework region substantially derived from a human immunoglobulin or antibody and complementarity determining regions (e.g., at least one CDR) substantially derived from a non-human immunoglobulin or antibody.

As used herein, an "inflammatory signaling inhibitor" or "ISI" is an agent that decreases the binding between a pro-inflammatory cytokine (e.g., TNF-alpha, TNF-beta, or IL-1) and its receptor (e.g., TNF receptor 1 or 2, or IL-1 receptor, respectively); decreases the binding of activating molecules to pro-inflammatory cell surface signaling molecules (e.g., CD20, CD25, CTLA-4, CD80/CD86, or CD28); or decreases the downstream activation of, or activity of, intracellular signaling molecules that are activated following the binding of pro-inflammatory cytokines to their receptors or the binding of activating molecules to pro-inflammatory cell surface signaling molecules (e.g., an agent that decreases the activation of, or activity of, signaling molecules in the p38 MAPK signaling pathway). The decrease mediated by an ISI may be a decrease in binding between a pro-inflammatory cytokine and its receptor, a decrease in binding of an activating molecule to a pro-inflammatory cell surface signaling molecule, or a decrease in intracellular signaling which occurs following the binding of pro-inflammatory cytokines to their receptors or activating molecules to pro-inflammatory cell surface signaling molecules. Preferably, such a decrease mediated by an ISI is a decrease of at least about 10%, preferably at least 20%, 30%, 40%, or 50%, more preferably at least 60%, 70%, 80%, or 90% (up to 100%). An ISI may act by reducing the amount of pro-inflammatory cytokine (e.g., TNF-alpha, TNF-beta, or IL-1) freely available to bind the receptor. For example, an ISI may be a soluble pro-inflammatory cytokine receptor protein (e.g., a soluble TNF receptor fusion protein such as etanercept (ENBREL®) or lenercept), or a soluble pro-inflammatory cell surface signaling molecule (e.g., a soluble CTLA-4 (abatacept)), or an antibody directed against a pro-inflammatory cytokine or a pro-inflammatory cell surface signaling molecule (e.g., an anti-TNF antibody, such as adalimumab, certolizumab, inflixamab, or golimumab; an anti-CD20 antibody, such as rituximab; or TRU-015 (Trubion Pharmaceuticals)). In addition, an 1S1 may act by disrupting the ability of the endogenous wild-type pro-inflammatory cytokine or the pro-inflammatory cell surface signaling molecule to bind to its receptor (e.g., TNF receptor 1 or 2, IL-1 receptor—e.g., anakinra, or CD11a—e.g., efalizumab (RAPTIVA®, Genentech)). Examples of dominant-negative TNF-alpha variants are XENP345 (a pegylated version of TNF variant A145R/197T) and Xpro™1595, and further variants disclosed in U.S. Patent Application Publication Nos. 20030166559 and 20050265962, herein incorporated by reference. An example of a dominant negative IL-1 variant is anakinra (KINERET®), which is a soluble form of IL-1 that binds to the IL-1 receptor without activating intracellular signaling pathways. Inflammatory signaling inhibitors, which can be used in the present invention, are also small molecules which inhibit or reduce the signaling pathways downstream of pro-inflammatory cytokine or pro-inflammatory cell surface signaling molecules (e.g., DE 096). Examples of ISIs of this kind include inhibitors of p38 MAP kinase, e.g., 5-amino-2-carbonylthiopene derivatives (as described in WO 04/089929, herein incorporated); ARRY-797; BIRB 796 BS, (1-5-tert-butyl-2-p-tolyl-2H-pyrazol-3-yl)-3-[4-2 (morpholin-4-yl-ethoxy)-naphtalen-1-yl]-urea); CHR-3620; CNI-1493; FR-167653 (Fujisawa Pharmaceutical, Osaka, Japan); ISIS 101757 (Isis Pharmaceuticals); ML3404; NPC31145; PD169316; PHZ1112; RJW67657, (4-(4-(4-fluorophenyl)-1-(3-phenylpropyl)-5-(4-pyridinyl)-1H-imidazol-2-yl)-3-butyn-1-ol; SC10-469; SB202190; SB203580, (4-(4-fluorophenyl)-2-(4-methylsulfinylphenyl)-5-(4-pyridyl)1H-imidazole); SB239063, trans-1-(4-hydroxycyclohexyl)-4-(4-fluorophenyl-methoxypyridimidin-4-yl)imidazole; SB242235; SD-282; SKF-86002; TAK 715; VX702; and VX745. Furthermore, an ISI may interfere with the processing of a pro-inflammatory cytokine (e.g., TNF-alpha and TNF-beta) from its membrane bound form to its soluble form. Inhibitors of TACE are ISIs of this class. Examples of inhibitors of TACE include BB-1101, BB-3103, BMS-561392, butynyloxyphenyl β-sulfone piperidine hydroxomates, CH4474, DPC333, DPH-067517, GM6001, GW3333, Ro 32-7315, TAPI-1, TAPI-2, and TMI 005. Additional examples of ISIs include short peptides derived from the E. coli heat shock proteins engineered for disease-specific immunomodulatory activity (e.g., dnaJP1).

By "integrin antagonist" is meant any agent that reduces or inhibits the biological activity of an integrin molecule (e.g., a reduction or inhibition of at least 10%, 20%, 30%, 40%, 50%, 60%, 70%, 80%, 90%, 95%, 99%, or more relative to the biological activity in the absence of the integrin antagonist), such as the α4 subunit of an integrin molecule. The agent may act directly or indirectly on the α4 integrin subunit (NCBI Accession No. P13612; Takada et al., *EMBO J.* 8:1361-1368 (1989)) by inhibiting the activity or expression of the α4 integrin subunit, or may act on a target to which the intact integrin containing an α4 subunit binds. For example, an antibody or blocking peptide that binds to vascular cell adhesion molecule-1 (VCAM-1), thus preventing the binding of α4β1 integrin to VCAM-1 is considered an integrin antagonist for purposes of the present invention. Non-limiting exemplary integrin antagonists suitable for use with the present invention may include proteins, blocking peptides, antibodies, such as natalizumab (TYSABRI®), and small molecule inhibitors. Examples of α4 integrin antagonists include, but are not limited to, natalizumab (Elan/Biogen Idec; see, e.g., U.S. Pat. Nos. 5,840,299; 6,033,665; 6,602,503; 5,168,062; 5,385,839; and 5,730,978; incorporated by reference herein), oMEPUPA-V (Biogen; U.S. Pat. No. 6,495,525; incorporated by reference herein), alefacept, CDP-323 (Celltech); firategrast (SB-68399; GlaxoSmithKline); TR-9109 (Pfizer); ISIS-107248 (Antisense Therapeutics); R-1295 (Roche); and TBC-4746 (Schering-Plough). Additional non-limiting examples of α4 integrin antagonists include the small molecules described in U.S. Pat. Nos. 5,821,231; 5,869,448; 5,936,065; 6,265,572; 6,288,267; 6,365,619; 6,423,728; 6,426,348; 6,458,844; 6.479,666; 6,482,849; 6,596,752; 6,667,331; 6,668,527; 6,685,617; 6,903,128; and 7,015,216 (each herein incorporated by reference); in U.S. Patent Application Publication Nos. 2002/0049236; 2003/0004196; 2003/0018016; 2003/0078249; 2003/0083267; 2003/0100585; 2004/0039040; 2004/0053907; 2004/0087574; 2004/0102496; 2004/0132809; 2004/0229858; 2006/0014966; 2006/0030553; 2006/0166866; 2006/0166961; 2006/0241132; 2007/0054909; and 2007/0232601 (each herein incorporated by reference); in European Patent Nos. EP 0842943; EP 0842944; EP 0842945; EP 0903353; and EP 0918059; and in PCT Publication Nos. WO 95/15973; WO 96/06108; WO 96/40781; WO 98/04247; WO 98/04913; WO 98/42656; WO 98/53814; WO 98/53817; WO 98/53818; WO 98/54207; WO 98/58902; WO 99/06390; WO 99/06431; WO 99/06432; WO 99/06433; WO 99/06434; WO 99/06435; WO 99/06436; WO 99/06437; WO 99/10312; WO 99/10313; WO 99/20272; WO 99/23063; WO 99/24398; WO 99/25685; WO 99/26615; WO 99/26921; WO 99/26922; WO 99/26923; WO 99/35163; WO 99/36393; WO 99/37605; WO 99/37618; WO 99/43642; WO 01/42215; and WO 02/28830; all of which are incorporated by reference herein. Additional examples of α4 integrin antagonists include the phenylalanine derivatives described in: U.S. Pat. Nos. 6,197,794; 6,229,011; 6,329,372; 6,388,084; 6,348,463; 6,362,204; 6,380,387; 6,445,550; 6,806,365; 6,835,738; 6,855,706; 6,872,719; 6,878,718; 6,911,451; 6,916,933; 7,105,520; 7,153,963; 7,160,874; 7,193,108; 7,250,516; and 7,291,645 (each herein incorporated by reference). Additional amino acid derivatives that are α4 integrin antagonists include those described in, e.g., U.S. Patent Application Publication Nos. 2004/0229859 and 2006/

0211630 (herein incorporated by reference), and PCT Publication Nos. WO 01/36376; WO 01/47868; and WO 01/70670; all of which are incorporated by reference herein. Other examples of α4 integrin antagonists include the peptides, and the peptide and semi-peptide compounds described in, e.g., PCT Publication Nos. WO 94/15958; WO 95/15973; WO 96/00581; WO 96/06108; WO 96/22966 (Leu-Asp-Val tripeptide; Biogen, Inc.); WO 97/02289; WO 97/03094; and WO 97/49731. An additional example of an α4 integrin antagonist is the pegylated molecule described in U.S. Patent Application Publication No. 2007/066533 (herein incorporated by reference). Examples of antibodies that are α4 integrin antagonists include those described in, e.g., PCT Publication Nos. WO 93/13798; WO 93/15764; WO 94/16094; and WO 95/19790. Additional examples of α4 integrin antagonists are described herein.

By "interferon" is meant a mammalian (e.g., a human) interferon-alpha, -beta, -gamma, or -tau polypeptide, or biologically-active fragment thereof, e.g., IFN-α (e.g., IFN-α-1a; see U.S. Patent Application No. 20070274950, incorporated herein by reference), IFN-α-1b, IFN-α-2a (see PCT Application No. WO 07/044083, herein incorporated by reference), and IFN-α-2b), IFN-β (e.g., described in U.S. Pat. No. 7,238,344, incorporated by reference; IFN-b-1a (AVONEX® and REBIF®), as described in U.S. Pat. No. 6,962,978, incorporated by reference, and IFN-β-1b (BETASERON®, as described in U.S. Pat. Nos. 4,588,585; 4,959,314; 4,737,462; and 4,450,103; incorporated by reference in their entirety), IFN-g, and IFN-t (as described in U.S. Pat. No. 5,738,845 and U.S. Patent Application Publication Nos. 20040247565 and 20070243163; incorporated by reference).

By "HSA linker conjugate" is meant a human serum albumin (HSA) linker in combination with (preferably covalently linked to) one or more binding moieties, peptide connectors, diagnostic agents, or therapeutic agents.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies can be prepared using any art recognized technique and those described herein such as, for example, a hybridoma method, as described by Kohler et al., *Nature* 256:495 (1975), a transgenic animal (e.g., Lonberg et al., *Nature* 368(6474):856-859 (1994)), recombinant DNA methods (e.g., U.S. Pat. No. 4,816,567), or using phage, yeast, or synthetic scaffold antibody libraries using the techniques described in, for example, Clackson et al., *Nature* 352:624-628 (1991) and Marks et al., *J. Mol. Biol.* 222:581-597 (1991).

By "pharmaceutically acceptable carrier" is meant a carrier which is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, for example, in *Remington's Pharmaceutical Sciences,* (18$^{th}$ edition), ed. A. Gennaro, 1990, Mack Publishing Company, Easton, Pa.

By "proliferative disease" or "cancer" is meant any condition characterized by abnormal or unregulated cell growth. Examples of proliferative diseases include, for example, solid tumors such as: sarcomas (e.g., clear cell sarcoma), carcinomas (e.g., renal cell carcinoma), and lymphomas; tumors of the breast, colon, rectum, lung, oropharynx, hypopharynx, esophagus, stomach, pancreas, liver, bilecyst, bile duct, small intestine, urinary system (including the kidney, bladder, and epithelium of the urinary tract), female genital system (including the uterine neck, uterus, ovary, chorioma, and gestational trophoblast), male genital system (including the prostate, seminal vesicle, and testicles), endocrine glands (including the thyroid gland, adrenal gland, and pituitary body), skin (including angioma, melanoma, sarcoma originating from bone or soft tissue, and Kaposi's sarcoma), brain and meninges (including astrocytoma, neuroastrocytoma, spongioblastoma, retinoblastoma, neuroma, neuroblastoma, neurinoma and neuroblastoma), nerves, eyes, hemopoietic system (including chloroleukemia, plasmacytoma and dermal T lymphoma/leukemia), and immune system (including lymphoma, e.g., Hodgkin's lymphoma and non-Hodgkin's lymphoma). An example of a non-solid tumor proliferative disease is leukemia (e.g., acute lymphoblastic leukemia).

The term "recombinant antibody," refers to an antibody prepared, expressed, created, or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage, yeast, or synthetic scaffold display, and (d) antibodies prepared, expressed, created, or isolated by any other means that involve splicing of immunoglobulin gene sequences (e.g., human immunoglobulin genes) to other DNA sequences.

By "specifically bind" is meant the preferential association of a binding moiety (e.g., an antibody, antibody fragment, receptor, ligand, or small molecule portion of an agent as described herein) to a target molecule (e.g., a secreted target molecule, such as a cytokine, chemokine, hormone, receptor, or ligand) or to a cell or tissue bearing the target molecule (e.g., a cell surface antigen, such as a receptor or ligand) and not to non-target cells or tissues lacking the target molecule. It is recognized that a certain degree of non-specific interaction may occur between a binding moiety and a non-target molecule (present alone or in combination with a cell or tissue). Nevertheless, specific binding may be distinguished as mediated through specific recognition of the target molecule. Specific binding results in a stronger association between the binding moiety (e.g., an antibody) and e.g., cells bearing the target molecule (e.g., an antigen) than between the binding moiety and e.g., cells lacking the target molecule. Specific binding typically results in greater than 2-fold, preferably greater than 5-fold, more preferably greater than 10-fold and most preferably greater than 100-fold increase in amount of bound binding moiety (per unit time) to e.g., a cell or tissue bearing the target molecule or marker as compared to a cell or tissue lacking that target molecule or marker. Binding moieties bind to the target molecule or marker with a dissociation constant of e.g., less than $10^{-6}$M, more preferably less than $10^{-7}$M, $10^{-8}$M, $10^{-9}$M, $10^{-10}$M, $10^{-11}$M, or $10^{-12}$M, and most preferably less than $10^{-13}$M, $10^{-14}$M, or $10^{-15}$M. Specific binding to a protein under such conditions requires a binding moiety that is selected for its specificity for that particular protein. A variety of assay formats are appropriate for selecting binding moieties (e.g., antibodies) capable of specifically binding to a particular target molecule. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

By "sequence identity" is meant (in the context of comparing a polynucleotide or polypeptide sequence to a reference sequence) that the polynucleotide or polypeptide sequence is the same as the reference sequence or has a specified percentage of nucleotides or amino acid residues that are the same at the corresponding locations within the reference sequence when the two sequences are optimally aligned.

By "surface-exposed amino acid residue" or "surface-exposed" is meant an amino acid residue that is present on the exterior face of the folded and conformationally-correct tertiary structure of a HSA polypeptide. Such residues can be substituted with e.g., other, chemically-reactive, amino acids (e.g., cysteine) to allow for site-specific conjugation of diagnostic or therapeutic agents. Additionally, surface-exposed amino acid residues can be substituted to allow (e.g., by addition of serine, threonine, or asparagine residues, or glycosylation motifs) or prevent (e.g., by removal of serine, threonine, or asparagine residues, or glycosylation motifs) glycosylation. Surface-exposed amino acid residues include, but are not limited to, threonine at position 496, serine at position 58, threonine at position 76, threonine at position 79, threonine at position 83, threonine at position 125, threonine at position 236, serine at position 270, serine at position 273, serine at position 304, serine at position 435, threonine at position 478, threonine at position 506, and threonine at position 508 (amino acid numbering is relative to e.g., the sequence of the HSA linker set forth in SEQ ID NO:1). Other surface-exposed residues can be identified by the skilled artisan using the HSA crystal structure (Sugio et al., "Crystal structure of human serum albumin at 2.5 A resolution," *Protein Eng.* 12:439-446 (1999)). A "subject" refers to a human patient or a nude mouse xenograft model comprising human tumor cells.

A "target molecule" or "target cell" is meant a molecule (e.g., a protein, epitope, antigen, receptor, or ligand) or cell to which a binding moiety (e.g., an antibody), or an HSA conjugate that contains one or more binding moieties (e.g., an HSA linker bonded to one or more antibodies or antibody fragments) can specifically bind. Preferred target molecules are exposed on the exterior of a target cell (e.g., a cell-surface or secreted protein) but target molecules may alternately or also be present in the interior of a target cell.

"Treating" preferably provides a reduction (e.g., by at least 10%, 15%, 20%, 25%, 30%, 35%, 40%, 45%, 50%, 60%, 70%, 80%, 90%, 95%, 99%, or even 100%) in the progression or severity of a human disease or disorder (e.g., an autoimmune or proliferative disease), or in the progression, severity, or frequency of one or more symptoms of the human disease or disorder in a subject.

BRIEF DESCRIPTION OF THE DRAWINGS

FIG. 17A), SKOV-3 (human ovarian adenocarcinoma; FIG. 17B), NCI-N87 (human gastric carcinoma; FIG. 17C), ACHN (human kidney adenocarcinoma; FIG. 17D), and MDA-MB-361 (human breast adenocarcinoma; FIG. 17E) xenograft model are shown. Mice were treated with 30 mg/kg of B2B3-1 every 3 days or HSA control at an equimolar dose to B2B3-1.

FIG. 20A includes fluorescent micrographs showing that B2B3-1 treatment of BT474-M3 breast tumor cells for 6 hours results in translocation of cell cycle inhibitor p27$^{kip1}$ to the nucleus. Hoechst stain was used to identify the nucleus. FIG. 20B is a Western blot of BT-474-M3 cells treated with B2B3-1 for 72 hours, which resulted in a decrease in the levels of the cell cycle regulator Cyclin D1. The cytoskeleton protein vinculin was probed as a protein loading control in this experiment.

FIG. 35 A-C shows the results of the experiments detailed in Example 43 in which B2B3-1 combination treatment with trastuzumab was studied in spheroids of various human breast cancer cell lines, which serve as a model for human breast tumors.

DETAILED DESCRIPTION

Figure 1:
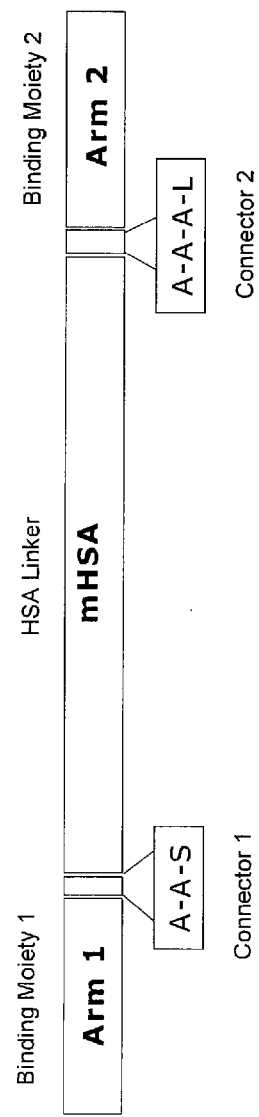
FIG. 1 is an illustration showing the schematic representation of an exemplary HSA linker conjugate. The connector between the amino terminal binding moiety and the HSA linker has a sequence of alanine, alanine and serine. The connector between the HSA linker and the carboxy terminal binding moiety has a sequence of alanine, alanine, alanine, leucine (SEQ ID NO:5).

This invention provides human serum albumin (HSA) linkers, as well as HSA linker conjugates (e.g., binding, diagnostic, or therapeutic agents) that comprise an HSA linker and one or more additional moieties such as binding moieties. Such HSA linker conjugates have desirable properties such as, for example, an increased in vivo half-life of between 6 hours and 7 days, and do not induce significant humoral or cell-mediated immune responses when administered in vivo to a mammal (e.g., a human). In one aspect, the invention provides a mutated HSA linker that has two defined amino acid substitutions (i.e., the "C34S" and "N503Q" substitutions, as set forth in SEQ ID NO:1). In another aspect, the invention provides an HSA linker bonded to one or more binding moieties (e.g., antibodies, antibody fragments, receptor/ligands, or small molecules) for diagnostic or therapeutic applications in a mammal (e.g., a human) in vivo or for use in vitro in connection with mammalian cells, tissues, or organs. In a further aspect, the HSA linker may be coupled to one or more immunomodulatory agents, cytotoxic or cytostatic agents, detectable labels, or radioactive agents for diagnostic or therapeutic applications in a mammal (or in connection with a mammalian cell, tissue, or organ). An HSA linker conjugate, which includes the HSA linker, can be optionally combined with one or more pharmaceutically acceptable carriers or excipients and can be formulated to be administered intravenously, intramuscularly, orally, by inhalation, parenterally, intraperitoneally, intraarterially, transdermally, sublingually, nasally, through use of suppositories, transbuccally, liposomally, adiposally, opthalmically, intraocularly, subcutaneously, intrathecally, topically, or locally. An HSA linker conjugate can, but need not, be combined or coadministered with one or more biologically-active agents (e.g., biological or chemical agents, such as chemotherapeutics and antineoplastic agents). In a further aspect, the invention provides a kit, with instructions, for the conjugation of binding moieties (e.g., antibodies, antibody fragments, receptors or ligands), immunomodulatory agents, cytotoxic or cytostatic agents, detectable labels, or radioactive agents to the HSA linker to prepare HSA linker conjugates that can be used for diagnostic or therapeutic applications.

Human Serum Albumin (HSA) Linkers

An HSA linker may comprise a wild-type HSA amino acid sequence, as set forth in SEQ ID NO:3. Alternatively, the HSA linker may comprise an altered, or mutated, sequence. One mutated HSA linker contains two amino acid mutations, at positions 34 and 503, relative to the wild-type HSA amino acid sequence set forth in SEQ ID NO:3. The cysteine residue at position 34 (i.e., C34) can be mutated to any amino acid residue other than cysteine (e.g., serine, threonine, or alanine). Likewise, the asparagine residue at position 503 (i.e., N503) can be mutated to any amino acid residue other than asparagine (e.g., glutamine, serine, histidine, or alanine). In one embodiment, the HSA linker has the amino acid and corresponding nucleotide sequence set forth in SEQ ID NOS:1 and 2, respectively. This mutated HSA linker contains two amino acid substitutions (i.e., serine for cysteine at amino acid residue 34 ("C34S") and glutamine for asparagine at amino acid residue 503 ("N503Q")). The HSA linker, when bonded to one or more binding moieties (e.g., antibodies, antibody fragments (e.g., single chain antibodies), or other targeting or biologically active agents (e.g., receptors and ligands)), confers several beneficial pharmacologic properties to those conjugates and to additional diagnostic or therapeutic agents also conjoined (e.g., immunomodulatory agents, cytotoxic or cytostatic agents, detectable labels, or radioactive agents)) relative to the pharmacologic properties of these agents in the absence of the HSA linker. These benefits can include decreased immunogenicity (e.g., decreased host antibody neutralization of linker-antibody conjugates), increased detection of HSA linker conjugates (e.g., by mass spectroscopy) and increased pharmacologic half-life (e.g., a half-life greater than 6 hours, 8 hours, 12 hours, 24 hours, 36 hours, 2 days, 3 days, 4 days, 5 days, 6 days, or 7 days) when administered to a mammal (e.g., a human). Specifically, the substitution of serine for cysteine at amino acid residue 34 results in reduced oxidation and protein heterogeneity of the HSA linker. In wild-type HSA, the asparagine at amino acid residue 503 is sensitive to deamination, likely resulting in reduced pharmacologic half-life. The substitution of glutamine for asparagine at amino acid residue 503 can result in increased pharmacologic half-life of the HSA linker, and correspondingly, of conjugate agents that include the HSA linker when administered to a mammal (e.g., a human) or cells, tissues, or organs thereof.

In other embodiments, the mutated HSA linker includes domain I of HSA (SEQ ID NO:53; residues 1-197 of SEQ ID NO:1), domain III of HSA (SEQ ID NO:55; residues 381-585 of SEQ ID NO:1), combination of domains I and III of HSA, or a combination of domain I or III of HSA with domain II of HSA (SEQ ID NO:54; residues 189-385 of SEQ ID NO:1). For example, an HSA linker can include domains I and II, I and III, or II and III. In addition, the cysteine residue at position 34 (i.e., C34) of domain I (SEQ ID NO:53) can be mutated to any amino acid residue other than cysteine (e.g., serine, threonine, or alanine). Likewise, the asparagine residue at position 503 (i.e., N503) of domain III (SEQ ID NO:55) can be mutated to any amino acid residue other than asparagine (e.g., glutamine, serine, histidine, or alanine). These HSA linkers can be incorporated into an HSA linker conjugate, which includes one or more of a peptide connector, a binding moiety, and therapeutic or diagnostic agents, each of which is described in detail below.

Peptide Connectors

To facilitate the conjugation of binding moieties, as defined herein, to the HSA linker, short (e.g., 2-20 amino acids in length) peptide connectors that can be bonded (e.g, covalently (e.g., a peptidic bond), ionically, or hydrophobically bonded, or via a high-affinity protein-protein binding interaction (e.g., biotin and avidin)) to the amino or carboxy termini of an HSA linker. These connectors provide flexible tethers to which any of the binding moieties described herein can be attached. A peptide connector may be 2, 3, 4, 5, 6, 7, 8, 9, 10, 11, 12, 13, 14, 15, 16, 17, 18, 19, 20 or more amino acids in length. In one embodiment, the connector is a sequence of, e.g., glycine, alanine, serine, glutamine, leucine, or valine residues. Although not specifically enumerated herein, the connector can be solely glycine, alanine, serine, glutamine, leucine, or valine residues, or it may be any combination of these residues up to about 20 amino acids in length. In a preferred embodiment, the connector attached to the amino terminus of an HSA linker has the amino acid sequence AAS or AAQ and the connector attached to the carboxy terminus has the amino acid sequence "AAAL" (SEQ ID NO:5). The connector can be covalently bound to the amino or carboxy terminal residue of the HSA linker, to an amino acid residue within the HSA linker, or can be included between one or more binding moieties, if present.

HSA Linker Manufacture

The HSA linker, with or without one or more peptide connectors described above, one or more of the binding moieties described below, polypeptide-based detectable labels, and other polypeptide-based therapeutic agents, can be produced recombinantly. For example, a nucleotide sequence encoding the HSA linker (and one or more of the optional elements) may be expressed (e.g., in a plasmid, viral vector, or transgenically) in a bacterial (e.g., E. coli), insect, yeast, or mammalian cell (e.g., a CHO cell), or a mammalian tissue, organ, or organism (e.g., a transgenic rodent, ungulate (e.g., a goat), or non-human primate). After expression of the HSA linker in the host cell, tissue, or organ, the skilled artisan may isolate and purify the HSA linker using standard protein purification methods (e.g., FPLC or affinity chromatography). A recombinant expression system for the production of an HSA linker in combination with two binding moieties is illustrated in FIG. 1.

Alternatively, the HSA linker, with or without one or more of the optional elements described above, can be synthetically produced. For example, the HSA linker or HSA linker conjugate can be prepared by techniques generally established in the art of peptide synthesis, such as the solid-phase approach. Solid-phase synthesis involves the stepwise addition of amino acid residues to a growing peptide chain that is linked to an insoluble support or matrix, such as polystyrene. The C-terminus residue of the peptide is first anchored to a commercially available support with its amino group protected with an N-protecting agent such as a t-butyloxycarbonyl group (tBoc) or a fluorenylmethoxycarbonyl (FMOC) group. The amino-protecting group is removed with suitable deprotecting agents such as TFA in the case of tBOC or piperidine for FMOC and the next amino acid residue (in N-protected form) is added with a coupling agent such as dicyclocarbodiimide (DCC). Upon formation of a peptide bond, the reagents are washed from the support. After addition of the final residue, the agent is cleaved from the support with a suitable reagent, such as trifluoroacetic acid (TFA) or hydrogen fluoride (HF). If desired, the HSA linker, with or without one or more of the optional elements described above, can be manufactured in one, two, three, or more segments, which can then be ligated to form the whole HSA linker construct.

Binding Moieties

HSA linker conjugates may include one or more binding moieties, such as antibodies, antibody fragments (as defined herein, e.g., a single chain Fv (scFv)) or receptor/ligands (i.e., protein or glycoprotein ligands or receptors)) that allow selective and specific binding of the HSA linker conjugate to a target cell, tissue, or organ. The binding moieties can be bonded to the HSA linker (e.g., via a covalent (e.g., a peptide bond), ionic, or hydrophobic bond, or via a high-affinity protein-protein binding interaction (e.g., biotin and avidin)).

One or more binding moieties can be bonded to an HSA linker. In one embodiment, two or more identical binding moieties (i.e., moieties having the same structure and binding affinities) are bonded to an HSA linker, one or more (e.g., in tandem) each at the amino and carboxy termini, the HSA linker thereby affording improved avidity of the binding moieties for their target antigen. Alternatively, two or more different binding moieties (e.g., an antibody, such as a scFv, with binding affinities for two or more different target molecules, or scFv with binding affinities for two or more different epitopes on the same target molecule) can be bonded to an HSA linker (e.g., a bispecific HSA linker conjugate) to allow multiple target antigens or epitopes to be bound by the HSA linker conjugate. In another embodiment, different species of binding moieties can also be bonded to an HSA linker to bestow, for example, two or more different binding specificities or agonistic/antagonistic biological properties on the linker conjugate. Useful combinations of binding moiety pairs for use in the preparation of bispecific HSA linker conjugates are disclosed in, e.g., International Patent Application Publications WO 2006/091209 and WO 2005/117973, herein incorporated by reference. In other embodiments, more than two binding moieties (e.g., the same or different binding moieties) can be bonded to an HSA linker to form an HSA linker conjugate.

The invention features an HSA linker conjugate having at least first and second binding moieties, each of which can be bound at either the amino or carboxy terminus of the HSA linker, or to peptide connectors, as defined herein, present at either or both termini. FIG. 1 illustrates an exemplary mutated HSA linker in which two binding moieties ("arm 1" and "arm 2") are bonded to the mutated HSA linker by the amino terminal peptide connector AAS and carboxy terminal peptide connector AAAL (SEQ ID NO:5). Binding moieties (e.g., an antibody or scFv) can also be bound to other loci (e.g., internal amino acid residues of the HSA linker), for example, covalently or ionically, e.g., using biotin-avidin interactions. Biotinylation of amine (e.g., lysine residues) and sulfhydryl (e.g., cysteine residues) amino acid side chains is known in the art and can be used to attach binding moieties to the HSA linker.

Binding moieties that can be included in an HSA linker conjugate include antibodies, antibody fragments, receptors, and ligands. Binding moieties bound to an HSA linker may be recombinant (e.g., human, murine, chimeric, or humanized), synthetic, or natural. Representative binding moieties include, for example, complete antibodies, domain antibodies, diabodies, triabodies, bi-specific antibodies, antibody fragments, Fab fragments, F(ab')2 molecules, single chain Fv (scFv) molecules, bispecific single chain Fv ((scFv')$_2$) molecules, tandem scFv fragments, antibody fusion proteins, hormones, receptors, ligands, and aptamers, and biologically-active fragments thereof.

Antibodies

Antibodies include the IgG, IgA, IgM, IgD, and IgE isotypes. Antibodies or antibody fragments thereof, as used herein, contain one or more complementarity determining regions (CDR) or binding peptides that bind to target proteins, glycoproteins, or epitopes present on the exterior or in the interior of target cells.

Many of the antibodies, or fragments thereof, described herein can undergo non-critical amino-acid substitutions, additions or deletions in both the variable and constant regions without loss of binding specificity or effector functions, or intolerable reduction of binding affinity (e.g., below about $10^{-7}$ M). Usually, an antibody or antibody fragment incorporating such alterations exhibits substantial sequence identity to a reference antibody or antibody fragment from which it is derived. Occasionally, a mutated antibody or antibody fragment can be selected having the same specificity and increased affinity compared with a reference antibody or antibody fragment from which it was derived. Phage-display technology offers powerful techniques for selecting such antibodies. See, e.g., Dower et al., WO 91/17271 McCafferty et al., WO 92/01047; and Huse, WO 92/06204, incorporated by reference herein.

The HSA linker can also be bonded to one or more fragments of an antibody that retain the ability to bind with specificity to a target antigen. Antibody fragments include separate variable heavy chains, variable light chains, Fab, Fab', F(ab')$_2$, Fabc, and scFv. Fragments can be produced by enzymatic or chemical separation of intact immunoglobulins. For example, a F(ab')$_2$ fragment can be obtained from an IgG molecule by proteolytic digestion with pepsin at pH 3.0-3.5 using standard methods such as those described in Harlow and Lane, Antibodies: A Laboratory Manual, Cold Spring Harbor Pubs., N.Y. (1988). Fab fragments may be obtained from F(ab')$_2$ fragments by limited reduction, or from whole antibody by digestion with papain in the presence of reducing agents. Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This manner of expression is advantageous for affinity-sharpening of antibodies.

Humanized Antibodies

Humanized antibodies may also be used in combination with the HSA linker, in which one or more of the antibody CDRs are derived from a non-human antibody sequence, and one or more, but preferably all, of the CDRs bind specifically to an antigen (e.g., a protein, glycoprotein, or other suitable epitope).

A humanized antibody contains constant framework regions derived substantially from a human antibody (termed an acceptor antibody), as well as, in some instances, a majority of the variable region derived from a human antibody. One or more of the CDRs (all or a portion thereof, as well as discreet amino acids surrounding one or more of the CDRs) are provided from a non-human antibody, such as a mouse antibody. The constant region(s) of the antibody, may or may not be present.

The substitution of one or more mouse CDRs into a human variable domain framework is most likely to result in retention of their correct spatial orientation if the human variable domain framework adopts the same or a similar conformation as the mouse variable framework from which the CDRs originated. This is achieved by obtaining the human variable domains from human antibodies whose framework sequences exhibit a high degree of sequence and structural identity with the murine variable framework domains from which the CDRs were derived. The heavy and light chain variable framework regions can be derived from the same or different human antibody sequences. The human antibody sequences can be the sequences of naturally occurring human antibodies, consensus sequences of several human antibodies, or can be human germline variable domain sequences. See, e.g., Kettleborough et al., *Protein Engineering* 4:773 (1991); Kolbinger et al., *Protein Engineering* 6:971 (1993).

Suitable human antibody sequences are identified by alignments of the amino acid sequences of the mouse variable regions with the sequences of known human antibodies. The comparison is performed separately for heavy and light chains but the principles are similar for each.

Methods of preparing chimeric and humanized antibodies and antibody fragments are described in, e.g., U.S. Pat. Nos. 4,816,567, 5,530,101, 5,622,701, 5,800,815, 5,874,540, 5,914,110, 5,928,904, 6,210,670, 6,677,436, and 7,067,313 and U.S. Patent Application Nos. 2002/0031508, 2004/0265311, and 2005/0226876. Preparation of antibody or fragments thereof is further described in, e.g., U.S. Pat. Nos. 6,331,415, 6,818,216, and 7,067,313.

Receptors and Ligands

Within certain HSA linker conjugates, protein or glycoprotein receptors or ligands are bound to an HSA linker. HSA linkers bonded with a receptor or ligand can be used, for example, to specifically target a secreted protein, a cell (e.g., a cancer cell), tissue, or organ. Furthermore, the specific binding of the HSA linker-receptor or -ligand conjugate to cognate target receptors or ligands can cause agonistic or antagonistic biological activity in intracellular or intercellular signaling pathways. As with the other binding moieties described herein, receptors and ligands, or fragments thereof, can be conjoined to the amino and/or carboxy termini of an HSA linker, to a peptide connector linked to the HSA linker or to an amino acid residue within the HSA linker.

Exemplary receptors and ligands that can be joined to an HSA linker include, but are not limited to, insulin-like growth factor 1 receptor (IGF1R), IGF2R, insulin-like growth factor (IGF), mesenchymal epithelial transition factor receptor (c-met; also known as hepatocyte growth factor receptor (HGFR)), hepatocyte growth factor (HGF), epidermal growth factor receptor (EGFR), epidermal growth factor (EGF), heregulin, fibroblast growth factor receptor (FGFR), platelet-derived growth factor receptor (PDGFR), platelet-derived growth factor (PDGF), vascular endothelial growth factor receptor (VEGFR), vascular endothelial growth factor (VEGF), tumor necrosis factor receptor (TNFR), tumor necrosis factor alpha (TNF-α), TNF-β, folate receptor (FOLR), folate, transferrin receptor (TfR), mesothelin, Fc receptor, c-kit receptor, c-kit, α4 integrin, P-selectin, sphingosine-1-phosphate receptor-1 (S1PR), hyaluronate receptor, leukocyte function antigen-1 (LFA-1), CD4, CD11, CD18, CD20, CD25, CD27, CD52, CD70, CD80, CD85, CD95 (Fas receptor), CD106 (vascular cell adhesion molecule 1 (VCAM1), CD166 (activated leukocyte cell adhesion molecule (ALCAM)), CD178 (Fas ligand), CD253 (TNF-related apoptosis-inducing ligand (TRAIL)), ICOS ligand, CCR2, CXCR3, CCR5, CXCL12 (stromal cell-derived factor 1 (SDF-1)), interleukin 1 (IL-1), CTLA-4, receptors alpha and beta, MART-1, gp100, MAGE-1, ephrin (Eph) receptor, mucosal addressin cell adhesion molecule 1 (MAdCAM-1), carcinoembryonic antigen (CEA), Lewis$^Y$, MUC-1, epithelial cell adhesion molecule (EpCAM), cancer antigen 125 (CA125), prostate specific membrane antigen (PSMA), TAG-72 antigen, and biologically-active fragments thereof.

Receptors and ligands can be expressed, isolated, or joined to an HSA linker using any of the methods described supra.

Diagnostic Agents

The HSA linker, or any binding moiety conjugated thereto (e.g., antibody, antibody fragment, receptor, or ligand), can be coupled to a chelating agent or to a detectable label to form a diagnostic agent. Also contemplated are HSA linker conjugates that include a detectable label, as described herein, as well as one or more of the therapeutic agents or binding moieties described herein.

The HSA linker (or HSA linker conjugate) and chelator components can be coupled by reacting the free amino group of a threonine residue of the HSA linker (or HSA linker conjugate) with an appropriate functional group of the chelator, such as a carboxyl group or activated ester. For example, a such coupling may be achieved by incorporating the chelator ethylenediaminetetraacetic acid (EDTA), which is common in the art of coordination chemistry, when functionalized with a carboxyl substituent on the ethylene chain. Synthesis of EDTA derivatives of this type are reported in Arya et al. (*Bioconjugate Chemistry* 2:323 (1991)), which describes blocking each of the four coordinating carboxyl groups with a t-butyl group while the carboxyl substituent on the ethylene chain is free to react with the amino group of a peptide portion of the agent.

An HSA linker or an HSA linker conjugate may incorporate a metal chelator component that is peptidic, i.e., compatible with solid-phase peptide synthesis. In this case, the chelator may be coupled in the same manner as EDTA described above or, more conveniently, the chelator and HSA linker or HSA linker conjugate are synthesized in toto starting from the C-terminal residue of the HSA linker or HSA linker conjugate and ending with the N-terminal residue of the chelator.

An HSA linker or an HSA linker conjugate may further incorporate a linking group component that serves to couple the HSA linker to the chelator while not adversely affecting the biological properties of the HSA linker, the targeting function of the binding moiety portion(s) of the HSA linker conjugate, or the metal binding function of the chelator. Suitable linking groups include amino acid chains and alkyl chains functionalized with reactive groups for coupling to the HSA linker or the HSA linker conjugate and to the chelator. An amino acid chain is the preferred linking group when the chelator is peptidic so that the HSA linker or HSA linker conjugate can be synthesized in toto by solid-phase techniques. An alkyl chain-linking group may be incorporated in the HSA linker or HSA linker conjugate by reacting the amino group of a threonine residue of a peptide portion of an HSA linker with a first functional group on the alkyl chain, such as a carboxyl group or an activated ester. Subsequently the chelator is attached to the alkyl chain to complete the formation of the HSA linker or HSA linker conjugate by reacting a second functional group on the alkyl chain with an appropriate group on the chelator. The second functional group on the alkyl chain is selected from substituents that are reactive with a functional group on the chelator while not being reactive with a threonine residue of the mutated HSA linker. For example, when the chelator incorporates a functional group such as a carboxyl group or an activated ester, the second functional group of the alkyl chain-linking group can be an amino group. It will be appreciated that formation of the HSA linker or HSA linker conjugate may require protection and deprotection of the functional groups present in order to avoid formation of undesired products. Protection and deprotection are accomplished using protecting groups, reagents, and protocols common in the art of organic synthesis. Particularly, protection and deprotection techniques employed in solid phase peptide synthesis described above may be used.

An alternative chemical linking group to an alkyl chain is polyethylene glycol (PEG), which is functionalized in the same manner as the alkyl chain described above for incorporation in the HSA linker or HSA linker conjugate. It will be appreciated that linking groups may alternatively be coupled first to the chelator and then to the HSA linker or HSA linker conjugate.

In one aspect, an HSA linker or HSA linker conjugate is coupled to a diagnostically useful metal capable of forming a complex. Suitable metals include, e.g., radionuclides, such as technetium and rhenium in their various forms (e.g., $^{99m}TcO^{3+}$, $^{99m}TcO_2^+$, $ReO^{3+}$, and $ReO_2^+$). Incorporation of the metal within the HSA linker or HSA linker conjugate can be achieved by various methods common in the art of coordination chemistry. When the metal is technetium-99 m, the following general procedure may be used to form a technetium complex. An HSA linker-chelator conjugate solution is formed initially by dissolving the HSA linker or HSA linker conjugate in aqueous alcohol such as ethanol. The solution is then degassed to remove oxygen then thiol protecting groups are removed with a suitable reagent, for example, with sodium hydroxide, and then neutralized with an organic acid, such as acetic acid (pH 6.0-6.5). In the labeling step, a stoichiometric excess of sodium pertechnetate, obtained from a molybdenum generator, is added to a solution of the conjugate with an amount of a reducing agent such as stannous chloride sufficient to reduce technetium and heated. The labeled HSA linker or HSA linker conjugate may be separated from contaminants $^{99m}TcO_4^-$ and colloidal $^{99m}TcO_2$ chromatographically, for example, with a C-18 Sep Pak cartridge.

In an alternative method, labeling of an HSA linker can be accomplished by a transchelation reaction. The technetium source is a solution of technetium complexed with labile ligands facilitating ligand exchange with the selected chelator. Suitable ligands for transchelation include tartarate, citrate, and heptagluconate. In this instance the preferred reducing reagent is sodium dithionite. It will be appreciated that the HSA linker or HSA linker conjugate may be labeled using the techniques described above, or alternatively the chelator itself may be labeled and subsequently coupled to an HSA linker to form an HSA linker-chelator conjugate; a process referred to as the "prelabeled ligand" method.

Another approach for labeling an HSA linker, or any agent conjugated thereto, involves immobilizing the HSA linker-chelator conjugate on a solid-phase support through a linkage that is cleaved upon metal chelation. This is achieved when the chelator is coupled to a functional group of the support by one of the complexing atoms. Preferably, a complexing sulfur atom is coupled to the support which is functionalized with a sulfur protecting group such as maleimide.

When labeled with a diagnostically useful metal, an agent that includes an HSA linker-chelator conjugate can be used to detect tissue at risk of developing cancer (e.g., lung cancer, breast cancer, colon cancer, and prostate cancer), age-related diseases (e.g., cardiovascular disease, cerebrovascular disease, or Alzheimer's disease), tobacco-related diseases (e.g., emphysema, aortic aneurysms, esophageal cancer, or squamous cell cancer of the head and neck) by procedures established in the art of diagnostic imaging. An agent that incorporates an HSA linker labeled with a radionuclide metal, such as technetium-99 m, may be administered to a mammal (e.g., a human) by intravenous injection in a pharmaceutically acceptable solution, such as isotonic saline, or by other methods described herein. The amount of a labeled agent appropriate for administration is dependent upon the distribution profile of the chosen HSA linker or HSA linker conjugate in the sense that an agent that incorporates a rapidly cleared HSA linker or HSA linker conjugate may be administered at higher doses than an agent that incorporates an HSA linker or HSA linker conjugate that clears less rapidly. Unit doses acceptable for imaging tissues are in the range of about 5-40 mCi for a 70 kg individual. The in vivo distribution and localization of an agent that incorporates a labeled HSA linker or HSA linker conjugate can be tracked by standard techniques described herein at an appropriate time subsequent to administration, typically between 30 minutes and 180 minutes and up to about 5 days depending upon the rate of accumulation at the target site with respect to the rate of clearance at non-target tissue.

An HSA linker, or any molecule or moiety conjugated thereto, can also be modified or labeled to facilitate diagnostic or therapeutic uses. Detectable labels such as a radioactive, fluorescent, heavy metal, or other molecules may be bound to any of the agents. Single, dual, or multiple labeling of an agent may be advantageous. For example, dual labeling with radioactive iodination of one or more residues combined with the additional coupling of, for example, $^{90}Y$ via a chelating group to amine-containing side or reactive groups, would allow combination labeling. This may be useful for specialized diagnostic needs such as identification of widely dispersed small neoplastic cell masses.

An HSA linker, or any molecule or moiety conjugated thereto, can also be modified, for example, by halogenation of the tyrosine residues of the peptide component. Halogens include fluorine, chlorine, bromine, iodine, and astatine. Such halogenated agents may be detectably labeled, e.g., if the halogen is a radioisotope, such as, for example, $^{18}$F, $^{75}$Br, $^{77}$Br, $^{122}$I, $^{123}$I, $^{124}$I, $^{125}$I, $^{129}$I, $^{131}$I, or $^{211}$At. Halogenated agents contain a halogen covalently bound to at least one amino acid, and preferably to D-Tyr residues in each agent molecule. Other suitable detectable modifications include binding of other compounds (e.g., a fluorochrome such as fluorescein) to a lysine residue of the agent, or analog, particularly an agent or analog having a linker including lysines.

Radioisotopes for radiolabeling an HSA linker, or any molecule or moiety conjugated thereto, include any radioisotope that can be covalently bound to a residue of the peptide component of the agent or analog thereof. The radioisotopes can also be selected from radioisotopes that emit either beta or gamma radiation, or alternatively, any of the agents can be modified to contain chelating groups that, for example, can be covalently bonded to lysine residue(s) of the HSA linker or any peptidic agent conjugated thereto. The chelating groups can then be modified to contain any of a variety of radioisotopes, such as gallium, indium, technetium, ytterbium, rhenium, or thallium (e.g., $^{125}$I, $^{67}$Ga, $^{111}$In, $^{99m}$Tc, $^{169}$Yb, $^{186}$Re).

An HSA linker, or any molecule or moiety conjugated thereto, can be modified by attachment of a radioisotope. Preferable radioisotopes are those having a radioactive half-life corresponding to, or longer than, the biological half-life of the HSA conjugate used. More preferably, the radioisotope is a radioisotope of a halogen atom (e.g. a radioisotope of fluorine, chlorine, bromine, iodine, and astatine), even more preferably $^{75}$Br, $^{77}$Br, $^{76}$Br, $^{122}$I, $^{123}$I, $^{124}$I, $^{125}$I, $^{129}$I, $^{131}$I, or $^{211}$At.

An agent that incorporates as HSA linker, or any molecule or moiety conjugated thereto, can be coupled to radioactive metals and used in radiographic imaging or radiotherapy. Preferred radioisotopes also include $^{99m}$Tc, $^{51}$Cr, $^{67}$Ga, $^{111}$In, $^{168}$Yb, $^{140}$La, $^{90}$Y, $^{88}$Y, $^{153}$Sm, $^{156}$Ho, $^{165}$Dy, $^{64}$Cu, $^{97}$Ru, $^{103}$Ru, $^{186}$Re, $^{188}$Re, $^{203}$Pb, $^{211}$Bi, $^{212}$Bi, $^{213}$Bi, and $^{214}$Bi. The Choice of metal is determined based on the desired therapeutic or diagnostic application.

An HSA linker, or any molecule or moiety conjugated thereto, can be coupled to a metal component, to produce a diagnostic or therapeutic agent. A detectable label may be a metal ion from heavy elements or rare earth ions, such as $Gd^{3+}$, $Fe^{3+}$, $Mn^{3+}$, or $Cr^{2+}$. Agents that incorporate an HSA linker having paramagnetic or superparamagnetic metals conjoined thereto are useful as diagnostic agents in MRI imaging applications. Paramagnetic metals include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III).

Chelating groups may be used to indirectly couple detectable labels or other molecules to an HSA linker or to an agent conjugated thereto. Chelating groups can link agents with radiolabels, such as a bifunctional stable chelator, or can be linked to one or more terminal or internal amino acid reactive groups. An HSA linker, or any molecule or moeity conjugated thereto, can be linked via an isothiocyanate β-Ala or appropriate non-α-amino acid linker which prevents Edman degradation. Examples of chelators known in the art include, for example, the ininocarboxylic and polyaminopolycarboxylic reactive groups, ininocarboxylic and polyaminopolycarboxylic reactive groups, diethylenetriaminepentaacetic acid (DTPA), and 1,4,7,10-tetraazacyclododecane-1,4,7,10-tetraacctic acid (DOTA).

An HSA linker, when expressed recombinantly, can be joined to a peptidic detectable label or diagnostic agent. Peptides and proteins that can be used as a detectable label with an HSA linker include, but are not limited to, fluorescent proteins, bioluminescent proteins, and epitope tags, each of which is discussed in detail below. One or more of these detectable labels can also be incorporated into an HSA linker conjugate that also includes a therapeutic, cytotoxic, or cytostatic agent.

Fluorescent proteins or fluorochromes, such as green fluorescent protein (GFP; SEQ ID NO:47), enhanced GFP (eGFP), yellow fluorescent protein (SEQ ID NO:48; YFP), cyan fluorescent protein (SEQ ID NO:49; CFP), and red fluorescent protein (SEQ ID NO:50; RFP or DsRed), can be used as detectable label joined to an HSA linker. Fluorescent proteins can be recombinantly expressed in a cell (e.g., a blood cell, such as a lymphocyte) following transfection or transduction of the cell with an expression vector that encodes the nucleotide sequence of the fluorescent protein. Upon exposure of the fluorescent protein to a stimulating frequency of light, the fluorescent protein will emit light at a low, medium, or high intensity that can be observed by eye under a microscope or by an optical imaging device. Exemplary fluorescent proteins suitable for use as the diagnostic sequence in agents are described in, e.g., U.S. Pat. Nos. 7,417, 131 and 7,413,874, each of which is herein incorporated by reference.

Bioluminescent proteins can also be used as a detectable label incorporated into an HSA linker. Bioluminescent proteins, such as luciferase (e.g., firefly (SEQ ID NO:51), *Renilla* (SEQ ID NO:52), and *Omphalotus* luciferase) and aequorin, emit light as part of a chemical reaction with a substrate (e.g., luciferin and coelenterazine). In one embodiment, a vector encoding a luciferase gene provides for the in vivo, in vitro, or ex vivo detection of cells (e.g., blood cells, such as lymphocytes) that have been transduced or transfected according to standard methods, such as those described herein. Exemplary bioluminescent proteins suitable for use as a diagnostic sequence and methods for their use are described in, e.g., U.S. Pat. Nos. 5,292,658, 5,670,356, 6,171,809, and 7,183,092, each of which is herein incorporated by reference.

Epitope tags are short amino acid sequences, e.g., 5-20 amino acid residues in length, that can be incorporated into an HSA linker conjugate as a detectable label to facilitate detection once expressed in a cell, secreted from the cell, or hound to a target cell. An agent that incorporates an epitope tag as a diagnostic sequence can be detected by virtue of its interaction with an antibody, antibody fragment, or other binding molecule specific for the epitope tag. Nucleotide sequences encoding the epitope tag are produced either by cloning appropriate portions of natural genes or by synthesizing a polynucleotide that encodes the epitope tag. An antibody, antibody fragment, or other binding molecule that binds an epitope tag can directly incorporate a detectable label (e.g., a fluorochrome, radiolabel, heavy metal, or enzyme such as horseradish peroxidase) or serve itself as a target for a secondary antibody, antibody fragment, or other binding molecule that incorporates such a label. Exemplary epitope tags that can be used as a diagnostic sequence include c-myc (SEQ ID NO:33), hemagglutinin (HA; SEQ ID NO:34), and histidine tag (His$_6$; SEQ ID NO:35). Furthermore, fluorescent (e.g., GFP) and bioluminescent proteins can also serve as epitope tags, as antibodies, antibody fragments, and other binding molecules are commercially available for the detection of these proteins.

The in vivo, in vitro, or ex vivo detection, imaging, or tracking of an HSA linker conjugate that incorporates a diagnostic sequence (e.g., a fluorescent protein, bioluminescent protein, or epitope tag) or any cell expressing or bound thereto can be accomplished using a microscope, flow cytometer, luminometer, or other state of the art optical imaging device, such as an IVIS® Imaging System (Caliper LifeSciences, Hopkinton, Mass.).

Therapeutic or Cytotoxic Agents Coupled to the HSA Linker

An HSA linker, or any molecule or moiety conjugated thereto, can be coupled to any known cytotoxic or therapeutic moiety to form an agent (an HSA linker conjugate) that can be administered to treat, inhibit, reduce, or ameliorate disease (e.g., a cancer, autoimmune disease, or cardiovascular disease) or one or more symptoms of disease. Examples include but are not limited to antineoplastic agents such as: acivicin; aclarubicin; acodazole hydrochloride; acronine; adozelesin; adriamycin; aldesleukin; altretamine; ambomycin; a. metantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; camptothecin; caracemide; carbetimer; carboplatin; carmustine; carubicin hydrochloride; carzelesin; cedefingol; chlorambucil; cirolemycin; cisplatin; cladribine; combretestatin a-4; crisnatol mesylate; cyclophosphamide; cytarabine; dacarbazine; daca (n-[2-(dimethyl-amino)ethyl]acridine-4-carboxamide); dactinomycin; daunorubicin hydrochloride; daunomycin; decitabine; dexormaplatin; dezaguanine; dezaguanine mesylate; diaziquone; docetaxel; dolasatins; doxorubicin; doxorubicin hydrochloride; droloxifene; droloxifene citrate; dromostanolone propionate; duazomycin; edatrexate; eflornithine hydrochloride; ellipticine; elsamitrucin; enloplatin; enpromate; epipropidine; epirubicin hydrochloride; erbulozole; esorubicin hydrochloride; estramustine; estramustine phosphate sodium; etanidazole; ethiodized oil i 131; etoposide; etoposide phosphate; etoprine; fadrozole hydrochloride; fazarabine; fenretinide; floxuridine; fludarabine phosphate; fluorouracil; 5-fdump; flurocitabine; fosquidone; fostriecin sodium; gemcitabine; gemcitabine hydrochloride; gold au 198; homocamptothecin; hydroxyurea; idarubicin hydrochloride; ifosfamide; ilmofosine; interferon alfa-2a; interferon alfa-2b; interferon alfa-nl; interferon alfa-n3; interferon beta-i a; interferon gamma-i b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peploycinsulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; rhizoxin; rhizoxin d; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; strontium chloride sr 89; sulofenur; talisomycin; taxane; taxoid; tecogalan sodium; tegafur; teloxantrone hydrochloride; temoporfin; teniposide; teroxirone; testolactone; thiamiprine; thioguanine; thiotepa; thymitaq; tiazofurin; tirapazamine; tomudex; top53; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine; vinblastine sulfate; vincristine; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 2-chlorodeoxyadenosine; 2' deoxyformycin; 9-aminocamptothecin; raltitrexed; N-propargyl-5,8-dideazafolic acid; 2chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N,N'-Bis(2-chloroethyl)-N-nitrosourea (BCNU); N-(2-chloroethyl)-N'cyclohexyl-N-nitrosourea (CCNU); N-(2-chloroethyl)-N'-(trans-4-methylcyclohexyl-N-nitrosourea (MeCCNU); N-(2-chloroethyl)-N-(diethyl)ethylphosphonate-N-nitrosourea (fotemustine); streptozotocin; diacarbazine (DTIC); mitozolomide; temozolomide; thiotepa; mitomycin C; AZQ; adozelesin; cisplatin; carboplatin; ormaplatin; oxaliplatin; C1-973; DWA 2114R; JM216; JM335; Bis (platinum); tomudex; azacitidine; cytarabine; gemcitabine; 6-mercaptopurine; 6-thioguanine; hypoxanthine; teniposide 9-amino camptothecin; topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-hydroxyphenyl) retinamide; 13-cis retinoic acid; 3-methyl TTNEB; 9-cis retinoic acid; fludarabine (2-F-ara-AMP); or 2-chlorodeoxyadenosine (2-Cda).

Other therapeutic compounds include, but are not limited to, 20-pi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxycamptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; merbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustinc; splcnopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

HSA linker conjugates can also include site-specifically conjugated molecules and moieties. Site-specific conjugation allows for the controlled stoichiometric attachment to specific residues in the HSA linker of cytotoxic, immunomodulatory, or cytostatic agents including, e.g., anti tubulin agents, DNA minor groove binders, DNA replication inhibitors, alkylating agents, anthracyclines, antibiotics, antifolates, antimetabolites, chemotherapy or radiation sensitizer, duocarmycins, etoposides, fluorinated pyrimidines, ionophores, lexitropsins, nitrosoureas, platinols, purine antimetabolites, puromycins, steroids, taxanes, topoisomerase inhibitors, and vinca alkaloids or any other molecules or moieties described herein.

Techniques for conjugating therapeutic agents to proteins, and in particular to antibodies, are well-known (e.g., Amon et al., "Monoclonal Antibodies For Immunotargeting Of Drugs In Cancer Therapy," in Monoclonal Antibodies And Cancer Therapy (Reisfeld et al., eds., Alan R. Liss, Inc., 1985); Hellstrom et al., "Antibodies For Drug Delivery," in Controlled Drug Delivery (Robinson et al., eds., Marcel Dekker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al., eds., 1985); "Analysis, Results, and Future Prospective of the Therapeutic Use of Radiolabeled Antibody In Cancer Therapy," in Monoclonal Antibodies For Cancer Detection And Therapy (Baldwin et al., eds., Academic Press, 1985); Thorpe et al., *Immunol. Rev.* 62:119-58 (1982); and Doronina et al., "Development of potent monoclonal antibody auristatin conjugates for cancer therapy," *Nature Biotech.* 21:(7) 778-784 (2003)). See also, e.g., PCT publication WO 89/12624.

An HSA linker, or any molecule or moiety conjugated thereto, can also be coupled to a lytic peptide. Such lytic peptides induce cell death and include, but are not limited to, streptolysin O; stoichactis toxin; phallolysin; staphylococcus alpha toxin; holothurin A; digitonin; melittin; lysolecithin; cardiotoxin; and cerebratulus A toxin (Kern et al., *J. Biol. Chem.* 253(16):5752-5757, 1978). An HSA linker, or any molecule or moiety conjugated thereto (e.g., antibody or antibody fragment conjugates), may be coupled to a synthetic peptide that shares some sequence homology or chemical characteristics with any of the naturally occurring peptide lysins; such characteristics include, but are not limited to, linearity, positive charge, amphipathicity, and formation of alpha-helical structures in a hydrophobic environment (Leuschner et al., *Biology of Reproduction* 73:860-865, 2005). An HSA linker, or any molecule or moiety conjugated thereto, can also be coupled to an agent that induces complement-mediated cell lysis such as, for example, the immunoglobulin $F_c$ subunit. An HSA linker, or any molecule or moiety conjugated thereto, can also be coupled to any member of the phospholipase family of enzymes (including phospholipase A, phospholipase B, phospholipase C, or phospholipase D) or to a catalytically-active subunit thereof.

An HSA linker, or any molecule or moiety conjugated thereto, can also be coupled to a radioactive agent to form an agent that can be used for detection or therapeutic applications. Radioactive agents that can be used include but are not limited to Fibrinogen $^{125}$I; Fludeoxyglucose $^{18}$F; Fluorodopa $^{18}$F; Insulin $^{125}$I; Insulin $^{131}$I; Iobenguane $^{123}$I; Iodipamide Sodium $^{131}$I; Iodoantipyrine $^{131}$I; Iodocholesterol $^{131}$I; Iodohippurate Sodium $^{123}$I; Iodohippurate Sodium $^{125}$I; Iodohippurate Sodium $^{131}$I; Iodopyracet $^{125}$I; Iodopyracet $^{131}$I; Iofetamine Hydrochloride $^{123}$I; Iomethin $^{125}$I; Iomethin $^{131}$I; Iothalamate Sodium $^{125}$I; Iothalamate Sodium $^{131}$I; tyrosine $^{131}$I; Liothyronine $^{125}$I; Liothyronine $^{131}$I; Merisoprol Acetate $^{197}$Hg; Merisoprol Acetate $^{203}$Hg; Merisoprol $^{197}$Hg; Selenomethionine $^{75}$Se; Technetium $^{99m}$Tc Antimony Trisulfide Colloid; Technetium $^{99m}$Tc Bicisate; Technetium $^{99m}$Tc Disofenin; Technetium $^{99m}$Tc Etidronate; Technetium $^{99m}$Tc Exametazime; Technetium $^{99m}$Tc Furifosmin; Technetium $^{99m}$Tc Gluceptate; Technetium $^{99m}$Tc Lidofenin; Technetium $^{99m}$Tc Mebrofenin; Technetium $^{99m}$Tc Medronate; Technetium $^{99m}$Tc Medronate Disodium; Technetium $^{99m}$Tc Mertiatide; Technetium $^{99m}$Tc Oxidronate; Technetium $^{99m}$Tc Pentetate; Technetium $^{99m}$Tc Pentetate Calcium Trisodium; Technetium $^{99m}$Tc Sestamibi; Technetium $^{99m}$Tc Siboroxime; Technetium $^{99m}$Tc; Succimer; Technetium $^{99m}$Tc Sulfur Colloid; Technetium $^{99m}$Tc Teboroxime; Technetium $^{99m}$Tc Tetrofosmin; Technetium $^{99m}$Tc Tiatide; Thyroxine $^{125}$I; Thyroxine $^{131}$I; Tolpovidone $^{131}$I; Triolein $^{125}$I; or Triolein $^{131}$I.

Additionally, a radioisotope can be site-specifically conjoined to an HSA linker or HSA linker conjugate. The available reactive groups could be used to conjugate site-specific bifunctional chelating agents for labeling of radioisotopes, including $^{123}$I, $^{124}$I, $^{125}$I, $^{131}$I, $^{99m}$Tc, $^{111}$In, $^{64}$Cu, $^{67}$Cu, $^{186}$Re, $^{177}$Lu, $^{90}$Y, $^{77}$As, $^{72}$As, $^{86}$Y, $^{89}$Zr, $^{211}$At, $^{212}$Bi, $^{213}$Bi, or $^{225}$Ac.

Therapeutic or cytotoxic agents incorporated into or coupled with an HSA linker or an HSA linker conjugate may further include, for example, anti-cancer Supplementary Potentiating Agents, including, but not limited to: tricyclic anti-depressant drugs (e.g., imipramine, desipramine, amitryptyline, clomipramine, trimipramine, doxepin, nortriptyline, protriptyline, amoxapine, and maprotiline); non-tricyclic anti-depressant drugs (e.g., sertraline, trazodone, and citalopram); $Ca^{2+}$ antagonists (e.g., verapamil, nifedipine, nitrendipine, and caroverine); Calmodulin inhibitors (e.g., prenylamine, trifluoroperazine, and clomipramine); Amphotericin B; Triparanol analogs (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

An agent that includes an HSA linker, or any molecule or moiety conjugated thereto, can also be coupled to or administered with one or more cytokines (e.g., granulocyte colony stimulating factor, interferon-alpha, and tumor necrosis factor-alpha). An HSA linker, or any molecule or moiety conjugated thereto, can also be coupled to an antimetabolic agent. Antimetabolic agents include, but are not limited to, the following compounds and their derivatives: azathioprine, cladribine, cytarabine, dacarbazine, fludarabine phosphate, fluorouracil, gencitabine chlorhydrate, mercaptopurine, methotrexate, mitobronitol, mitotane, proguanil chlorohydrate, pyrimethamine, raltitrexed, trimetrexate glucuronate, urethane, vinblastine sulfate, vincristine sulfate, etc. More preferably, an HSA linker or conjugate can be coupled to a folic acid-type antimetabolite, a class of agents that includes, for example, methotrexate, proguanil chlorhydrate, pyrimethanime, trimethoprime, or trimetrexate glucuronate, or derivatives of these compounds.

An HSA linker, or any molecule or moiety conjugated thereto, can also be coupled to a member of the anthracycline family of neoplastic agents, including but not limited to aclarubicine chlorhydrate, daunorubicine chlorhydrate, doxorubicine chlorhydrate, epirubicine chlorhydrate, idarubicine chlorhydrate, pirarubicine, or zorubicine chlorhydrate; a camptothecin, or its derivatives or related compounds, such as 10,11 methylenedioxycamptothecin; or a member of the maytansinoid family of compounds, which includes a variety of structurally-related compounds, e.g., ansamitocin P3, maytansine, 2'-N-demethylmaytanbutine, and maytanbicyclinol.

An HSA linker, or any molecule or moiety conjugated thereto, can be coupled directly to a cytotoxic or therapeutic agent using known chemical methods, or coupled indirectly to a cytotoxic or therapeutic agent via an indirect linkage. For example, an HSA linker can be attached to a chelating group that is attached to the cytotoxic or therapeutic agent. Chelating groups include, but are not limited to, ininocarboxylic and polyaminopolycarboxylic reactive groups, diethylenetriaminepentaacetic acid (DTPA), and 1,4,7,10-tetraazacyclododecane-1,4,7,10-tetraacetic acid (DOTA). For general methods, see, e.g., Liu et al., *Bioconjugate Chem.* 12(4):653, 2001; Cheng et al., WO 89/12631; Kieffer et al., WO 93/12112; Albert et al., U.S. Pat. No. 5,753,627; and WO 91/01144 (each of which are hereby incorporated by reference).

An HSA linker conjugate that includes, e.g., an HSA linker, one or more binding moieties (with or without intervening peptide connectors, as defined herein), and a therapeutic or cytotoxic agent, can be specifically targeted by the binding moiety (e.g., antibody, antibody fragment, or receptor/ligand) to a cell or tissue, thereby allowing selective destruction of the target cell or tissue to which the binding moiety is directed. For example, an HSA linker conjugate can be used to target and destroy cancer cells of the lung, breast, prostate, and colon in order to prevent, stabilize, inhibit the progression of, or treat cancers originating in these organs when the HSA linker conjugate includes a binding moiety that specifically binds to the cancer cells in these organs. Also, for example, an HSA linker conjugate can be used to target and destroy cells of the vasculature, brain, liver, kidney, heart, lung, prostate, colon, nasopharynx, oropharynx, larynx, bronchus, and skin in order to prevent, stabilize, inhibit the progression of, or treat age-related, tobacco-related, or autoimmune diseases or conditions relating to these organs by targeting, in the case of autoimmune disease for example, autoreactive T cells (e.g., by binding to and agonizing tumor necrosis factor receptor 2 (TNFR2) present on the autoreactive T cells).

An HSA linker, when expressed recombinantly, can be joined to a cytotoxic polypeptide. Cytotoxic polypeptides, when brought into contact with a target cell (e.g., a cancer cell), exerts cytotoxic or cytostatic effects on the cell. For example, a cytotoxic polypeptide, when joined with an HSA linker, can induce events in a target cell upon binding of the target cell that leads to cell death through, for example, apoptosis, necrosis, or senescence. Alternatively, a cytotoxic polypeptide joined with an HSA linker can interfere or inhibit normal cellular biological activities, such as division, metabolism, and growth, or abnormal cellular biological activities, such as metastasis.

For example, an HSA linker joined to caspase 3 will bind a target cell (e.g., a cancer cell) and undergo endocytosis. Once internalized by the target cell, the caspase portion of the HSA linker conjugate can initiate the pro-apoptotic caspase cascade, ultimately resulting in the apoptosis of the target cell.

In a preferred embodiment, an HSA linker conjugate includes a cytotoxic polypeptide capable of killing a cancer cell. In another embodiment, the cytotoxic polypeptide inhibits the growth or metastasis of a cancer cell. The cytotoxic polypeptide joined with an HSA linker can also be used to kill or inhibit the growth of cells associated with, necessary for, or beneficial to cancer growth, such as endothelial cells that form blood vessels that perfuse solid tumors.

In an embodiment, an HSA linker conjugate can include two or more cytotoxic polypeptides so as to modulate (e.g., increase) the specificity, intensity, or duration of the cytotoxic or cytostatic effect on a target cell (e.g., a cancer cell).

In another embodiment, the HSA linker is joined to an activatable form of cytotoxic polypeptide (e.g., a biologically-inactive pro-agent that is capable of activation upon cleavage by an enzyme or drug). In this embodiment, texposure (e.g., in vivo) of the cytotoxic polypeptide pro-agent to an enzyme or drug capable of cleaving the cytotoxic polypeptide, renders the cytotoxic polypeptide biologically-active (e.g., cytotoxic or cytostatic). An example of a biologically-inactive cytotoxic polypeptide that can be converted to a biologically-active form for use with an HSA linker is a procaspase (e.g., procaspase 8 or 3). For example, the procaspase 8 domain of an HSA linker can be cleaved by TRAIL or FasL upon internalization by a target cell (e.g., a cancer cell). Once cleaved, the biologically active caspase 8 can promote apoptosis of the target cell.

In one embodiment, the cytotoxic polypeptide joined to an HSA linker can include a full-length peptide, polypeptide, or protein, or biologically-active fragment thereof (e.g., a "death domain"), known to have cytotoxic or cytostatic properties. Peptides, polypeptides, or proteins with cytotoxic or cytostatic properties can be altered (e.g., by making amino acid substitutions, mutations, truncations, or additions) to facilitate incorporation of the cytotoxic sequence into an agent as described herein. Desirable alterations include, for example, changes to the amino acid sequence that facilitate protein expression, longevity, cell secretion, and target cell toxicity.

The present invention also provides a nucleic acid molecule encoding a cytotoxic polypeptide as a fusion protein with an HSA linker, optionally including binding moieties and peptide connectors. The nucleic acid molecule can be incorporated into a vector (e.g., an expression vector), such that, upon expression of the HSA linker in a cell transfected or transduced with the vector, the cytotoxic polypeptide, HSA linker, and binding moieties, if present, are operably linked (e.g., fused, contiguously-joined, or tethered together). Examples of peptides, polypeptides, and proteins that can be used as a cytotoxic polypeptide of the present invention include, but are not limited to, apoptosis-inducing proteins such as cytochrome c (SEQ ID NO:39); caspases (e.g., caspase 3 (SEQ ID NO:36) and caspase 8 (SEQ ID NO:37)); procaspases, granzymes (e.g., granzymes A and B (SEQ ID NO:38)); tumor necrosis factor (TNF) and TNF receptor family members, including TNF-alpha (TNFα; SEQ ID NO:40)), TNF-beta, Fas (SEQ ID NO:41) and Fas ligand; Fas-associated death domain-like IL-1β converting enzyme (FLICE); TRAIL/APO2L (SEQ ID NO:45) and TWEAK/APO3L (see, e.g., U.S. Patent Application Publication No. 2005/0187177, herein incorporated by reference); pro-apoptotic members of the Bcl-2 family, including Bax (SEQ ID NO:46), Bid, Bik, Bad (SEQ ID NO:42), Bak, and RICK (see, e.g., U.S. Patent Application Publication No. 2004/0224389, herein incorporate by reference); vascular apoptosis inducing proteins 1 and 2 (VAP1 and VAP2; Masuda et al., *Biochem. Biophys. Res. Commun.* 278:197-204 (2000)); pierisin (SEQ ID NO:44; Watanabe et al., *Biochemistry* 96:10608-10613 (1999)); apoptosis-inducing protein (SEQ ID NO:43; AIP; Murawaka et al., *Nature* 8:298-307 (2001)); IL-1α propiece polypeptide (see, e.g., U.S. Pat. No. 6,191,269, herein incorporated by reference); apoptin and apoptin-associated proteins such as AAP-1 (see, e.g., European Patent Application Publication No. EP 1083224, herein incorporated by reference); anti-angiogenic factors such as endostatin and angiostatin; and other apoptosis-inducing proteins, including those described in the following International and U.S. Patent Application Publications, each herein incorporated by reference: U.S. 2003/0054994, U.S. 2003/0086919, U.S. 2007/0031423, WO 2004/078112, WO 2007/012430, and WO 2006/0125001 (intracellular domain of delta 1 and jagged 1).

Wild-Type HSA Linker Conjugates

The present invention also encompasses a naturally-occurring wild-type HSA linker, the amino acid and nucleotide sequences of which are provided in SEQ ID NOS:3 and 4, respectively, in the formation of binding, diagnostic, or therapeutic agents. In all embodiments utilizing an HSA linker with the amino acid sequence listed in SEQ ID NO:3, one or more peptide connectors, as described above, are covalently attached to the amino and/or carboxy termini of the HSA linker, or to an amino acid residue within the HSA linker sequence, to facilitate conjugation of one or more binding moieties.

Truncations

The invention further provides an HSA linker conjugate that is formed using a truncated wild-type HSA polypeptide, optionally combined with one or more peptide connectors or binding moieties. A wild-type HSA polypeptide lacking 1, 2, 3, 4, 5, 10, 15, 20, 50, 100, 200 or more amino acids of the full-length wild-type HSA amino acid sequence (i.e., SEQ ID NO:3) can be conjoined to any of the binding moieties or diagnostic or therapeutic agents described herein. Truncations can occur at one or both ends of the HSA linker, or can include a deletion of internal residues. Truncation of more than one amino acid residue need not be linear (i.e., consecutive). Examples of wild-type HSA linkers include those having, in combination with one or more peptide connectors or binding moieties, one or more of domain I (SEQ ID NO:56; residues 1-197 of SEQ ID NO:3), domain II (SEQ ID NO:54; residues 189-385 of SEQ ID NO:3), or domain III (SEQ ID NO:57; residues 381-585 of SEQ ID NO:3), or combinations thereof, e.g., domains I and II, I and III, and II and III.

Serum clearance rates of a conjugate (e.g., a bispecific HSA-drug or radioisotope-containing agent), can be optimized by testing conjugates containing a truncated wild-type HSA linker, as described above.

Additional HSA Linker Modifications

HSA linkers may, but need not, be modified by site-specific chemical modification of amino acid residues in the HSA linker. The correctly-folded tertiary structure of HSA displays certain amino acid residues on the external face of the protein. Chemically-reactive amino acid residues (e.g., cysteine) can be substituted for these surface-exposed residues to allow site-specific conjugation of a diagnostic or therapeutic agent.

Alternatively, or in addition, HSA linkers may optionally be modified by the addition or removal of asparagine, serine, or threonine residues from an HSA linker sequence to alter glycosylation of these amino acid residues. Glycosylation sites added to an HSA linker are preferably surface-exposed, as discussed herein. Glycosyl or other carbohydrate moieties introduced to an HSA linker can be directly conjugated to diagnostic, therapeutic, or cytotoxic agents.

Cysteine (Thiol) Conjugation

Surface-exposed amino acid residues of the HSA linker may be substituted with cysteine residues to allow for chemical conjugation of diagnostic, therapeutic, or cytotoxic agents. Cysteine residues exposed on the surface of the HSA linker (when folded into its native tertiary structure) allow the specific conjugation of a diagnostic, therapeutic, or cytotoxic agent to a thiol reactive group such as maleimide or haloacetyl. The nucleophilic reactivity of the thiol functionality of a cysteine residue to a maleimide group is about 1000 times higher compared to any other amino acid functionality in a protein, such as the amino group of a lysine residue or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London). The amount of free thiol in a protein may be estimated using the standard Ellman's assay. In some instances, reduction of the disulfide bonds with a reagent such as dithiothreitol (DTT) or selenol (Singh et al., *Anal. Biochem.* 304:147-156 (2002)) is required to generate the reactive free thiol.

Sites for cysteine substitution can be identified by analysis of surface accessibility of the HSA linker (e.g., the identification of serine and threonine residues as suitable for substitution are described in Example 1 below). The surface accessibility can be expressed as the surface area (e.g., square angstroms) that can be contacted by a solvent molecule, e.g., water. The occupied space of water is approximated as a sphere with a 1.4 angstrom radius. Software for calculating the surface accessibility of each amino acid of a protein is freely available or licensable. For example, the CCP4 Suite of crystallography programs which employ algorithms to calculate the surface accessibility of each amino acid of a protein with known x-ray crystallography derived coordinates ("The CCP4 Suite: Programs for Protein Crystallography" *Acta. Cryst. D*50:760-763 (1994); www.ccp4.ac.uk/dist/html/IN-DEX.html). Solvent accessibility may also be assessed using the free software DeepView Swiss PDB Viewer downloaded from the Swiss Institute of Bioinformatics. The substitution of cysteines at surface-exposed sites allows for conjugation of the reactive cysteine to a thiol reactive group linked to the diagnostic or therapeutic agent.

Glycosylation

In addition, altered serum clearance rates can be achieved by engineering glycosylation sites into the HSA linker. In certain embodiments, an HSA linker is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X represents any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the HSA linker is conveniently accomplished by altering the amino acid sequence such that one or more of the above-described tripeptide sequences (for N-linked glycosylation sites) is created. The alteration may also be made by the addition, deletion, or substitution of one or more serine or threonine residues to the sequence of the original HSA linker (for 0-linked glycosylation sites). The resulting carbohydrate structures on HSA can also be used for site-specific conjugation of cytotoxic, immunomodulatory or cytostatic agents as described above.

HSA Linker Conjugates in Combination with Other Therapeutic Agents

HSA linker conjugates described herein may be administered with one or more of the therapeutic, cytotoxic, or cytostatic agents described herein. For example, a patient suffering from breast cancer can be administered an HSA linker containing ErbB2 and ErbB3 scFvs (e.g., B2B3-1) can be co-administered with, e.g., doxorubicin, cyclophosphamide, and paclitaxel, a common chemotherapeutic regimen for the treatment of breast cancer. A preferred therapeutic agent for use in this regard is trastuzumab. Data regarding this combination are set forth in Examples 42-44 below. Additional biological and chemical agents useful for the treatment of cancer are set forth herein, e.g., in Appendix 2.

HSA Linker Conjugates in Combination with Radiotherapy or Surgery

HSA linker conjugates may be administered prior to, concurrent with, or following radiotherapy or surgery. For example, a patient suffering from a proliferative disorder (e.g., breast cancer) can receive an HSA linker conjugate, alone or in combination with other therapeutic, cytotoxic, or cytotoxic agents as described herein concurrent with targeted radiotherapy or surgical intervention (e.g., lumpectomy or mastectomy) at the site of the cancerous tissue. Radiotherapies suitable for use in combination with HSA linker conjugates include brachytherapy and targeted intraoperative radiotherapy (TARGIT).

Pharmaceutical Compositions

Pharmaceutical compositions provided herein contain a therapeutically or diagnostically effective amount of an HSA linker conjugate that includes one or more of a binding moiety (e.g., antibodies or antibody fragments), a diagnostic agent (e.g., radionuclide or chelating agents), or a therapeutic agent (e.g., cytotoxic or immunomodulatory agents) agent. The active ingredients, an HSA linker conjugate (prepared with one or more of a binding moiety, diagnostic agent, or therapeutic agent) can be formulated for use in a variety of drug delivery systems. One or more physiologically acceptable excipients or carriers can also be included in the compositions for proper formulation. Suitable formulations for use in the present invention are found in *Remington's Pharmaceutical Sciences*, Mack Publishing Company, Philadelphia, Pa., 17th ed. (1985). For a brief review of methods for drug delivery, see, Langer *Science* 249:1527-1533 (1990).

The pharmaceutical compositions are intended for parenteral, intranasal, topical, oral, or local administration, such as by a transdermal means, for prophylactic and/or therapeutic treatment. Commonly, the pharmaceutical compositions are administered parenterally (e.g., by intravenous, intramuscular, or subcutaneous injection), or by oral ingestion, or by topical application. Thus, compositions for parenteral administration may include an HSA linker, with or without one or more binding, diagnostic, and/or therapeutic agent conjugated thereto, dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of an HSA linker conjugate (prepared with one or more of a binding, diagnostic, and/or therapeutic agent) in a sealed package of tablets or capsules, for example. The composition in solid form can also be packaged in a container for a flexible quantity, such as in a squeezable tube designed for a topically applicable cream or ointment.

The compositions containing an effective amount of an HSA linker conjugate (prepared with one or more of a binding, diagnostic, and/or therapeutic agent) can be administered to a mammal (e.g., a human) for prophylactic and/or therapeutic treatments. In prophylactic applications, compositions containing an HSA linker conjugate (prepared with one or more of a binding, diagnostic, and/or therapeutic agent) are administered to a patient susceptible to or otherwise at risk of developing a disease or condition (e.g., a cancer, autoimmune disease, or cardiovascular disease). Such an amount is defined to be a "prophylactically effective dose." In this use, the precise amounts again depend on the patient's state of health, but generally range from about 0.5 mg to about 400 mg of an HSA linker conjugate (prepared with one or more of a binding, diagnostic, and/or therapeutic agent) per dose (e.g., 10 mg, 50 mg, 100 mg, 200 mg, 300 mg, or 400 mg or more per dose) and from about 0.1 μg to about 300 mg of one or more immunomodulatory agents per dose (e.g., 10 μg, 30 μg, 50 μg, 0.1 mg, 10 mg, 50 mg, 100 mg, or 200 mg per dose). A dose of an HSA linker conjugate (prepared with one or more of a binding, diagnostic, and/or therapeutic agent) can be administered prophylactically to a patient one or more times per hour, day, week, month, or year (e.g., 2, 4, 5, 6, 7, 8, 9, 10, 11, or 12 times per hour, day, week, month, or year). More commonly, a single dose per week of an HSA linker conjugate (prepared with one or more of a binding, diagnostic, and/or therapeutic agent) is administered.

In therapeutic applications, a dose of an HSA linker conjugate (prepared with one or more of a binding, diagnostic, and/or therapeutic agent) is administered to a mammal (e.g., a human) already suffering from a disease or condition (e.g., a cancer, autoimmune disease, or cardiovascular disease) in an amount sufficient to cure or at least partially arrest or alleviate one or more of the symptoms of the disease or condition and its complications. An amount adequate to accomplish this purpose is defined as a "therapeutically effective dose." Amounts effective for this use may depend on the severity of the disease or condition and general state of the patient, but generally range from about 0.5 mg to about 400 mg of an HSA linker conjugate (prepared with one or more of a binding, diagnostic, and/or therapeutic agent) per dose (e.g., 10 mg, 50 mg, 100 mg, 200 mg, 300 mg, or 400 mg or more per dose). A dose of an HSA linker conjugate (prepared with one or more of a binding, diagnostic, and/or therapeutic agent) can be administered therapeutically to a patient one or more times per hour, day, week, month, or year (e.g., 2, 4, 5, 6, 7, 8, 9, 10, 11, or 12 times per hour, day, week, month, or year). More commonly, a single dose per week of an HSA linker conjugate (prepared with one or more of a binding, diagnostic, and/or therapeutic agent) is administered.

In several embodiments, the patient may receive an HSA linker conjugate (prepared with one or more of a binding, diagnostic, and/or therapeutic agent) in the range of about 0.5 to about 400 mg per dose one or more times per week (e.g., 2, 3, 4, 5, 6, or 7 or more per week), preferably about 5 mg to about 300 mg per dose one or more times per week, and even more preferably about 5 mg to about 200 mg per dose one or more times per week. The patient may also receive a biweekly dose of an HSA linker conjugate (prepared with one or more of a binding, diagnostic, and/or therapeutic agent) in the range of about 50 mg to about 800 mg or a monthly dose of an HSA linker, or any binding, diagnostic, and/or therapeutic agent conjugated thereto, in the range of about 50 mg to about 1,200 mg.

In other embodiments, an HSA linker conjugate (prepared with one or more of a binding, diagnostic, and/or therapeutic agent) may be administered to a patient in a typical dosage range of about 0.5 mg per week to about 2000 mg per week, about 1.0 mg per week to about 1000 mg per week, about 5 mg per week to about 500 mg per week, about 10 mg per week to about 100 mg per week, about 20 mg per week to about 80 mg per week, about 100 mg per week to about 300 mg per week, or about 100 mg per week to about 200 mg per week. In another aspect, the dosages for administration to a 70 kg patient can range from, for example, about 1 μg to about 5000 mg, about 2 μg to about 4500 mg, about 3 μg to about 4000 mg, about 4 μg to about 3,500 mg, about 5 μg to about 3000 mg, about 6 μg to about 2500 mg, about 7 μg to about 2000 mg, about μg to about 1900 mg, about 9 μg to about 1,800 mg, about 10 μg to about 1,700 mg, about 15 μg to about 1,600 mg, about 20 μg to about 1,575 mg, about 30 μg to about 1,550 mg, about 40 μg to about 1,500 mg, about 50 μg to about 1,475 mg, about 100 μg to about 1,450 mg, about 200 μg to about 1,425 mg, about 300 μg to about 1,000 mg, about 400 μg to about 975 mg, about 500 μg to about 650 mg, about 0.5 mg to about 625 mg, about 1 mg to about 600 mg, about 1.25 mg to about 575 mg, about 1.5 mg to about 550 mg, about 2.0 mg to about 525 mg, about 2.5 mg to about 500 mg, about 3.0 mg to about 475 mg, about 3.5 mg to about 450 mg, about 4.0 mg to about 425 mg, about 4.5 mg to about 400 mg, about 5 mg to about 375 mg, about 10 mg to about 350 mg, about 20 mg to about 325 mg, about 30 mg to about 300 mg, about 40 mg to about 275 mg, about 50 mg to about 250 mg, about 100 mg to about 225 mg, about 90 mg to about 200 mg, about 80 mg to about 175 mg, about 70 mg to about 150 mg, or about 60 mg to about 125 mg, of an HSA linker conjugate provided herein. Dosage regimen may be adjusted to provide the optimum therapeutic response. In another aspect, an HSA linker conjugate (prepared with one or more of a binding, diagnostic, and/or therapeutic agent) may be administered in the range of about 0.5 mg every other day to about 500 mg every other day, preferably about 5 mg every other day to about 75 mg every other day, more preferably about 10 mg every other day to about 50 mg every other day, and even more preferably 20 mg every other day to about 40 mg every other day. An HSA linker conjugate (prepared with one or more of a binding, diagnostic, and/or therapeutic agent) may also be administered in the range of about 0.5 mg three times per week to about 100 mg three times per week, preferably about 5 mg three times per week to about 75 mg three times per week, more preferably about 10 mg three times per week to about 50 mg three times per week, and even more preferably about 20 mg three times per week to about 40 mg three times per week.

In non-limiting embodiments of the methods of the present invention, an HSA linker conjugate (prepared with one or more of a binding, diagnostic, and/or therapeutic agent) is administered to a mammal (e.g., a human) continuously for 1, 2, 3, or 4 hours; 1, 2, 3, or 4 times a day; every other day or every third, fourth, fifth, or sixth day; 1, 2, 3, 4, 5, 6, 7, 8, 9, or 10 times a week; biweekly; 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 times a month; bimonthly; 1, 2, 3, 4, 5, 6, 7, 8, 9, or 10 times every six months; 1, 2, 3, 4, 5, 6, 7, 8, 9, 10, 11, 12, 13, 14, 15, 16, 17, 18, 19, or 20 times a year; or biannually. An HSA linker conjugate (prepared with one or more of a binding, diagnostic, and/or therapeutic agent) may be administered at different frequencies during a therapeutic regime. In additional embodiments, an HSA linker conjugate (prepared with one or more of a binding, diagnostic, and/or therapeutic agent) may be administered to a patient at the same frequency or at a different frequency.

The amount of one or more diagnostic or therapeutic agents and an HSA linker, or any agent conjugated thereto, required to achieve the desired therapeutic effect depends on a number of factors, such as the specific diagnostic or therapeutic agent(s) chosen, the mode of administration, and clinical condition of the recipient. A skilled artisan will be able to determine the appropriate dosages of one or more diagnostic or therapeutic agents and an HSA linker, or any agent conjugated thereto, to achieve the desired results.

Single or multiple administrations of the compositions comprising an effective amount of an HSA linker conjugate (prepared with one or more of a binding, diagnostic, and/or therapeutic agent) can be carried out with dose levels and pattern being selected by the treating physician. The dose and administration schedule can be determined and adjusted based on the severity of the disease or condition in a mammal (e.g., a human), which may be monitored throughout the course of treatment according to the methods commonly practiced by clinicians or those described herein.

An HSA linker conjugate (prepared with one or more of a binding, diagnostic, and/or therapeutic agent) can be administered to a mammalian subject, such as a human, directly or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in *Remington's Pharmaceutical Sciences*, (18$^{th}$ edition), ed. A. Gennaro, 1990, Mack Publishing Company, Easton, Pa.

Diagnostic and Therapeutic Applications

HSA linker conjugates can be used for diagnostic and therapeutic applications in a human, including, for example, the diagnosis or treatment of proliferative diseases (e.g., cancers, such as melanoma, clear cell sarcoma, and renal cancer) and autoimmune diseases (e.g., multiple sclerosis, rheumatoid arthritis, and uveitis). The following discussion of human proliferative and autoimmune diseases is meant to provide the skilled practitioner with a general understanding of how HSA linker conjugates can be applied in diagnostic and therapeutic applications and is not meant to limit the scope of the present invention.

Proliferative Diseases (Cancer)

An HSA linker conjugate can be used to diagnose, treat, prevent, or eliminate proliferative diseases such as, but not limited to, breast cancer, melanoma, clear cell sarcoma, renal cancer (e.g., renal cell carcinoma), prostate cancer, lung cancer, gastric cancer, and ovarian cancer. Binding moieties to be conjoined with an HSA linker for diagnostic or therapeutic application in a patient suspected of having or suffering from a proliferative disease may be chosen based on their ability to specifically bind, agonize, activate, antagonize, or inhibit target molecules (e.g., cell surface receptors such as tyrosine kinase receptors) associated with a proliferative disease. Binding moieties that target, for example, insulin-like growth factor receptor (IGFR, e.g., IGF1R and IGF2R), fibroblast growth factor receptor (FGFR), platelet-derived growth factor receptor (PDGFR), vascular endothelial growth factor receptor (VEGFR), tumor necrosis factor receptor (TNFR), epidermal growth factor receptor (EGFR, e.g., ErbB2 (HER2/neu)), Fc receptor, c-kit receptor, or mesenchymal epithelial transition factor receptor (c-met; also known as hepatocyte growth factor receptor (HGFR)) can be conjoined to an HSA linker to diagnose or treat a proliferative disease. Specific binding of a cancer cell by an HSA linker conjugate can allow for detection (e.g., an HSA linker conjoined to a detectable label, as defined herein) or destruction (e.g., an HSA linker conjoined to a cytotoxic agent) of the bound cancer cell. Specific application of HSA linker conjugates for the treatment of breast and renal cancer is described below.

Breast Cancer

Common forms of breast cancer include invasive ductal carcinoma, a malignant cancer in the breast's ducts, and invasive lobular carcinoma, a malignant cancer in the breast's lobules. Some types of breast cancer cells are known to express high levels of epidermal growth factor receptors, especially ErbB2 (i.e., HER2/neu). Aberrant signaling or unregulated activation of EGFRs has been linked to the development and progression of many cancers, including breast cancer. Uncontrolled cellular proliferation mediated via dysfunctional EGFR pathways can be found in a wide variety of solid tumors of epithelial origin and data have linked tumor EGFR expression, overexpression, and dysregulation to advanced disease, metastatic phenotype, resistance to chemotherapy, and an overall poorer prognosis.

An HSA linker conjoined to one or more binding moieties specific for an EGFR (e.g., anti-ErbB2; trastuzumab) can be used with a diagnostic (e.g., a detectable label) or cytotoxic, cytostatic, or therapeutic agent, as described herein, to diagnose or treat breast cancer. Alternatively, a bispecific HSA linker conjugate that comprises binding moieties specific for ErbB2 and ErbB3, such as "B2B3-1," described further herein, can be employed to diagnose or treat cancers, e.g., breast, kidney, ovarian, and lung cancers.

As described above, an HSA linker conjugate used to treat breast cancer can be administered prior to (e.g., neoadjuvant chemotherapy), concurrent with, or following (e.g., adjuvant chemotherapy) radiotherapy or surgical intervention. An HSA linker conjugate can also be co-administered with other compounds (e.g., antineoplastic agents, such as biological or chemical therapeutics) useful for the treatment of breast cancer. For example, the antineoplastic agents listed in Table 1, including mitotic inhibitors (e.g., taxanes), topoisomerase inhibitors, alkylating agents (including, e.g., platinum-based agents), selective estrogen modulators (SERM), aromatase inhibitors, antimetabolites, antitumor antibiotics (e.g., anthracycline antibiotics), anti-VEGF agents, anti-ErbB2 (HER2/neu) agents, and anti-ErbB3 agents, are known to be particularly useful for the treatment of breast cancer. An HSA linker conjugate can be administered by a clinician in combination with any compound, including those listed in Appendix 2, known or thought to be beneficial for the treatment of breast cancer.

TABLE 1

Exemplary antineoplastic agents for treatment of breast cancer in combination with HSA linker conjugates.

| Therapeutic Class | Exemplary Agent (Generic/Tradename) | Exemplary Dose |
|---|---|---|
| Mitotic Inhibitors | paclitaxel (TAXOL ®; ABRAXANE ®) | 175 mg/m$^2$ |
|  | docetaxel (TAXOTERE ®) | 60-100 mg/m$^2$ |
| Topoisomerase Inhibitors | camptothecin |  |
|  | topotecan hydrochloride (HYCAMTIN ®) |  |
|  | etoposide (EPOSIN ®) |  |
| Alkylating Agents | cyclophosphamide (CYTOXAN ®) | 600 mg/m$^2$ |
| Platinum-Based Agents | Cisplatin | 20-100 mg/m$^2$ |
|  | carboplatin (PARAPLATIN ®) | 300 mg/m$^2$ |
|  | nedaplatin (AQUPLA ®) |  |
|  | oxaliplatin (ELOXATIN ®) | 65-85 mg/m$^2$ |
|  | satraplatin (SPERA ®) |  |
|  | triplatin tetranitrate |  |
| Selective Estrogen Modulators (SERM) | tamoxifen (NOLVADEX ®) | 20-40 mg/day |
|  | raloxifene (EVISTA ®) | 60 mg/day |
|  | toremifene (FARESTON ®) |  |
| Antimetabolites | methotrexate | 40 mg/m$^2$ |
|  | Fluorouracil (5-FU) | 500 mg/m$^2$ |
|  | Raltitrexed |  |
| Antitumor Antibiotics | Doxorubicin (ADRIAMYCIN ®) | 40-75 mg/m$^2$ |
|  | epirubicin (ELLENCE ®) | 60-120 mg/m$^2$ |
| Aromatase Inhibitors | aminoglutethimide (CYTADREN ®) | 250-2000 mg/day |
|  | anastrozole (ARIMIDEX ®) | 1 mg/day |
|  | letrozole (FEMARA ®) | 2.5 mg/day |
|  | Vorozole |  |
|  | exemestane (AROMASIN ®) | 25-50 mg/day |
|  | Testolactone |  |
|  | fadrozole (AFEMA ®) |  |
| Anti-VEGF Agents | bevacizumab (AVASTIN ®) | 10 mg/kg |
| Anti-ErbB2 (HER2/neu) Agents | trastuzumab (HERCEPTIN ®) | 2-8 mg/kg |
|  | Pertuzumab (OMNITARG ®) |  |
| Anti-ErbB3 (HER3) Agents | U3-1287 (AMG 888) |  |

Renal Cancer

Kidney cancers, such as renal cell carcinoma, are particularly resistant to traditional radiological and chemical therapies. As such, the application of biological therapeutics, conjoined with an HSA linker, represents an attractive option for patients suffering from these cancers. For example, an HSA linker conjoined with binding moieties that agonize type I interferon or interleukin 2 receptors can be used to treat a renal cancer. As a solid tumor, binding moieties that target and inhibit tumor vascularization (e.g., anti-vascular endothelial growth factor (VEGF) antibodies such as bevacizumab) can also be used for therapeutic effect.

Autoimmune Diseases

An HSA linker conjugate can be used to diagnose, treat, prevent, or stabilize autoimmune diseases and disorders in e.g., a human patient, such as, e.g., multiple sclerosis (MS), insulin-dependent diabetes mellitus (IDDM), rheumatoid arthritis (RA), uveitis, Sjögren's syndrome, Grave's disease, psoriasis, and myasthenia gravis. Autoimmune diseases and disorders are caused by self-reactive elements of the immune system (e.g., T cells, B cells, and self-reactive antibodies). As such, binding moieties that inhibit, block, antagonize, or deplete (e.g., anti-lymphocyte or anti-thymocyte globulins; basiliximab, daclizumab, or muromonab-CD3 monoclonal antibodies) self-reactive immune cells and antibodies can be conjoined with an HSA linker for therapeutic use. Binding moieties that function as inflammatory signaling inhibitors (ISI), as defined herein, can be conjoined to an HSA linker for the treatment of autoimmunity. In addition, binding moieties that inhibit or antagonize integrin function (e.g., an integrin antagonist, as defined herein) can ameliorate or halt disease progression.

In other embodiments, the binding moiety is a soluble TNF receptor, such as etanercept or lenercept; an antibody directed against a pro-inflammatory cytokine or a pro-inflammatory cell surface signaling molecule, such as adalimumab, certolizumab, inflixamab, golimumab, and rituxan; a dominant-negative pro-inflammatory cytokine variant, such as XENP345, XPRO™1595, anakinra, and variants disclosed in U.S. Patent Application Publication Nos. 20030166559 and 20050265962; an inhibitor of the signaling pathways downstream of pro-inflammatory cytokine or pro-inflammatory cell surface signaling molecules, such as DE 096, 5-amino-2-carbonylthiopene derivatives (as described in W02004089929), ARRY-797, BIRB 796 BS, (1-5-tert-butyl-2-p-tolyl-2H-pyrazol-3-yl)-3-[4-2(morpholin-4-yl-ethoxy)-naphtalen-1-yl]-urea, CHR-3620, CNI-1493, FR-167653 (Fujisawa Pharmaceutical, Osaka, Japan), ISIS 101757 (Isis Pharmaceuticals), ML3404, NPC31145, PD169316, PHZ1112, RJW67657, 4-(4-(4-fluorophenyl)-1-(3-phenyl-propyl)-5-(4-pyridinyl)-1H-imidazol-2-yl)-3-butyn-1-ol, SCIO-469, SB202190, SB203580, (4-(4-fluorophenyl)-2-(4-methylsulfinylphenyl)-5-(4-pyridyl)1H-imidazole), SB239063, trans-1-(4-hydroxycyclohexyl)-4-(4-fluorophenyl-methoxypyridimidin-4-yl)imidazole, SB242235, SD-282, SKF-86002, TAK 715, VX702, and VX745; or an inhibitor of TNF-alpha converting enzyme (TACE), such as BB-1101, BB-3103, BMS-561392, butynyloxyphenyl β-sulfone piperidine hydroxomates, CH4474, DPC333, DPH-067517, GM6001, GW3333, Ro 32-7315, TAPI-1, TAPI-2, and TMI 005); or an anti-idiotypic agent, such as monoclonal antibodies, LJP 394 (abetimus, RIQUENT®, La Jolla Pharmaceuticals).

In other embodiments, the binding moiety is an interferon, as described herein. Binding moieties that can be conjoined to an HSA linker include, e.g., interferon-beta (REBIF® (IFN-β-1a), AVONEX® (IFN-β-1a), and BETASERON® (IFN-β-1b)), interferon-t (TAUFERON™), interferon-alpha (e.g., ROFERON-A® (IFN-α-2a), INTRON-A® (IFN-α-2b), REBETRON® (IFN-α-2b), ALFERON-N® (IFN-α-n3), PEG-INTRON® (IFN-α-2b covalently conjugated with monomethoxy polyethylene glycol), INFERGEN® (a non-naturally occurring type 1 interferon with 88% homology to IFN-α-2b), or PEGASYS® (pegylated IFN-α-1a)), and ACTIMMUNE® (IFN-g-1b).

The present invention further provides HSA linker conjugates with binding moieties that antagonize these pro-inflammatory molecules or their specific receptors to treat autoimmunity. Specific application of HSA linker conjugates for the diagnosis and treatment of MS and RA are described below.

Multiple Sclerosis

Multiple sclerosis (MS) is a neurological disease characterized by irreversible degeneration of the nerves of the central nervous system (CNS). Although the underlying cause is unclear, the neurodegeneration in MS is the direct result of demyelination, or the stripping of myelin, a protein that normally lines the outer layer and insulates the nerves. T cells play a key role in the development of MS. Inflamed MS lesions, but not normal white matter, can have infiltrating $CD4^+$ T cells that respond to self antigens presented by MHC class II-linked molecules such as human HLA-DR2. The infiltrating CD4 T cells ($T_H1$ cells) produce the pro-inflammatory cytokines IL-2, IFN-γ, and TNF-α that activate antigen-presenting cells (APCs) such as macrophages to produce additional pro-inflammatory cytokines (e.g., IL-1β, IL-6, IL-8, and IL-12. IL-12 induces further IFN-γ synthesis. The result is progressive demyelination of neuronal sheaths, leading to human disease.

HSA linker conjugates can be used to aid in the diagnosis of MS. Diagnostic HSA linker conjugates that include binding moieties that specifically target one or more (e.g., a bispecific HSA linker conjugate) immune cell activation markers (e.g., CD69, CD28, HLA-DR, and CD45). An imbalance of one or more of these pro-inflammatory or immune cell activation mediators relative to other factors or cells may be measured using an HSA linker conjugate conjoined with a diagnostic agent (e.g., a radioisotope or fluorochrome).

An HSA linker conjugate can be used to treat a person at risk of developing or suffering from MS or to prevent, ameliorate, or cure the symptoms of the disease. For example, binding moieties that specifically target and antagonize α4 integrin (e.g., natalizumab), CD52 (e.g., alemtuzumab), CD80, P-selectin, sphingosine-1-phosphate receptor-1 (S1PR1), hyaluronate receptor, leukocyte function antigen-1 (LFA-1), CD11 (e.g., efalizumab), CD18, CD20 (e.g., rituximab), CD85, ICOS ligand, CCR2, CXCR3, or CCR5 can be useful when conjoined to an HSA linker for therapeutic use in a patient suffering from MS. Similary, binding moieties that neutralize type I interferons (e.g., interferons-alpha and -beta) or that antagonize type I interferon receptors (e.g., IFNαR1) can also be conjoined to an HSA linker for therapeutic application.

Rheumatoid Arthritis

Rheumatoid arthritis (RA) is a chronic, inflammatory autoimmune disorder that causes the immune system to attack the joints. It is a disabling and painful inflammatory condition, which can lead to substantial loss of mobility due to pain and joint destruction. RA is a systemic disease, often affecting extra-articular tissues throughout the body including the skin, blood vessels, heart, lungs, and muscles.

Patients suffering from RA frequently have an increase in cellular expression of the HLA-DR4/DR1 cluster. HSA linker conjugates specific for one or both of these cell surface molecules are useful for the diagnosis of RA.

An HSA linker conjugate can be used to treat a person at risk of developing of suffering from RA to prevent, ameliorate, or cure the symptoms of the disease. For example, binding moieties, as defined herein, that specifically target and antagonize TNF-α (e.g., etanercept, infliximab, and adalimumab), IL-1 (e.g., anakinra), or CTLA-4 (e.g., abatacept). Binding moieties that specifically target and deplete B cells (e.g., an anti-CD20 antibody, such as rituximab) can also be conjoined to the HSA linker described herein to treat or prevent RA.

Uveitis

Uveitis specifically refers to inflammation of the middle layer of the eye, but may refer to any inflammatory process involving the interior of the eye. Uveitis may be autoimmune or idiopathic in origin An HSA linker conjugate can be used to treat a person at risk of developing of suffering from autoimmune uveitis to prevent, ameliorate, or cure the symptoms of the disease. For example, alpha-fetoprotein (e.g., human AFP; NCBI Accession No. NM_001134), or biologically-active fragments thereof, can be conjoined to an HSA linker to reduce or eliminate inflammation associated with autoimmune or idiopathic uveitis.

Kits

The present invention further provides kits that include a pharmaceutical composition containing an HSA linker, and one or more of a binding moiety (e.g., antibodies or antibody fragments), a diagnostic agent (e.g., radionuclide or chelating agents), and a therapeutic agent (e.g., cytotoxic or immunomodulatory agents) with reagents that can be used to conjugate them to the HSA linker, if necessary, and including a pharmaceutically-acceptable carrier, in a therapeutically effective amount for treating a disease or condition (e.g., a cancer, autoimmune disease, or cardiovascular disease). The kits include instructions to allow a practitioner (e.g., a physician, nurse, or patient) to administer the composition contained therein.

Preferably, the kits include multiple packages of the single-dose pharmaceutical composition(s) containing an effective amount of an HSA linker, or any binding (e.g., antibodies or antibody fragments (e.g., scFv)), diagnostic (e.g., radionuclide or chelating agents), and/or therapeutic (e.g., cytotoxic or immunomodulatory agents) conjugate thereof. Optionally, instruments or devices necessary for administering the pharmaceutical composition(s) may be included in the kits. For instance, a kit may provide one or more pre-filled syringes containing an effective amount of an HSA linker, or any binding, diagnostic, and/or therapeutic agent conjugated thereto. Furthermore, the kits may also include additional components such as instructions or administration schedules for a patient suffering from a disease or condition (e.g., a cancer, autoimmune disease, or cardiovascular disease) to use the pharmaceutical composition(s) containing an HSA linker, or any binding, diagnostic, and/or therapeutic agent conjugated thereto.

It will be apparent to those skilled in the art that various modifications and variations can be made in the compositions, methods, and kits of the present invention without departing from the spirit or scope of the invention. Thus, it is intended that the present invention cover the modifications and variations of this invention provided they come within the scope of the appended claims and their equivalents.

EXAMPLES

The following examples are provided by way of illustration only and not by way of limitation. Those of skill in the art will readily recognize a variety of non-critical parameters that could be changed or modified to yield essentially the same or similar results.

Example 1

Methods to Identify Residues in the HSA Linker for Site-Specific Conjugation of Cytotoxic or Cytostatic Drugs To identify sites for specific conjugation of drug to HSA the crystal structure is studied and surface exposed serine and threonine residues are identified. These particular surface-exposed amino acids can then be mutated to cysteine allowing drug conjugation to the substituted cysteine using a thiol-specific conjugating agent such as maleimide. Mild reduction may be required prior to drug conjugation. The number of drugs conjugated is controlled by the number of surface exposed cysteine residues introduced into HSA. Serine and threonine are selected as the most suitable residues for mutation as they share the most structural identity with cysteine, however, other surface exposed residues may also be mutated to cysteine and successfully conjugated to cytostatic or cytotoxic drugs.

The crystal structure of HSA is deposited in the RSCB Protein Data Bank (1 bm0—Sugio et al., "Crystal structure of human serum albumin at 2.5 A resolution," *Protein Eng.* 12:439-446 (1999)). This structure is analyzed using the DeepView Swiss PDB Viewer downloaded from the Swiss Institute of Bioinformatics. Serine and threonine residues with 50%, 40%, and 30% surface exposure were identified as the most suitable for mutation to cysteine (Table 2). Mutations can be introduced using standard molecular biology procedures. Conjugation of a thiol reactive drug or chelating agent to introduced cysteines can be tested using standard protein chemistry techniques.

TABLE 2

| % Surface Exposure | Residue |
|---|---|
| 50 | T496 |
| 40 | S58 |
| 30 | T76, T79, T83, T125, T236, S270, S273, S304, S435, T478, T506, T508 |

Example 2

Methods to Identify Residues in the HSA Linker for Introduction of Asparagine-Linked Glycosylation Sites To identify regions for introduction of asparagine-linked glycosylation sites in HSA, the crystal structure is studied to identify surface exposed (>30%) asparagine, serine and threonine residues that would be suitable for mutation. Glycosylation occurs on asparagine residues when the consensus sequence asparagine-x-serine/threonine is present, where x cannot be a proline. Table 2 lists possible mutation sites in HSA for the introduction of asparagine-linked glycosylation.

TABLE 3

| Residue | Proposed Mutation |
|---|---|
| Gln32 | Asn |
| Val46 | Ser/Thr |
| Asp56 | Asn |
| Asp63 | Ser/Thr* |
| Glu231 | Asn |
| Asp237 | Asn |
| Gln268 | Asn |
| Asp269 | Ser/Thr |
| Glu285 | Asn |
| Ala320 | Ser/Thr* |
| Asp340 | Asn |
| Glu354 | Asn |
| Gln437 | Asn |
| Glu425 | Asn |
| Glu465 | Asn |
| Asp494 | Asn* |

*These mutations have also been reported to occur very rarely in HSA (Carlson et al., "Alloalbuminemia in Sweden: Structural study and phenotypic distribution of nine albumin variants," *Proc. Nat. Acad. Sci. USA* 89: 8225-8229 (1992); Madison et al., "Genetic variants of human serum albumin in Italy: point mutants and a carboxyl-terminal variant," *Proc. Nat. Acad. Sci. USA* 91: 6476-6480 (1994); Hutchinson et al., "The N-terminal sequence of albumin Redhill, a variant of human serum albumin," *FEBS Lett.* 193: 211-212 (1985); Brennan et al., "AlbuminRedhill (-1 Arg, 320 Ala-Thr): a glycoprotein variant of human serum albumin whose precursor has an aberrant signal peptidase cleavage site," *Proc. Nat. Acad. Sci. USA* 87: 26-30 (1990); Minchiotti et al., "Structural characterization of four genetic variants of human serumal bumin associated with alloalbuminemia in Italy," *Eur. J. Biochem.* 247: 476-482 (1997); Peach et al., "Structural characterization of a glycoprotein variant of human serum albumin: albumin Casebrook (494 Asp-Asn)," *Biochim. Biophys. Acta* 1097: 49-54 (1991).

Example 3

B2B3-1 is a bispecific scFv antibody fusion molecule comprising B1D2, a human anti-ErbB2 scFv antibody (SEQ ID NO:27) and H3, a human anti-ErbB3 scFv (SEQ ID NO:26). The two scFvs are joined by a modified human serum albumin (HSA) linker. The anti-ErbB3 scFv, H3, is recombinantly fused to the amino terminus of the HSA linker incorporating a short connector polypeptide and the anti-ErbB2 scFv, B1D2, is recombinantly fused to the carboxy terminus of the modified HSA linker incorporating an additional short connector polypeptide. Each connector polypeptide is selected based on protease resistance properties. The modified HSA linker contains two amino acid substitutions. A cysteine residue at position 34 of native HSA is mutated to serine in order to reduce potential protein heterogeneity due to oxidation at this site. An asparagine residue at amino acid 503 of native HSA, which in native HSA may be sensitive to deamidation which can result in decreased pharmacologic half-life, is mutated to glutamine. It is believed that B2B3-1 selectively binds ErbB2 over-expressing tumors by virtue of its high affinity anti-ErbB2 scFv binding moiety, which has a kD in the range of 10.0 nM to 0.01 nM and more preferably a kD of about 0.3 nM. Subsequent binding of ErbB3 by the anti-ErbB3 scFv, which has a kD in the range of 50 to 1 nM and more preferably about 16 nM, inhibits HRG induced phosphorylation of ErbB3. The modified HSA linker confers an extended circulating half-life on the bispecific molecule. B2B3-1 has a molecular weight of 119.6 kDa and is preferably not glycosylated.

B2B3-1 inhibits ligand-induced phosphorylation of ErbB3 with sub-nanomolar potency; this activity is believed to be due, at least in part, to the abundant expression of its dimerization partner, ErbB2, which facilitates specific targeting of cancer cells that express both receptors.

Example 4

Figure 2:
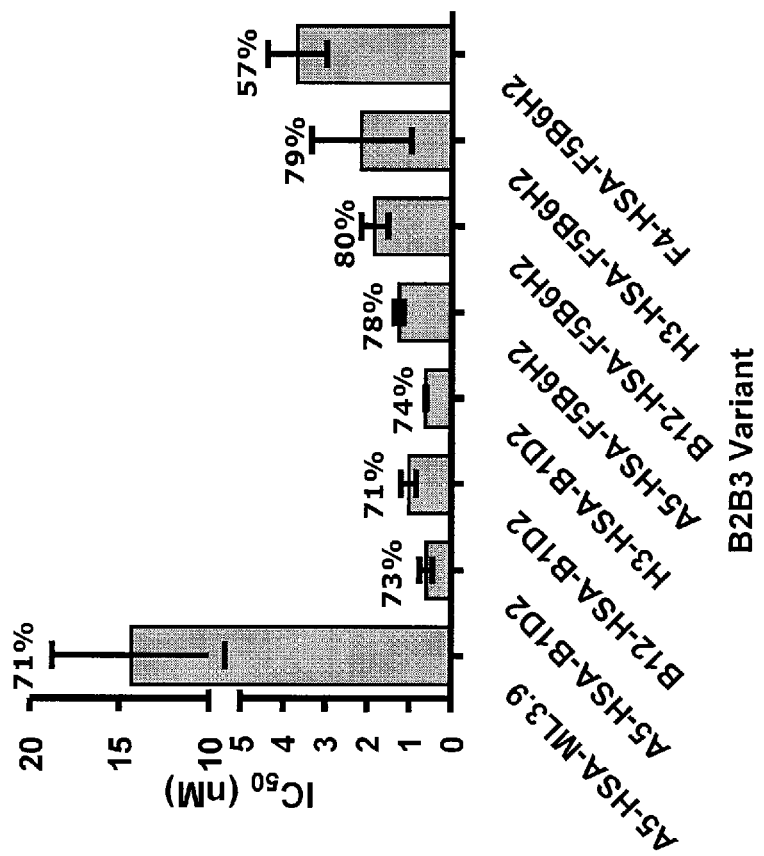
FIG. 2 is a graph showing that B2B3 variants inhibit HRG-induced pErbB3 in ZR75-1 breast cancer cells.
Figure 3A:
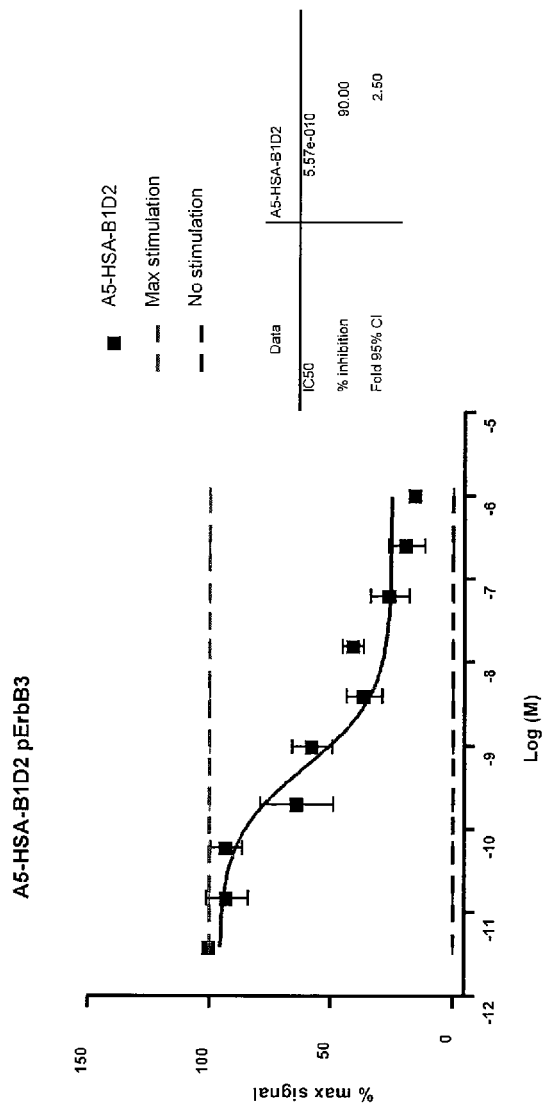
FIGS. 3A-D are graphs showing the inhibition of phosphorylated ErbB3 in BT474 breast cancer cells following 24 hour pre-treatment with the B2B3 HSA linker conjugates B1D2-2 (A5-HSA-B1D2, FIG. 3A), B1D2-1 (H3-HSA-B1D2, FIG. 3B), B2B3-10 (H3-HSA-F5B6H2, FIG. 3C), and B2B3-8 (F4-HSA-F5B6H2, FIG. 3D). Further details regarding these HSA linker conjugates is set forth below, e.g., in Table 6.
Figure 3B:
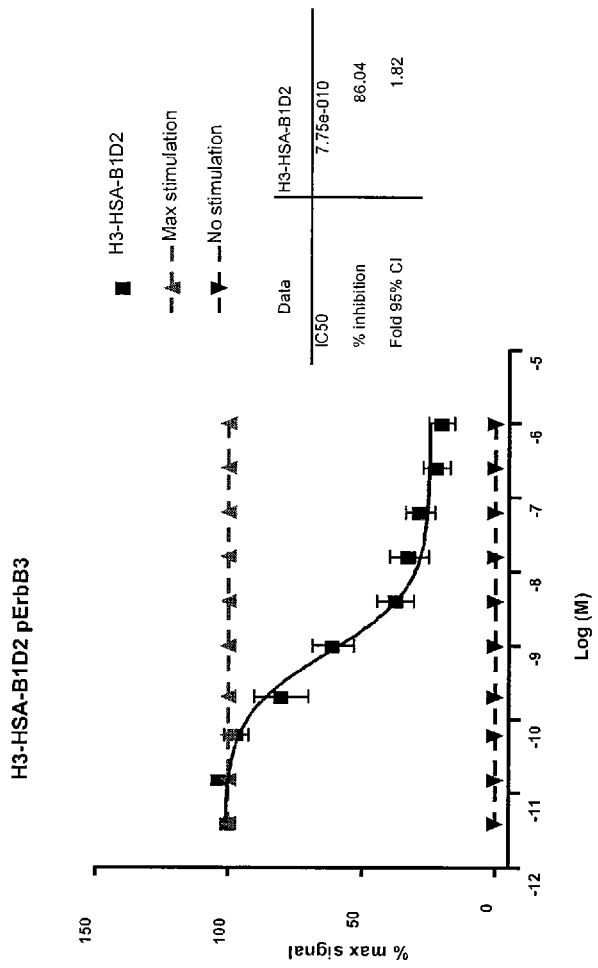
Figure 3C:
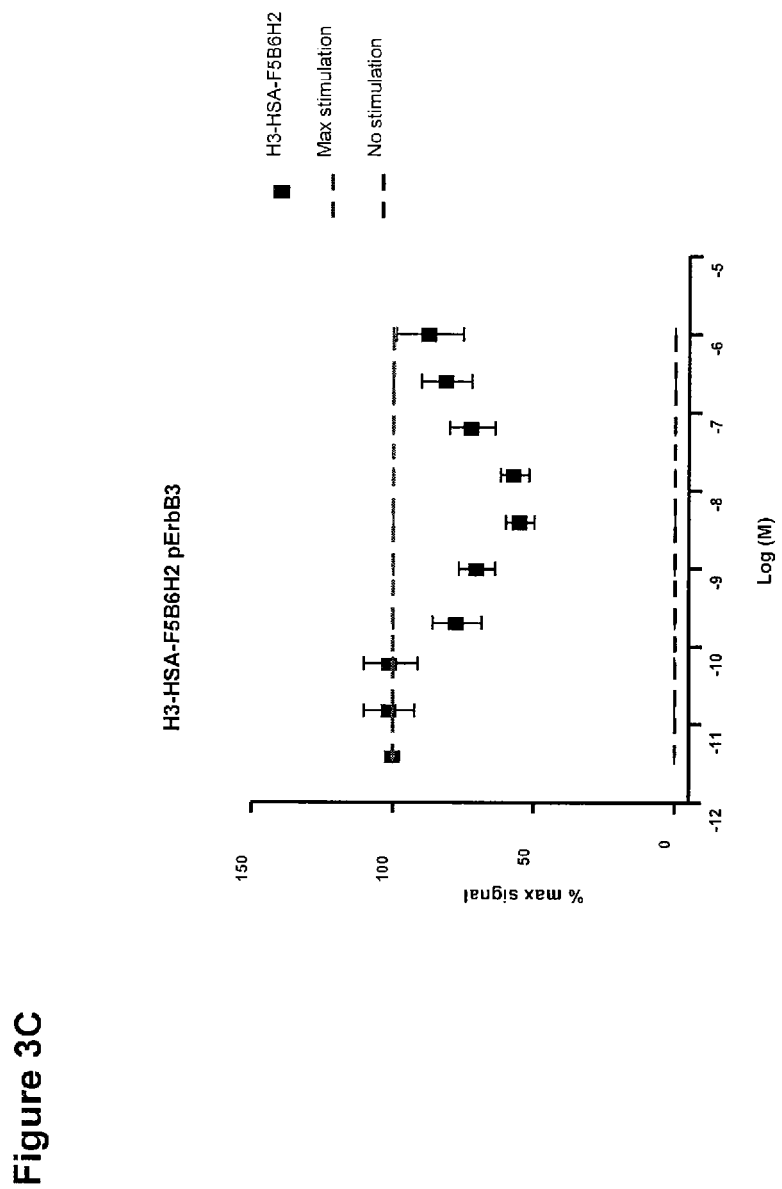
Figure 3D:
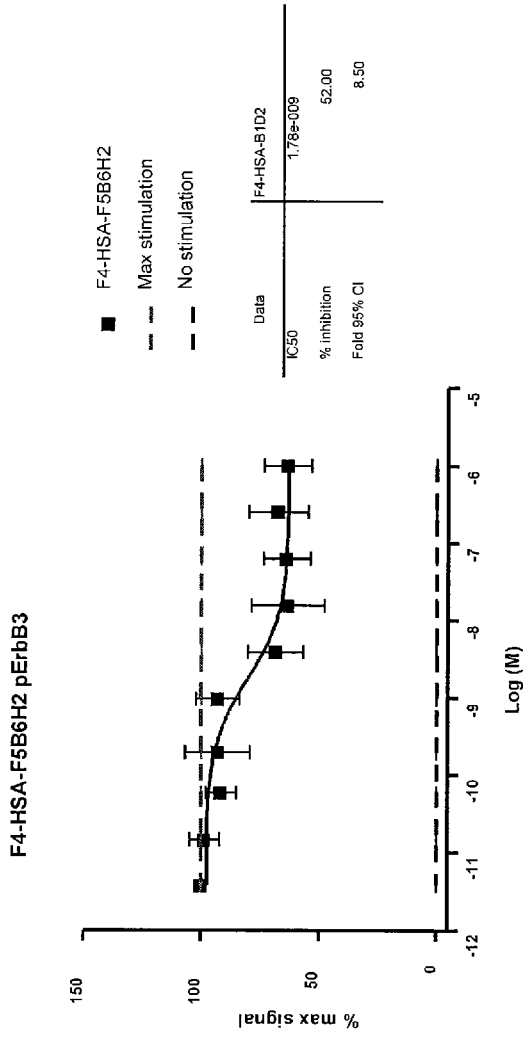
Figure 4A:
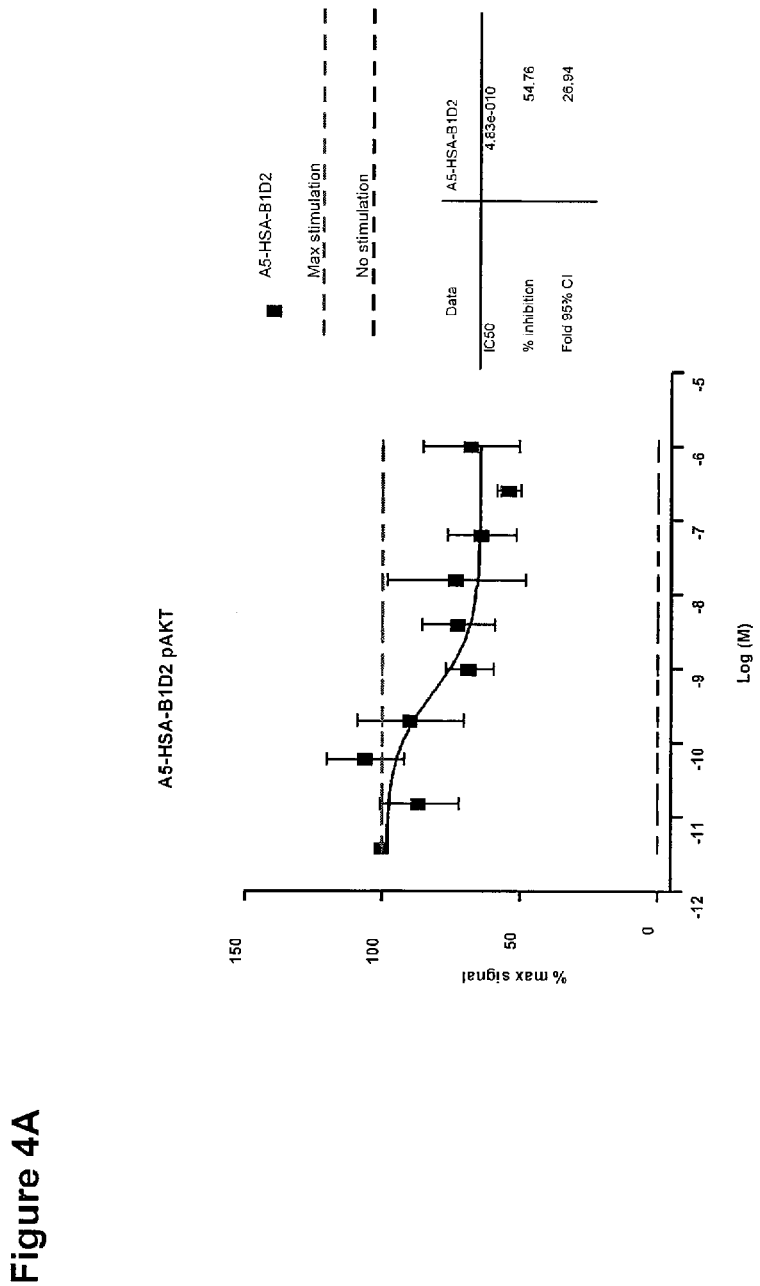
FIGS. 4A-D are graphs showing the inhibition of phosphorylated AKT in BT474 breast cancer cells following 24 hour pre-treatment with the B2B3 HSA linker conjugates B1D2-2 (A5-HSA-B1D2, FIG. 4A), B1D2-1 (H3-HSA-B1D2, FIG. 4B), B2B3-10 (H3-HSA-F5B6H2, FIG. 4C), and B2B3-8 (F4-HSA-F5B6H2, FIG. 4D). Further details regarding these HSA linker conjugates is set forth below, e.g., in Table 6.
Figure 4B:
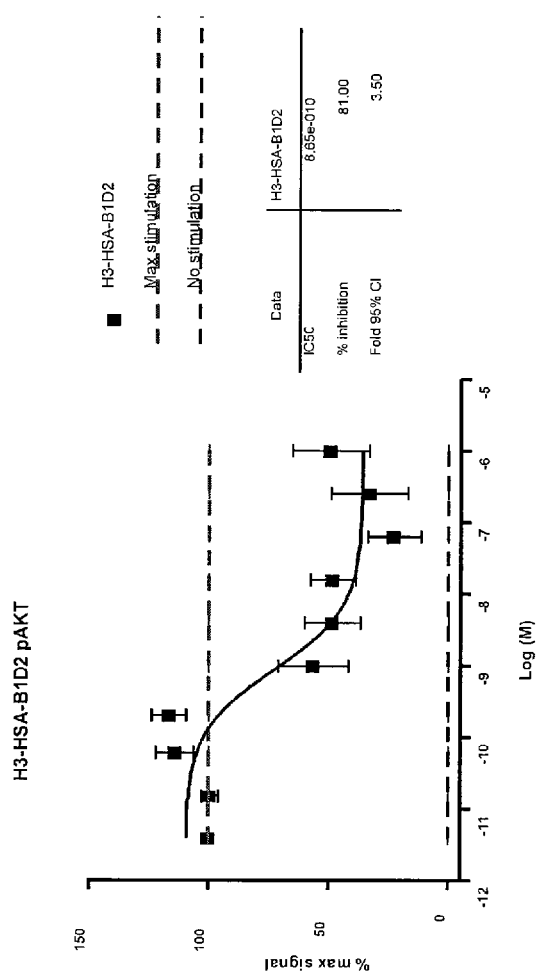
Figure 4C:
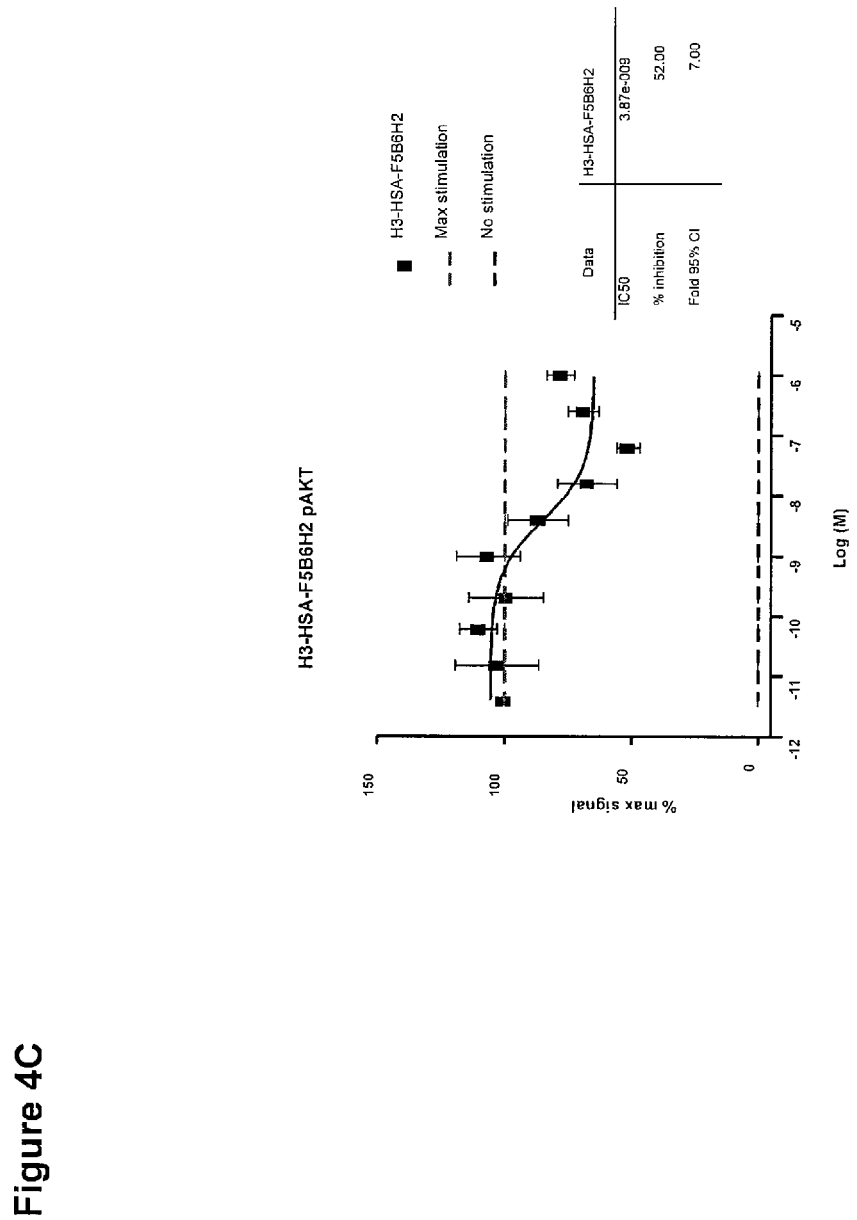
Figure 4D:
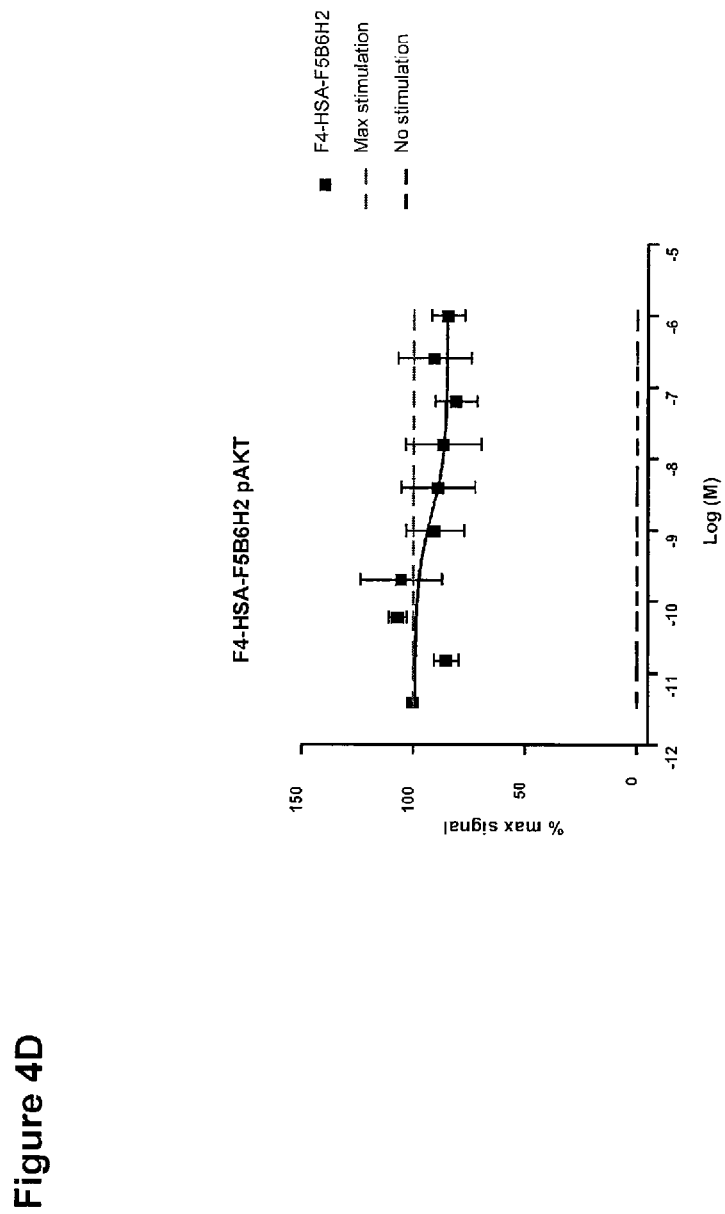
Figure 5A:
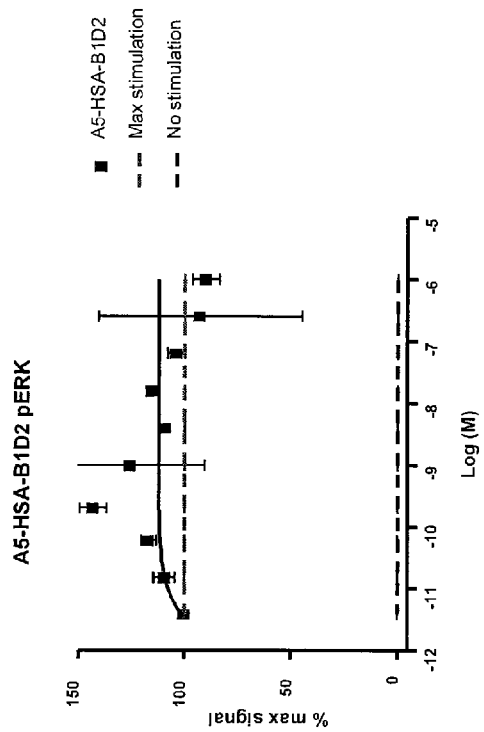
FIGS. 5A-D are graphs showing that inhibition of phosphorylated ERK in BT474 breast cancer cells following 24 hour pre-treatment with the B2B3 HSA linker conjugates B1D2-2 (A5-HSA-B1D2, FIG. 5A), B1D2-1 (H3-HSA-B1D2, FIG. 5B), B2B3-10 (H3-HSA-F5B6H2, FIG. 5C), and B2B3-8 (F4-HSA-F5B6H2, FIG. 5D). Further details regarding these HSA linker conjugates is set forth below, e.g., in Table 6
Figure 5B:
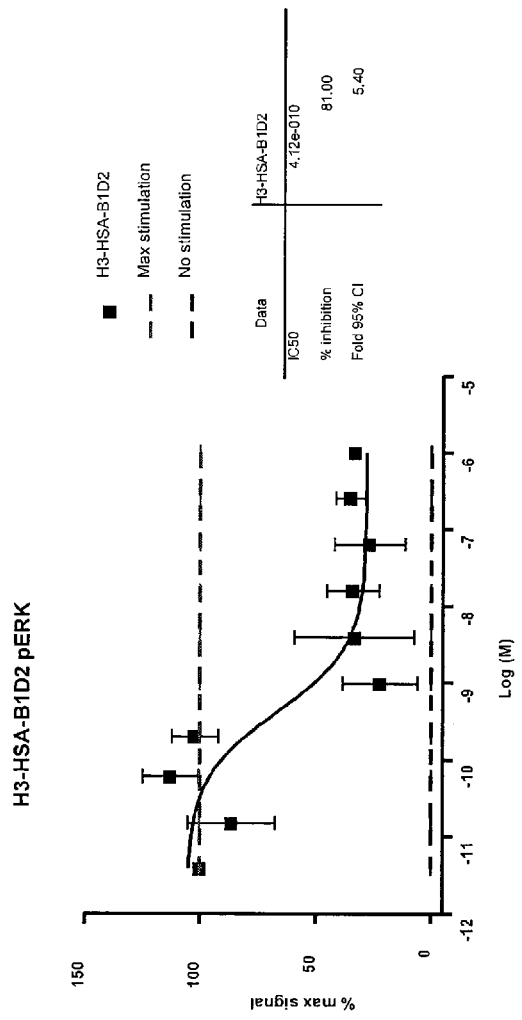
Figure 5C:
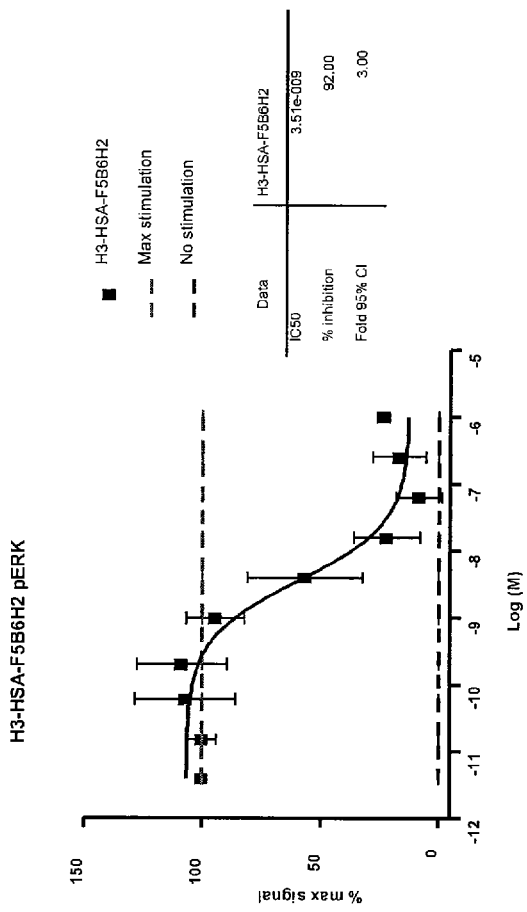
Figure 5D:
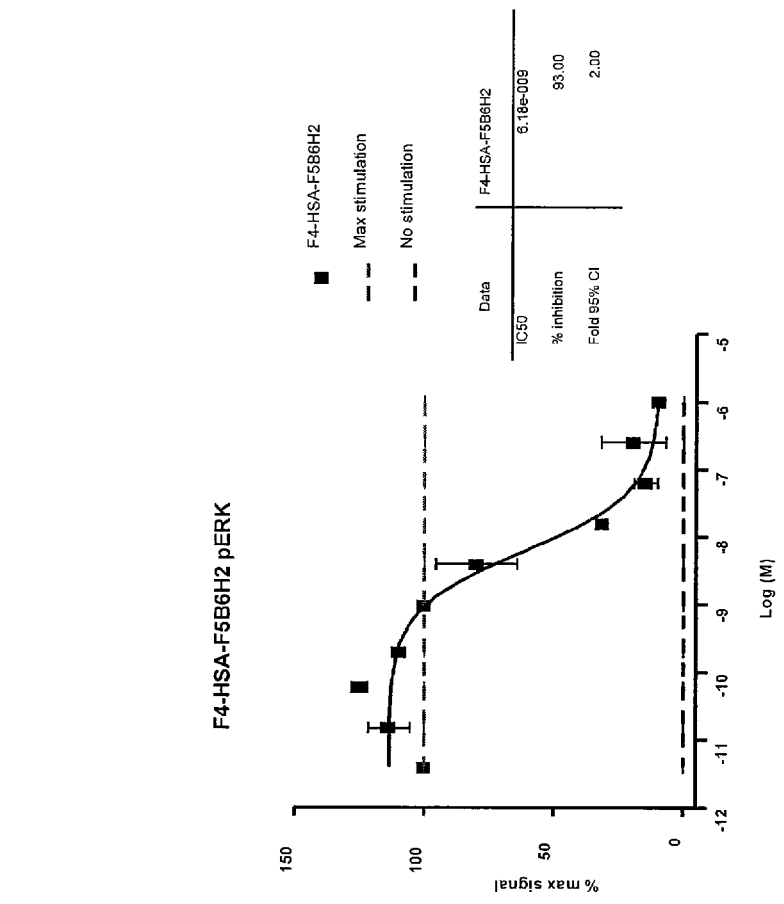

As shown in FIG. 2, B2B3-1 variants inhibit HRG-induced pErbB3 in ZR75-1 breast cancer cells. ZR75-1 breast cancer cells are treated with a dose range of B2B3-1 variants for 24 hours followed by HRG stimulation. pErbB3 levels are measured in cell lysates by ELISA and $IC_{50}$ values are calculated together with the percent of inhibition. Shown are the mean $IC_{50}$ values (Y axis) with error bars representing replicate experiments. Percent inhibition values are shown above the corresponding bar.

ELISA Assays

Except as noted, ELISA reagents for total and phospho-ErbB3 ELISAs are purchased from R&D Systems as DUOSET kits. 96-well NUNC MAXISORB plates are coated with 50 µl of an antibody and incubated overnight at room temperature. Next morning, plates are washed 3 times with 1000 µl/well in a BIOTEK plate washer with Dulbecco's phosphate buffered saline without calcium or magnesium (PBS) with added Tween detergent (PBST) (0.05% Tween-20). Plates are subsequently blocked for about 1 hr at room temperature with 2% BSA in PBS. The plates are washed 3 times with 1000 µl/well in the BIOTEK plate washer with PBST. Cells are grown at 37° C. and 5% carbon dioxide, washed with cold PBS, then harvested with mammalian protein extract (MPER) lysis buffer (Pierce, 78505) to which 150 mM NaCl, 5 mM sodium pyrophosphate, 10 uM bpV (phen), 50 uM phenylarsine, 1 mM sodium orthovanadate, and protease inhibitor cocktail (Sigma, P2714) is added. 504 of cell lysates and standards diluted in 50% Lysis buffer and 1% BSA are used in duplicates for further processing. Samples are incubated for 2 hrs at 4° C. on a plate shaker and washed as before. About 50 µl of a detection antibody diluted in 2% BSA, PBST is added and incubated for about 1-2 hrs at room temperature. For phospho-ErbB3, the detection antibody is directly conjugated to horseradish peroxidase (HRP), while for total ErbB3 and biotinylated mouse anti-human ErbB3 secondary detection antibody is used. The plate is washed as before. For total ErbB3 about 50 µl of Streptavidin-HRP is added and incubation is for 30 min. and the plates washed as before. About 50 µL of SUPERSIGNAL ELISA Pico (Thermo Scientific) substrate is added and the plate is read using a FUSION plate reader. Duplicate samples are averaged and, where shown, error bars represent the standard deviation between the two replicates.

Example 5

Inhibition of phosphorylated ErbB3 (FIGS. 3A-D), AKT (FIGS. 4A-D), and ERK (FIGS. 5A-D) following 24 hour pre-treatment with B2B3-1 variants A5-HSA-B1D2 (panel A of FIGS. 3-5), H3-HSA-B1D2 (panel B of FIGS. 3-5), H3-HSA-F5B6H2 (panel C of FIGS. 3-5), and F4-HSA-F5B6H2 (panel D of FIGS. 3-5) is measured. BT474 breast cancer cells are treated with a dose range of B2B3-1 variants for 24 hours followed by HRG stimulation. pErbB3, pAKT, and pERK levels are measured in cell lysates by ELISA and $IC_{50}$ values are calculated together with the percent of inhibition. These results demonstrate that B1B2-1 is the only HSA linker conjugate of those tested that provides greater than 50% inhibition of HRG-induced phosphorylation of AKT, ERK, and ErbB3 at a concentration of $10^{-8}$ molar and above.

Example 6

Figure 6:
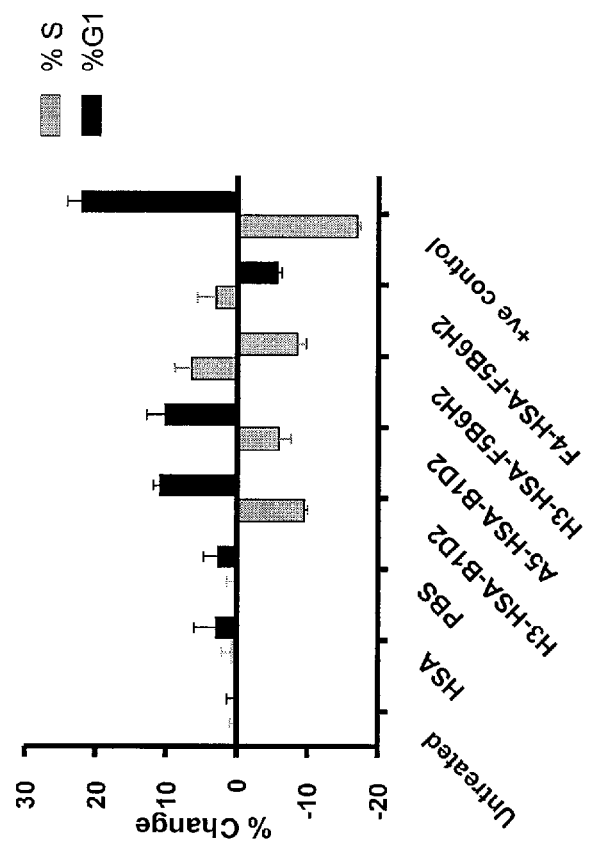
FIG. 6 is a graph showing that treatment of BT474 breast cancer cells with B2B3-1 variants causes G1 arrest and a decrease in the number of cells in S phase.

As shown in FIG. 6, treatment of BT474 breast tumor cells with B2B3-1 variants causes G1 cell cycle arrest and a decrease in the population of cells in S phase. BT474 cells are treated with 1 µM of B2B3-1 variants and controls for 72 hours. After the end of treatment, cells are trypsinized, gently resuspended in hypotonic solution containing propidium iodide and single cells are analyzed by flow cytometry. Cell cycle distribution in G1 and S phases is measured using curve-fitting algorithms designed for cell cycle analysis (FlowJo software cell cycle platform).

Example 7

B2B3-1 (SEQ ID NO:16) inhibits ErbB3 activation, utilizing the abundant expression of its dimerization partner, ErbB2, to target tumor cells. A high affinity anti-ErbB2 scFv antibody, B1D2, facilitates targeting of B2B3-1 to tumor cells over-expressing ErbB2. B1D2 is connected by a modified HSA linker to a lower affinity anti-ErbB3 scFv antibody, H3, which blocks binding of ErbB3's ligand, HRG. It is believed that the inhibition of ErbB3 phosphorylation and downstream AKT signaling mediated by B2B3-1 is due to this blockade. The ErbB2 binding scFv, B1D2, is derived from parent scFv C6.5, which possesses neither agonistic nor antagonistic activity at ErbB2. B1D2, therefore, likely functions solely as a targeting agent. The lower affinity binding of the ErbB3 binding scFv is believed to prevent strong binding of B2B3-1 to normal, non-cancerous tissues which express ErbB3 but little or no ErbB2, thereby reducing the potential for non-specific toxicity. In tumor cells expressing both ErbB2 and ErbB3, there is an avidity effect of bispecific B2B3-1 binding to both receptors that overcomes the low affinity of the ErbB3 scFv allowing strong inhibition of HRG interaction with ErbB3 receptor complexes.

Figure 7:
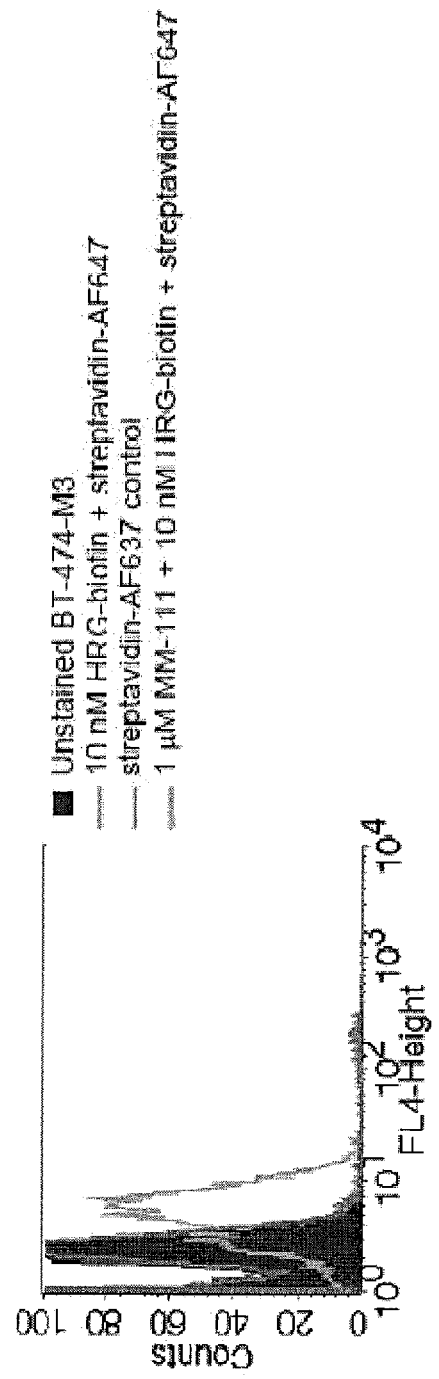
FIG. 7 is a flow cytometry histogram showing that pre-incubation of BT-474-M3 cells with 1 µM B2B3-1 substantially blocks binding of HRG.
Figure 8:
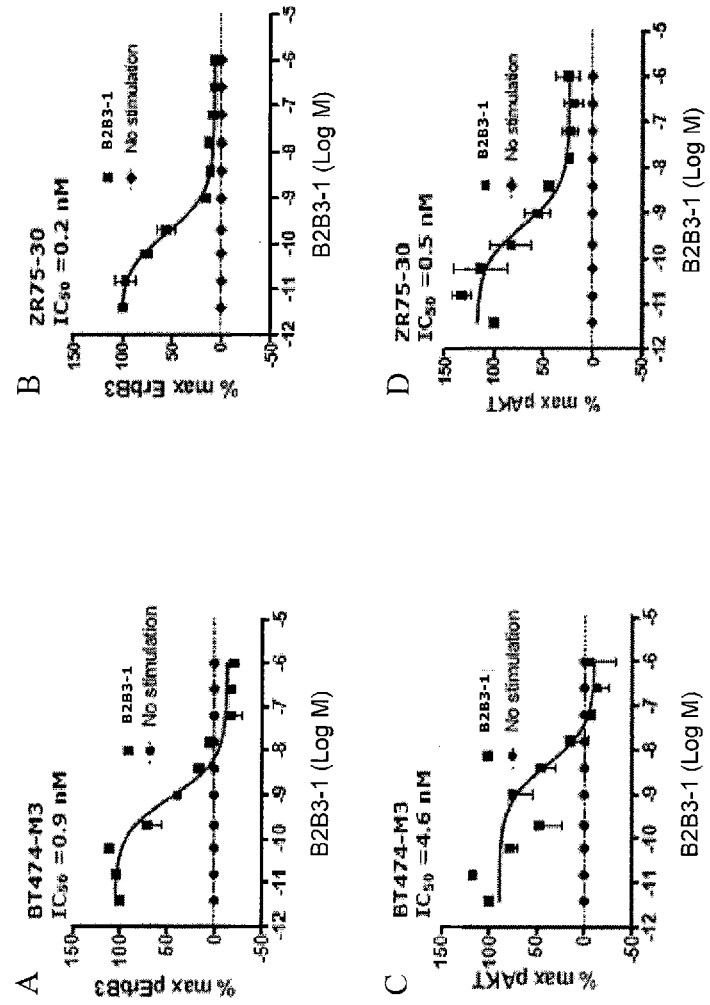
FIGS. 8A-D are graphs showing that B2B3-1 inhibits ErbB3 and AKT phosphorylation in B-T474-M3 and ZR75-30 cell lines. Breast cancer cell lines BT-474-M3 (FIGS. 8A and 8C) and ZR75-3 0 (FIGS. 8B and 8D) were pre-treated with a dose titration of B2B3-1 for 24 hours and then stimulated for 10 minutes with 5 nM of HRG 1β EGF domain. The phosphorylation status of ErbB3 and AKT was then examined using an ELISA assay.

The ability of B2B3-1 to inhibit HRG binding to ErbB3 is investigated using flow cytometry (FACS). Cells of the breast cancer cell line human (a variant of BT-474 that over-express ErbB2), are pretreated with 1 µM B2B3-1 then incubated with 10 nM biotinylated HRG 1β EGF domain. After extensive washing, binding is assessed using streptavidin-AlexaFluor 647 conjugate. All incubations are performed at 4° C. FIG. 7 shows that B2B3-1 is capable of blocking the binding of HRG to ErbB3. and appears to provide 100% blockade at a concentration of 1 μM.

Example 8

After demonstrating B2B3-1's ability to block HRG binding to ErbB3, the effect of B2B3-1 on ErbB3 signaling in vitro on two cell lines that express ErbB3 and over-express ErbB2 is investigated. Human breast cancer cell lines BT-474-M3 (described in, e.g., Drummond et al. (2005) *Clin. Cancer Res.* 11:3392; Park et al. (2002) *Clin. Cancer Res.* 8:1172; Kirpotin et al. (2006) *Cancer Res.* 66:6732) and ZR7530 (obtainable from the US NIH Lawrence Berkeley National Laboratory breast cancer cell collection) are serum starved overnight, pre-treated with a dose titration of B2B3-1 for 24 hours and then stimulated for 10 minutes with 5 nM of HRG 1β EGF domain. The phosphorylation status of ErbB3 and AKT is then examined using ELISA assays generally as described above. The results show that B2B3-1 inhibits HRG induced activation of both ErbB3 and AKT phosphorylation in a dose-dependent manner and with potent $IC_{50}$s in both cell lines (FIGS. 8A-D).

Example 9

Figure 9:
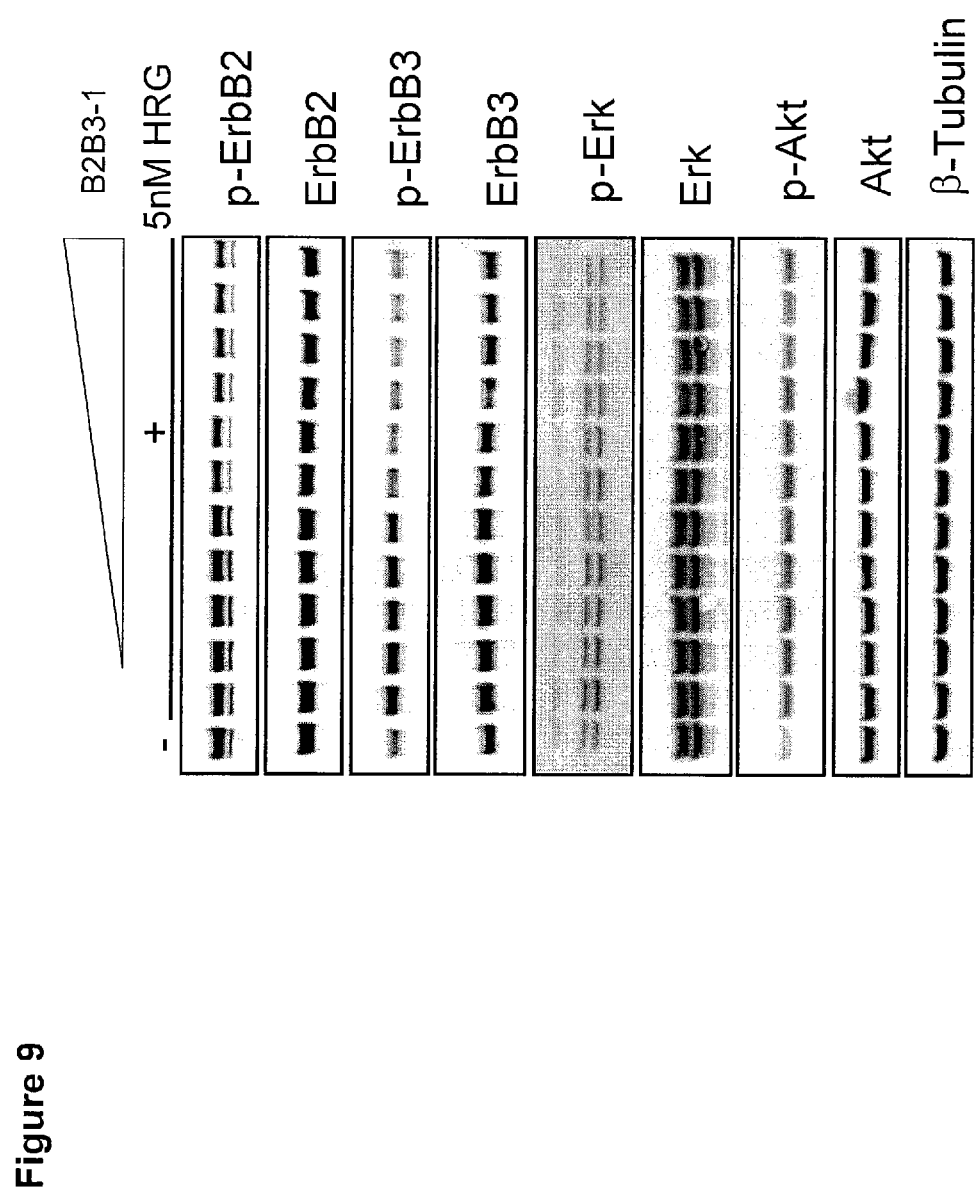
FIG. 9 is a photograph of a Western blot that shows the effect of treatment with increasing concentrations of B2B3-1 on signaling proteins in BT474 breast cancer cells. "p-" indicates the tyrosine-posphorylated form of the signaling protein. Beta tubulin (not a signaling protein in this context) provides a loading control. Beta tubulin (not a signaling protein in this context) provides a loading control.

FIG. 9 shows the effect of B2B3-1 treatment on signaling proteins in BT474 breast cancer cells. Cells are treated with a dose range of B2B3-1 for 24 hours, followed by heregulin stimulation. Levels of pErbB2, pErbB3, pErk and pAKT and their corresponding total protein levels are determined on cell lysates by Western blot analysis. Results indicate that levels of at least pErbB2 and pErbB3 are reduced in a dose-dependent manner by B2B3-1 treatment.

Example 10

Figure 10:
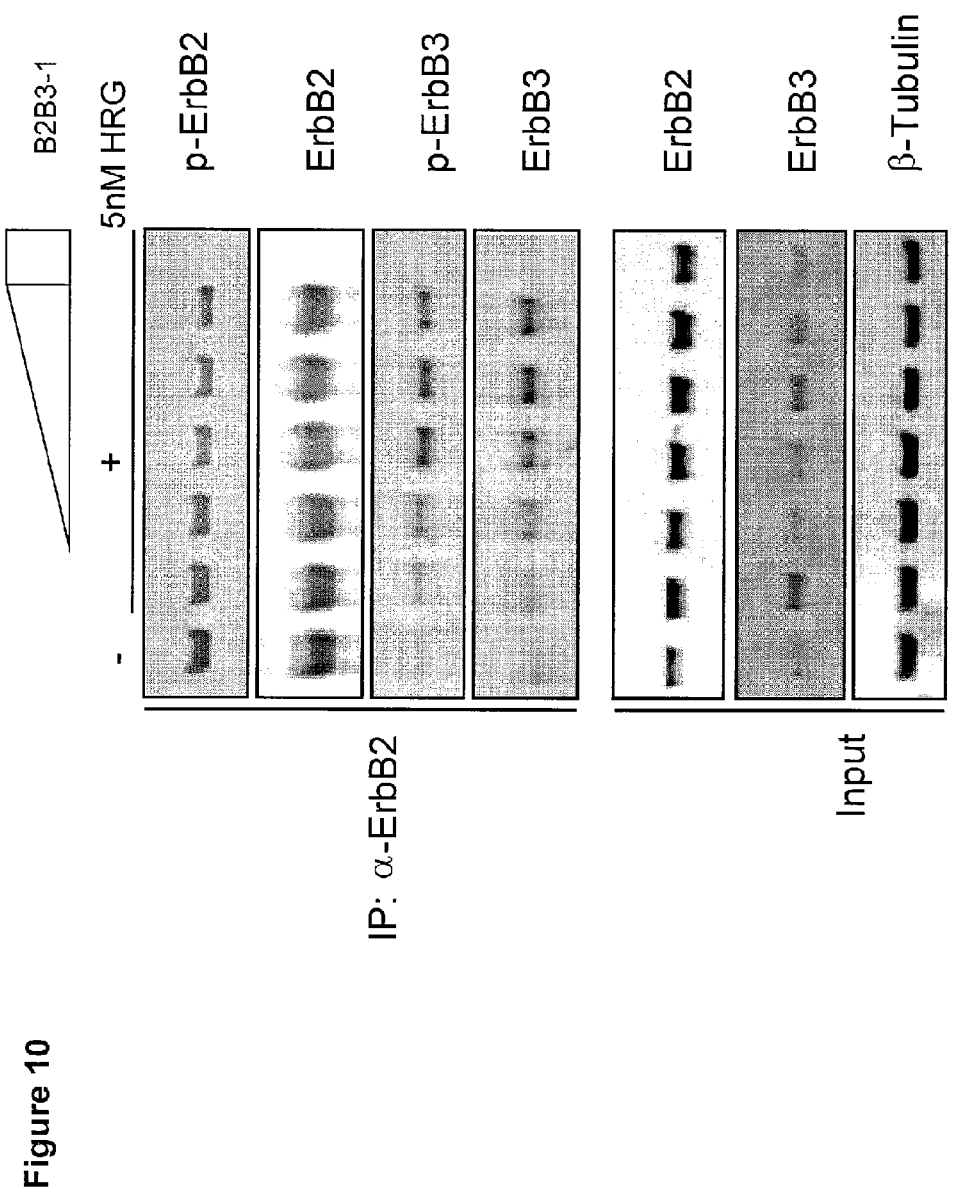
FIG. 10 is a photograph of a Western blot that shows the immunoprecipitation of B2B3-1 treated BT474 breast cancer cells. Beta tubulin provides a control for levels of cellular proteins input into the immunoprecipitation reactions.

FIG. 10 shows the immunoprecipitation-Western blot analysis of B2B3-1 treated BT474 breast cancer cells. Cells are treated with a dose range of B2B3-1 for 24 hours, followed by heregulin stimulation. ErbB2-associated complexes are isolated from cell lysates using an anti-ErbB2 antibody followed by Western blot analysis to detect pErbB2 and pErbB3 and the corresponding total protein levels. The results show that B2B3-1 crosslinks ErbB2 to ErbB3, so that substantially more ErbB3 and phospho-ErbB3 is precipitated by the anti-ErbB2 antibody.

Example 11

Figure 11:
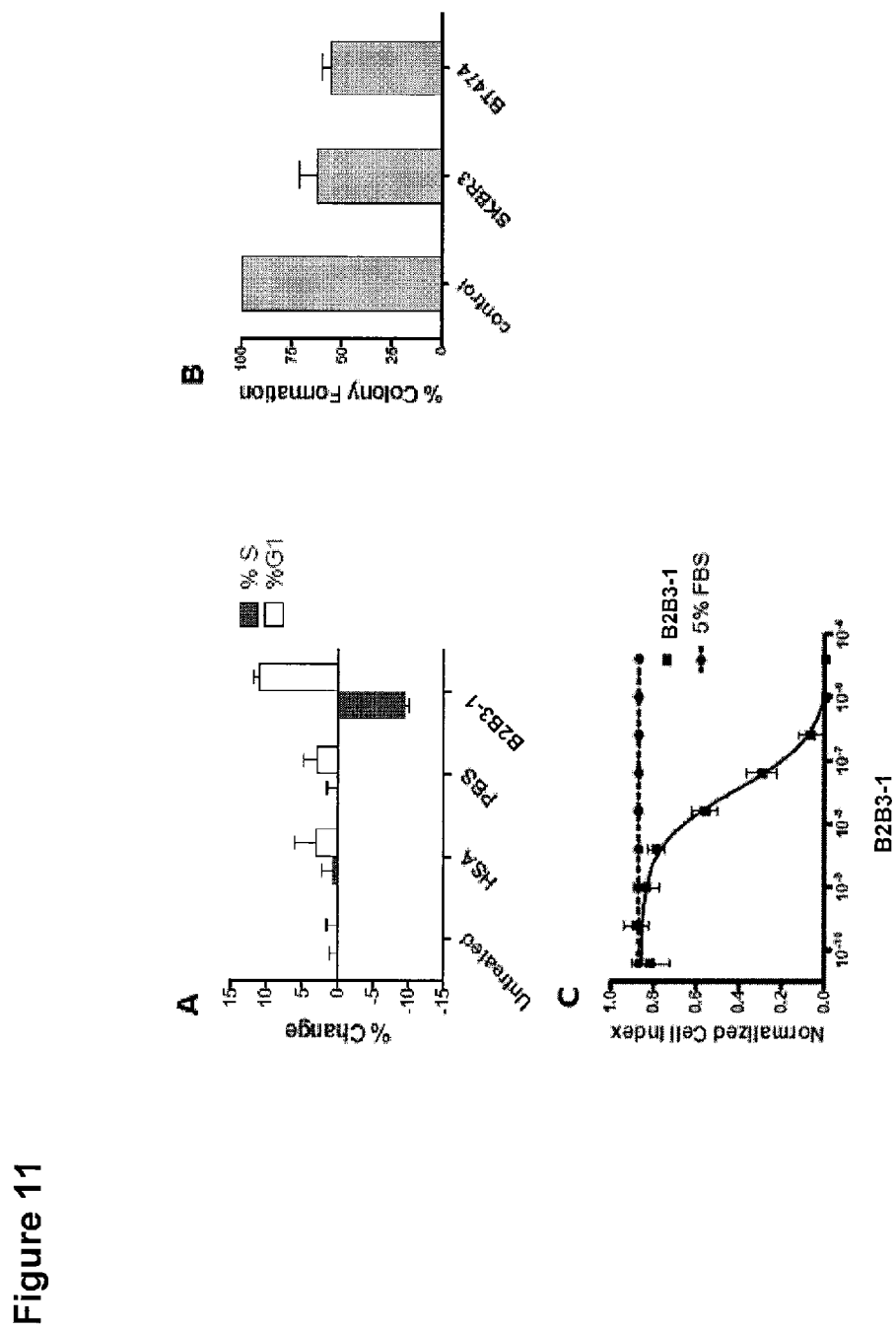
FIGS. 11A-C are graphs showing B2B3-1 treatment of BT-474 cell line causes G1 arrest and a decrease in the population of cells in S phase (FIG. 11A), and inhibits colony formation in both BT-474 and SKBr3 cells compared to untreated cells (FIG. 11B). In addition, B2B3-1 inhibits proliferation of BT-474-M3 cells in a cell impedance assay (FIG. 11C).

The anti-tumor activity of B2B3-1 is investigated in vitro using a number of assays. In the first assay, the effect of B2B3-1 on the accumulation of BT-474 or SKBR3 cells in G1 phase and the concomitant decrease in S phase of the cell cycle is examined. Briefly, cells are treated with 1 μM B2B3-1 or PBS vehicle for 72 hours. After the end of treatment, cells are trypsinized, gently resuspended in hypotonic solution containing propidium iodide and single cells are analyzed by flow cytometry. Cell cycle distribution in G1 and S phases is measured using curve-fitting algorithms designed for cell cycle analysis (FlowJo software cell cycle platform, Tree Star, Inc.). B2B3-1 was found to modestly decrease the percentage of cells in S phase and increase the population of cells in G1 phase (FIG. 11A). In a second experiment, the number of cell colonies formed following treatment with B2B3-1 is studied. BT-474 and SKBR3 breast cancer cells are plated in the presence of 1 μM B2B3-1 and compared to cells plated in media only. Media only or media including treatment is replenished every 3 days. After 14 days the number of colonies is counted and compared to untreated cells. FIG. 11B illustrates the 40-45% decrease in the number of colonies formed when cells are treated with B2B3-1 compared to control cells. Finally, the ability of B2B3-1 to inhibit cell proliferation is assessed in a cell impedance assay using a Real-Time Cell Electronic Sensing System (RT-CES: ACEA Biosciences). BT-474 cells are seeded on plates integrated with microelectronic sensor arrays and treated with a dose titration of B2B3-1 or media only for 72 hours. Data reflecting the generation of cell-electrode impedance response are collected every hour for 72 hours and $IC_{50}$ values are calculated 68 hours after treatment. FIG. 11C illustrates that B2B3-1 was able to inhibit impedance of BT-474 cells with an $IC_{50}$ of 33 nM.

Example 12

Figure 12:
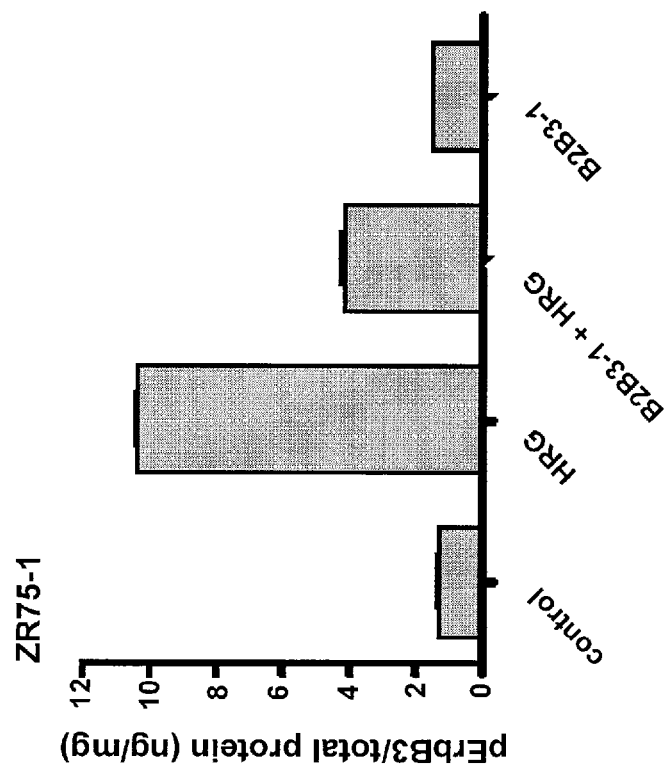
FIG. 12 is a graph showing that B2B3-1 does not stimulate ErbB3 phosphorylation in ZR75-1 cells.

We also investigated whether B2B3-1 exhibits agonistic activity based on its ability to simultaneously bind and cross-link ErbB2 and ErbB3 receptors. Serum starved ZR75-1 breast cancer cells are incubated with 1 μM B2B3-1 or PBS vehicle for 24 hours. Cells are also treated with B2B3-1 or PBS vehicle for 24 hours followed by a 10-minute stimulation with 5 nM HRG 1β EGF domain. Cells are lysed and the pErbB3 content of the lysates is assessed by ELISA generally as described above. FIG. 12 shows that cells treated with B2B3-1 alone contained levels of phosphorylated ErbB3 that were comparable to the levels in untreated cells, indicating that B2B3-1 does not act as an agonist promonting ErbB3 phosphorylation.

Example 13

Figure 13:
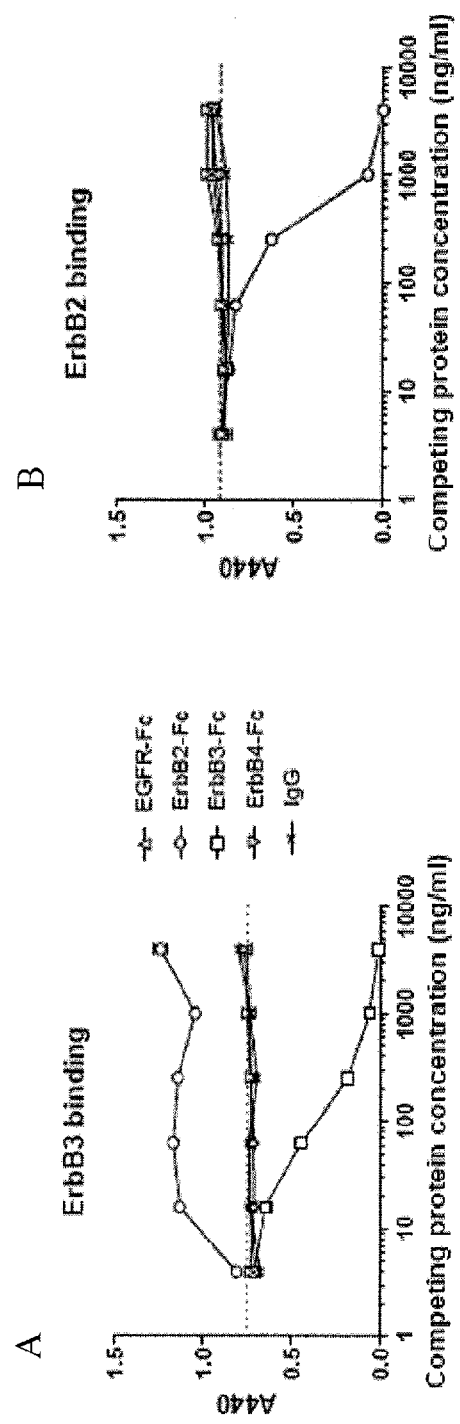
FIGS. 13A-B are graphs showing that B2B3-1 binds specifically to ErbB3 (FIG. 13A) and ErbB2 (FIG. 13B).

The ability of B2B3-1 to bind with specificity to ErbB2 and ErbB3 and not to related ErbB family members, EGFR and ErbB4, is investigated by ELISA. Plates are coated with the recombinant extracellular domain of either ErbB2 or ErbB3. Plates are blocked and incubated with a half-maximal binding concentration of B2B3-1 in the presence of a dilution series of competing recombinant extracellular domains of EGFR, ErbB2, ErbB3 or ErbB4. The results show only soluble ErbB2 extracellular domain blocked B2B3-1 binding to ErbB2-coated plates (FIG. 13A). Likewise, only soluble ErbB3 extracellular domain blocked B2B3-1 binding to ErbB3-coated plates (FIG. 13B). These results are believed to demonstrate the specificity of the anti-ErbB2 arm B1D2 for ErbB2, and of the anti-ErbB3 arm H3 for ErbB3. The increased signal observed when soluble ErbB2 extracellular domain was incubated with B2B3-1 on the ErbB3 coated plate is assumed to be due to formation of an ErbB2, ErbB3, B2B3-1 complex on the plate.

Example 14

The ability of B2B3-1 to bind to tumor cells expressing both ErbB2 and ErbB3 is studied using monospecific variants of B3B3-1. SKO-2 (SEQ ID NO:67) and SKO-3 (SEQ ID NO:68) are variants of B2B3-1 that lack the ability to interact with ErbB2 or ErbB3, respectively.

SKO-2 and SKO-3 are constructed using the QUIKCHANGE Site Directed Mutagenesis kit (STRATAGENE) which uses oligonucleotide primer pairs, each complementary to opposite strands of the template vector. These are extended during temperature cycling generating a mutated plasmid containing staggered nicks. Following temperature cycling, the product is treated with Dpn I, which is used to digest the parental DNA template. The nicked vector DNA containing the desired mutations is then transformed into XL1-BLUE supercompetent cells STRATAGENE) to propogate plasmid DNA.

To create SKO-2, 5 nucleotides in the VH CDR3 loop of the anti-ErbB2 scFv, B1D2, are mutated to create the following amino acid substitutions; H95A, W100hA, and E100jA. Mutations at these positions have been demonstrated to knock-out binding of the B1D2 parent scFv, C6.5, to ErbB2 (Schier et al, 1996 JMB). Mutations are introduced to the B2B3-1 plasmid pMP9043 (SEQ ID NO:60) in a stepwise manner. First, mutations c295g and a296c are generated using primers 5'-GTA CTT TTG TGC CCG GGC CGA TGT GGG CTA CTG C-3' (SEQ ID NO:61) and 5'-GCA GTA GCC CAC ATC GGC CCG GGC ACA AAA GTA C-3' (SEQ ID NO:62) and temperature cycling of 95° C. for 1 minute followed by 30 cycles of 95° C. for 1 minute, 55° C. for minute, and 65° C. for 17.2 minutes. Mutations are confirmed by DNA sequencing of plasmid DNA. To introduce mutations at t334g, g335c, and a341c, a second round of site-directed mutagenesis is performed on the plasmid with sequence-confirmed mutations at c295g and a296c using primers 5'-GAC ATG TGC CAA GGC CCC CGC GTG GCT GGG AGT G-3' (SEQ ID NO:63) and 5'-CAC TCC CAG CCA CGC GGG GGC CTT GGC ACA TGT C-3' (SEQ ID NO:64) and temperature cycling of 95° C. for 30 seconds and 18 cycles of 95° C. for 30 seconds, 55° C. for 1 minute and 68° C. for 17.2 minutes. Mutations are confirmed by DNA sequencing of resulting plasmid DNA.

To create SKO-3, the mutated B1D2 scFv is subcloned into the original B2B3-1 plasmid to replace the anti-ErbB3 scFv, H3. Primers annealing to SKO-2, 5'ACAGTGGCGGCCGC-CACCATGGGCTGGCTCTGATCCTGCTGT-
TCCTGGTGG CCGTGGCCACGCGTGTGCTGTC-CCAGGGCAGCTCGTCCAGAGCGGCGC (SEQ ID NO:65) and 5'GGAGGCGGCGCCCAGGACTGTCAGCT-TGGTGCCACCGCCG (SEQ ID NO:66) are used to isolate the mutated B1D2 scFv from SKO-2 and to introduce Kas I and Not I restriction sites for subcloning into Kas I/Not I restriction digested B2B3-1 plasmid. PCR is performed as follows: 94° C. for 1 minute followed by 30 cycles of 94° C. for 30 seconds, 58° C. for 1 minute, 72° C. for 1 minute, followed by one cycle of 72° C. for 5 minutes to amplify the mutant B1D2. Successful cloning is monitored by DNA sequencing. SKO-2 and SKO-3 plasmids are stably expressed from CHO-K1 cells in shake flasks or 10L WAVE bags and purified from conditioned media using Blue SEPHAROSE and cation exchange chromatography.

Figure 14:
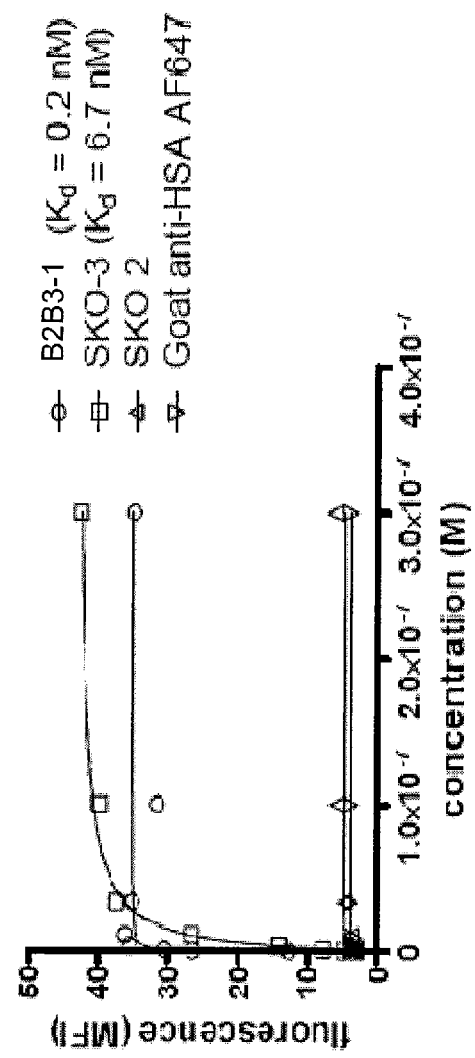
FIG. 14 is a graph showing that avidity binding of B2B3-1 to MALME-3 cells results in a significant increase in apparent binding affinity compared to ErbB2-only binding variant, SKO-3, and ErbB3-only binding variant, SKO-2.

MALME-3M melanoma cells, which express approximately equal numbers of ErbB2 and ErbB3 receptors, are incubated with a dilution series of B2B3-1, SKO-2, or SKO-3 in the presence of saturating concentrations of a goat anti-HSA Alexafluor-647 conjugated antibody. Cell binding is assessed by flow cytometry and apparent binding affinities are determined for each molecule. Control cells are incubated with secondary antibody alone. No measurable cell binding is observed for SKO-2, which retains only the low affinity binding to ErbB3 mediated by H3 and lacks ErbB2 binding activity. SKO-3, which retains a functional, high affinity ErbB2 binding B1 D2 scFv but lacks the ability to bind ErbB3 had a $K_D$ of 6.7 nM. B2B3-1 bound cells with a $K_D$ of 0.2 nM, demonstrating the increased binding mediated by the bispecific design of this molecule (FIG. 14).

Example 15

Figure 15:
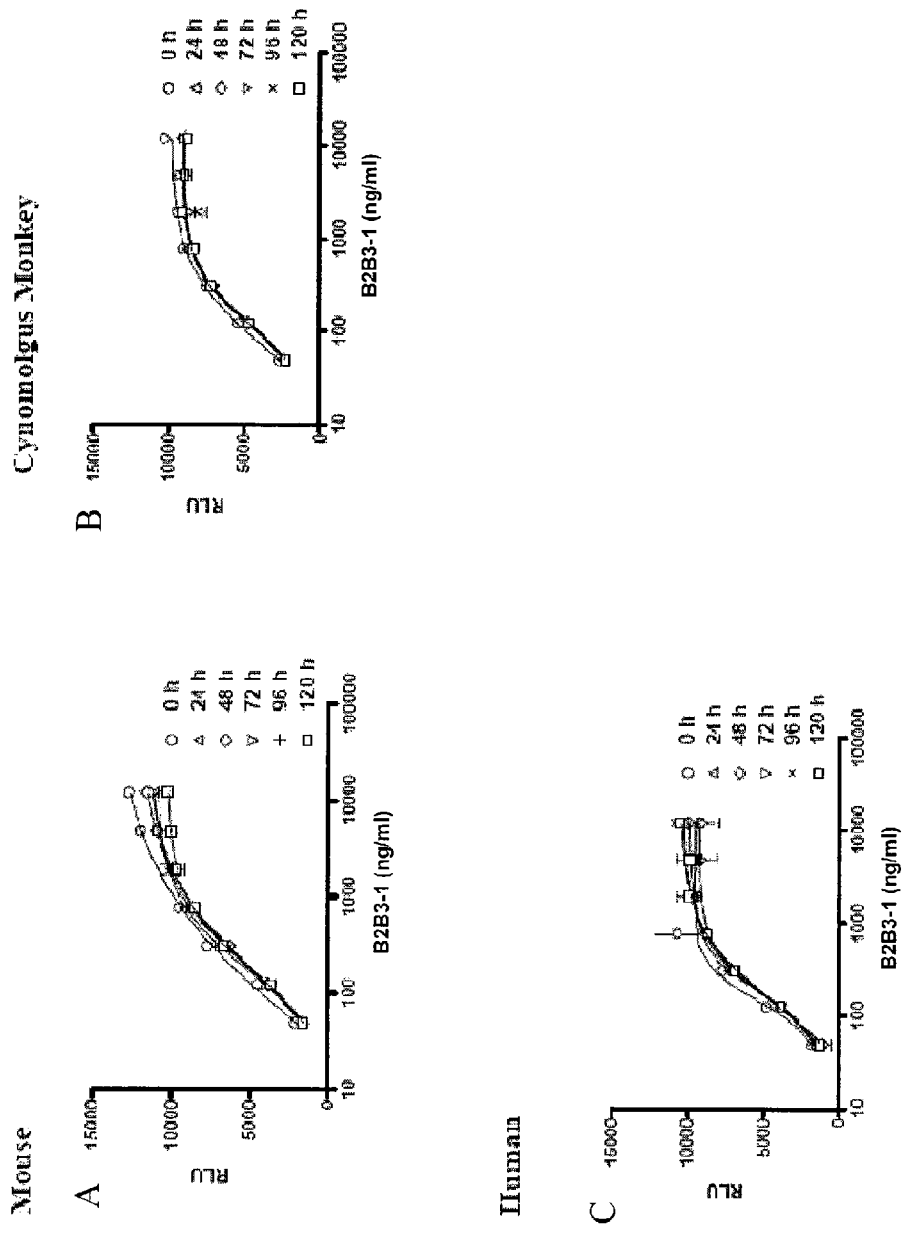
FIGS. 15A-C are graphs showing the stability of B2B3-1 in mouse, Cynomolgus monkey, and human serum. 100 nM B2B3-1 was incubated in mouse (FIG. 15A), Cynomolgus monkey (FIG. 15B), or human (FIG. 15C) serum at 37° C. for a period of 120 hours. Samples were removed at 0, 24, 48, 72, 96 and 120 hours and the ability of B2B3-1 to bind both ErbB2 and ErbB3 was measured by ELISA (RLU=relative light units).

The stability of B2B3-1 under physiological conditions is assessed by incubating 100 nM B2B3-1 in human, Cynomolgus monkey, or mouse serum at 37° C. for a period of 120 hours. Samples are removed at 0, 24, 48, 72, 96 and 120 hours and the ability of B2B3-1 to bind both ErbB2 and ErbB3 is measured by ELISA. This ELISA involves coating a 96-well plate with recombinant ErbB2 extracellular domain overnight followed by a blocking step and then incubation with a dilution series of B2B3-1. Plates are then incubated with an Fc-ErbB3 extracellular domain fusion protein followed by a goat antihuman-Fc-HRP conjugate. Plates are developed by addition of supersignal chemiluminescense substrate. FIGS. 15A-C show that B2B3-1 remains stable in serum from all three species under physiological conditions, retaining comparable ability to bind both ErbB2 and ErbB3 at all time points measured.

Example 16

B2B3-1 Dose Response in BT-474-M3 Human Breast Cancer in vivo Xenograft Model

Figure 16:
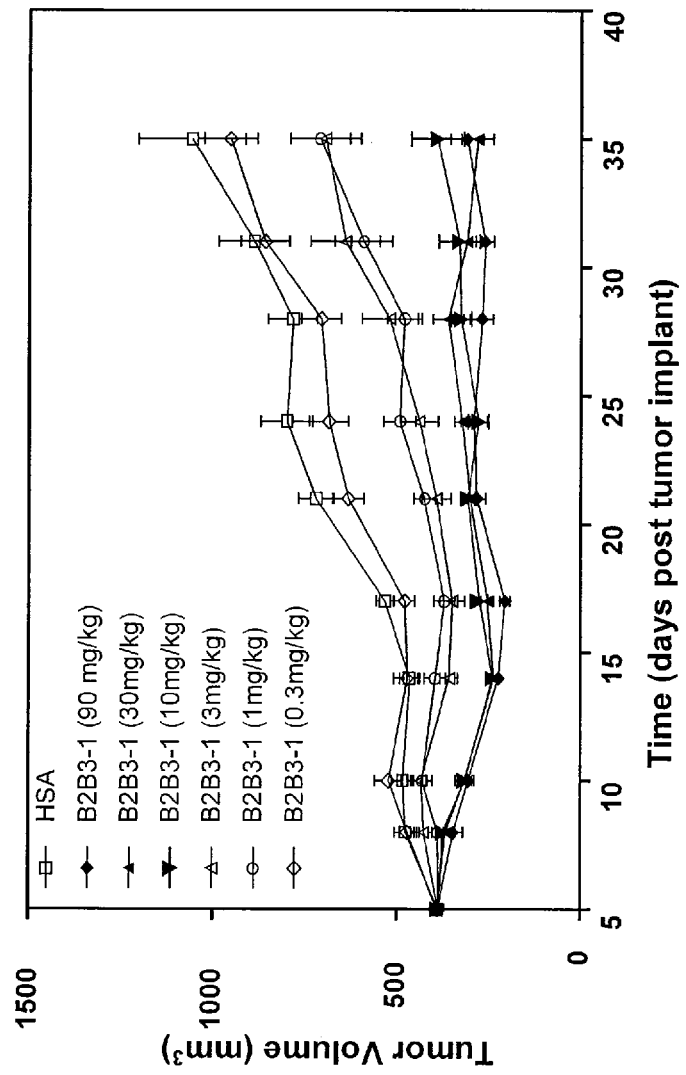
FIG. 16 is a graph showing B2B3-1 dose response in a BT-474-M3 breast cancer xenograft model. The relationship of B2B3-1 dose on tumor response was assessed in the BT-474-M3 breast tumor line at the doses indicated. HSA was given at 52.5 mg/kg, which is an equimolar dose to the 90 mg/kg B2B3-1 dose.
Figure 17:
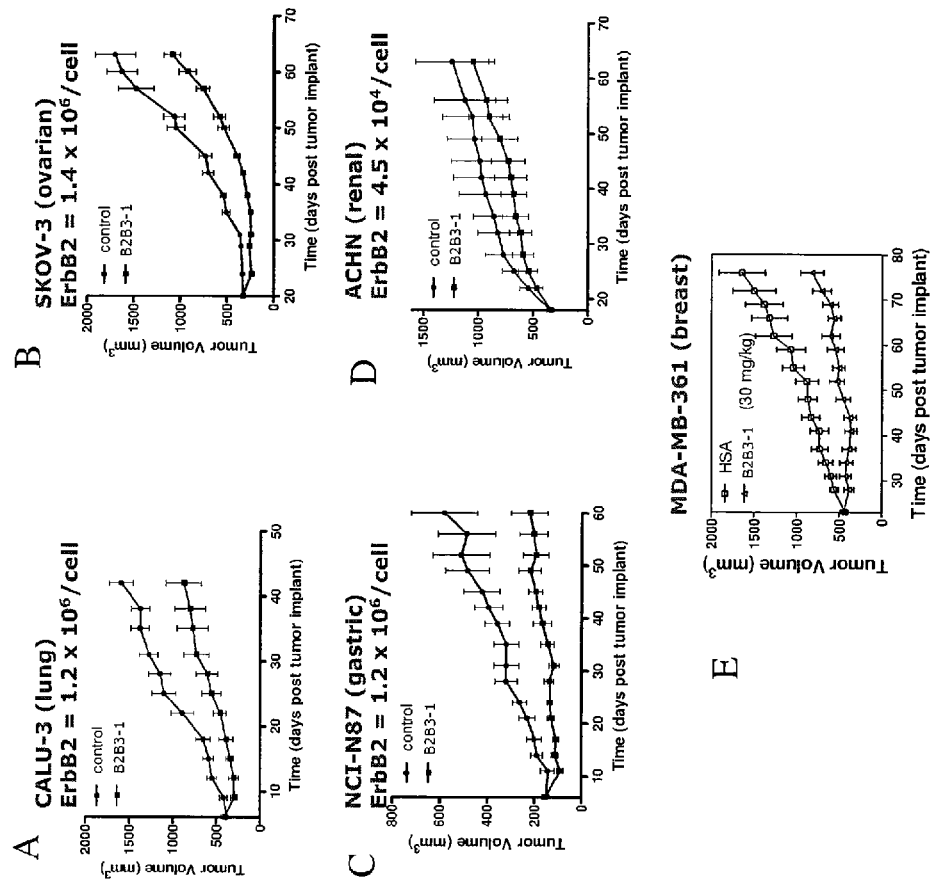
FIGS. 17A-E are graphs showing that B2B3-1 is effective in multiple xenograft models in an ErbB2 dependent manner. Calu-3 (human lung adenocarcinoma.

The efficacy of B2B3-1 in vivo is assessed using nude mice bearing human BT-474-M3 xenografts. Ten mice per group are treated with 12 doses of 0.3, 1, 3, 10, 30 or 90 mg/kg of B2B3-1 every 3 days. Control groups are administered PBS vehicle or HSA at an equimolar dose to the 90 mg/kg B2B3-1 dose. All doses are administered interperitoneally (i.p.). Tumor size is measured twice a week and the corresponding tumor volume is calculated. The results show that B2B3-1 treatment leads to significant reduction in BT-474-M3 tumor size as compared to the control group (FIG. 16). Complete regressions were observed in each of the B2B3-1 treatment groups except mice treated with the lowest dose of B2B3-1 (0.1 mg/kg).

Example 17

As shown in FIGS. 17A-E, B2B3-1 reduces tumor size in multiple xenograft models in an ErbB2 dependent manner. B2B3-1 was efficacious in the Calu-3 (FIG. 17A), SKOV-3 (FIG. 17B), NCI-N87 (FIG. 17C), and MDA-MB-361 (FIG. 17E) xenograft models expressing ErbB2 at >1×10$^5$ receptors/cell but worked less well in the ACHN (FIG. 17D) xenograft model which expresses 4.5×10$^4$ ErbB2 receptors/cell. Mice were treated with 30 mg/kg of B2B3-1 every 3 days.

Example 18

Figure 18A:
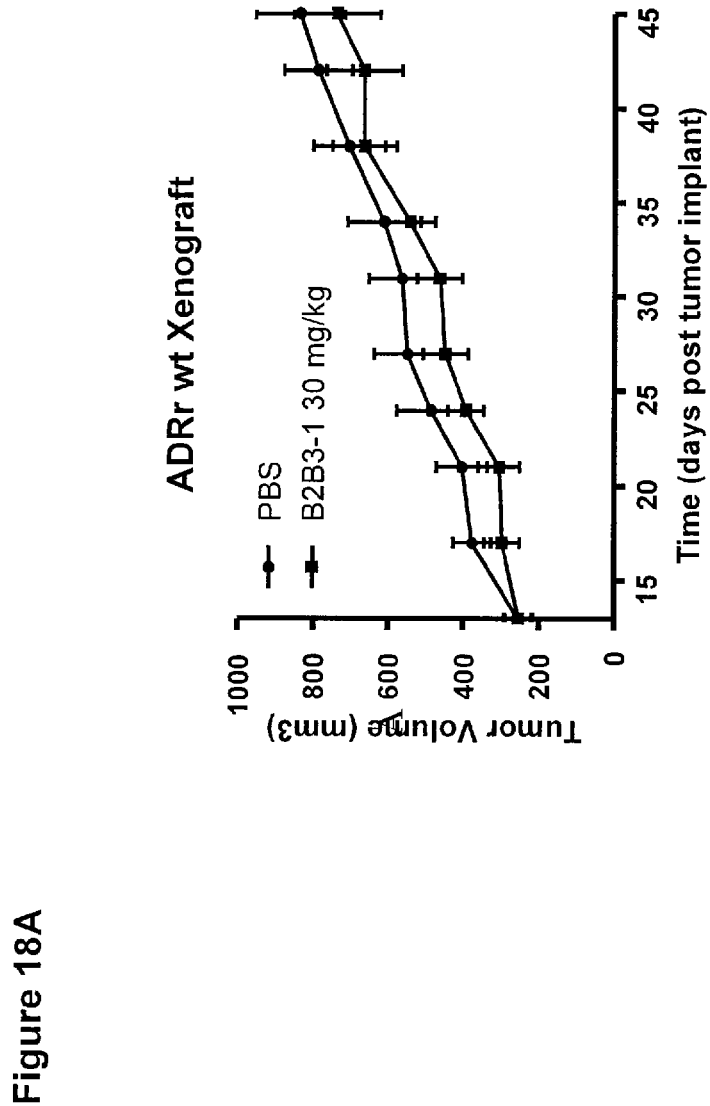
FIGS. 18A-B are graphs showing that the over-expression of ErbB2 converts B2B3-1 non-responder ADRr breast cancer xenograft model into a responder. ErbB2 was over-expressed in wild type ADRr xenografts (FIG. 18A) and ADRr-E2 xenografts (FIG. 18B) using a retroviral expression system.
Figure 18B:
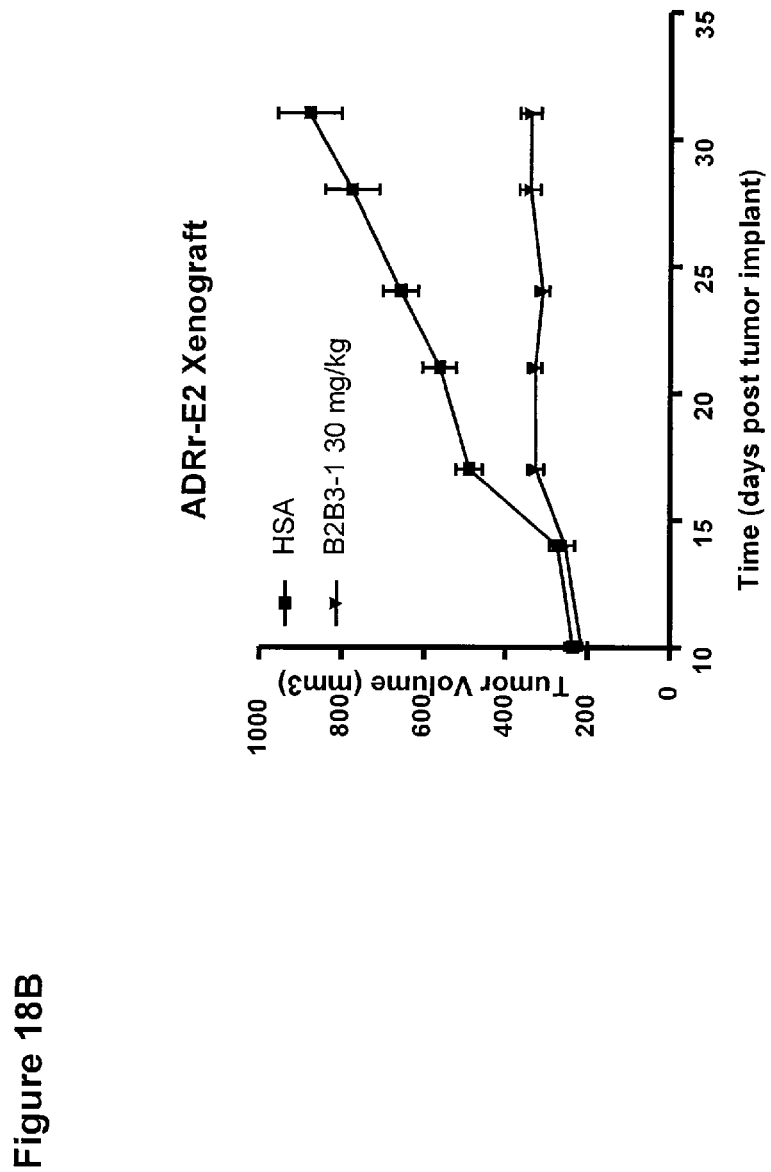

Over-expression of ErbB2 converts B2B3-1 non-responder ADRr breast cancer xenograft model into a responder to B2B3-1 (FIGS. 18A and 18B). ErbB2 is over-expressed in ADRr breast cancer cells using a retroviral expression system. Transfected cells expressing high levels of ErbB2 (ADRr-E2) are selected using FACS and subsequently injected subcutaneously into nude mice to establish xenograft tumors. Mice are treated with 30 mg/kg of B2B3-1 every 3 days. While no response to B2B3-1 was observed in wild type ADRr xenografts (FIG. 18A), ADRr-E2 xenografts (FIG. 18B) responded to B2B3-1.

Example 19

Figure 19A:
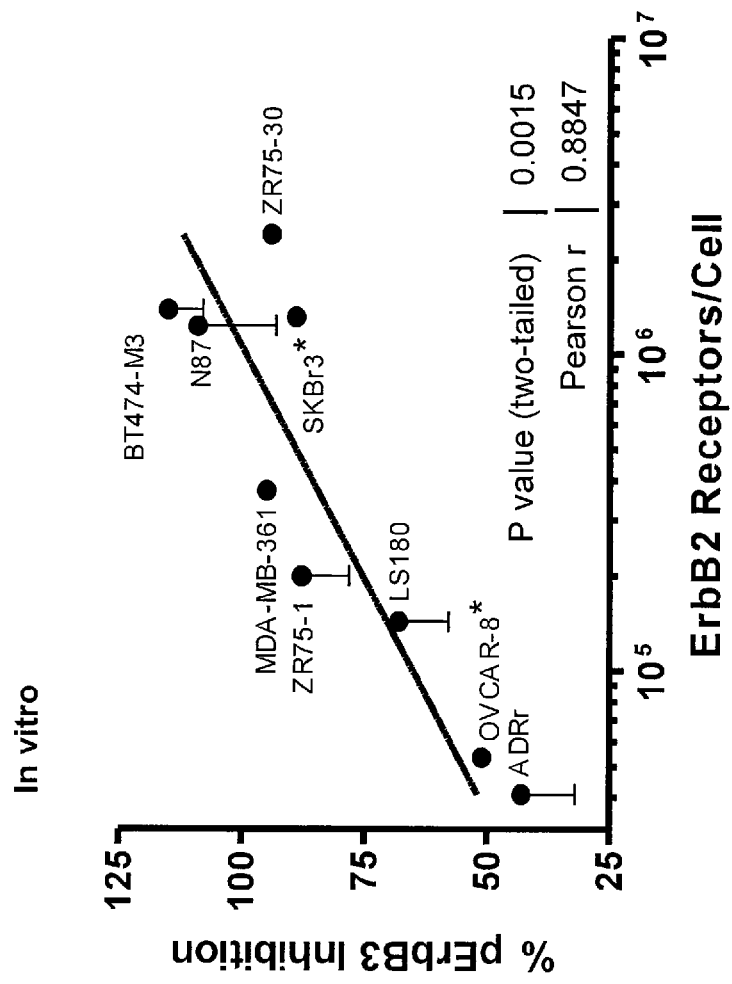
FIGS. 19A-B are graphs showing that B2B3-1 activity correlates positively with ErbB2 expression levels in vitro (FIG. 19A) and in vivo (FIG. 19B).
Figure 19B:
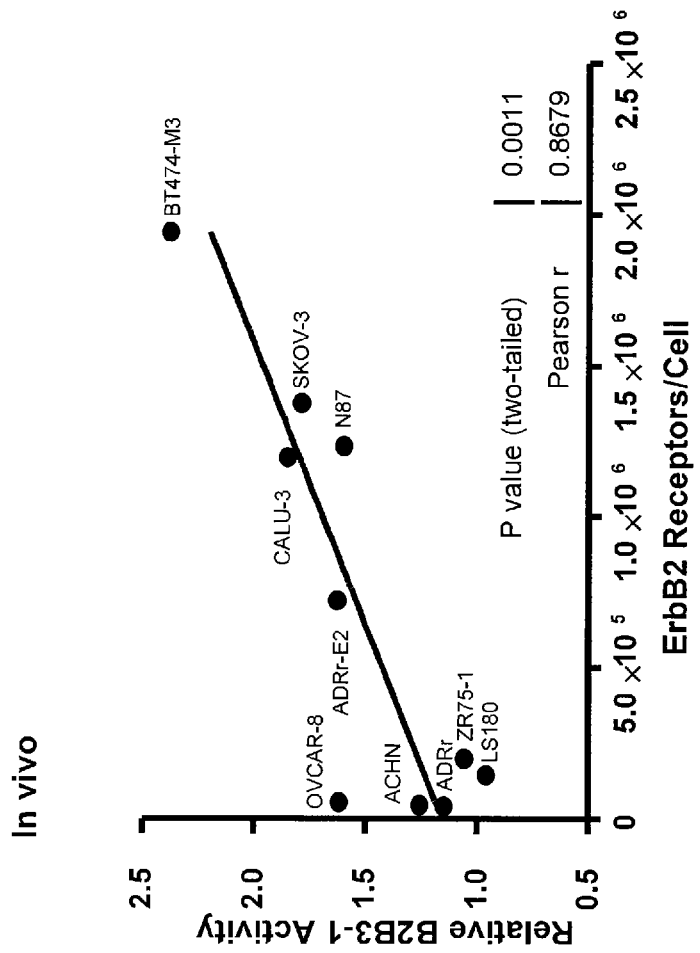

As shown in FIGS. 19A-B, B2B3-1 activity correlates positively with ErbB2 expression levels in vitro (FIG. 19A)

and in vivo (FIG. 19B). B2B3-1 inhibition of ErbB3 phosphorylation is determined in 9 tumor cell lines with expression levels of ErbB2 ranging from $5 \times 10^4$ receptors/cell to $2.4 \times 10^6$ receptors/cell using an ELISA assay. The extent of B2B3-1's ability to inhibit ErbB3 phosphorylation to basal levels (% pErbB3 inhibition) was found to correlate positively with ErbB2 expression levels. Similarly, B2B3-1 activity is assessed in 10 tumor xenograft models expressing low to high levels of ErbB2. Xenograft response also correlated positively with ErbB2 expression levels.

Example 20

Figure 20:
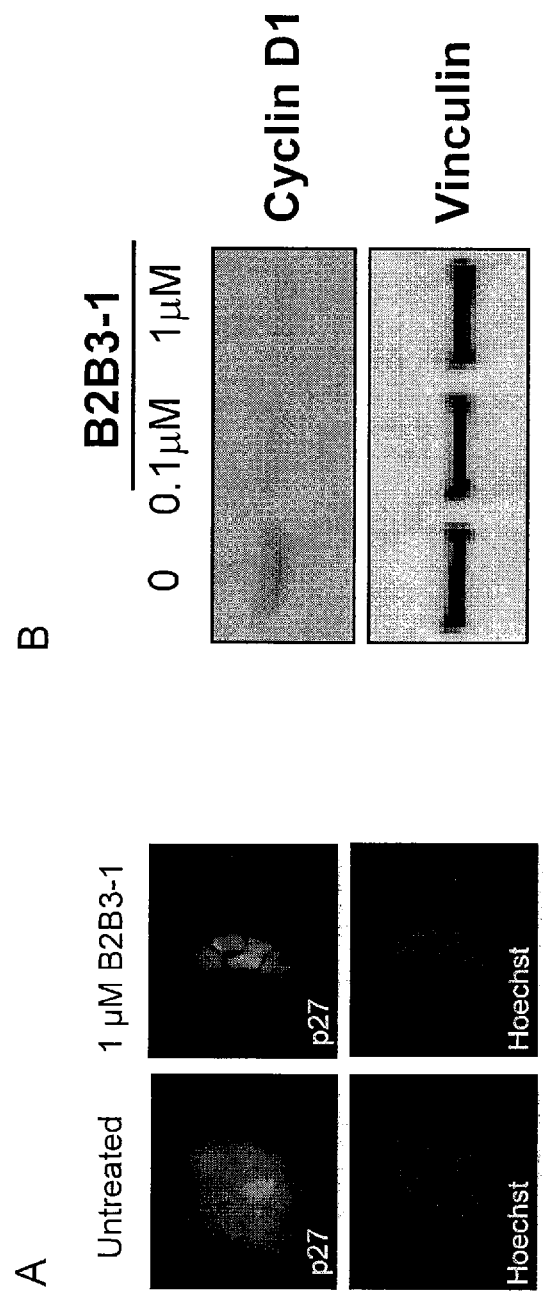
FIG. 20A-B show that B2B3-1 treatment modifies tumor cell cycling.

B2B3-1 treatment of BT474-M3 breast tumor cells results in translocation of p27$^{kip1}$ to the nucleus (FIG. 20A). BT474-M3 cells are treated with 1 µM of B2B3-1 for 6 hours. The sub-cellular location of p27$^{kip1}$ is assessed using immunofluorescence techniques. In cells treated with B2B3-1, p27$^{kip1}$ translocated to the nucleus, which has been shown to result in inhibition of cell proliferation. p27$^{kip1}$ remained in the cytoplasm of untreated cells.

To further study the effect of B2B3-1 on the cell cycle, BT-474-M3 cells treated with B2B3-1 for 72 hours are probed for the cell cycle regulator Cyclin D1 using Western blot analysis (FIG. 20B). The cytoskeleton protein vinculin is used as a protein loading control in this experiment. B2B3-1 treatment resulted in a decrease in the levels of Cyclin D1 compared to untreated cells.

Example 21

Figure 21:
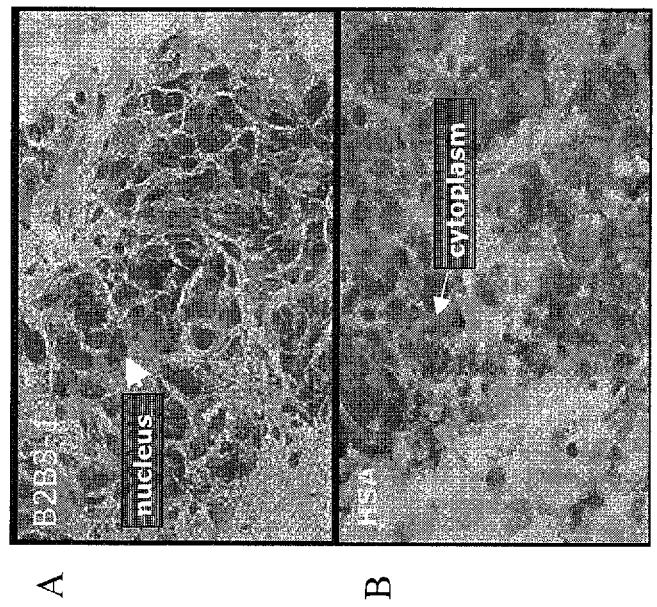
FIGS. 21A-B are micrographs showing that B2B3-1 treatment of BT474 breast tumor xenografts results in translocation of p27$^{kip1}$ to the nucleus. BT474 breast tumor xenografts were treated with B2B3-1 (FIG. 21A) at a dose of 30 mg/kg or an equimolar dose of HSA (FIG. 21B) every 3 days for a total of 4 doses and stained for p27$^{kip1}$.

As shown in FIGS. 21A-B, B2B3-1 treatment of BT474-M3 breast tumor xenografts results in translocation of p27$^{kip1}$ to the nucleus. BT474 breast tumor xenografts are treated with B2B3-1 (FIG. 21A) at a dose of 30 mg/kg or an equimolar dose of HSA (FIG. 21B) every 3 days for a total of 4 doses. Increased nuclear staining for p27$^{kip1}$ was observed in B2B3-1 treated tumors compared to HSA control tumors indicating an anti-proliferative effect of B2B3-1 in vivo.

Example 22

Figure 22:
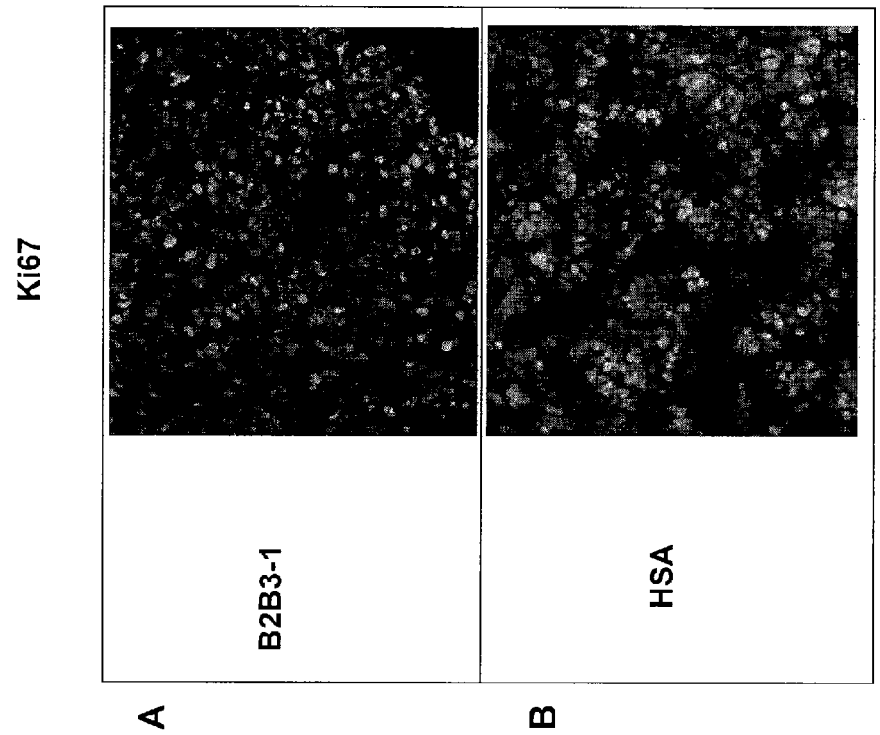
FIG. 22A-B are fluorescent micrographs showing that B2B3-1 treatment results in a reduction of the proliferation marker Ki67 in BT474-M3 breast cancer xenograft. BT474-M3 breast tumor xenografts were treated with B2B3-1 (FIG. 22A) at a dose of 30 mg/kg or an equimolar dose of HSA (FIG. 22B) every 3 days for a total of 4 doses.

B2B3-1 treatment results in a reduction of the proliferation marker Ki67 in BT474 breast cancer xenograft tumors. BT474-M3 breast tumor xenografts are treated with B2B3-1 (FIG. 22A) at a dose of 30 mg/kg or an equimolar dose of HSA (FIG. 22B) every 3 days for a total of 4 doses. Subsequent staining of tumor sections for Ki67 demonstrated a reduced expression pattern for B2B3-1 treated tumors compared to HSA treated tumors.

Example 23

Figure 23:
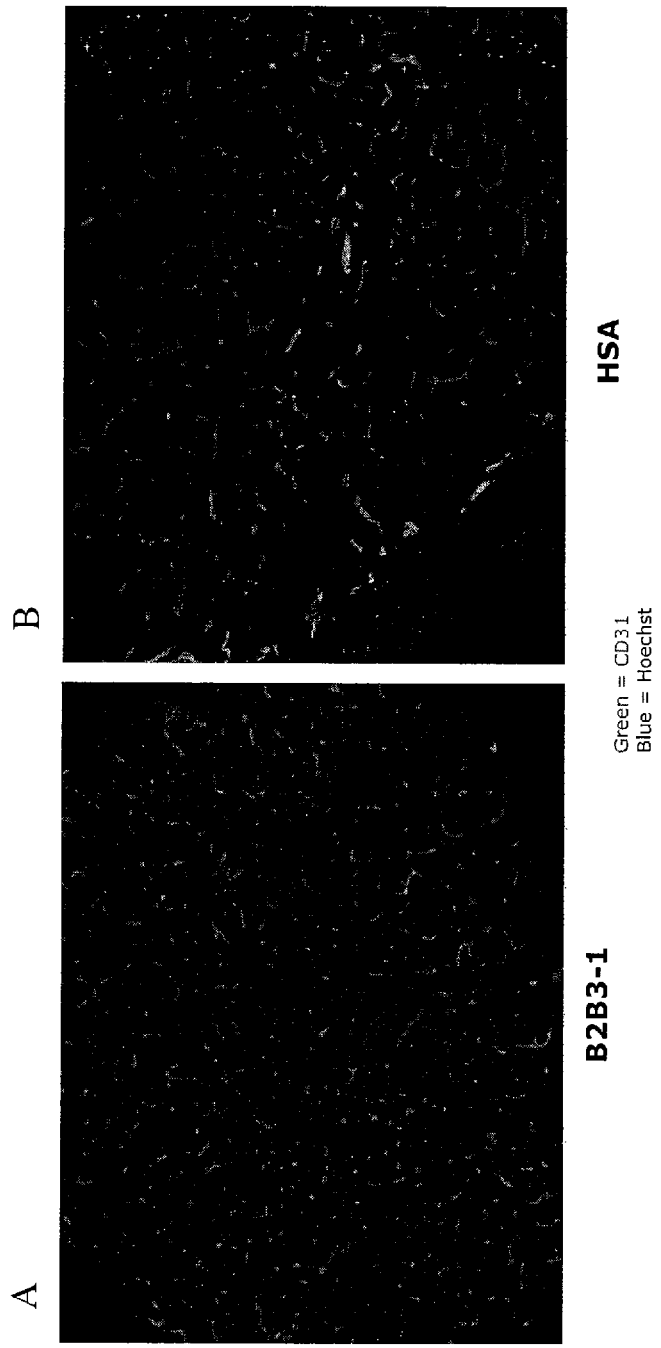
FIGS. 23A-B are fluorescent micrographs showing that B2B3-1 treatment results in a reduction of vessel density in BT474-M3 breast cancer xenograft tumors (as determined by a reduction in CD31 staining). BT474-M3 breast tumor xenografts were treated with B2B3-1 (FIG. 23A) at a dose of 30 mg/kg or an equimolar dose of HSA (FIG. 23B) every 3 days for a total of 4 doses.

B2B3-1 treatment results in a reduction of vessel density in BT474-M3 breast cancer xenograft tumors, as determined by assaying for CD31 expression (FIGS. 23A-B). BT474 breast tumor xenografts are treated with B2B3-1 (FIG. 23A) at a dose of 30 mg/kg or an equimolar dose of HSA (FIG. 23B) every 3 days for a total of 4 doses. Tumors are stained for the presence of vascular marker CD31. Tumors treated with B2B3-1 show a marked decrease in vessel density compared to control tumors treated with HSA.

Example 24

B2B3-1 Inhibits Phosphorylation of ErbB3 In Vivo

Figure 24:
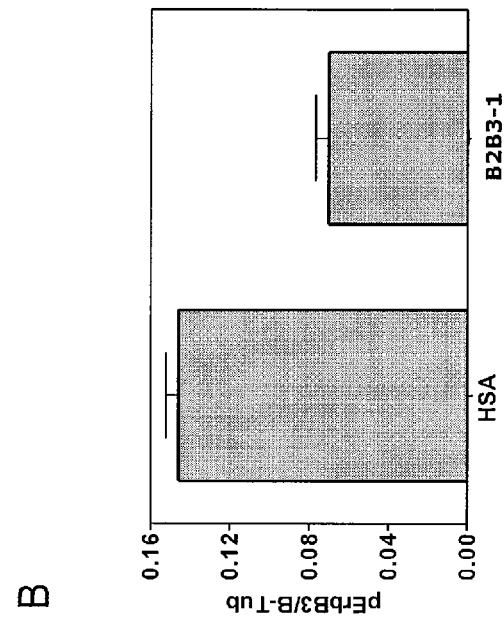
FIGS. 24A-B are graphs showing that B2B3-1 inhibits phosphorylation of ErbB3 in vivo. Lysates from individual BT-474-M3 xenograft tumors treated with B2B3-1 (M1-M5) or control HSA (H1-H2) were subjected to SDS-PAGE and probed for pErbB3 and beta tubulin using Western blot analysis (FIG. 24A). Normalization of the mean pErbB3 signal to the mean beta tubulin signal demonstrated that B2B3-1 treated tumors contained significantly less pErbB3 than HSA tumors (FIG. 24B).
Figure 24:
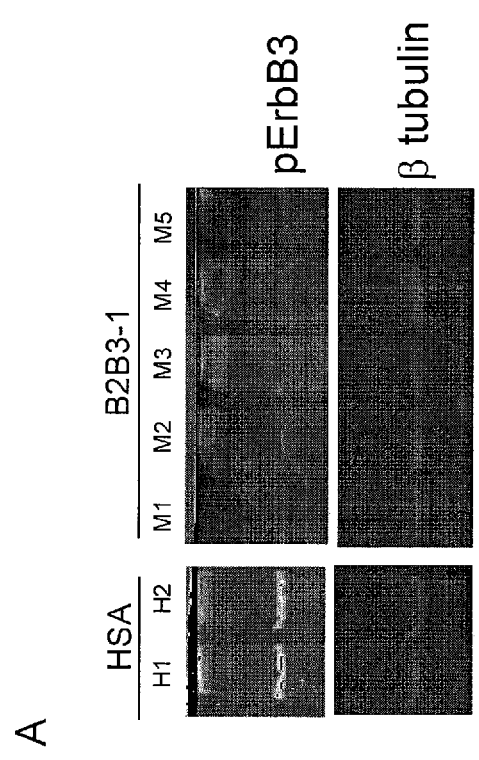

BT-474-M3 xenograft tumors are treated with 30 mg/kg B2B3-1 or 17.5 mg/kg HSA every 3 days for a total of 4 doses and tumors are harvested 24 hours after the final dose. Tumors are lysed and subjected to SDS-PAGE followed by Western analysis to assess relative levels of phosphorylation of B2B3-1's target ErbB3. Equal quantities of protein are loaded in each lane and total protein levels are controlled by probing for beta tubulin. Western blot analysis using antibodies specific for phosphorylated ErbB3 show that B2B3-1 treated tumors contain less pErbB3 than HSA treated tumors (FIG. 24A). Densitometry of the western blot analysis followed by normalization of the mean pErbB3 integral band intensity to the mean beta tubulin integral band intensity demonstrated that B2B3-1 treated tumors contained significantly less pErbB3 than control HSA treated tumors (FIG. 24B). These data confirmed that B2B3-1 inhibits phosphorylation of its target ErbB3 in vivo.

Example 25

In vivo Activity of B2B3-1 in BT-474-M3 Xenografts which have Reduced PTEN Activity ShRNA technology is applied to knock out the activity of the tumor suppressor gene phosphatase and tensin homolog (PTEN) in BT-474-M3 breast cancer cells. Briefly, cultured BT-474-M3 cells are transfected with shPTEN or shControl RNA by retroviral transfection. Transfected cells with reduced PTEN are selected using FACS and subsequently injected subcutaneously into the right flank of nude mice to establish xenograft tumors. Cells transfected with a control vector are injected into the left flank of the same mouse. Mice are treated with 30 mg/kg B2B3-1 every 3 days or 10 mg/kg trastuzumab every week. HSA is injected as a control at an equimolar dose to B2B3-1. All injections are done i.p.

Figure 25A:
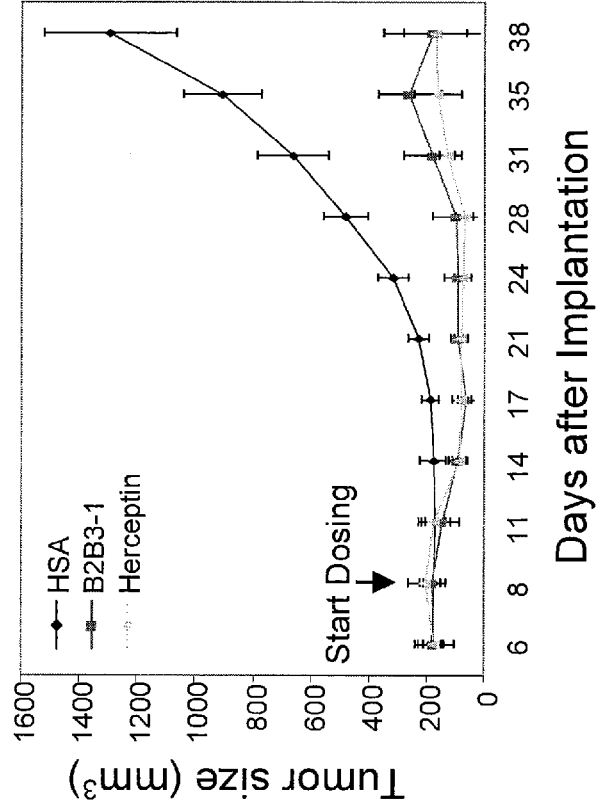
FIGS. 25A and B are graphs showing the in vivo activity of B2B3-1 in BT-474-M3 shPTEN and shControl xenografts. Cultured BT-474-M3 tumor cells were transfected with a control vector (FIG. 25A) or with a retroviral vector expressing shPTEN (FIG. 25B), which knocks out PTEN activity. BT-474-M3 breast cancer cells thus engineered to knock out PTEN activity were injected into the right flank of mice, while cells transfected with control vector were injected into the left flank of the same mouse. Mice were treated with 30 mg/kg B2B3-1 every 3 days or 10 mg/kg Herceptin every week and HSA was injected as a control at an equimolar dose to B2B3-1. B2B3-1 and Herceptin promoted a reduction in the size of tumors formed by control BT-474-M3 breast cancer cells (FIG. 25A), whereas only B2B3-1 (and not Herceptin) promoted a reduction in the size of tumors formed by BT-474-M3 breast cancer cells lacking expression of PTEN (FIG. 25B).
Figure 25B:
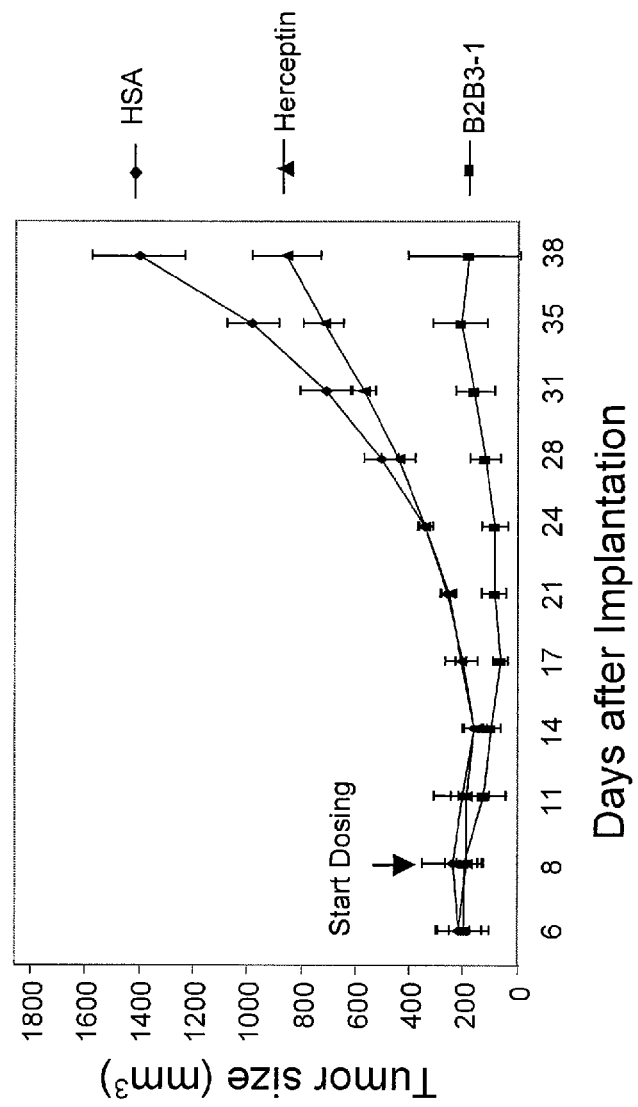

B2B3-1 and trastuzumab promoted a reduction in the size of tumors formed by control BT-474-M3 breast cancer cells (FIG. 25A), whereas only B2B3-1 (and not trastuzumab) promoted a reduction in the size of tumors formed by BT-474-M3 human breast cancer cells lacking expression of PTEN (FIG. 25B).

Example 26

Figure 26A:
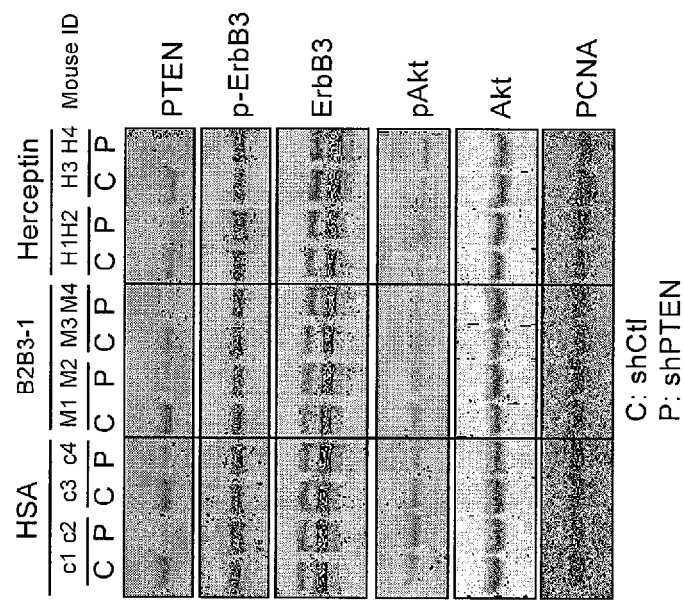
FIGS. 26A-B show that B2B3-1 inhibits phosphorylation of AKT in BT-474-M3 xenografts that have reduced PTEN activity. Tumors were lysed following the completion of treatment (q3dx11) and tested for PTEN, pErbB3, and pAKT expression levels by Western blot analysis (FIG. 26A). Densitometry on the band intensity for pAKT normalized to total AKT and total protein demonstrate that B2B3-1 was able to inhibit phosphorylation of this protein, when Herceptin did not (FIG. 26B).
Figure 26B:
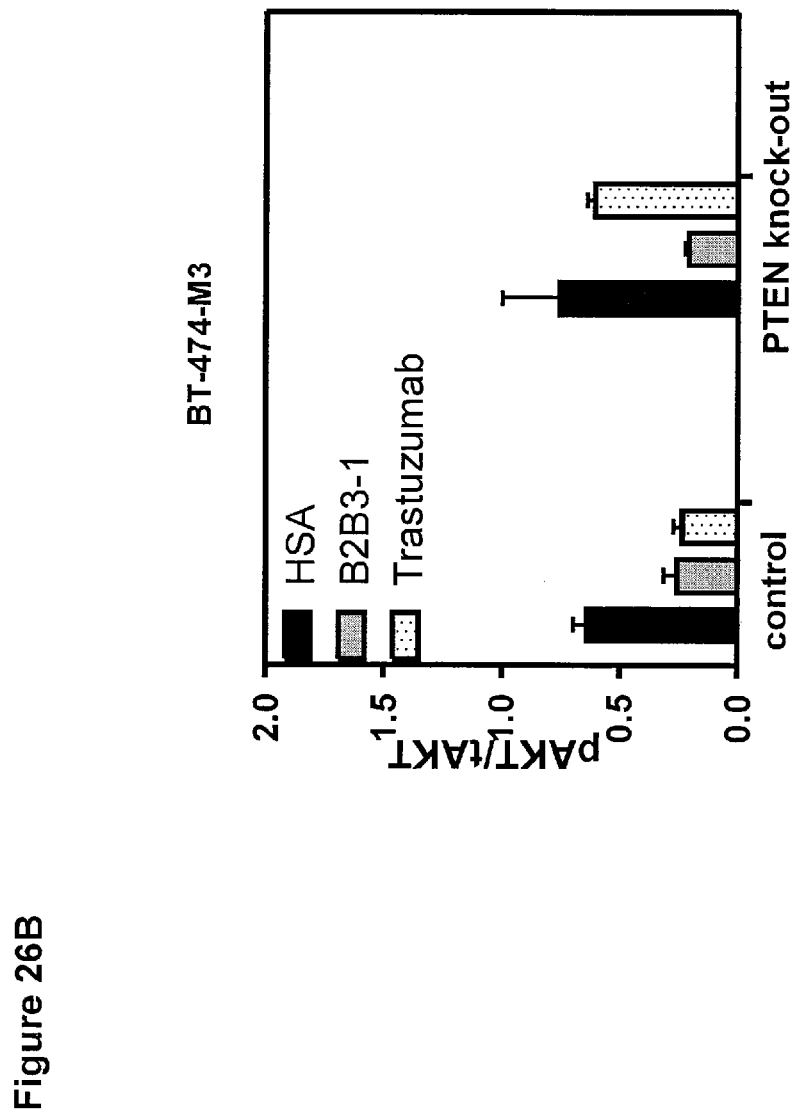
Figure 27:
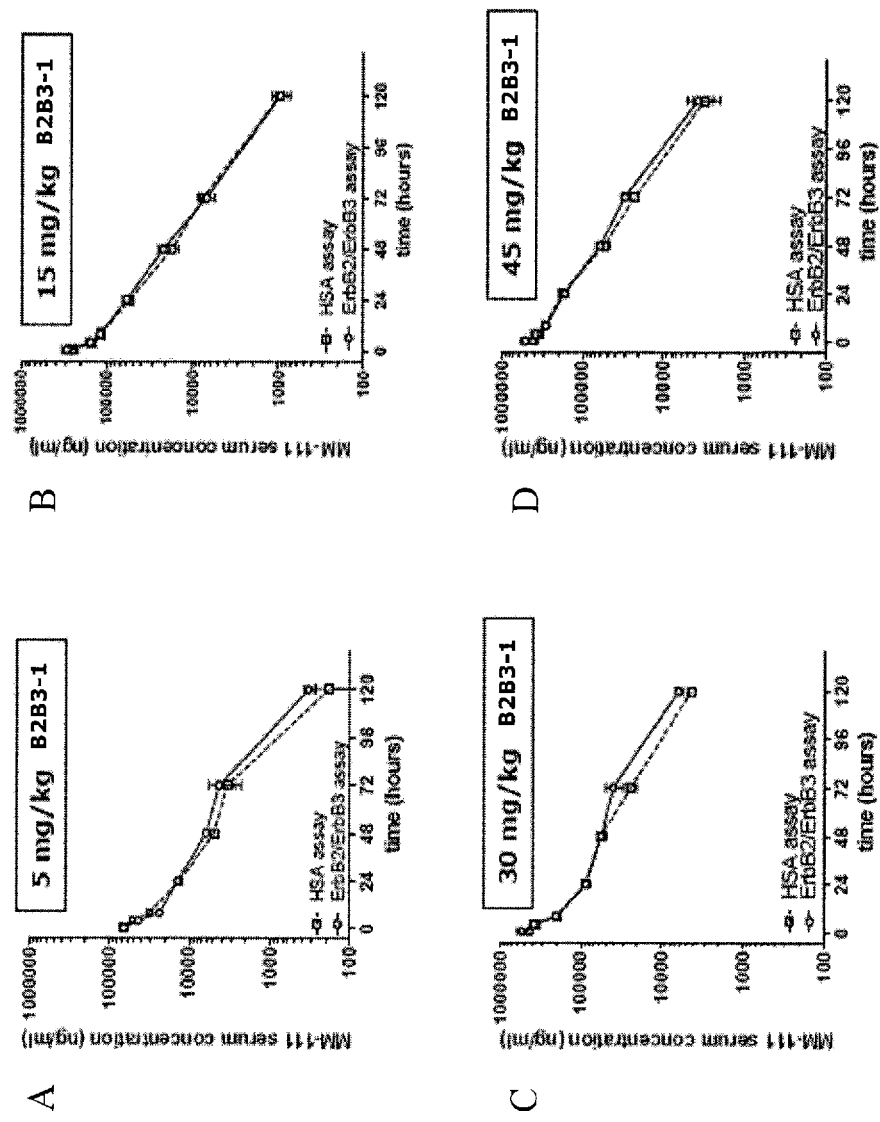
FIGS. 27A-D are graphs showing the single dose pharmacokinetic properties of 5 (FIG. 27A), 15 (FIG. 27B), 30 (FIG. 27C), and 45 (FIG. 27D) mg/kg bolus dose of B2B3-1 in nu/nu mice. B2B3-1 serum concentrations are comparable measured by the HSA assay or ErbB2/ErbB3 assay, indicating that the antigen binding activity of B2B3-1 is retained in circulation.

B2B3-1 Inhibits ErbB3 Signaling in BT-474-M3 Breast Cancer Cells having Reduced PTEN Activity The ability of B2B3-1 to inhibit phosphorylation of ErbB3 signaling in tumor xenografts is studied using the PTEN deficient BT-474-M3 model described above. Xenograft tumors of the engineered cell line or control cell line are treated with 30 mg/kg B2B3-1, 17.5 mg/kg HSA every 3 days or 10 mg/kg trastuzumab weekly and tumors are harvested 24 hours after the final dose. Tumors are lysed and subjected to SDS-PAGE followed by Western analysis to assess relative levels of phosphorylation of B2B3-1's target ErbB3, AKT and total PTEN levels. Equal quantities of protein are loaded in each lane and total protein levels are controlled by probing for PCNA. Western blot analysis using antibodies specific for phosphorylated ErbB3 shows that B2B3-1 treated tumors contain less pAKT than HSA treated or Herceptin treated tumors (FIG. 26A). Densitometry of the western blot analysis followed by normalization of the mean pAKT integral band intensity to the mean PCNA integral band intensity demonstrated that B2B3-1 treated tumors contained significantly less pAKT than control HSA treated and Herceptin-treated tumors (FIG. 26B).

Example 27

The pharmacokinetic parameters for B2B3-1 are investigated in nu/nu mice. Animals are randomized into groups and administered intravenous (IV) with a single dose of 5, 15, 30, or 45 mg/kg B2B3-1 (FIGS. 27A-D, respectively). Blood is collected pre-dose and at 0.5, 4, 8, 24, 48, 72, and 120 hours post dose. Three mice are used for each time point. Serum levels of B2B3-1 are measured using two ELISA methods. The first method requires functional binding of B2B3-1 to both ErbB2 and ErbB3 while the second method measures only the HSA component of B2B3-1 in the serum. The HSA ELISA utilizes a polyclonal-anti HSA capture antibody and a HRP-conjugated polyclonal anti-HSA detection antibody. A reduction in B2B3-1 serum concentration measured using the ErbB2/ErbB3 binding method versus the HSA method would indicate a loss in functional B2B3-1. FIGS. 27A-D show that the pharmacokinetic properties of B2B3-1 are comparable when assessed using either ELISA method, indicating that B2B3-1 is stable in circulation in mice.

Example 28

Figure 28:
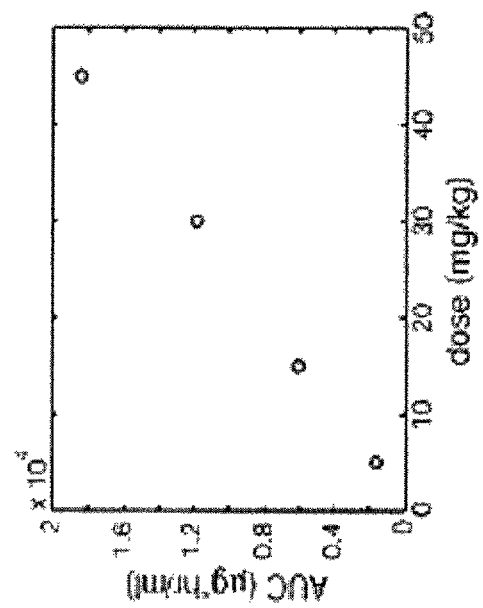
FIG. 28 is a graph showing the dose-exposure relationship for 5, 15, 30, and 45 mg/kg bolus doses of B2B3-1 in nude mice. Increases in dose result in a linear increase in overall exposure to B2B3-1.

B2B3-1 serum concentrations are fit using a two-compartment, biexponential model and show biphasic disposition. Terminal half-lives were calculated to be 17, 16, 23, and 18 hrs for the 5, 15, 30, or 45 mg/kg doses, respectively, and are shown in Table 4. Increases in B2B3-1 dose resulted in a linear increase in exposure (FIG. 28).

TABLE 4

Pharmacokinetic properties of B2B3-1 in mice and Cynomolgus monkeys.

| Dose (mg/kg) | Species | N | T½β (hrs) | AUC (hr-µg/ml) | Clearance (ml/hr/kg) |
|---|---|---|---|---|---|
| 5 | Mouse (single dose) | 3 | 16.9 | 1.58E+03 | 3.19 |
| 15 | Mouse (single dose) | 3 | 16.2 | 6.10E+03 | 2.47 |
| 30 | Mouse (single dose) | 3 | 22.6 | 1.18E+04 | 2.54 |
| 45 | Mouse (single dose) | 3 | 17.5 | 1.84E+04 | 2.46 |
| 4 | Cynomolgus monkey (1st dose) | 2 | 39.1 | 3.44E+03 | 1.17 |
| 4 | Cynomolgus monkey (4th dose) | 2 | 44.9 | 7.20E+03 | 0.60 |
| 20 | Cynomolgus monkey (1st dose) | 2 | 33.1 | 2.29E+04 | 0.88 |
| 20 | Cynomolgus monkey (4th dose) | 2 | 122.5 | 8.20E+04 | 0.25 |
| 200 | Cynomolgus monkey (1st dose) | 4 | 68.8 | 3.18E+05 | 0.64 |
| 200 | Cynomolgus monkey (4th dose) | 2 | 69.7 | 5.72E+05 | 0.35 |
| 200 | Cynomolgus monkey (4th dose)* | 2 | 66.6 | 5.99E+05 | 0.34 |

*recovery animals

Example 29

Blood samples for pharmacokinetic analysis are also obtained from a dose range-finding toxicology study in female Cynomolgus monkeys. In this study, animals are infused with 4, 20 or 200 mg/kg of B2B3-1 administered every 3 days for 4 doses. Sampling occurred prior to and 5 minutes after dosing on each dosing day (study days 1, 4, 7 and 10) to provide pre-dose and peak/trough concentrations, and at 1, 2, 4, 8, 24 and 48 hours after the end of the first infusion on day 1 and at 1, 2, 4, 8, 24, 48, 72 and 120 hours after the last infusion on day 10. For recovery animals dosed at 200 mg/kg serum samples are also collected at 168, 336 and 456 hours after the last infusion.

Figure 29:
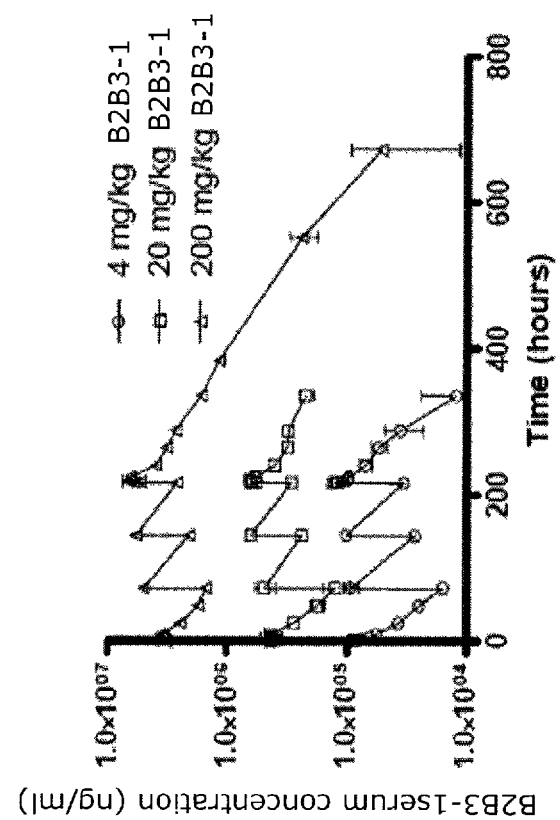
FIG. 29 is a graph showing the B2B3-1 serum concentrations measured in Cynomolgus monkeys dosed every three days for 4 doses with 4 mg/kg (n=2), 20 mg/kg (n=2) and 200 mg/kg (up to 336 hour n=4, for 384, 552 and 672 hour time points n=2).

Cynomolgus monkey serum samples are assayed using the ErbB2/ErbB3 ELISA method described previously. Serum concentrations for each dose over the time course are shown in FIG. 29. The analysis shows that mean concentration-time profiles for serum B2B3-1 after dosing on days 1 and 10 were qualitatively similar with concentrations generally declining with time from Cmax. Mean half-life estimates ranged from 38.3-67.2 hours on day 1 and 45.0 to 121.0 hours on day 10 (Table 4).

Example 30

The plasmid encoding the B2B3-1 bispecific scFv antibody fusion protein is created combining gene sequences of a unique human anti-ErbB3 scFv (designated "H3"), a human anti-ErbB2 scFv (designated "B1D2"), and a modified human serum albumin (HSA) linker. The anti-ErbB3 scFv, H3, is recombinantly linked to the amino terminus of the HSA linker via a connecting peptide (Ala-Ala-Ser) and the anti-ErbB2 scFv, B1D2, is genetically linked the carboxy terminus of the HSA linker via a connecting peptide (Ala-Ala-Ala-Leu—SEQ ID NO:5). The peptide connectors are formed through the introduction of restriction sites during construction of the mammalian expression vector and are synthesized with optimized codon usage for mammalian expression together with the single chain antibody fragments and HSA linker.

The B1D2 scFv is selected from a combinatorial phage display library created by mutagenesis of the ErbB2-binding scFv C6.5, which is selected from a non-immune phage display library. The H3 scFv is selected from a non-immune phage display library originally made by Sheets et al. The gene sequences encoding the B1D2 and H3 single chain antibody fragments are optimized for CHO cell codon preferences and synthesized for subsequent construction of the B2B3-1 encoding plasmid.

The modified HSA linker contains two amino acid substitutions. A cysteine residue at position 34 is mutated to serine in order to reduce potential protein heterogeneity due to oxidation at this site. An asparagine residue at amino acid 503 is mutated to glutamine, which in wild type HSA is sensitive to deamination and can result in decreased pharmacologic half-life.

The gene sequence encoding the modified HSA linker is synthesized with optimized codon usage for mammalian expression for subsequent construction of the B2B3-1 encoding plasmid.

Example 31

Figure 30:
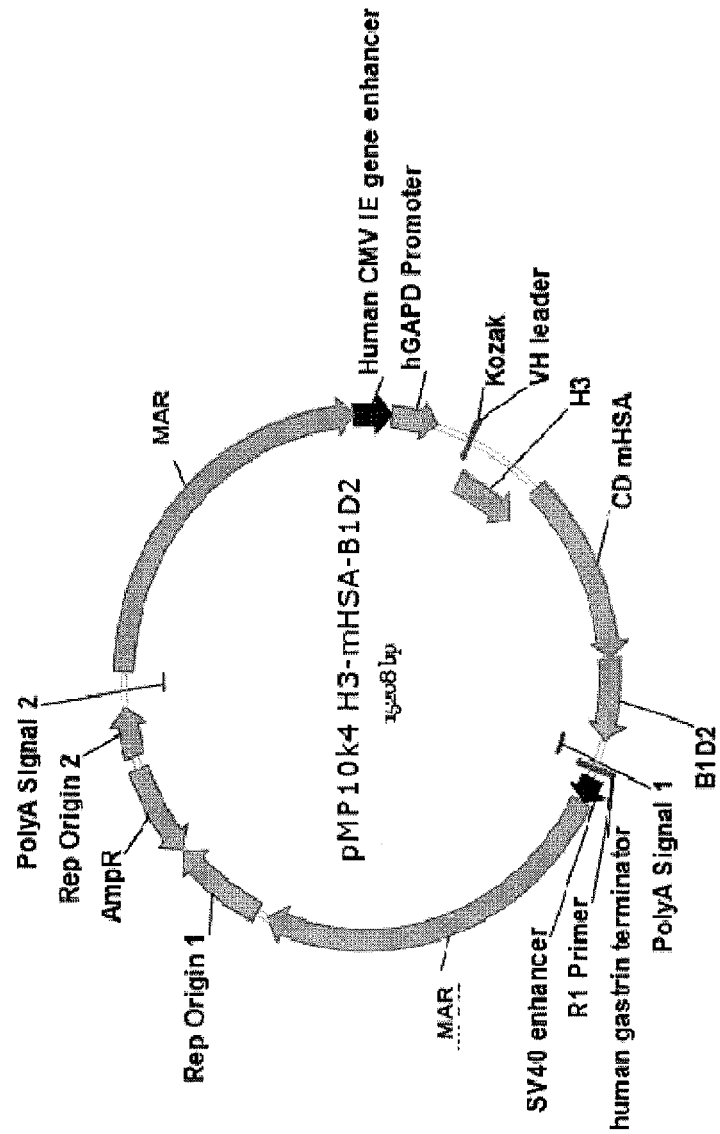
FIG. 30 is an illustration of the B2B3-1 expression plasmid pMP10k4H3-mHSA-B1D2.
Figure 31:
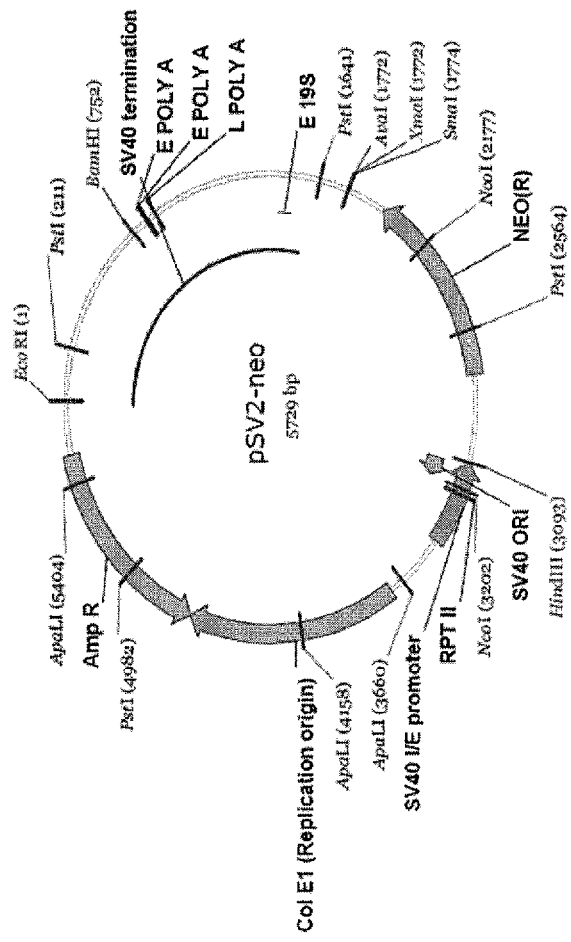
FIG. 31 is an illustration of the neomycin resistance plasmid pSV2-neo.
Figure 32:
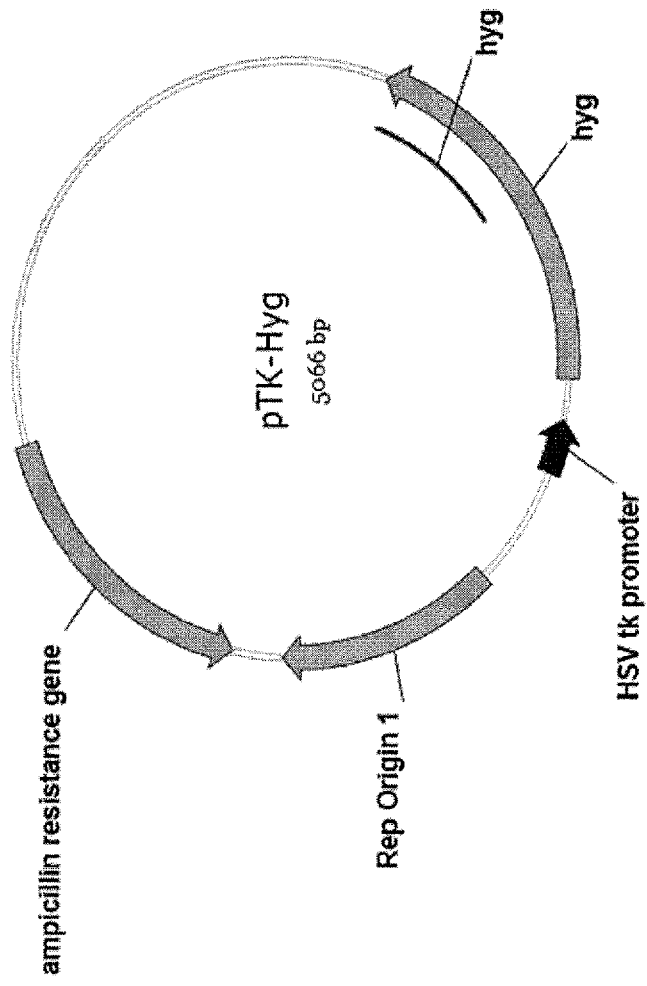
FIG. 32 is an illustration of the hygromycin resistance plasmid pTK-Hyg.

The B2B3-1 coding sequence is cloned into pMP10k base vector using standard molecular biology techniques to create plasmid pMP10k4H3-mHSA-B1D2, shown in FIG. 30. For the most part this construct employs commonly used genetic elements. B2B3-1 expression is driven by the human GAPD promoter. This vector utilizes genetic elements referred to as Matrix Attachment Regions or MAR elements. The MAR genetic elements control the dynamic organization of chromatin, and insulate nearby genes from the effect of surrounding chromatin thereby increasing copy number dependent, position-independent, expression of genes. MAR elements have been shown to improve the probability of isolating a clone exhibiting the desired level of expression for the production of a recombinant protein and to increase the stability of production. The MAR elements used in the B2B3-1 constructs are non-coding human MAR elements. In addition to the B2B3-1 plasmid, a neomycin antibiotic resistance plasmid (FIG. 31) and a hygromycin resistance plasmid (FIG. 32) are also used to select for stable transformants.

Example 32

First Round of Gene Transfection

Chinese Hamster Ovary CHO-K1 cells are purchased from ATCC (ATCC #CCL-61). The CHO-K1 cell line is a serum and proline dependent adherent sub-clone of the parental CHO cell line created by T.T. Puck. The CHO-K1 cells used for B2B3-1 transfection are pre-adapted for suspension growth in serum free media prior to transfection. An iterative transfection procedure is used to develop the B2B3-1 cell line. Twenty-four hours before transfection, CHO-K1 cells are sub passaged to $1.0 \times 10^6$ cells/mL in SFM4CHO (Serum Free) medium (HyClone, Logan, Utah) supplemented with 8 mM L-glutamine, 0.1 mM sodium hypoxanthine, and 0.016 mM thymidine. On the day of transfection, cells are resuspended in OptiMEM medium (Invitrogen Corp, Carlsbad, Calif.) and 40,000 cells are placed in each well of a twenty-four well plate. In the first transfection, the B2B3-1 expression plasmid (pMP10k4H3-mHSA-B1D2) and the neomycin resistance plasmid (FIG. 30; pSV2-neo (Selexis, Inc., Marlborough, Mass.) are mixed together using a molar plasmid ratio of 75:1 (B2B3-1:neomycin resistance). The plasmid mixture is subsequently mixed with a cationic lipid transfection reagent (Lipofectamine LTX, Invitrogen Corp, Carlsbad, Calif.) and lipid/DNA complexes are allowed to form for thirty minutes. The DNA/Lipid complex is then added to the CHO-K1 cells and the 24-well plates are placed in a 37° C., 5% $CO_2$ incubator.

Example 33

Selection and Screening for High Producers

The contents of each transfection well are washed with PBS, trypsinized and distributed across two, ninety-six well plates. The growth media used consists of DIMEM/F12 (Invitrogen Corp, Carlsbad, Calif.) with 10% FBS (Invitrogen Corp, Carlsbad, Calif.) and 500 mg/L of geneticin (G418; Invitrogen Corp, Carlsbad, Calif.). Media in the 96-well plates is changed on day 4 to SFM4CHO medium supplemented with 8 mM L-glutamine, 0.1 mM sodium hypoxanthine, 0.016 mM thymidine, and 500 mg/L geneticin. Following an additional two weeks of culture in selection medium, surviving cells have formed well-defined colonies. The clones are evaluated using quantitative spot blot techniques. The top producing colonies are trypsinized, and expanded to a single well of a 24-well plate.

A seven day productivity assay is used to screen for high B2B3-1 producing colonies. Upon expansion the cells in 24-well plates are allowed to proliferate for seven days in SFM4CHO medium supplemented with 8 mM L-glutamine, 0.1 mM sodium hypoxanthine, and 0.016 mM thymidine. The B2B3-1 concentration in the spent media is determined. Top clones from the 24-well scale are expanded into 125 mL baffled shake flasks. A seven day study in the shake flask in SFM4CHO medium supplemented with 8 mM L-glutamine, 0.1 mM sodium hypoxanthine, and 0.016 mM thymidine is used to screen the cell pools for growth and B2B3-1 production.

Example 34

Second Round of Gene Transfection

The highest producing cell pool determined from the first round of transfection (supra) is transfected a second time to increase production. Twenty-four hours before transfection, the cell pool is sub passaged to $1.0 \times 10^6$ cells/mL in SFM4CHO (Serum Free) medium supplemented with 8 mM L-glutamine, 0.1 mM sodium hypoxanthine, and 0.016 mM thymidine. On the day of transfection, cells are resuspended in OptiMEM medium (Invitrogen Corp, Carlsbad, Calif.) and 40,000 cells re placed in each well of a twenty-four well plate. In the first transfection, the B2B3-1 and hygromycin resistance plasmid (FIG. 32; pTK-Hyg (Clontech, Mountain View, Calif.)) are mixed together using a molar plasmid ratio of 50:1 (B2B3-1:hygromycin resistance). The plasmid mixture is subsequently mixed with a cationic lipid transfection reagent (Lipofectamine LTX, Invitrogen Corp) and lipid/DNA complexes are allowed to form for thirty minutes. The DNA/Lipid complex is then added to the cell pool and the 24-well plates are placed in a 37° C., 5% $CO_2$ incubator.

Example 35

Selection and Screening for High Producers From Second Transfection

The contents of each transfection well are washed with PBS, trypsinized and distributed across two, 96-well plates. The growth media used consists of DMEM/F12 supplemented with 10% FBS and 400 mg/L of hygromycin B (Invitrogen Corp). Media in the 96-well plates is changed on day 4 to Hyclone SFM4CHO medium supplemented with 8 mM L-glutamine, 0.1 mM sodium hypoxanthine, 0.016 mM thymidine, and 400 mg/L of hygromycin B. After an additional two weeks of selection, surviving cells have formed well-defined colonies. The clones are evaluated using quantitative spot blot techniques. The top producing colonies are trypsinized, and expanded to a single well of a 24-well plate.

A seven day productivity assay is used to screen for high B2B3-1 producing colonies.
Upon expansion the cells are allowed to proliferate for seven days, and the B2B3-1 concentration in the spent media is determined.

Top clones from the 24-well plates are expanded into 125 mL baffled shaker flasks in the Hyclone SFM4CHO medium supplemented with 8 mM L-glutamine, 0.1 mM sodium hypoxanthine, and 0.016 mM thymidine. A seven day study in shake flask is used to screen the cell pools for growth and B2B3-1 production. The spent media is quantitated using Protein Aresin and an HPLC instrument.

Example 36

Limiting Dilution Cloning

The best growing and highest B2B3-1-producing colony identified by the productivity assay is transferred from the 125 mL shaker flask and plated in five 96-well plates at a cell concentration calculated to give one cell/well. The 96-well plates are placed in an incubator at 37° C. and 5% $CO_2$. The wells are examined bi-weekly to track formation of colonies. Colonies arising from a single cell are identified based on the symmetrical shape of the colony. Wells containing such colonies are marked for further screening by 24-well 7-day assessment, and 125 mL shaker flask 7-day assessment.

The second round of limiting dilution cloning is performed in a similar manner to the first round. An additional 100 ml, fed batch evaluation is performed to confirm clone choice. A pre-seed bank is cryopreserved.

Example 37

Formulation of B2B3-1

B2B3-1 is administered once a week via intravenous infusion over a period of 60 or 90 minutes, depending on patient tolerability. B2B3-1 is formulated in a sterile 20 mM L-histidine hydrochloride, 150 mM sodium chloride, pH 6.5 solution at a concentration of 25 mg/mL for administration to a patient (e.g., a human).

Example 38

Treatment of Breast Cancer

If a patient's cancer is believed to be expressing high levels of epidermal growth factor receptors, including ErbB2 (HER2/neu), then treatment with an HSA linker conjoined to an ErbB2 biding moiety, such as B2B3-1, B2B3-2, v-3, B2B3-4, B2B3-5, B2B3-6, B2B3-7, B2B3-8, B2B3-9, or B3-10 (see Table 6, below) would be indicated. Such would be the case where genotypic or histologic screens of cancer biopsies reveals increased expression of ErbB2 in the patient's tumor.

A B2B3 HSA linker conjugate (e.g., B2B3-1, SEQ ID NO:16) is administered to a patient diagnosed with breast cancer once a week or twice a week via intravenous infusion over a period of, e.g., 60 or 90 minutes, depending on patient tolerability, at a dose no higher than 30 mg/kg. The B2B3 HSA linker conjugate is formulated in a sterile 20 mM L-histidine hydrochloride, 150 mM sodium chloride, pH 6.5 solution at a concentration of 25 mg/mL for administration to the patient. A clinician supervising the administration of the B2B3 HSA linker conjugate follows common formulation and dosing practices to determine the proper course of therapy for the patient.

The clinician may further co-administer one or more therapies with the B2B3 HSA linker conjugate. E.g., one or more therapeutic drugs or compounds may be administered in combination with the B2B3 HSA linker conjugate, such as the common chemotherapeutic regimen for the treatment of breast cancer, which includes doxorubicin, cyclophosphamide, and paclitaxel. Alternatively, a clinician can administer the B2B3 HSA linker conjugate in combination with surgical or radiation therapy to treat breast cancer the patient.

Example 39

Treatment of Ovarian Cancer

If a patient's cancer is believed to be expressing high levels of epidermal growth factor receptors, including ErbB2 (HER2/neu), then treatment with an HSA linker conjoined to an ErbB2 biding moiety, such as B2B3-1, B2B3-2, v-3, B2B3-4, B2B3-5, B2B3-6, B2B3-7, B2B3-8, B2B3-9, or B3B3-10 (see Table 6, below) would be indicated. Such would be the case where genotypic or histologic screens of cancer biopsies reveals increased expression of ErbB2 in the patient's tumor.

A B2B3 HSA linker conjugate (e.g., B2B3-1, SEQ ID NO:16) is administered to the patient diagnosed with ovarian cancer alone or in combination with one or more other therapies essentially as described in the preceding Example.

Example 40

Additional HSA Linker Conjugates

HSA linker conjugates are constructed using one or more of the elements (groups A-E) listed in Table 5 below. In particular, an HSA linker conjugate, which is shown as Group C in Table 5 below, incorporates one or more binding moieties selected from groups A and E shown in Table 5. In addition, the HSA linker conjugates can also include one or more peptide connectors, which are selected from groups B and D in Table 5, at each of the amino and carboxy terminal ends of the HSA linker. Peptide connectors can be repeated or truncated to increase or decrease the length of the connector sequence.

TABLE 5

| Group A<br>Amino Terminal<br>Binding Moiety | Group B<br>Amino Terminal<br>Peptide Connector | Group C<br>HSA | Group D<br>Carboxy Terminal<br>Peptide Connector | Group E<br>Carboxy Terminal<br>Binding Moiety |
|---|---|---|---|---|
| H3 (SEQ ID NO:26)<br>B1D2 (SEQ ID NO:27)<br>A5 (SEQ ID NO:28)<br>ML3.9 (SEQ ID NO:29)<br>B12 (SEQ ID NO:30)<br>F4 (SEQ ID NO:31)<br>F5B6H2 (SEQ ID NO:32) | AAAL (SEQ ID NO:5)<br>AAS<br>AAQ | mHSA (SEQ ID NO:1)<br>wtHSA (SEQ ID NO:3) | AAAL (SEQ ID NO:5)<br>AAS<br>AAQ | H3 (SEQ ID NO:26)<br>B1D2 (SEQ ID NO:27)<br>A5 (SEQ ID NO:28)<br>ML3.9 (SEQ ID NO:29)<br>B12 (SEQ ID NO:30)<br>F4 (SEQ ID NO:31)<br>F5B6H2 (SEQ ID NO:32) |

Example 41

In Vivo, B2B3-1 Dosed q7d Shows Equivalent Efficacy as B2B3-1 Dosed q3d

Figure 33:
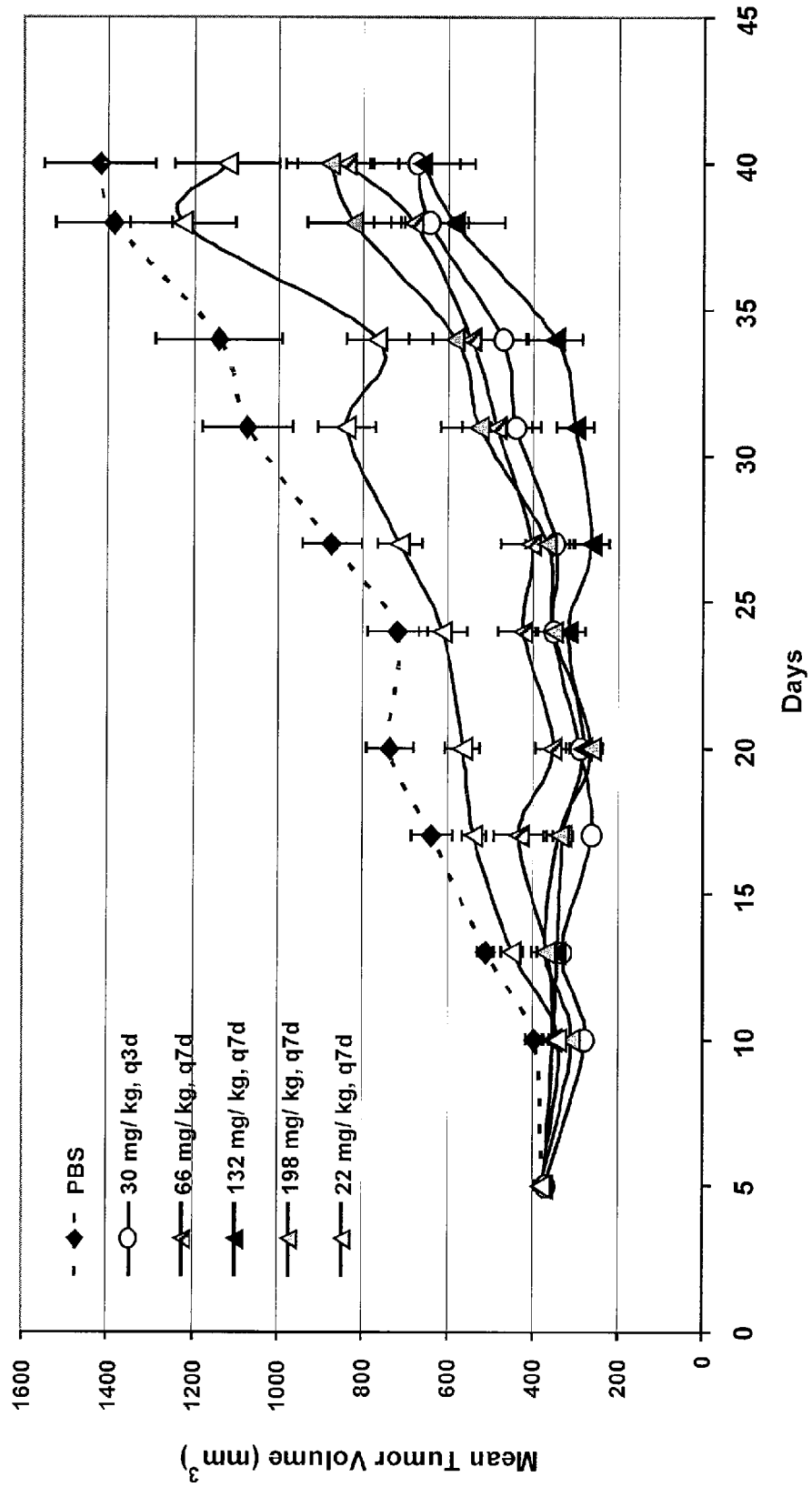
FIG. 33 shows data demonstrating that B2B3-1 dosed q7d shows equivalent efficacy to q3d dosing.

B2B3-1 efficacy using a q7d (once every 7 days) dosing regimen is determined in in female athymic nude mice (nu/nu) from Charles River Labs, 5-6 weeks of age bearing xenograft tumors of the human breast cancer cell line BT-474-M3 (FIG. 33). Mice receive a subcutaneous estrogen-releasing implant in the opposite flank (0.72 mg pellet, 60 day, slow-release, Innovative Research of America, Sarasota, Fla.) 24 h prior to the injection of $20 \times 10^6$ human BT-474-M3 cells in PBS. Dosing is initiated when tumor growth is established (tumor volumes of approximately 400 mm3) and B2B3-1 is administered to 10 mice per group either once every 3 days (q3d) at 30 mg/kg for the course of the study or once every 7 days at 22 mg/kg, 66 mg/kg, 132 mg/kg or 198 mg/kg by intraperitoneal injection. Tumors are measured twice a week using digital calipers. Tumor volume is calculated using the formula: $\pi/6 \times (W^2 \times L)$, where W is the short diameter and L is the long diameter. Pharmacokinetic calculations suggest that a 66 mg/kg dose q7d should give a similar exposure of B2B3-1 to the xenograft tumor as a 30 mg/kg dose q3d. PBS vehicle is used as a negative control. B2B3-1 efficacy was equivalent for the 30 mg/kg, q3d dose and the 3 highest doses of B2B3-1 administered q7d, indicating a q7d dosing schedule for B2B3-1 is suitable in this model.

Example 42

B2B3-1 and Trastuzumab have Different Mechanisms of ErbB3 Inhibition

Figure 34:
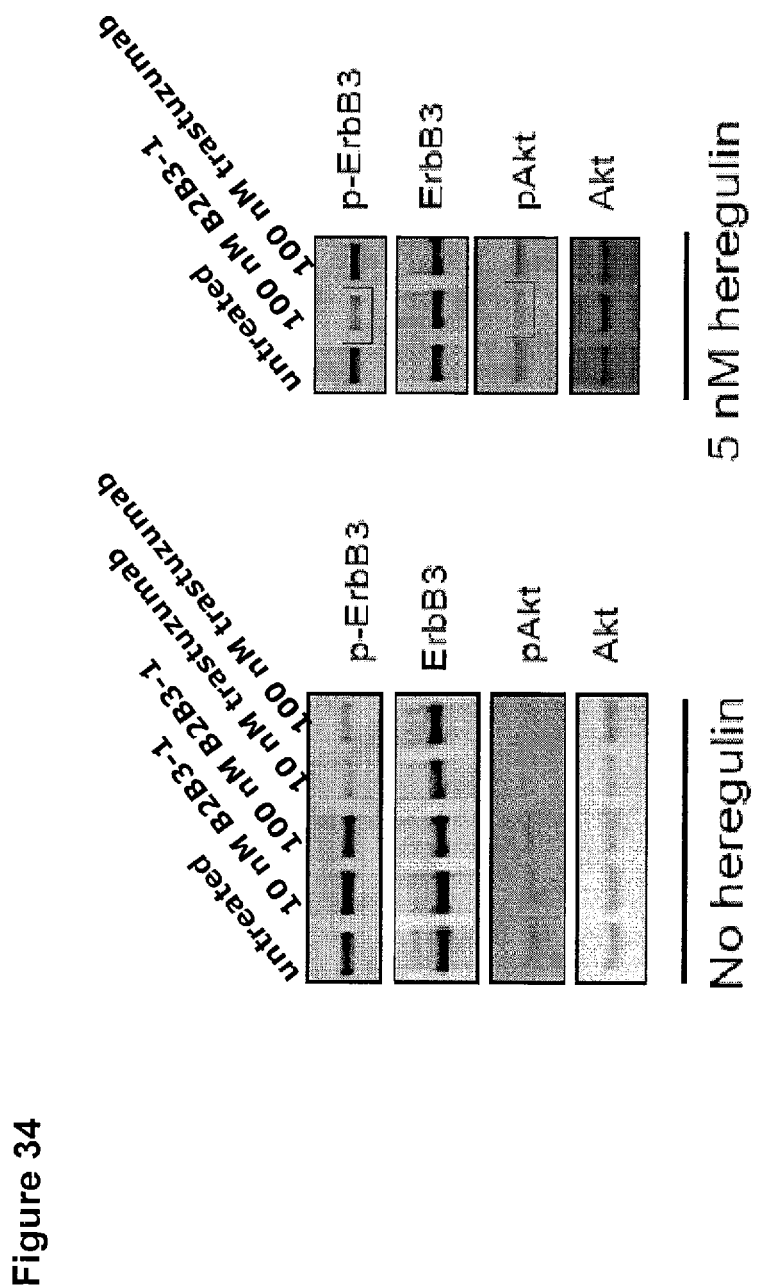
FIG. 34 shows western blot data demonstrating that B2B3-1 and trastuzumab exhibit different mechanisms of ErbB3 inhibition.

The ability of B2B3-1 to inhibit heregulin induced ErbB3 activity is tested using Western blot analysis. Monolayers of serum-starved BT-474-M3 cells are treated for 24 hours with 100 nM B2B3-1 or trastuzumab and then stimulated with 5 nM HRG 1β EGF for 10 minutes. Cells are also treated with 10 nM and 100 nM B2B3-1 or 10 nM and 100 nM trastuzumab and left unstimulated. Lysates are subjected to immunoblot analysis for ErbB3, pErb3, AKT, and pAKT. Western blot analysis (FIG. 34) demonstrated that B2B3-1 treatment results in inhibition of pErbB3 and pAKT in a ligand dependent manner, whereas inhibition of pErbB3 and pAKT by trastuzumab was only seen in the absence of ligand.

Example 43

B2B3-1 has an Additive Effect when Administered with Trastuzumab In Vitro

Figure 35A:
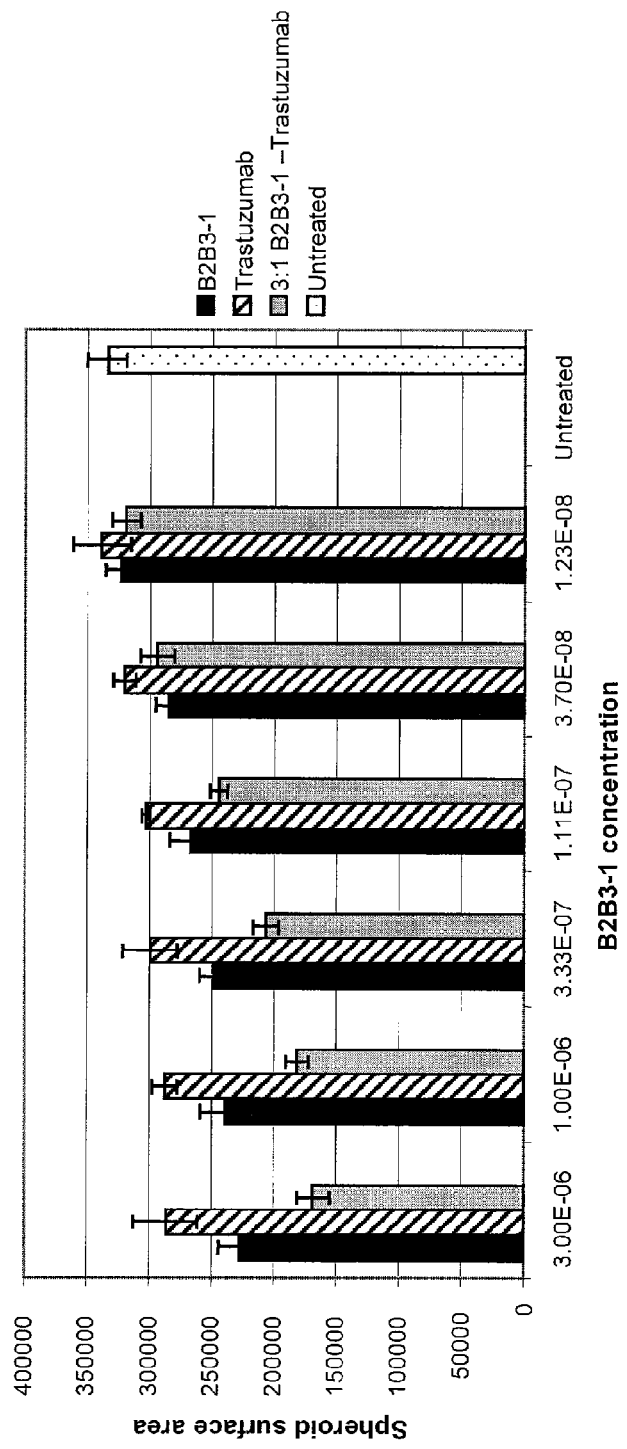
FIG. 35A shows data obtained using BT-474-M3 cells.
Figure 35B:
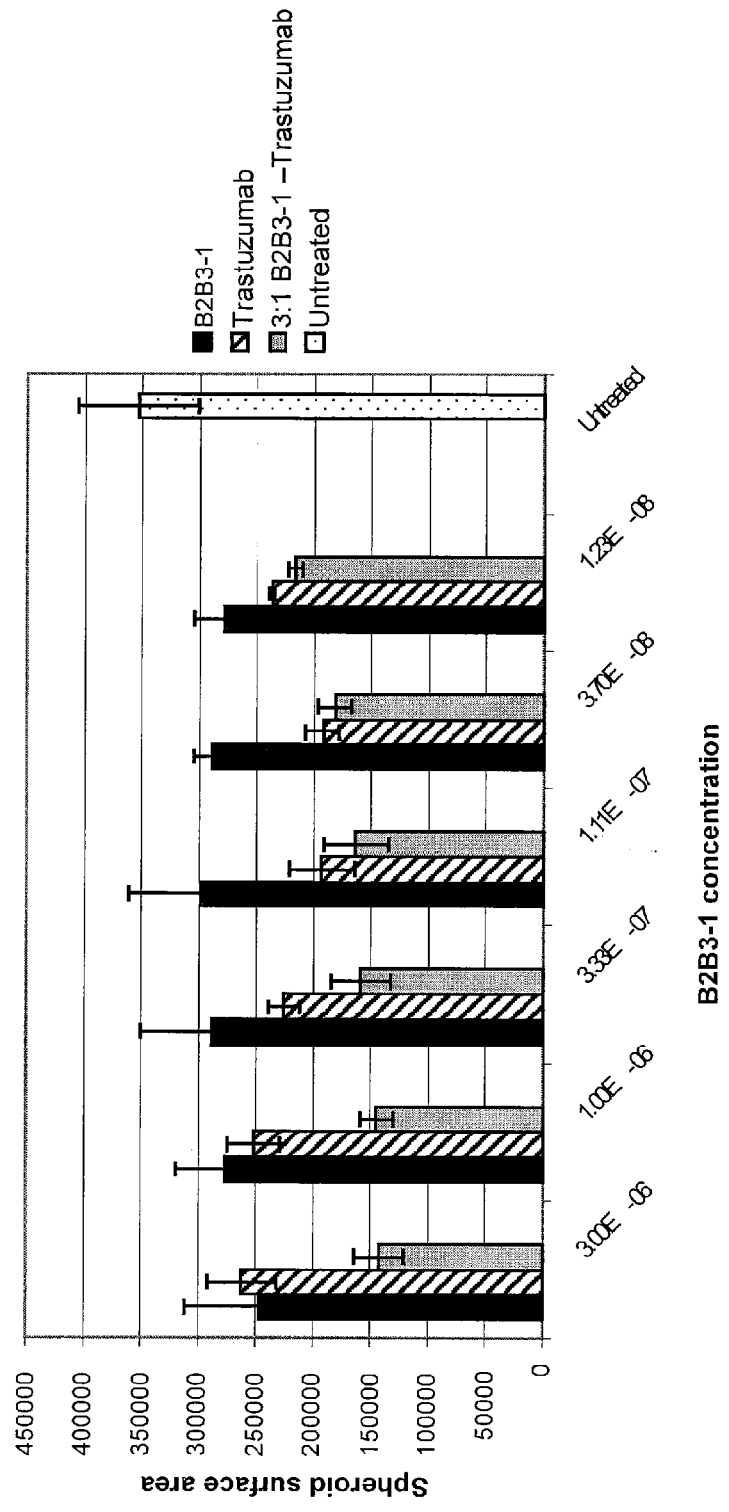
FIG. 35B shows data obtained using SKBR3 cells.
Figure 35C:
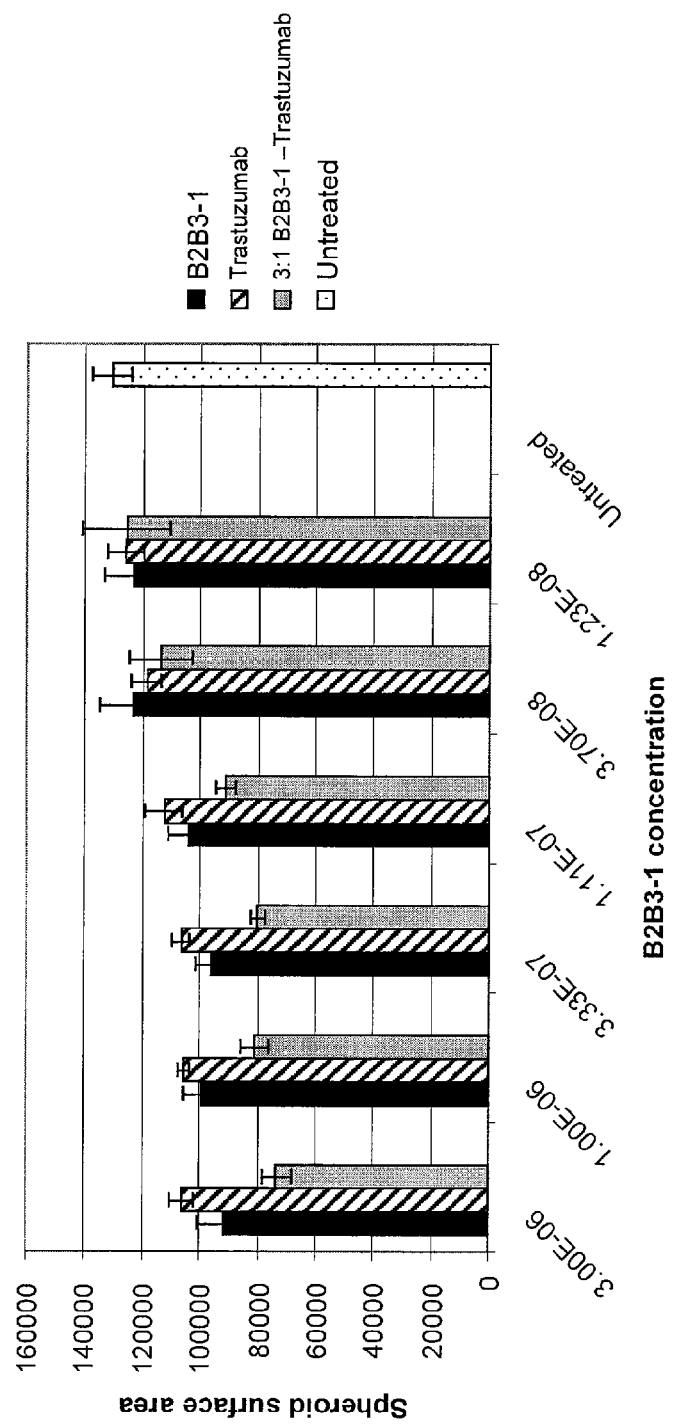
FIG. 35C shows data obtained using MDA-MB-361 cells. The molar concentration of B2B3-1, alone or in combination, is given along the X-axis. The molar concentration of trastuzumab, alone or in combination is one third that of each indicated concentration of B2B3-1.

The effects of B2B3-1, trastuzumab and the combination of both drugs on the growth of cancer cell spheroids was examined using four different breast cancer cell lines. 2,000 cells of BT-474-M3, SKBR3 (ATCC), or MDA-MB-361 (ATCC) human breast cancer cells were seeded in round-bottom low adherence 96-well plates (Corning® 96 Well Clear Round Bottom Ultra Low Attachment Microplate—Product #7007) and the following day the spheroids were measured and treated with a dose range of B2B3-1, trastuzumab or a combination of both at a ratio of 3 fold molar excess B2B3-1 to trastuzumab. After 12 days of growth the surface area of the spheroids was measured and compared to untreated cells. As can be seen in FIGS. 35A-C, the combination of B2B3-1 with trastuzumab over a range of concentrations resulted in greater inhibition of spheroid growth compared to the single agents in all cell lines tested at all but the lowest concentrations of drug(s). These results also indicate that B2B3-1 does not compete with trastuzumab for binding to ErbB2 (HER2).

Example 44

B2B3-1 has an Additive Effect when Administered with Trastuzumab In Vivo

The effects of B2B3-1 when co-administered with trastuzumab in vivo is studied in female athymic nude mice (nu/nu) from Charles River Labs, 5-6 weeks of age, using a BT-474-M3 xenograft model. Mice receive a subcutaneous estrogen-releasing implant in the opposite flank (0.72 mg pellet, 60 day, slow-release, Innovative Research of America, Sarasota, Fla.) 24 h prior to the injection of $20 \times 10^6$ human BT-474-M3 cells in PBS. Dosing is initiated when tumor growth is established (tumor volumes of approximately 400 mm$^3$). Tumors are measured twice a week using digital calipers. Tumor volume is calculated using the formula: $\pi/6 \times (W^2 \times L)$, where W is the short diameter and L is the long diameter. Ten mice per group are administered B2B3-1 at 3 mg/kg or 10 mg/kg q3d, trastuzumab at 1 mg/kg or 0.1 mg/kg q7d or the combination of both drugs for the course of the study by intraperitoneal injection. All combinations of B2B3-1 and trastuzumab (10 mg/kg B2B3-1+1 mg/kg trastuzumab, 10 mg/kg B2B3-1+0.1 mg/kg trastuzumab, 3 mg/kg B2B3-1+1 mg/kg trastuzumab, 3 mg/kg B2B3-1+0.1 mg/kg trastuzumab) are dosed as for the corresponding single agent.

Figure 36:
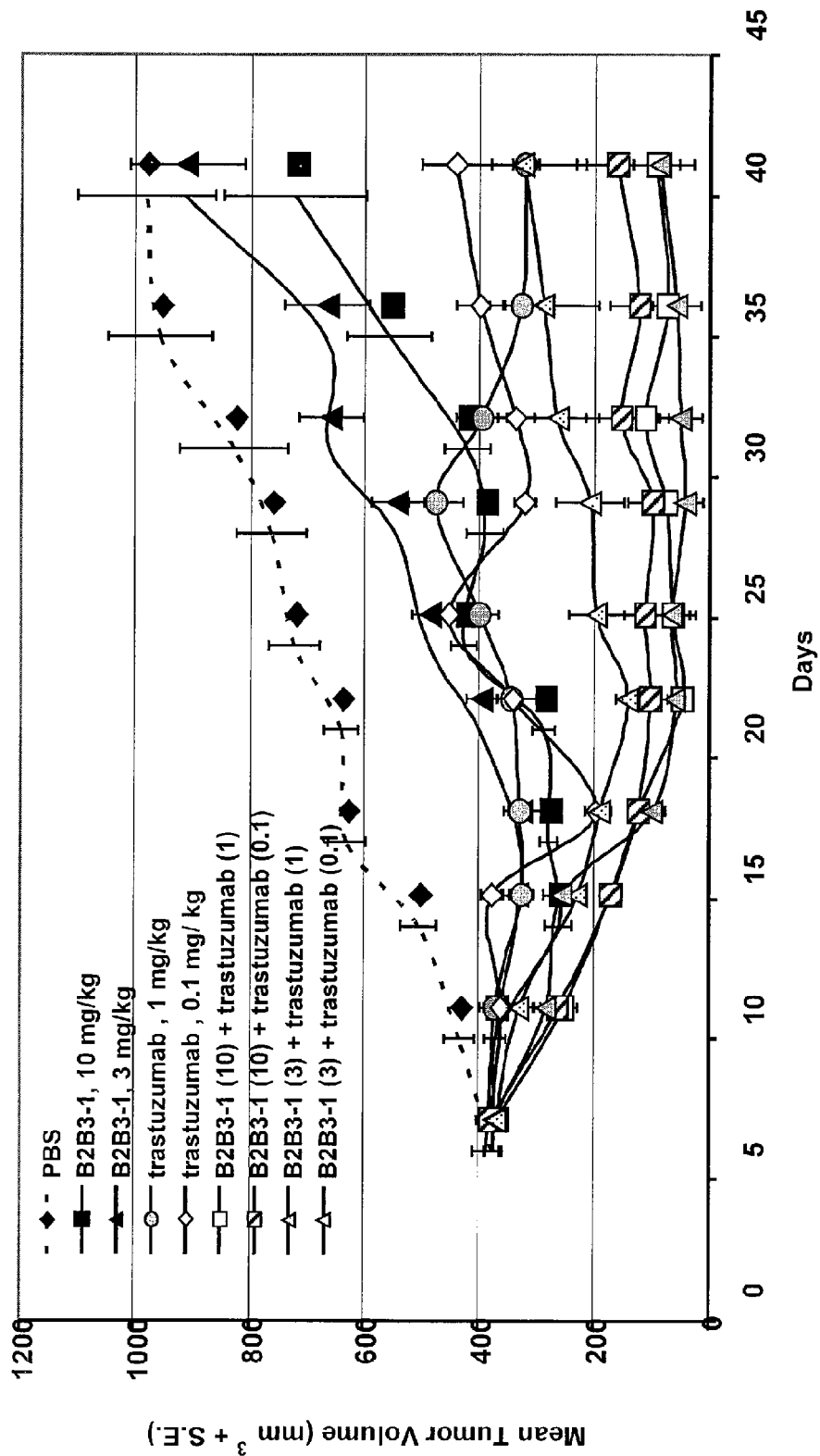
FIG. 36 show the results of the in vivo tumor xenograft experiments detailed in Example 44. "Days" on the X-axis indicates days post tumor implant. Error bars for each data point represent the response for at least two independent xenografts.
Figure 37:
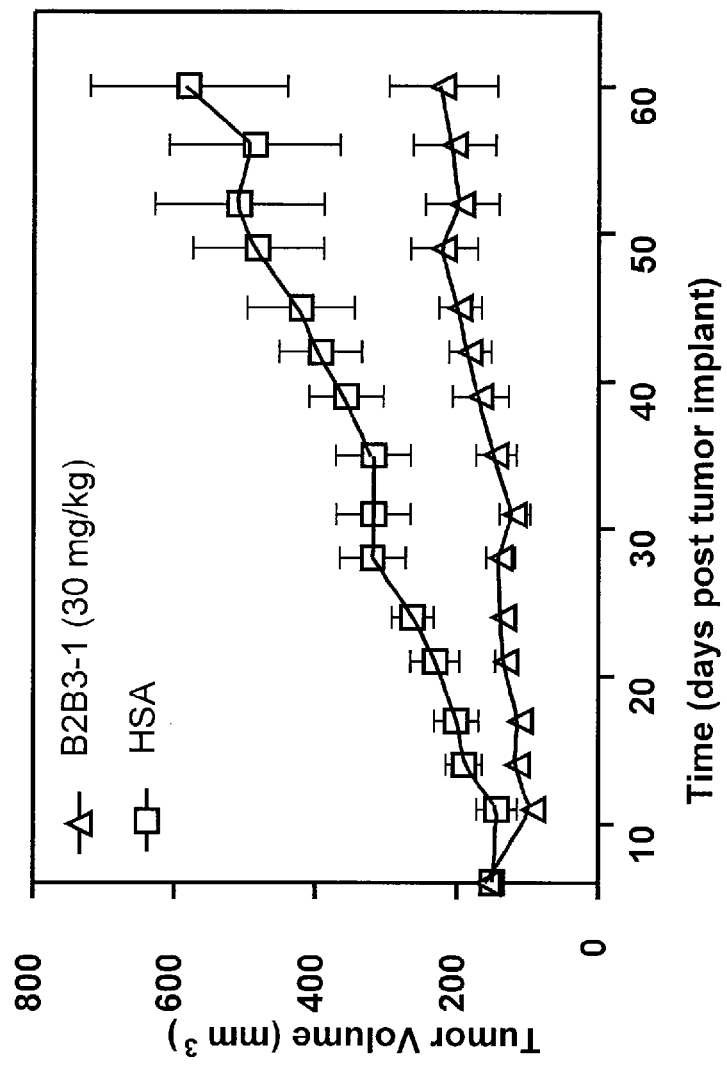
FIG. 37 shows data obtained from a xenograft model essentially as described in Example 44, except that the tumor cells used are N-87 gastric tumor cells which may be obtained from the US National Cancer Institute.
Figure 38:
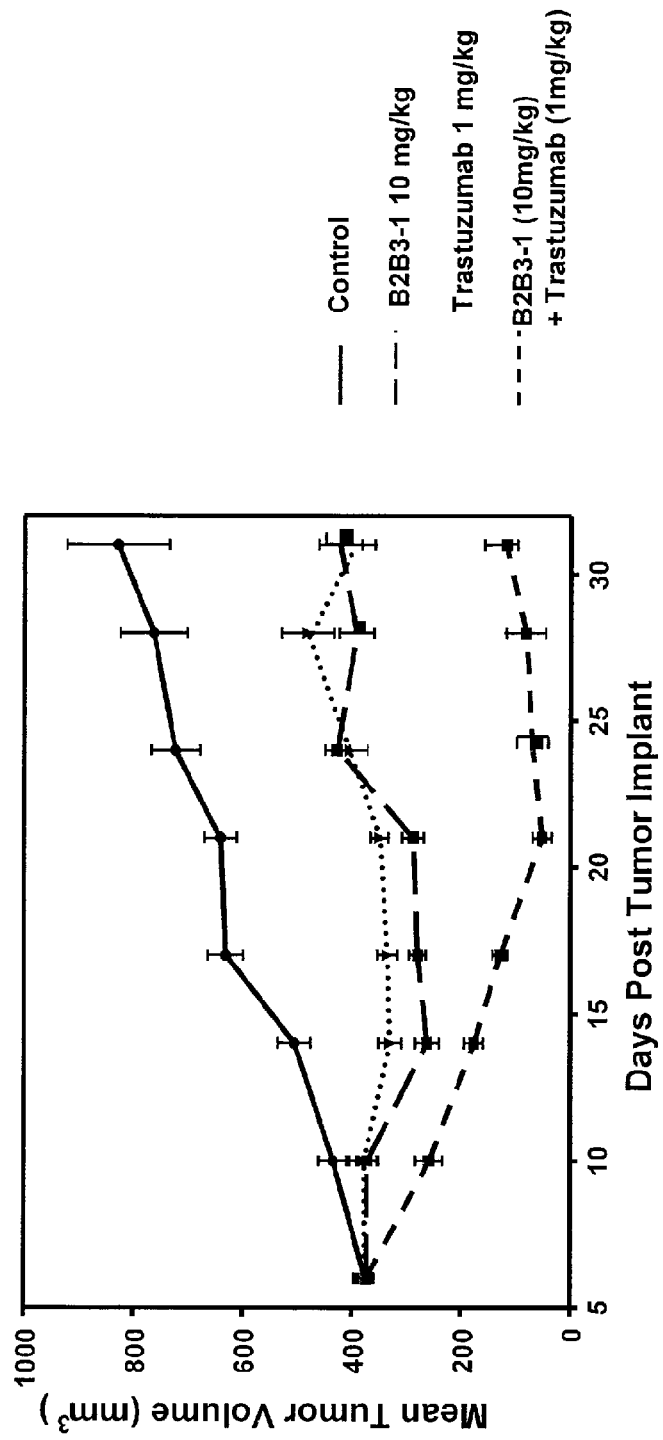
FIG. 38 shows a subset of the data presented in FIG. 36.

As shown in FIG. 36, substantially greater efficacy was seen for all the combinations compared to the single agents and significant efficacy was observed from at least as early as day 20 onward for the combination groups dosed with 10 mg/kg B2B3-1 and both doses of trastuzumab and with 3 mg/kg B2B3-1 and 1 mg/kg trastuzumab. In the 10 mg/kg B2B3-1+1 mg/kg trastuzumab combination group, 5 out of the 10 mice had completely regressed tumors compared to 0 out of 10 for the single agent groups given equivalent doses as the combination. In the 3 mg/kg B2B3-1+1 mg/kg trastuzumab combination group, 7 out of 10 mice had completely regressed tumors compared to 0 out of 10 for the single agent groups given equivalent doses as the combination. These results indicate that B2B3-1 does not compete with trastuzumab for binding to ErbB2 (HER2). These results also demonstrate that treatment with a combination of at least 3 mg/kg of B2B3-1 and at least 0.1 mg/kg trastuzumab is more effective than treatment with 3 mg/kg or 10 mg/kg of B2B3-1 alone or with 0.1 mg/kg or 1 mg/kg of trastuzumab alone. In particular, the combination of at least 3 mg/kg of B2B3-1 and 1 mg/kg trastuzumab induces essentially complete tumor regression in at least about 50% of nude mice carrying human breast tumor cell xenografts, while the same concentrations of either B2B3-1 or trastuzumab alone do not provide complete regression in even 10% of such mice.

Further provided are specific embodiments of the HSA linkers, peptide connectors, and binding moieties discussed above. Table 6, below, lists ten HSA linker conjugates with varying ErbB2-specific or ErbB3-specific binding moieties, as well as peptide connectors, at the amino and carboxy termini of an HSA linker.

Those skilled in the art will recognize, and will be able to ascertain and implement using no more than routine experimentation, many equivalents of the specific embodiments described herein. Such equivalents are intended to be encompassed by the following claims. Any combinations of the embodiments disclosed in the dependent claims are contemplated to be within the scope of the disclosure.

The disclosure of each and every US and foreign patent and pending patent application and publication referred to herein is hereby incorporated herein by reference in its entirety.

TABLE 6

| HSA Linker Conjugate | Amino Terminal Binding Moiety | N-Terminal Connector | HSA | C-Terminal Connector | Carboxy Terminal Binding Moiety |
|---|---|---|---|---|---|
| B2B3-1 (SEQ ID NO: 16) | H3 (SEQ ID NO: 26) | AAS | mHSA (SEQ ID NO: 1) | AAAL (SEQ ID NO: 5) | B1D2 (SEQ ID NO: 27) |
| B2B3-2 (SEQ ID NO: 17) | A5 (SEQ ID NO: 28) | AAS | mHSA (SEQ ID NO: 1) | AAAL (SEQ ID NO: 5) | B1D2 (SEQ ID NO: 27) |
| B2B3-3 (SEQ ID NO: 18) | A5 (SEQ ID NO: 28) | AAS | mHSA (SEQ ID NO: 1) | AAAL (SEQ ID NO: 5) | F5B6H2 (SEQ ID NO: 32) |

TABLE 6-continued

| HSA Linker Conjugate | Amino Terminal Binding Moiety | N-Terminal Connector | HSA | C-Terminal Connector | Carboxy Terminal Binding Moiety |
|---|---|---|---|---|---|
| B2B3-4 (SEQ ID NO: 19) | A5 (SEQ ID NO: 28) | AAS | mHSA (SEQ ID NO: 1) | AAAL (SEQ ID NO: 5) | ML3.9 (SEQ ID NO: 29) |
| B2B3-5 (SEQ ID NO: 20) | B12 (SEQ ID NO: 30) | AAS | mHSA (SEQ ID NO: 1) | AAAL (SEQ ID NO: 5) | B1D2 (SEQ ID NO: 27) |
| B2B3-6 (SEQ ID NO: 21) | B12 (SEQ ID NO: 30) | AAS | mHSA (SEQ ID NO: 1) | AAAL (SEQ ID NO: 5) | F5B6H2 (SEQ ID NO: 32) |
| B2B3-7 (SEQ ID NO: 22) | F4 (SEQ ID NO: 31) | AAS | mHSA (SEQ ID NO: 1) | AAAL (SEQ ID NO: 5) | B1D2 (SEQ ID NO: 27) |
| B2B3-8 (SEQ ID NO: 23) | F4 (SEQ ID NO: 31) | AAS | mHSA (SEQ ID NO: 1) | AAAL (SEQ ID NO: 5) | F5B6H2 (SEQ ID NO: 32) |
| B2B3-9 (SEQ ID NO: 24) | H3 (SEQ ID NO: 26) | AAS | HSA (SEQ ID NO: 3) | AAAL (SEQ ID NO: 5) | B1D2 (SEQ ID NO: 27) |
| B2B3-10 (SEQ ID NO: 25) | H3 (SEQ ID NO: 26) | AAS | mHSA (SEQ ID NO: 1) | AAAL (SEQ ID NO: 5) | F5B6H2 (SEQ ID NO: 32) |

APPENDIX 1

Sequences, Sequence Annotations and Sequence Alignments

SEQ ID NO: 60
pMP9043
gtgccgacgatagagcagacctcgctaaatatatctgcgagaatcaggat
tccattagctctaagctgaaagaatgttgcgagaagcccctcctggaaaa
gagtcattgtatcgccgaggtggaaaacgacgagatgccagcagatctgc
catcactcgctgccgactttgtggaatccaaagatgtctgcaagaattac
gcagaggctaaagacgtgttcctggggatgtttctgtatgagtacgcccg
gcgtcaccccgattatagcgtcgtgctcctgctccgactggcaaagacct
acgaaacaactctggagaaatgttgcgctgccgcagaccctcatgaatgt
tatgctaaggtgttcgatgagtttaagccactcgtcgaagagccccagaa
cctgattaaacagaattgcgaactgttcgagcagctcggtgaatacaagt
ttcagaacgccctgctcgtgcgttataccaaaaaggtccctcaggtgtct
acaccaactctggtggaggtcagtaggaatctgggcaaagtgggatcaaa
gtgttgcaaacaccccgaggcaaagagaatgccttgtgctgaagattacc
tctccgtcgtgctgaaccagctctgcgtgctgcatgaaaagaccccagtc
agcgatcgggtgacaaaatgttgcaccgaatctctggtcaatcgccgacc
ctgtttcagtgccctcgaagtggacgaaacttatgtgcctaaggagtttc
aggctgaaacattcaccttcacgccgatatctgcactctgtccgagaaa
gaaaggcagattaagaaacagacagcactggtcgagctcgtgaagcataa
accaaaggctaccaaggagcagctgaaagccgtcatggacgatttcgcag
cttttgtggaaaagtgttgcaaagccgacgataaggagacttgtttcgca
gaagaggggaaaagctcgtggctgccagccaggcagctctgggtctggc
cgcagctctgcaggtgcagctcgtccagagcggcgctgaggtgaagaagc
caggcgagtcccctgaagatcctcctgtaagggctccggctacagcttcacc -continued
tcctactggatcgcttgggtgaggcagatgccaggaaagggactggagta
catgggcctgatctaccctggcgactccgacaccaagtactccccatcct
tccaggccaggtgaccatcagcgtggacaagtccgtgtctaccgcctac
ctgcaatggtcctccctgaagccttctgactctgccgtgtacttttgtgc
ccggcacgatgtgggctactgcaccgaccggacatgtgccaagtggcccg
agtggctgggagtgtggggacagggaacactggtgacagtgagttctggc
ggtggcggctcttccggcggtggctctggtggcggcggatctcagagcgt
gctgacacagccacctagcgtgtccgctgcccctggccagaaggtgacaa
tcagctgctccggcagctcttccaacatcggcaacaactacgtgtcttgg
tatcagcagctgccccggaacagctccaaaactgctgatctatgaccacac
caatcggcctgccggcgtgccagatcggttctctggctctaagagcggca
cctccgccagcctggctatctctggcttcagatctgaggatgaggctgac
tactattgtgcctcctgggactacaccctgtctggctgggtgttcggcgg
tggcaccaagctgacagtcctgggatgatgactcgagtctagagggcccg
tttaaacccgctgatcagcctcgactgtgccttctagttgccagccatct
gttgtttgcccctcccccgtgccttccttgaccctggaaggtgccactcc
cactgtcctttcctaataaaatgaggaaattgcatcgcattgtctgagta
ggtgtcattctattctggggggtggggtggggcaggacagcaagggggag
gattgggaagacaatagcaggcatgctggggatgcggtgggctctatggc
ttctgaggcggaaagaaccagctggggctctaggggggtatccccacgcgc
cctgtagcggcgcattaagcgcggcgggtgtggtggttacgcgcagcgtg
accgctacacttgccagcgccctagcgcccgctcctttcgctttcttccc
ttcctttctcgccacgttcgccggctttccccgtcaagctctaaatcggg
ggctccctttagggttccgatttagtgctttacggcacctcgaccccaaa
aacttgattagggtgatggttcacgtacctagaagttcctattccgaagt
tcctattctctagaaagtataggaacttccttggccaaaaagcctgaact -continued caccgcgacgtctgtcgagaagtttctgatcgaaaagttcgacagcgtct
ccgacctgatgcagctctcggagggcgaagaatctcgtgctttcagcttc
gatgtaggagggcgtggatatgtcctgcgggtaaatagctgcgccgatgg
tttctacaaagatcgttatgtttatcggcactttgcatcggccgcgctcc
cgattccggaagtgcttgacattggggaattcagcgagagcctgacctat
tgcatctcccgccgtgcacagggtgtcacgttgcaagacctgcctgaaac
cgaactgcccgctgttctgcagccggtcgcggaggccatggatgcgatcg
ctgcggccgatcttagccagacgagcgggttcggcccattcggaccgcaa
ggaatcggtcaatacactacatggcgtgatttcatatgcgcgattgctga
tcccatgtgtatcactggcaaactgtgatggacgacaccgtcagtgcgt
ccgtcgcgcaggctctcgatgagctgatgctttgggccgaggactgcccc
gaagtccggcacctcgtgcacgcggatttcggctccaacaatgtcctgac
ggacaatggccgcataacagcggtcattgactggagcgaggcgatgttcg
gggattcccaatacgaggtcgccaacatcttcttctggaggccgtggttg
gcttgtatggagcagcagacgcgctacttcgagcggaggcatccggagct
tgcaggatcgccgcggctccgggcgtatatgctccgcattggtcttgacc
aactctatcagagcttggttgacggcaatttcgatgatgcagcttgggcg
cagggtcgatgcgacgcaatcgtccgatccggagccgggactgtcgggcg
tacacaaatcgcccgcagaagcgcggccgtctggaccgatggctgtgtag
aagtactcgccgatagtggaaaccgacgccccagcactcgtccgagggca
aaggaatagcacgtactacgagatttcgattccaccgccgccttctatga
aaggtttgggcttcggaatcgttttccgggacgccggctggatgatcctcc
agcgcggggatctcatgctggagttcttcgcccaccccaacttgtttatt
gcagcttataatggttacaaataaagcaatagcatcacaaatttcacaaa
taaagcattttttttcactgcattctagttgtggtttgtccaaactcatca
atgtatcttatcatgtctgtataccgtcgacctctagctagagcttggcg
taatcatggtcatagctgtttcctgtgtgaaattgttatccgctcacaat
tccacacaacatacgagccggaagcataaagtgtaaagcctggggtgcct
aatgagtgagctaactcacattaattgcgttgcgctcactgcccgctttc
cagtcgggaaacctgtcgtgccagctgcattaatgaatcggccaacgcgc
ggggagaggcggtttgcgtattgggcgctcttccgcttcctcgctcactg
actcgctgcgctcggtcgttcggctgcggcgagcggtatcagctcactca
aaggcggtaatacggttatccacagaatcaggggataacgcaggaaagaa
catgtgagcaaaaggccagcaaaaggccaggaaccgtaaaaaggccgcgt
tgctggcgtttttccataggctccgcccccctgacgagcatcacaaaaat
cgacgctcaagtcagaggtggcgaaacccgacaggactataaagatacca
ggcgtttccccctggaagctccctcgtgcgctctcctgttccgaccctgc
cgcttaccggatacctgtccgcctttctcccttcgggaagcgtggcgctt
tctcatagctcacgctgtaggtatctcagttcggtgtaggtcgttcgctc
caagctgggctgtgtgcacgaaccccccgttcagcccgaccgctgcgcct
tatccggtaactatcgtcttgagtccaacccggtaagacacgacttatcg -continued ccactggcagcagccactggtaacaggattagcagagcgaggtatgtagg
cggtgctacagagttcttgaagtggtggcctaactacggctacactagaa
ggacagtatttggtatctgcgctctgctgaagccagttaccttcggaaaa
agagttggtagctcttgatccggcaaacaaaccaccgctggtagcggtgg
tttttttgtttgcaagcagcagattacgcgcagaaaaaaaggatctcaag
aagatcctttgatcttttctacggggtctgacgctcagtggaacgaaaac
tcacgttaagggattttggtcatgagattatcaaaaaggatcttcaccta
gatccttttaaattaaaaatgaagttttaaatcaatctaaagtatatatg
agtaaacttggtctgacagttaccaatgcttaatcagtgaggcacctatc
tcagcgatctgtctatttcgttcatccatagttgcctgactccccgtcgt
gtagataactacgatacgggagggcttaccatctggccccagtgctgcaa
tgataccgcgagacccacgctcaccggctccagatttatcagcaataaac
cagccagccggaagggccgagcgcagaagtggtcctgcaactttatccgc
ctccatccagtctattaattgttgccgggaagctagagtaagtagttcgc
cagttaatagtttgcgcaacgttgttgccattgctacaggcatcgtggtg
tcacgctcgtcgtttggtatggcttcattcagctccggttcccaacgatc
aaggcgagttacatgatccccatgttgtgcaaaaaagcggttagctcct
tcggtcctccgatcgttgtcagaagtaagttggccgcagtgttatcactc
atggttatggcagcactgcataattctcttactgtcatgccatccgtaag
atgcttttctgtgactggtgagtactcaaccaagtcattctgagaatagt
gtatgcggcgaccgagttgctcttgcccggcgtcaatacggataatacc
gcgccacatagcagaactttaaaagtgctcatcattggaaaacgttcttc
ggggcgaaaactctcaaggatcttaccgctgttgagatccagttcgatgt
aacccactcgtgcacccaactgatcttcagcatcttttactttcaccagc
gtttctgggtgagcaaaaacaggaaggcaaaatgccgcaaaaaagggaat
aagggcgacacggaaatgttgaatactcatactcttcctttttcaatatt
attgaagcatttatcagggttattgtctcatgagcggatacatatttgaa
tgtatttagaaaaataaacaaataggggttccgcgcacatttccccgaaa
agtgccacctgacgtcgacggatcgggagatctcccgatcccctatggtg
cactctcagtacaatctgctctgatgccgcatagttaagccagtatctgc
tccctgcttgtgtgttggaggtcgctgagtagtgcgcgagcaaaatttaa
gctacaacaaggcaaggcttgaccgacaattgcatgaagaatctgcttag
ggttaggcgttttgcgctgcttcgcgatgtacgggccagatatacgcgtt
gacattgattattgactagttattaatagtaatcaattacggggtcatta
gttcatagcccatatatggagttccgcgttacataacttacggtaaatgg
cccgcctggctgaccgcccaacgacccccgcccattgacgtcaataatga
cgtatgttcccatagtaacgccaataggactttccattgacgtcaatgg
gtggagtatttacggtaaactgcccacttggcagtacatcaagtgtatca
tatgccaagtacgccccctattgacgtcaatgacggtaaatggcccgcct
ggcattatgcccagtacatgaccttatgggactttcctacttggcagtac
atctacgtattagtcatcgctattaccatggtgatgcggttttggcagta -continued

```
catcaatgggcgtggatagcggtttgactcacggggatttccaagtctcc
acccccattgacgtcaatgggagtttgttttggcaccaaaatcaacgggac
tttccaaaatgtcgtaacaactccgccccattgacgcaaatgggcggtag
gcgtgtacggtgggaggtctatataagcagagctctctggctaactagag
aacccactgcttactggcttatcgaaattaatacgactcactatagggag
acccaagcttctagaattcgctgtctgcgagggccagctgttgggtgag
tactccctctcaaaagcgggcatgacttctgcgctaagattgtcagtttc
caaaaacgaggaggatttgatattcacctggcccgcggtgatgcctttga
gggtggccgcgtccatctggtcagaaaagacaatcttttttgttgtcaagc
ttgaggtgtggcaggcttgagatctggccatacacttgagtgacaatgac
atccactttgcctttctctccacaggtgtccactcccaggtccaactgca
gatatccagcacagtggcggccgccaccatgggctggtctctgatcctgc
tgttcctggtggccgtggccacgcgtgtgctgtcccaggtgcagctgcag
gagtctggcggcggactggtgaagcctggcggctccctgcggctgtcctg
cgccgcctccggcttcaccttctcctcctactggatgtcctgggtgcggc
aggcccctggcaagggcctggagtgggtggccaacatcaaccgggacggc
tccgcctcctactacgtggactccgtgaagggccggttcaccatctcccg
ggacgacgccaagaactccctgtacctgcagatgaactccctgcgggccg
aggacaccgccgtgtactactgcgccagggaccggggcgtggctacttc
gacctgtggggcaggggcaccctggtgaccgtgtcctccgctagtactgg
cggcggaggatctggcggaggagggagcggggcggtggatcccagtccg
ccctgacccagcctgcctccgtgtccggctccctggccagtccatcacc
atcagctgcaccggcacctcctccgacgtgggcggctacaacttcgtgtc
ctggtatcagcagcaccccggcaaggcccctaagctgatgatctacgacg
tgtccgaccggccttccggcgtgtccgacaggttctccggctccaagtcc
ggcaacaccgcctccctgatcatcagcggcctgcaggcagacgacgaggc
cgactactactgctcctcctacggctcctcctccacccacgtgatctttg
gcggcggaacaaaggtgaccgtgctggcgccgcctccgacgctcacaag
agcgaagtggcacataggttcaaagatctgggcgaagagaactttaaggc
cctcgtcctgatcgctttcgcacagtacctccagcagtctccctttgaag
atcacgtgaaactggtcaatgaggtgaccgaatttgccaagacatgcgtg
gctgatgagagtgcagaaaactgtgacaaatcactgcatactctctttgg
agataagctgtgcaccgtcgccacactcagagagacttatggggaaatgg
ctgactgttgcgcaaaacaggagcctgaacggaatgagtgtttcctccag
cacaaggatgacaacccaaatctgccccgcctcgtgcgacctgaggtcga
tgtgatgtgcaccgcctttcatgacaacgaagagacattcctgaagaaat
acctgtatgaaattgctcgtaggcaccatactttatgccccgagctc
ctgttctttgcaaagagatacaaagctgccttcactgaatgttgccaggc
agctgataaggccatgtctcctgcctaaactggacgagctccgggatg
aaggtaaggcttccagcgccaaacagcgcctgaagtgcgcttctctccag
aagtttggcgagcgagcattcaaagcctgggctgtggccgtctcagtca
```

-continued
```
gaggtttccaaaggcagaatttgctgaggtctcaaaactggtgaccgacc
tcacaaaggtccatactgagtgttgccacggagatctgctggaat
```

SEQ ID NO: 67
QVQLVQSGAEVKKPGESLKISCKGSGYSFTSYWIAWVRQMPGKGLEYMGL
IYPGDSDTKYSPSFQGQVTISVDKSVSTAYLQWSSLKPSDSAVYFCARAD
VGYCTDRTCAKAPAWLGVWGQGTLVTVSSGGGGSSGGGSGGGGSQSVLTQ
PPSVSAAPGQKVTISCSGSSSNIGNNYVSWYQQLPGTAPKLLIYDHTNRP
AGVPDRFSGSKSGTSASLAISGFRSEDEADYYCASWDYTLSGWVFGGGTK
LTVLGAASDAHKSEVAHRFKDLGEENFKALVLIAFAQYLQQSPFEDHVKL
VNEVTEFAKTCVADESAENCDKSLHTLFGDKLCTVATLRETYGEMADCCA
KQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKAS
SAKQRLKCASLQKFGERAFKAWAVARLSQRFPKAEFAEVSKLVTDLTKVH
TECCHGDLLECADDRADLAKYICENQDSISSKLKECCEKPLLEKSHCIAE
VENDEMPADLPSLAADFVESKDVCKNYAEAKDVFLGMFLYEYARRHPDYS
VVLLLRLAKTYETTLEKCCAAADPHECYAKVFDEFKPLVEEPQNLIKQNC
ELFEQLGEYKFQNALLVRYTKKVPQVSTPTLVEVSRNLGKVGSKCCKHPE
AKRMPCAEDYLSVVLNQLCVLHEKTPVSDRVTKCCTESLVNRRPCFSALE
VDETYVPKEFQAETFTFHADICTLSEKERQIKKQTALVELVKHKPKATKE
QLKAVMDDFAAFVEKCCKADDKETCFAEEGKKLVAASQAALGLAAALQVQ
LVQSGAEVKKPGESLKISCKGSGYSFTSYWIAWVRQMPGKGLEYMGLIYP
GDSDTKYSPSFQGQVTISVDKSVSTAYLQWSSLKPSDSAVYFCARHDVGY
CTDRTCAKWPEWLGVWGQGTLVTVSSGGGGSSGGGSGGGGSQSVLTQPPS
VSAAPGQKVTISCSGSSSNIGNNYVSWYQQLPGTAPKLLIYDHTNRPAGV
PDRFSGSKSGTSASLAISGFRSEDEADYYCASWDYTLSGWVFGGGTKLTV
LG

SEQ ID NO: 68
QVQLQESGGGLVKPGGSLRLSCAASGFTFSSYWMSWVRQAPGKGLEWVAN
INRDGSASYYVDSVKGRFTISRDDAKNSLYLQMNSLRAEDTAVYYCARDR
GVGYFDLWGRGTLVTVSSASTGGGGSGGGGSGGGGSQSALTQPASVSGSP
GQSITISCTGTSSDVGGYNFVSWYQQHPGKAPKLMIYDVSDRPSGVSDRF
SGSKSGNTASLIISGLQADDEADYYCSSYGSSSTHVIFGGGTKVTVLGAA
SDAHKSEVAHRFKDLGEENFKALVLIAFAQYLQQSPFEDHVKLVNEVTEF
AKTCVADESAENCDKSLHTLFGDKLCTVATLRETYGEMADCCAKQEPERN
ECFLQHKDDNPNLPRLVRPEVDVMCTAFHDNEETFLKKYLYEIARRHPYF
YAPELLFFAKRYKAAFTECCQAADKAACLLPKLDELRDEGKASSAKQRLK
CASLQKFGERAFKAWAVARLSQRFPKAEFAEVSKLVTDLTKVHTECCHGD
LLECADDRADLAKYICENQDSISSKLKECCEKPLLEKSHCIAEVENDEMP
ADLPSLAADFVESKDVCKNYAEAKDVFLGMFLYEYARRHPDYSVVLLLRL
AKTYETTLEKCCAAADPHECYAKVFDEFKPLVEEPQNLIKQNCELFEQLG
EYKFQNALLVRYTKKVPQVSTPTLVEVSRNLGKVGSKCCKHPEAKRMPCA
EDYLSVVLNQLCVLHEKTPVSDRVTKCCTESLVNRRPCFSALEVDETYVP
```

-continued
```
KEFQAETFTFHADICTLSEKERQIKKQTALVELVKHKPKATKEQLKAVMD

DFAAFVEKCCKADDKETCFAEEGKKLVAASQAALGLAAALQVQLVQSGAE

VKKPGESLKISCKGSYSFTSYWIAWVRQMPGKGLEYMGLIYPGDSDTKY    5

SPSFQGQVTISVDKSVSTAYLQWSSLKPSDSAVYFCARADVGYCTDRTCA

KAPAWLGVWGQGTLVTVSSGGGGSSGGGSGGGSQSVLTQPPSVSAAPGQ

KVTISCSGSSSNIGNNYVSWYQQLPGTAPKLLIYDHTNRPAGVPDRFSGS   10

KSGTSASLAISGFRSEDEADYYCASWDYTLSGWVFGGGTKLTVLG
```

| B2B3-1 (H3-mHSA-B1D2) |
|---|

```
   1 QVQLQESGGG LVKPGGSLRL SCAASGFTFS SYWMSWVRQA PGKGLEWVAN
  51 INRDGSASYY VDSVKGRFTI SRDDAKNSLY LQMNSLRAED TAVYYCARDR
 101 GVGYFDLWGR GTLVTVSSAS TGGGGSGGGG SGGGGSQSAL TQPASVSGSP
 151 GQSITISCTG TSSDVGGYNF VSWYQQHPGL APKLMIYDVS DRPSGVSDRF
 201 SGSKSGNTAS LIISGLQADD EADYYCSSYG SSSTHVIFGG GTKVTVLGAA
 251 SDAHKSEVAH RFKDLGEENF KALVLIAFAQ YLQQSPFEDH VKLVNEVTEF
 301 AKTCVADESA ENCDKSLHTL FGDKLCTVAT LRETYGEMAD CCAKQEPERN
 351 ECFLQHKDDN PNLPRLVRPE VDVMCTAFHD NEETFLKKYL YEIARRHPYF
 401 YAPELLFFAK RYKAAFTECC QAADKAACLL PKLDELRDEG KASSAKQRLK
 451 CASLQKFGER AFKAWAVARL SQRFPKAEFA EVSKLVTDLT KVHTECCHGD
 501 LLECADDRAD LAKYICENQD SISSKLKECC EKPLLEKSHC IAEVENDEMP
 551 ADLPSLAADF VESKDVCKNY AEAKDVFLGM FLYEYARRHP DYSVVLLLRL
 601 AKTYETTLEK CCAAADPHEC YAKVFDEFKP LVEEPQNLIK QNCELFEQLG
 651 EYKFQNALLV RYTKKVPQVS TPTLVEVSRN LGKVGSKCCK HPEAKRMPCA
 701 EDYLSVVLNQ LCVLHEKTPV SDRVTKCCTE SLVNRRPCFS ALEVDETYVP
 751 KEFQAETFTF HADICTLSEK ERQIKKQTAL VELVKHKPKA TKEQLKAVMD
 801 DFAAFVEKCC KADDKETCFA EEGKKLVAAS QAALGLAAAL QVQLVQSGAE
 851 VKKPGESLKI SCKGSGYSFT SYWIAWVRQM PGKGLEYMGL IYPGDSDTKY
 901 SPSFQGQVTI SVDKSVSTAY LQWSSLKPSD SAVYFCARHD VGYCTDRTCA
 951 KWPEWLGVWG QGTLVTVSSG GGGSSGGGSG GGGSQSVLTQ PPSVSAAPGQ
1001 KVTISCSGSS SNIGNNYVSW YQQLPGTAPK LLIYDHTNRP AGVPDRFSGS
1051 KSGTSASLAI SGFRSEDEAD YYCASWDYTL SGWVFGGGTK LTVLG
```

CDR loops are highlighted within H3 (underlined 1-248 with bold italicized CDRs) and B1D2 (underlined 841-1095 with bold italicized CDRs). Connectors to modified HSA are dotted-underlined.

Sequence Alignments for Various HSA Linker Conjugates Comprising B2B3 and mHSA

```
                              1                                           45
A5-mHSA-ML3.9    (1) QVQLVQSGGGLVKPGGSLRLSCAASGFSFNTYDMNWVRQAPGKGL
A5-mHSA-B1D2     (1) QVQLVQSGGGLVKPGGSLRLSCAASGFSFNTYDMNWVRQAPGKGL
A5-mHSA-F5B6H2   (1) QVQLVQSGGGLVKPGGSLRLSCAASGFSFNTYDMNWVRQAPGKGL
B12-mHSA-B1D2    (1) QVQLVQSGGGLVQPGRSLRLSCAASGFTFDDYAMHWVRQAPGKGL
B12-mHSA-F5B6H2  (1) QVQLVQSGGGLVQPGRSLRLSCAASGFTFDDYAMHWVRQAPGKGL
F4-mHSA-B1D2     (1) QVQLQESGGGLVKPGGSLRLSCAASGFTFSSYAMSWVRQAPGKGL
F4-mHSA-F5B6H2   (1) QVQLQESGGGLVKPGGSLRLSCAASGFTFSSYAMSWVRQAPGKGL
```

-continued

```
                        46                                          90
A5-mHSA-ML3.9    (46)   EWVSSISSSSSYIYYADSVKGRFTISRDNAKNSLYLQMNSLRAED
A5-mHSA-B1D2     (46)   EWVSSISSSSSYIYYADSVKGRFTISRDNAKNSLYLQMNSLRAED
A5-mHSA-F5B6H2   (46)   EWVSSISSSSSYIYYADSVKGRFTISRDNAKNSLYLQMNSLRAED
B12-mHSA-B1D2    (46)   EWVSGISWNSGSIGYADSVKGRFTISRDNAKNSLYLQMNSLRPED
B12-mHSA-F5B6H2  (46)   EWVSGISWNSGSIGYADSVKGRFTISRDNAKNSLYLQMNSLRPED
F4-mHSA-B1D2     (46)   EWVSTISGSGGSTYYADSVKGRFTISRDNSKNTLYLQMNSLRAED
F4-mHSA-F5B6H2   (46)   EWVSTISGSGGSTYYADSVKGRFTISRDNSKNTLYLQMNSLRAED
H3-mHSA-B1D2     (46)   EWVANINRDGSASYYVDSVKGRFTISRDDAKNSLYLQMNSLRAED
H3-mHSA-F5B6H2   (46)   EWVANINRDGSASYYVDSVKGRFTISRDDAKNSLYLQMNSLRAED 91                                         135
A5-mHSA-ML3.9    (91)   TAVYYCARDG---VATTPFDYWGQGTLVTVS---SGGGGSGGGGS
A5-mHSA-B1D2     (91)   TAVYYCARDG---VATTPFDYWGQGTLVTVS---SGGGGSGGGGS
A5-mHSA-F5B6H2   (91)   TAVYYCARDG---VATTPFDYWGQGTLVTVS---SGGGGSGGGGS
B12-mHSA-B1D2    (91)   TAVYYCARDLGAKQWLEGFDYWGQGTLVTVSSASTGGGGSGGGGS
B12-mHSA-F5B6H2  (91)   TAVYYCARDLGAKQWLEGFDYWGQGTLVTVSSASTGGGGSGGGGS
F4-mHSA-B1D2     (91)   TAVYYCAKGYSSSWSEVASGYWGQGTLVTVSSASTGGGGSGGGGS
F4-mHSA-F5B6H2   (91)   TAVYYCAKGYSSSWSEVASGYWGQGTLVTVSSASTGGGGSGGGGS
H3-mHSA-B1D2     (91)   TAVYYCARDR----GVGYFDLWGRGTLVTVSSASTGGGGSGGGGS
H3-mHSA-F5B6H2   (91)   TAVYYCARDR----GVGYFDLWGRGTLVTVSSASTGGGGSGGGGS 136                                        180
A5-mHSA-ML3.9    (130)  GGGGSQSVLTQPPS-VSGAPGQRVTISCTGSSSNIGAGYDVHWYQ
A5-mHSA-B1D2     (130)  GGGGSQSVLTQPPS-VSGAPGQRVTISCTGSSSNIGAGYDVHWYQ
A5-mHSA-F5B6H2   (130)  GGGGSQSVLTQPPS-VSGAPGQRVTISCTGSSSNIGAGYDVHWYQ
B12-mHSA-B1D2    (136)  GGGGSSYELTQDPA-VSVALGQTVRITCQGDSLRS---YYASWYQ
B12-mHSA-F5B6H2  (136)  GGGGSSYELTQDPA-VSVALGQTVRITCQGDSLRS---YYASWYQ
F4-mHSA-B1D2     (136)  GGGGSAIVMTQSPSSLSASVGDRVTITCRASQGIR---NDLGWYQ
F4-mHSA-F5B6H2   (136)  GGGGSAIVMTQSPSSLSASVGDRVTITCRASQGIR---NDLGWYQ
H3-mHSA-B1D2     (132)  GGGGSQSALTQPAS-VSGSPGQSITISCTGTSSDVGGYNFVSWYQ
H3-mHSA-F5B6H2   (132)  GGGGSQSALTQPAS-VSGSPGQSITISCTGTSSDVGGYNFVSWYQ 181                                        225
A5-mHSA-ML3.9    (174)  QLPGTAPKLLIYGNSNRPSGVPDRFSGSKSGTSASLAITGLQAED
A5-mHSA-B1D2     (174)  QLPGTAPKLLIYGNSNRPSGVPDRFSGSKSGTSASLAITGLQAED
A5-mHSA-F5B6H2   (174)  QLPGTAPKLLIYGNSNRPSGVPDRFSGSKSGTSASLAITGLQAED
B12-mHSA-B1D2    (177)  QKPGQAPVLVIYGKNNRPSGIPDRFSGSTSGNSASLTITGAQAED
B12-mHSA-F5B6H2  (177)  QKPGQAPVLVIYGKNNRPSGIPDRFSGSTSGNSASLTITGAQAED
F4-mHSA-B1D2     (178)  QKAGKAPKLLIYAASSLQSGVPSRFSGSGSGTDFTLTISSLQPDD
F4-mHSA-F5B6H2   (178)  QKAGKAPKLLIYAASSLQSGVPSRFSGSGSGTDFTLTISSLQPDD
H3-mHSA-B1D2     (176)  QHPGKAPKLMIYDVSDRPSGVSDRFSGSKSGNTASLIISGLQADD
H3-mHSA-F5B6H2   (176)  QHPGKAPKLMIYDVSDRPSGVSDRFSGSKSGNTASLIISGLQADD 226                                        270
A5-mHSA-ML3.9    (219)  EADYYCQSYDSS-LSALFGGGTKLTVLG-AASDAHKSEVAHRFKD
A5-mHSA-B1D2     (219)  EADYYCQSYDSS-LSALFGGGTKLTVLG-AASDAHKSEVAHRFKD
A5-mHSA-F5B6H2   (219)  EADYYCQSYDSS-LSALFGGGTKLTVLG-AASDAHKSEVAHRFKD
B12-mHSA-B1D2    (222)  EADYYCNSRDSSGNHWVEGGGTKVTVLG-AASDAHKSEVAHRFKD
B12-mHSA-F5B6H2  (222)  EADYYCNSRDSSGNHWVFGGGTKVTVLG-AASDAHKSEVAHRFKD
F4-mHSA-B1D2     (223)  FATYFCQQAHSF--PPTFGGGTKVEIKRGAASDAHKSEVAHRFKD
F4-mHSA-F5B6H2   (223)  FATYFCQQAHSF--PPTFGGGTKVEIKRGAASDAHKSEVAHRFKD
H3-mHSA-B1D2     (221)  EADYYCSBYGSSSTHVIFGGGTKVTVLG-AASDAHKSEVAHRFKD
H3-mHSA-F5B6H2   (221)  EADYYCSSYGSSSTHVIFGGGTKVTVLG-AASDAHKSEVAHRFKD 271                                        315
A5-mHSA-ML3.9    (262)  LGEENFKALVLIAFAQYLQQSPFEDHVKLVNEVTEFAKTCVADES
A5-mHSA-B1D2     (262)  LGEENFKALVLIAFAQYLQQSPFEDHVKLVNEVTEFAKTCVADES
A5-mHSA-F5B6H2   (262)  LGEENFKALVLIAFAQYLQQSPFEDHVKLVNEVTEFAKTCVADES
B12-mHSA-B1D2    (266)  LGEENFKALVLIAFAQYLQQSPFEDHVKLVNEVTEFAKTCVADES
B12-mHSA-F5B6H2  (266)  LGEENFKALVLIAFAQYLQQSPFEDHVKLVNEVTEFAKTCVADES
F4-mHSA-B1D2     (266)  LGEENFKALVLIAFAQYLQQSPFEDHVKLVNEVTEFAKTCVADES
F4-mHSA-F5B6H2   (266)  LGEENFKALVLIAFAQYLQQSPFEDHVKLVNEVTEFAKTCVADES
H3-mHSA-B1D2     (265)  LGEENFKALVLIAFAQYLQQSPFEDHVKLVNEVTEFAKTCVADES
H3-mHSA-F5B6H2   (265)  LGEENFKALVLIAFAQYLQQSPFEDHVKLVNEVTEFAKTCVADES 316                                        360
A5-mHSA-ML3.9    (307)  AENCDKSLHTLFGDKLCTVATLRETYGEMADCCAKQEPERNECFL
A5-mHSA-B1D2     (307)  AENCDKSLHTLFGDKLCTVATLRETYGEMADCCAKQEPERNECFL
A5-mHSA-F5B6H2   (307)  AENCDKSLHTLFGDKLCTVATLRETYGEMADCCAKQEPERNECFL
B12-mHSA-B1D2    (311)  AENCDKSLHTLFGDKLCTVATLRETYGEMADCCAKQEPERNECFL
B12-mHSA-F5B6H2  (311)  AENCDKSLHTLFGDKLCTVATLRETYGEMADCCAKQEPERNECFL
F4-mHSA-B1D2     (311)  AENCDKSLHTLFGDKLCTVATLRETYGEMADCCAKQEPERNECFL
F4-mHSA-F5B6H2   (311)  AENCDKSLHTLFGDKLCTVATLRETYGEMADCCAKQEPERNECFL
H3-mHSA-B1D2     (310)  AENCDKSLHTLFGDKLCTVATLRETYGEMADCCAKQEPERNECFL
H3-mHSA-F5B6H2   (310)  AENCDKSLHTLFGDKLCTVATLRETYGEMADCCAKQEPERNECFL
```

H3-mHSA-B1D2     (1)    QVQLQESGGGLVKPGGSLRLSCAASGFTFSSYWMSWVRQAPGKGL
H3-mHSA-F5B6H2   (1)    QVQLQESGGGLVKPGGSLRLSCAASGFTFSSYWMSWVRQAPGKGL

-continued

```
                         361                                           405
A5-mHSA-ML3.9    (352) QHKDDNPNLPRLVRPEVDVMCTAFHDNEETFLKKYLYEIARRHPY
A5-mHSA-B1D2     (352) QHKDDNPNLPRLVRPEVDVMCTAFHDNEETFLKKYLYEIARRHPY
A5-mHSA-F5B6H2   (352) QHKDDNPNLPRLVRPEVDVMCTAFHDNEETFLKKYLYEIARRHPY
B12-mHSA-B1D2    (356) QHKDDNPNLPRLVRPEVDVMCTAFHDNEETFLKKYLYEIARRHPY
B12-mHSA-F5B6H2  (356) QHKDDNPNLPRLVRPEVDVMCTAFHDNEETFLKKYLYEIARRHPY
F4-mHSA-B1D2     (356) QHKDDNPNLPRLVRPEVDVMCTAFHDNEETFLKKYLYEIARRHPY
F4-mHSA-F5B6H2   (356) QHKDDNPNLPRLVRPEVDVMCTAFHDNEETFLKKYLYEIARRHPY
H3-mHSA-B1D2     (355) QHKDDNPNLPRLVRPEVDVMCTAFHDNEETFLKKYLYEIARRHPY
H3-m3SA-F5B6H2   (355) QHKDDNPNLPRLVRPEVDVMCTAFHDNEETFLKKYLYEIARRHPY 406                                           450
A5-mHSA-ML3.9    (397) FYAPELLFFAKRYKAAFTECCQAADKAACLLPKLDELRDEGKASS
A5-mHSA-B1D2     (397) FYAPELLFFAKRYKAAFTECCQAADKAACLLPKLDELRDEGKASS
A5-mHSA-F5B6H2   (397) FYAPELLFFAKRYKAAFTECCQAADKAACLLPKLDELRDEGKASS
B12-mHSA-B1D2    (401) FYAPELLFFAKRYKAAFTECCQAADKAACLLPKLDELRDEGKASS
B12-mHSA-F5B6H2  (401) FYAPELLFFAKRYKAAFTECCQAADKAACLLPKLDELRDEGKASS
F4-mHSA-B1D2     (401) FYAPELLFFAKRYKAAFTECCQAADKAACLLPKLDELRDEGKASS
F4-mHSA-F5B6H2   (401) FYAPELLFFAKRYKAAFTECCQAADKAACLLPKLDELRDEGKASS
H3-mHSA-B1D2     (400) FYAPELLFFAKRYKAAFTECCQAADKAACLLPKLDELRDEGKASS
H3-mHSA-F5B6H2   (400) FYAPELLFFAKRYKAAFTECCQAADKAACLLPKLDELRDEGKASS 451                                           495
A5-mHSA-ML3.9    (442) AKQRLKCASLQKFGERAFKAWAVARLSQRFPKAEFAEVSKLVTDL
A5-mHSA-B1D2     (442) AKQRLKCASLQKFGERAFKAWAVARLSQRFPKAEFAEVSKLVTDL
A5-mHSA-F5B6H2   (442) AKQRLKCASLQKFGERAFKAWAVARLSQRFPKAEFAEVSKLVTDL
B12-mHSA-B1D2    (446) AKQRLKCASLQKFGERAFKAWAVARLSQRFPKAEFAEVSKLVTDL
B12-mHSA-F5B6H2  (446) AKQRLKCASLQKFGERAFKAWAVARLSQRFPKAEFAEVSKLVTDL
F4-mHSA-B1D2     (446) AKQRLKCASLQKFGERAFKAWAVARLSQRFPKAEFAEVSKLVTDL
F4-mHSA-F5B6H2   (446) AKQRLKCASLQKFGERAFKAWAVARLSQRFPKAEFAEVSKLVTDL
H3-mHSA-B1D2     (445) AKQRLKCASLQKFGERAFKAWAVARLSQRFPKAEFAEVSKLVTDL
H3-mHSA-F5B6H2   (445) AKQRLKCASLQKFGERAFKAWAVARLSQRFPKAEFAEVSKLVTDL 496                                           540
A5-mHSA-ML3.9    (487) TKVHTECCHGDLLECADDRADLAKYICENQDSISSKLKECCEKPL
A5-mHSA-B1D2     (487) TKVHTECCHGDLLECADDRADLAKYICENQDSISSKLKECCEKPL
A5-mHSA-F5B6H2   (487) TKVHTECCHGDLLECADDRADLAKYTCENQDSISSKLKECCEKPL
B12-mHSA-B1D2    (491) TKVHTECCHGDLLECADDRADLAKYICENQDSISSKLKECCEKPL
B12-mHSA-F5B6H2  (491) TKVHTECCHGDLLECADDRADLAKYICENQDSISSKLKECCEKPL
F4-mHSA-B1D2     (491) TKVHTECCHGDLLECADDRADLAKYICENQDSISSKLKECCEKPL
F4-mHSA-F5B6H2   (491) TKVHTECCHGDLLECADDRADLAKYICENQDSISSKLKECCEKPL
H3-mHSA-B1D2     (490) TKVHTECCHGDLLECADDRADLAKYICENQDSISSKLKECCEKPL
H3-mHSA-F586H2   (490) TKVHTECCHGDLLECADDRADLAKYICENQDSISSKLKECCEKPL 541                                           585
A5-mHSA-ML3.9    (532) LEKSHCIAEVENDEMPADLPSLAADFVESKDVCKNYAEAKDVFLG
A5-mHSA-B1D2     (532) LEKSHCIAEVENDEMPADLPSLAADFVESKDVCKNYAEAKDVFLG
A5-mHSA-F5B6H2   (532) LEKSHCIAEVENDEMPADLPSLAADFVESKDVCKNYAEAKDVFLG
B12-mHSA-B1D2    (536) LEKSHCIAEVENDEMPADLPSLAADFVESKDVCKNYAEAKDVFLG
B12-mHSA-F5B6H2  (536) LEKSHCIAEVENDEMPADLPSLAADFVESKDVCKNYAEAKDVFLG
F4-mHSA-B1D2     (536) LEKSHCIAEVENDEMPADLPSLAADFVESKDVCKNYAEAKDVFLG
F4-mHSA-F5B6H2   (536) LEKSHCIAEVENDEMPADLPSLAADFVESKDVCKNYAEAKDVFLG
H3-mHSA-B1D2     (535) LEKSHCIAEVENDEMPADLPSLAADFVESKDVCKNYAEAKDVFLG
H3-mHSA-F5B6H2   (535) LEKSHCIAEVENDEMPADLPSLAADFVESKDVCKNYAEAKDVFLG 586                                           630
A5-mHSA-ML3.9    (577) MFLYEYARRHPDYSVVLLLRLAKTYETTLEKCCAAADPHECYAKV
A5-mHSA-B1D2     (577) MFLYEYARRHPDYSVVLLLRLAKTYETTLEKCCAAADPHECYAKV
A5-mHSA-F5B6H2   (577) MFLYEYARRHPDYSVVLLLRLAKTYETTLEKCCAAADPHECYAKV
B12-mHSA-B1D2    (581) MFLYEYARRHPDYSVVLLLRLAKTYETTLEKCCAAADPHECYAKV
B12-mHSA-F586H2  (581) MFLYEYARRHPDYSVVLLLRLAKTYETTLEKCCAAADPHECYAKV
F4-mHSA-B1D2     (581) MFLYEYARRHPDYSVVLLLRLAKTYETTLEKCCAAADPHECYAKV
F4-mHSA-F5B6H2   (581) MFLYEYARRHPDYSVVLLLRLAKTYETTLEKCCAAADPHECYAKV
H3-mHSA-B1D2     (580) MFLYEYARRHPDYSVVLLLRLAKTYETTLEKCCAAADPHECYAKV
H3-mHSA-F5B6H2   (580) MFLYEYARRHPDYSVVLLLRLAKTYETTLEKCCAAADPHECYAKV 631                                           675
A5-mHSA-ML3.9    (622) FDEFKPLVEEPQNLIKQNCELFEQLGEYKFQNALLVRYTKKVPQV
A5-mHSA-B1D2     (622) FDEFKPLVEEPQNLIKQNCELFEQLGEYKFQNALLVRYTKKVPQV
A5-mHSA-F5B6H2   (622) FDEFKPLVEEPQNLIKQNCELFEQLGEYKFQNALLVRYTKKVPQV
B12-mHSA-B1D2    (626) FDEFKPLVEEPQNLIKQNCELFEQLGEYKFQNALLVRYTKKVPQV
B12-mHSA-F5B6H2  (626) FDEFKPLVEEPQNLIKQNCELFEQLGEYKFQNALLVRYTKKVPQV
F4-mHSA-B1D2     (626) FDEFKPLVEEPQNLIKQNCELFEQLGEYKFQNALLVRYTKKVPQV
F4-mHSA-F5B6H2   (626) FDEFKPLVEEPQNLIKQNCELFEQLGEYKFQNALLVRYTKKVPQV
H3-mHSA-B1D2     (625) FDEFKPLVEEPQNLIKQNCELFEQLGEYKFQNALLVRYTKKVPQV
H3-mHSA-F5B6H2   (625) FDEFKPLVEEPQNLIKQNCELFEQLGEYKFQNALLVRYTKKVPQV 676                                           720
A5-mHSA-ML3.9    (667) STPTLVEVSRNLGKVGSKCCKHPEAKRMPCAEDYLSVVLNQLCVL
A5-mHSA-B1D2     (667) STPTLVEVSRNLGKVGSKCCKHPEAKRMPCAEDYLSVVLNQLCVL
A5-mHSA-F5B6H2   (667) STPTLVEVSRNLGKVGSKCCKHPEAKRMPCAEDYLSVVLNQLCVL
```

```
                            -continued
B12-mHSA-B1D2    (671) STPTLVEVSRNLGKVGSKCCKHPEAKRMPCAEDYLSVVLNQLCVL
B12-mHSA-F5B6H2  (671) STPTLVEVSRNLGKVGSKCCKHPEAKRMPCAEDYLSVVLNQLCVL
F4-mHSA-B1D2     (671) STPTLVEVSRNLGKVGSKCCKHPEAKRMPCAEDYLSVVLNQLCVL
F4-mHSA-F5B6H2   (671) STPTLVEVSRNLGKVGSKCCKHPEAKRMPCAEDYLSVVLNQLCVL
H3-mHSA-B1D2     (670) STPTLVEVSRNLGKVGSKCCKHPEAKRMPCAEDYLSVVLNQLCVL
H3-mHSA-F5B6H2   (670) STPTLVEVSRNLGKVGSKCCKHPEAKRMPCAEDYLSVVLNQLCVL 721                                         765
A5-mHSA-ML3.9    (712) HEKTPVSDRVTKCCTESLVNRRPCFSALEVDETYVPKEFQAETFT
A5-mHSA-B1D2     (712) HEKTPVSDRVTKCCTESLVNRRPCFSALEVDETYVPKEFQAETFT
A5-mHSA-F5B6H2   (712) HEKTPVSDRVTKCCTESLVNRRPCFSALEVDETYVPKEFQAETFT
B12-mHSA-B1D2    (716) HEKTPVSDRVTKCCTESLVNRRPCFSALEVDETYVPKEFQAETFT
B12-mHSA-F5B6H2  (716) HEKTPVSDRVTKCCTESLVNRRPCFSALEVDETYVPKEFQAETFT
F4-mHSA-B1D2     (716) HEKTPVSDRVTKCCTESLVNRRPCFSALEVDETYVPKEFQAETFT
F4-mHSA-F5B6H2   (716) HEKTPVSDRVTKCCTESLVNRRPCFSALEVDETYVPKEFQAETFT
H3-mHSA-B1D2     (715) HEKTPVSDRVTKCCTESLVNRRPCFSALEVDETYVPKEFQAETFT
H3-mHSA-F5B6H2   (715) HEKTPVSDRVTKCCTESLVNRRPCFSALEVDETYVPKEFQAETFT 766                                         810
A5-mHSA-ML3.9    (757) FHADICTLSEKERQIKKQTALVELVKHKPKATKEQLKAVMDDFAA
A5-mHSA-B1D2     (757) FHADICTLSEKERQIKKQTALVELVKHKPKATKEQLKAVMDDFAA
A5-mHSA-F5B6H2   (757) FHADICTLSEKERQIKKQTALVELVKHKPKATKEQLKAVMDDFAA
B12-mHSA-B1D2    (761) FHADICTLSEKERQIKKQTALVELVKHKPKATKEQLKAVMDDFAA
B12-mHSA-F5B6H2  (761) FHADICTLSEKERQIKKQTALVELVKHKPKATKEQLKAVMDDFAA
F4-mHSA-B1D2     (761) FHADICTLSEKERQIKKQTALVELVKHKPKATKEQLKAVMDDFAA
F4-mHSA-F5B6H2   (761) FHADICTLSEKERQIKKQTALVELVKHKPKATKEQLKAVMDDFAA
H3-mHSA-B1D2     (760) FHADICTLSEKERQIKKQTALVELVKHKPKATKEQLKAVMDDFAA
H3-mHSA-F5B6H2   (760) FHADICTLSEKERQIKKQTALVELVKHKPKATKEQLKAVMDDFAA 811                                         855
A5-mHSA-ML3.9    (802) FVEKCCKADDKETCFAEEGKKLVAASQAALGLAAALQVQLVQSGA
A5-mHSA-B1D2     (802) FVEKCCKADDKETCFAEEGKKLVAASQAALGLAAALQVQLVQSGA
A5-mHSA-F5B6H2   (802) FVEKCCKADDKETCFAEEGKKLVAASQAALGLAAALQVQLVESGG
B12-mHSA-B1D2    (806) FVEKCCKADDKETCFAEEGKKLVAASQAALGLAAALQVQLVQSGA
B12-mHSA-F5B6H2  (806) FVEKCCKADDKETCFAEEGKKLVAASQAALGLAAALQVQLVESGG
F4-mHSA-B1D2     (806) FVEKCCKADDKETCFAEEGKKLVAASQAALGLAAALQVQLVQSGA
F4-mHSA-F5B6H2   (806) FVEKCCKADDKETCFAEEGKKLVAASQAALGLAAALQVQLVESGG
H3-mHSA-B1D2     (805) FVEKCCKADDKETCFAEEGKKLVAASQAALGLAAALQVQLVQSGA
H3-mHSA-F5B6H2   (805) FVEKCCKADDKETCFAEEGKKLVAASQAALGLAAALQVQLVESGG 856                                         900
A5-mHSA-ML3.9    (847) EVKKPCESLKISCKGSGYSFTSYWIAWVRQMPGKGLEYMGLIYPG
A5-mHSA-B1D2     (847) EVKKPGESLKISCKGSGYSFTSYWIAWVRQMPGKGLEYMGLIYPG
A5-mHSA-F5B6H2   (847) GLVQPGGSLRLSCAASGFTFRSYAMSWVRQAPGKGLEWVSAISGR
B12-mHSA-B1D2    (851) EVKKPGESLKISCKGSGYSFTSYWIAWVRQMPGKGLEYMGLIYPG
B12-mHSA-F5B6H2  (851) GLVQPGGSLRLSCAASGFTFRSYAMSWVRQAPGKGLEWVSAISGR
F4-mHSA-B1D2     (851) EVKKPGESLKISCKGSGYSFTSYWIAWVRQMPGKGLEYMGLIYPG
F4-mHSA-F5B6H2   (851) GLVQPGGSLRLSCAASGFTFRSYAMSWVRQAPGKGLEWVSAISGR
H3-mHSA-B1D2     (850) EVKKPGESLKISCKGSGYSFTSYWIAWVRQMPGKGLEYMGLIYPG
H3-mHSA-F5B6H2   (850) GLVQPGGSLRLSCAASGFTFRSYAMSWVRQAPGKGLEWVSAISGR 901                                         945
A5-mHSA-ML3.9    (892) DSDTKYSPSFQGQVTISVDKSVSTAYLQWSSLKPSDSAVYFCARH
A5-mHSA-B1D2     (892) DSDTKYSPSFQGQVTISVDKSVSTAYLQWSSLKPSDSAVYFCARH
A5-mHSA-F5B6H2   (892) GDNTYYADSVKGRFTISRDNSKNTLYLQMNSLRAEDTAVYYCAKM
B12-mHSA-B1D2    (896) DSDTKYSPSFQGQVTISVDKSVSTAYLQWSSLKPSDSAVYFCARH
B12-mHSA-F5B6H2  (896) GDNTYYADSVKGRFTISRDNSKNTLYLQMNSLRAEDTAVYYCAKM
F4-mHSA-B1D2     (896) DSDTKYSPSFQGQVTISVDKSVSTAYLQWSSLKPSDSAVYFCARH
F4-mHSA-F5B6H2   (896) GDNTYYADSVKGRFTISRDNSKNTLYLQMNSLRAEDTAVYYCAKM
H3-mHSA-B1D2     (895) DSDTKYSPSFQGQVTISVDKSVSTAYLQWSSLKPSDSAVYFCARH
H3-mHSA-F5B6H2   (895) GDNTYYADSVKGRFTISRDNSKNTLYLQMNSLRAEDTAVYYCAKM 946                                         990
A5-mHSA-ML3.9    (937) DVGYCSSSNCAKWPEYFQHWGQGTLVTVSSGGGGSSGGGGSGGGGS
A5-mHSA-B1D2     (937) DVGYCTDRTCAKWPEWLGVWGQGTLVTVSSGGGGSSGGGSGGGGS
A5-mHSA-F5B6H2   (937) TSNAVG---------FDYWGQGTLVTVSSGGGGSGGGGSGGGGSG
B12-mHSA-B1D2    (941) DVGYCTDRTCAKWPEWLGVWGQGTLVTVSSGGGGSSGGGSGGGGS
B12-mHSA-F5B6H2  (941) TSNAVG---------FDYWGQGTLVTVSSGGGGSGGGGSGGGGSG
F4-mHSA-B1D2     (941) DVGYCTDRTCAKWPEWLGVWGQGTLVTVSSGGGGSSGGGSGGGGS
F4-mHSA-F5B6H2   (941) TS---------NAVGFDYWGQGTLVTVSSGGGGSGGGGSGGGGSG
H3-mHSA-B1D2     (940) DVGYCTDRTCAKWPEWLGVWGQGTLVTVSSGGGGSSGGGSGGGGS
H3-mHSA-F5B6H2   (940) TSNAVG---------FDYWGQGTLVTVSSGGGGSGGGGSGGGGSG 991                                        1035
A5-mHSA-ML3.9    (982) QSVLTQPPSVSAAPGQKVTISCSGSSSNIGNNY-VSWYQQLPGTA
A5-mHSA-B1D2     (982) QSVLTQPPSVSAAPGQKVTISCSGSSSNIGNNY-VSWYQQLPGTA
A5-mHSA-F5B6H2   (972) QSVLTQPPSVSGAPGQRVTISCTGRHSNIGLGYGVHWYQQLPGTA
B12-mHSA-B1D2    (986) QSVLTQPPSVSAAPGQKVTISCSGSSSNIGNNY-VSWYQQLPGTA
B12-mHSA-F5B6H2  (976) QSVLTQPPSVSGAPGQRVTISCTGRHSNIGLGYGVHWYQQLPGTA
F4-mHSA-B1D2     (986) QSVLTQPPSVSAAPGQKVTISCSGSSSNIGNNY-VSWYQQLPGTA
F4-mHSA-F5B6H2   (976) QSVLTQPPSVSGAPGQRVTISCTGRHSNIGLGYGVHWYQQLPGTA
```

```
                        -continued
H3-mHSA-B1D2      (985) QSVLTQPPSVSAAPGQKVTISCSGSSSNIGNNY-VSWYQQLPGTA
H3-mHSA-F5B6H2    (975) QSVLTQPPSVSGAPGQRVTISCTGRHSNIGLGYGVHWYQQLPGTA 1036                                      1080
A5-mHSA-ML3.9    (1026) PKLLIYDHTNRPAGVPDRFSGSKSGTSASLAISGFRSEDEADYYC
A5-mHSA-B1D2     (1026) PKLLIYDHTNRPAGVPDRFSGSKSGTSASLAISGFRSEDEADYYC
A5-mHSA-F5B6H2   (1017) PKLLIYGNTNRPSGVPDRFSGFKSGTSASLAITGLQAEDEADYYC
B12-mHSA-B1D2    (1030) PKLLIYDHTNRPAGVPDRFSGSKSGTSASLAISGFRSEDEADYYC
B12-mHSA-F5B6H2  (1021) PKLLIYGNTNRPSGVPDRFSGFKSGTSASLAITGLQAEDEADYYC
F4-mHSA-B1D2     (1030) PKLLIYDHTNRPAGVPDRFSGSKSGTSASLAISGFRSEDEADYYC
F4-mHSA-F5B6H2   (1021) PKLLIYGNTNRPSGVPDRFSGFKSGTSASLAITGLQAEDEADYYC
H3-mHSA-B1D2     (1029) PKLLIYDHTNRPAGVPDRFSGSKSGTSASLAISGFRSEDEADYYC
H3-mHSA-F5B6H2   (1020) PKLLIYGNTNRPSGVPDRFSGFKSGTSASLAITGLQAEDEADYYC 1081          1104
A5-mHSA-ML3.9    (1071) ASWDYTLSGWVFGGGTKLTVLG--
A5-mHSA-B1D2     (1071) ASWDYTLSGWVFGGGTKLTVLG--
A5-mHSA-F5B6H2   (1062) QSYDRRTPGWVFGGGTKLTVLG--
B12-mHSA-B1D2    (1075) ASWDYTLSGWVFGGGTKLTVLG--
```

APPENDIX 2

Anticancer Agents

| Anticancer agents for combination with B2B3-1 | Brand Name(s) | Manufacturer/Proprietor |
|---|---|---|
| Anti-IGF1R Antibodies | | |
| AMG 479 (fully humanized mAb) | | Amgen |
| IMCA12 (fully humanized mAb) | | ImClone |
| NSC-742460 | | Dyax |
| 19D12 (fully humanized mAb) | | |
| CP751-871 (fully humanized mAb) | | Pfizer |
| H7C10 (humanized mAb) | | |
| alphaIR3 (mouse) | | |
| scFV/FC (mouse/human chimera) | | |
| EM/164 (mouse) | | |
| MK-0646, F50035 | | Pierre Fabre Medicament, Merck |
| Small Molecules Targeting IGF1R | | |
| NVP-AEW541 | | Novartis |
| BMS-536,924 (1H-benzoimidazol-2-yl)-1H-pyridin-2-one) | | Bristol-Myers Squibb |
| BMS-554,417 | | Bristol-Myers Squibb |
| Cycloligan | | |
| TAE226 | | |
| PQ401 | | |
| Anti-EGFR Monoclonal Antibodies | | |
| INCB7839 | | Incyte |
| Bevacizumab | Avastin ® | Genentech |
| Cetuximab | Erbitux ® | IMCLONE |
| mAb 806 | | |
| Matuzumab (EMD72000) | | |
| Nimotuzumab (TheraCIM) | | |
| Panitumumab | Vectibix ® | Amgen |
| Anti-ErbB3 Therapeutics | — | — |
| U3-1287/AMG888 | | U3 Pharma/Amgen |
| MM-121 | | Merrimack Pharmaceuticals |
| Anti-ErbB2 Therapeutics | — | — |
| trastuzumab | Herceptin ® | Genentech |
| HKI-272 - neratinib | | Wyeth |
| KOS-953 - tanespimycin | | Kosan Biosciences |
| Her/ErbB Dimerization Inhibitors | | |
| 2C4, R1273 - Pertuzumab | , Omnitarg ® | Genentech, Roche |
| Small Molecules Targeting EGFR | | |
| CI-1033 (PD 183805) | | Pzifer, Inc. |
| EKB-569 | | |
| Gefitinib | IRESSA ™ | AstraZeneca |
| Lapatinib (GW572016) | | GlaxoSmithKline |
| Lapatinib Ditosylate | Tykerb ® | SmithKline Beecham |

| | | |
|---|---|---|
| Erlotinib HCl (OSI-774) | Tarceva ® | OSI Pharms |
| PD158780 | | |
| PKI-166 | | Novartis |
| Tyrphostin AG 1478 (4-(3-Chloroanillino)-6,7-dimethoxyquinazoline) | | |
| Anti-cmet Antibody Therapies | | |
| AVEO (AV299) | | AVEO |
| AMG102 | | Amgen |
| 5D5 (OA-5D5) | | Genentech |
| Small Molecules Targeting cmet | | |
| PHA665752 | | |
| ARQ-650RP | | ArQule |
| ARQ 197 | | ArQule |
| Alkylating Agents | | |
| BCNU→ 1,3-bis t2-chloroethyl)-nitrosourea | | |
| Bendamustine | | |
| Busulfan | Myleran | GlaxoSmithKline |
| Carboplatin | Paraplatin | Bristol-Myers Squibb |
| Carboquone | | |
| Carmustine | | |
| CCNU→ 1,-(2-chloroethyl)-3-cyclohexyl-1-nitrosourea (methyl CCNU) | | |
| Chlorambucil | Leukeran ® | Smithkline Beecham |
| Chlormethine | | |
| Cisplatin (Cisplatinum, CDDP) | Platinol | Bristol-Myers |
| | Cytoxan | Bristol-Myers Squibb |
| Cyclophosphamide | Neosar | Teva Parenteral |
| Dacarbazine (DTIC) | | |
| Fotemustine | | |
| Hexamethylmelamine (Altretamine, HMM) | Hexalen ® | MGI Pharma, Inc. |
| Ifosfamide | Mitoxana ® | ASTA Medica |
| Lomustine | | |
| Mannosulfan | | |
| Melphalan | Alkeran ® | GlaxoSmithKline |
| Nedaplatin | | |
| Nimustine | | |
| Oxaliplatin | Eloxatin ® | Sanofi-Aventis US |
| Prednimustine, | | |
| Procarbazine HCL | Matulane | Sigma-Tau Pharmaceuticals, Inc. |
| Ribonucleotide Reductase Inhibitor (RNR) | | |
| Ranimustine | | |
| Satraplatin | | |
| Semustine | | |
| Streptozocin | | |
| Temozolomide | | |
| Treosulfan | | |
| Triaziquone | | |
| Triethylene Melamine | | |
| ThioTEPA | | Bedford, Abraxis, Teva |
| Triplatin tetranitrate | | |
| Trofosfamide | | |
| Uramustine | | |
| Antimetabolites | | |
| 5-azacytidine | | |
| Flourouracil (5-FU)/Capecitabine | | |
| 6-mercaptopurine (Mercaptopurine, 6-MP) | | |
| 6-Thioguanine (6-TG) | Purinethol ® | Teva |
| Cytosine Arabinoside (Cytarabine, Ara-C) | Thioguanine ® | GlaxoSmithKline |
| Azathioprine | Azasan ® | AAIPHARMA LLC |
| Capecitabine | XELODA ® | HLR (Roche) |
| Cladribine (2-CdA, 2-chlorodeoxyadenosine) | Leustatin ® | Ortho Biotech |
| 5-Trifluoromethyl-2'-deoxyuridine | | |
| Fludarabine phosphate | Fludara ® | Bayer Health Care |
| Floxuridine (5-fluoro-2) | FUDR ® | Hospira, Inc. |
| Methotrexate sodium | Trexall | Barr |
| Pemetrexed | Alimta ® | Lilly |

-continued

| | | |
|---|---|---|
| Pentostatin | Nipent ® | Hospira, Inc. |
| Raltitrexed | Tomudex ® | AstraZeneca |
| Tegafur | | |
| Aromatose Inhibitor | | |
| | | |
| Ketoconazole | | |
| Glucocorticoids | | |
| | | |
| Dexamethasone | Decadron ® Dexasone, Diodex, Hexadrol, Maxidex | Wyeth, Inc. |
| Prednisolone | | |
| Prednisone | Deltasone, Orasone, Liquid Pred, Sterapred ® | |
| Immunotherapeutics | | |
| | | |
| Alpha interferon | | |
| Angiogenesis Inhibitor | Avastin ® | Genentech |
| IL-12→ Interleukin 12 | | |
| IL-2→ Interleukin 2 (Aldesleukin) | Proleukin ® | Chiron |
| Kinase Inhibitors | | |
| | | |
| AMG 386 | | Amgen |
| Axitinib ((AG-013736) | | Pfizer, Inc |
| Bosutinib (SKI-606) | | Wyeth |
| Brivanib alalinate (BMS-582664) | | BMS |
| Cediranib (AZD2171) | Recentin | AstraVeneca |
| Dasatinib (BMS-354825) | Sprycel ® | Bristol-Myers Squibb |
| Imatinib mesylate | Gleevec | Novartis |
| Lestaurtinib (CEP-701) | | Cephalon |
| Motesanib diphosphate (AMG-706) | | Amgen/Takeda |
| Nilotinib hydrochloride monohydrate | Tasigna ® | Novartis |
| Pazopanib HCL (GW786034) | Armala | GSK |
| Semaxanib (SU5416) | | Pharmacia, |
| Sorafenib tosylate | Nexavar ® | Bayer |
| Sunitinib malate | Sutent ® | Pfizer, Inc. |
| Vandetanib (AZD647) | Zactima | AstraZeneca |
| Vatalanib; PTK-787 | | Novartis; Bayer Schering Pharma |
| XL184, NSC718781 | | Exelixis, GSK |
| Microtubule-Targeting Agents | | |
| | | |
| Colchicine | | |
| Docetaxel | Taxotere ® | Sanofi-Aventis US |
| Ixabepilone | IXEMPRA ™ | Bristol-Myers Squibb |
| Larotaxel | | Sanofi-aventis |
| Ortataxel | | Spectrum Pharmaceuticals |
| Nanoparticle paclitaxel (ABI-007) | Abraxane ® | Abraxis BioScience, Inc. |
| Paclitaxel | Taxol ® | Bristol-Myers Squibb |
| Tesetaxel | | Genta |
| Vinblastine sulfate | Velban ® | Lilly |
| Vincristine | Oncovin ® | Lilly |
| Vindesine sulphate | Eldisine ® | Lilly |
| Vinflunine | | Pierre Fabre |
| Vinorelbine tartrate | Navelbine ® | Pierre Fabre |
| mTOR Inhibitors | | |
| | | |
| Deforolimus (AP23573, MK 8669) | | ARIAD Pharmaceuticals, Inc |
| Everolimus (RAD001, RAD001C) | Certican ®, Afinitor | Novartis |
| Sirolimus (Rapamycin) | Rapamune ® | Wyeth Pharama |
| Temsirolimus (CCI-779) | Torisel ® | Wyeth Pharama |
| Protein Synthesis Inhibitor | | |
| | | |
| L-asparaginase | Elspar ® | Merck & Co. |
| Somatostatin Analogue | | |
| | | |
| Octreotide acetate | Sandostatin ® | Novartis |
| Topoisomerase Inhibitors | | |
| | | |
| Actinomycin D | | |
| Camptothecin (CPT) | | |
| Belotecan | | |
| Daunorubicin citrate | Daunoxome ® | Gilead |
| Doxorubicin hydrochloride | Doxil ® | Alza |
| | Vepesid ® | Bristol-Myers Squibb |
| Etoposide | Etopophos | Hospira, Bedford, Teva Parenteral, Etc. |
| Irinotecan HCL (CPT-11) | Camptosar ® | Pharmacia & Upjohn |

| | | |
|---|---|---|
| Mitoxantrone HCL | Novantrone | EMD Serono |
| Rubitecan | | |
| Teniposide (VM-26) | Vumon ® | Bristol-Myers Squibb |
| Topotecan HCL | Hycamtin ® | GlaxoSmithKline |
| Chemotherapeutic Agents | | |
| Adriamycin, 5-Fluorouracil, Cytoxin, Bleomycin, Mitomycin C, Daunomycin, Carminomycin, Aminopterin, Dactinomycin, Mitomycins, Esperamicins Clofarabine, Mercaptopurine, Pentostatin, Thioguanine, Cytarabine, Decitabine, Floxuridine, Gemcitabine (Gemzar), Enocitabine, Sapacitabine | | |
| Hormonal Therapies | | |
| Abarelix | Plenaxis ™ | Amgen |
| Abiraterone acetate | CB7630 | BTG plc |
| Afimoxifene | TamoGel | Ascend Therapeutics, Inc. |
| Anastrazole | Arimidex ® | AstraZeneca |
| Aromatase inhibitor | Atamestane plus toremifene | Intarcia Therapeutics, Inc. |
| | Arzoxifene | Eli Lilly & Co. |
| Asentar; DN-101 | | Novartis; Oregon Health & Science Univ. |
| Bicalutamide | Casodex ® | AstraZeneca |
| Buserelin | Suprefact ® | Sanofi Aventis |
| Cetrorelix | Cetrotide ® | EMD Serono |
| Exemestane | Aromasin ® | Pfizer |
| Exemestane | Xtane | Natco Pharma, Ltd. |
| Fadrozole (CGS 16949A) | | |
| Flutamide | Eulexin ® | Schering |
| Flutamide | Prostacur | Laboratorios Almirall, S.A. |
| Fulvestrant | Faslodex ® | AstraZeneca |
| Goserelin acetate | Zoladex ® | AstraZeneca |
| Letrozole | Femara ® | Novartis |
| Letrozole (CGS20267) | Femara | Chugai Pharmaceutical Co., Ltd. |
| Letrozole | Estrochek | Jagsonpal Pharmaceuticals, Ltd. |
| Letrozole | Letrozole | Indchemie Health Specialities |
| Leuprolide acetate | Eligard ® | Sanofi Aventis |
| Leuprolide acetate | Leopril | VHB Life Sciences, Inc. |
| Leuprolide acetate | Lupron ®/Lupron Depot | TAP Pharma |
| Leuprolide acetate | Viador | Bayer AG |
| Megestrol acetate | Megace ® | Bristol-Myers Squibb |
| Magestrol acetate | Estradiol Valerate (Delestrogen) | Jagsonpal Pharmaceuticals, Ltd. |
| Medroxyprogesterone acetate | Veraplex | Combiphar |
| MT206 | | Medisyn Technologies, Inc. |
| Nafarelin | | |
| Nandrolone decanoate | Zestabolin | Mankind Pharma, Ltd. |
| Nilutamide | Nilandron ® | Aventis Pharmaceuticals |
| Raloxifene HCL | Evista ® | Lilly |
| Tamoxifen | Taxifen | Yung Shin Pharmaceutical |
| Tamoxifen | Tomifen | Alkem Laboratories, Ltd. |
| Tamoxifen citrate | Nolvadex | AstraZeneca |
| Tamoxifen citrate | Soltamox | EUSA Pharma, Inc. |
| Tamoxifen citrate | Tamoxifen citrate SOPHARMA | Sopharma JSCo. |
| Toremifene citrate | Fareston ® | GTX, Inc. |
| Triptorelin pamoate | Trelstar ® | Watson Labs |
| Triptorelin pamoate | Trelstar Depot | Paladin Labs, Inc. |
| Protein Kinase B (PKB) Inhibitors | | |
| Akt Inhibitor ASTEX | | Astex Therapeutics |
| Akt Inhibitors NERVIANO | | Nerviano Medical Sciences |
| AKT Kinase Inhibitor TELIK | | Telik, Inc. |
| AKT DECIPHERA | | Deciphera Pharmaceuticals, LLC |
| Perifosine (KRX0401, D-21266) | | Keryx Biopharmaceuticals, Inc., AEterna Zentaris, Inc. |
| Perifosine with Docetaxel | | Keryx Biopharmaceuticals, Inc., AEterna Zentaris, Inc. |
| Perifosine with Gemcitabine | | AEterna Zentaris, Inc. |
| Perifosine with Paclitaxel | | Keryx Biopharmaceuticals, Inc, AEterna Zentaris, Inc. |
| Protein Kinase-B inhibitor DEVELOGEN | | DeveloGen AG |
| PX316 | | Oncothyreon, Inc. |
| RX0183 | | Rexahn Pharmaceuticals, Inc. |
| RX0201 | | Rexahn Pharmaceuticals, Inc. |
| VQD002 | | VioQuest Pharmaceuticals, Inc. |
| XL418 | | Exelixis, Inc. |

-continued

| | | |
|---|---|---|
| ZEN027 | | AEterna Zentaris, Inc. |
| Phosphatidylinositol 3-Kinase (PI3K) Inhibitors | | |
| BEZ235 | | Novartis AG |
| BGT226 | | Novartis AG |
| CAL101 | | Calistoga Pharmaceuticals, Inc. |
| CHR4432 | | Chroma Therapeutics, Ltd. |
| Erk/PI3K Inhibitors ETERNA | | AEterna Zentaris, Inc. |
| GDC0941 | | Genentech Inc./Piramed Limited/Roche Holdings, Ltd. |
| Enzastaurin HCL (LY317615) | Enzastaurin | Eli Lilly |
| LY294002/Wortmannin | | |
| PI3K Inhibitors SEMAFORE | | Semafore Pharmaceuticals |
| PX866 | | Oncothyreon, Inc. |
| SF1126 | | Semafore Pharmaceuticals |
| VMD-8000 | | VM Discovery, Inc. |
| XL147 | | Exelixis, Inc. |
| XL147 with XL647 | | Exelixis, Inc. |
| XL765 | | Exelixis, Inc. |
| PI-103 | | Roche/Piramed |
| Cyclin-dependent kinase inhibitors | | |
| CYC200, r-roscovitine | Seliciclib | Cyclacel Pharma |
| NSC-649890, L86-8275, HMR-1275 | Alvocidib | NCI |
| TLr9, CD289 | | |
| IMOxine | | Merck KGaA |
| HYB2055 | | Idera |
| IMO-2055 | | Isis Pharma |
| 1018 ISS | | Dynavax Technologies/UCSF |
| PF-3512676 | | Pfizer |
| Enzyme Inhibitor | | |
| Lonafarnib (SCH66336) | Sarasar | SuperGen, U Arizona |
| Anti-TRAIL | | |
| AMG-655 | | Aeterna Zentaris, Keryx Biopharma |
| Apo2L/TRAIL, AMG951 | | Genentech, Amgen |
| Apomab (fully humanized mAb) | | Genentech |

| | | |
|---|---|---|
| Anticancer agents for combination with B2B3-1 | | |
| Other | Target | Manufacturer/Proprietor |
| Imprime PGG | | Biothera |
| CHR-2797 | AminopeptidaseM1 | Chroma Therapeutics |
| E7820, NSC 719239 | Integrin-alpha2 | Eisai |
| INCB007839 | ADAM 17, TACE | Incyte |
| CNF2024, BIIB021 | Hsp90 | Biogen Idec |
| MP470, HPK-56 | Kit/Met/Ret | Shering-Plough |
| SNDX-275/MS-275 | HDAC | Syndax |
| Zarnestra, Tipifarnib, R115777 | Ras | Janssen Pharma |
| Voloximab; Eos 200-4, M200 | alpha581 integrin | Biogen Idec; Eli Lilly/UCSF/PDL BioPharma |
| Apricoxib (TP2001) | COX-2 Inhibitor | Daiichi Sankyo; Tragara Pharma |

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All patents and patent applications mentioned in this specification are herein incorporated by reference to the same extent as if each independent patent or patent application was specifically and individually indicated to be incorporated by reference in its entirety.

SEQUENCE LISTING

<160> NUMBER OF SEQ ID NOS: 68

<210> SEQ ID NO 1
<211> LENGTH: 585
<212> TYPE: PRT
<213> ORGANISM: Artificial Sequence

```
<220> FEATURE:
<223> OTHER INFORMATION: Synthetic construct

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ser Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400
```

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Gln Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 2
<211> LENGTH: 1755
<212> TYPE: DNA
<213> ORGANISM: Artificial Sequence
<220> FEATURE:
<223> OTHER INFORMATION: Synthetic construct

<400> SEQUENCE: 2
gacgctcaca agagcgaagt ggcacatagg ttcaaagatc tgggcgaaga gaactttaag     60
gccctcgtcc tgatcgcttt cgcacagtac ctccagcagt ctcccttttga agatcacgtg    120 aaactggtca tgaggtgac cgaatttgcc aagacatgcg tggctgatga gagtgcagaa     180
aactgtgaca atcactgca tactctcttt ggagataagc tgtgcaccgt cgccacactc     240
agagagactt atgggaaat ggctgactgt tgcgcaaaac aggagcctga acggaatgag    300
tgtttcctcc agcacaagga tgacaaccca atctgccccc gctcgtgcg acctgaggtc    360 gatgtgatgt gcaccgcctt tcatgacaac gaagagacat cctgaagaa atacctgtat    420 gaaattgctc gtaggcaccc atactttat gcccccgagc tcctgttctt tgcaaagaga    480
tacaaagctg ccttcactga atgttgccag gcagctgata aggccgcatg tctcctgcct    540
aaactggacg agctccggga tgaaggtaag gcttccagcg ccaaacagcg cctgaagtgc    600
gcttctctcc agaagtttgg cgagcgagca ttcaaagcct gggctgtggc ccgtctcagt    660
cagaggtttc caaaggcaga atttgctgag gtctcaaaac tggtgaccga cctcacaaag    720
gtccatactg agtgttgcca cggagatctg ctggaatgtg ccgacgatag agcagacctc    780
gctaaatata tctgcgagaa tcaggattcc attagctcta agctgaaaga atgttgcgag    840
aagcccctcc tggaaaagag tcattgtatc gccgaggtgg aaaacgacga gatgccagca    900
gatctgccat cactcgctgc cgactttgtg aatccaaag atgtctgcaa gaattacgca    960

-continued

```
gaggctaaag acgtgttcct ggggatgttt ctgtatgagt acgcccggcg tcaccccgat    1020
tatagcgtcg tgctcctgct ccgactggca aagacctacg aaacaactct ggagaaatgt    1080
tgcgctgccg cagaccctca tgaatgttat gctaaggtgt tcgatgagtt taagccactc    1140
gtcgaagagc cccagaacct gattaaacag aattgcgaac tgttcgagca gctcggtgaa    1200
tacaagtttc agaacgccct gctcgtgcgt tataccaaaa aggtccctca ggtgtctaca    1260
ccaactctgg tggaggtcag taggaatctg ggcaaagtgg gatcaaagtg ttgcaaacac    1320
cccgaggcaa agagaatgcc ttgtgctgaa gattacctct ccgtcgtgct gaaccagctc    1380
tgcgtgctgc atgaaaagac cccagtcagc gatcgggtga caaaatgttg caccgaatct    1440
ctggtcaatc gccgaccctg tttcagtgcc ctcgaagtgg acgaaactta tgtgcctaag    1500
gagtttcagg ctgaaacatt caccttcac gccgatatct gcactctgtc cgagaaagaa    1560
aggcagatta agaaacagac agcactggtc gagctcgtga agcataaacc aaaggctacc    1620
aaggagcagc tgaaagccgt catggacgat ttcgcagctt ttgtggaaaa gtgttgcaaa    1680
gccgacgata aggagacttg tttcgcagaa gagggaaaa agctcgtggc tgccagccag    1740
gcagctctgg gtctg                                                     1755
```

<210> SEQ ID NO 3
<211> LENGTH: 585
<212> TYPE: PRT
<213> ORGANISM: Homo sapiens

<400> SEQUENCE: 3

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
```

```
            225                 230                 235                 240
Val His Thr Glu Cys Cys His Gly Asp Leu Leu Glu Cys Ala Asp Asp
                    245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
        290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
        370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
Val Gly Ser Lys Cys Cys Lys His Pro Glu Ala Lys Arg Met Pro Cys
            435                 440                 445
Ala Glu Asp Tyr Leu Ser Val Val Leu Asn Gln Leu Cys Val Leu His
        450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
        530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 4
<211> LENGTH: 1755
<212> TYPE: DNA
<213> ORGANISM: Homo sapiens

<400> SEQUENCE: 4
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
```

```
aaattagtga atgaagtaac tgaatttgca aaaacatgtg tagctgatga gtcagctgaa    180
aattgtgaca aatcacttca tacccttttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca aacctccccc gattggtgag accagaggtt    360
gatgtgatgt gcactgcttt tcatgacaat gaagagacat ttttgaaaaa atacttatat    420
gaaattgcca aagacatcc ttactttat gccccggaac tccttttctt tgctaaaagg     480
tataaagctg cttttacaga atgttgccaa gctgctgata agctgccctg cctgttgcca    540
aagctcgatg aacttcggga tgaagggaag gcttcgtctg ccaaacagag actcaaatgt    600
gccagtctcc aaaaatttgg agaaagagct ttcaaagcat gggcagtggc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag ggcggacctt    780
gccaagtata tctgtgaaaa tcaggattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aactgtgagc ttttttaagca gcttggagag   1200 tacaaattcc agaatgcgct attagttcgt tacaccaaga aagtaccccca agtgtcaact   1260 ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca caaatgctg cacagagtcc    1440 ttggtgaaca ggcgaccatg cttttcagct ctggaagtcg atgaaacata cgttcccaaa   1500
gagtttaatg ctgaaacatt caccttccat gcagatatat gcacactttc tgagaaggag   1560
agacaaatca agaaacaaac tgcacttgtt gagcttgtga acacaagcc caaggcaaca    1620 aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gctta                                                    1755
```

<210> SEQ ID NO 5
<211> LENGTH: 4
<212> TYPE: PRT
<213> ORGANISM: Artificial sequence
<220> FEATURE:
<223> OTHER INFORMATION: Synthetic Construct

<400> SEQUENCE: 5

Ala Ala Ala Leu
1

<210> SEQ ID NO 6
<211> LENGTH: 588
<212> TYPE: PRT
<213> ORGANISM: Artificial sequence
<220> FEATURE:
<223> OTHER INFORMATION: Synthetic Construct

<400> SEQUENCE: 6

```
Ala Ala Ser Asp Ala His Lys Ser Glu Val Ala His Arg Phe Lys Asp
1               5                   10                  15

Leu Gly Glu Glu Asn Phe Lys Ala Leu Val Leu Ile Ala Phe Ala Gln
            20                  25                  30

Tyr Leu Gln Gln Ser Pro Phe Glu Asp His Val Lys Leu Val Asn Glu
        35                  40                  45

Val Thr Glu Phe Ala Lys Thr Cys Val Ala Asp Glu Ser Ala Glu Asn
    50                  55                  60

Cys Asp Lys Ser Leu His Thr Leu Phe Gly Asp Lys Leu Cys Thr Val
65                      70                  75                  80

Ala Thr Leu Arg Glu Thr Tyr Gly Glu Met Ala Asp Cys Cys Ala Lys
                85                  90                  95

Gln Glu Pro Glu Arg Asn Glu Cys Phe Leu Gln His Lys Asp Asp Asn
            100                 105                 110

Pro Asn Leu Pro Arg Leu Val Arg Pro Glu Val Asp Val Met Cys Thr
        115                 120                 125

Ala Phe His Asp Asn Glu Glu Thr Phe Leu Lys Lys Tyr Leu Tyr Glu
    130                 135                 140

Ile Ala Arg Arg His Pro Tyr Phe Tyr Ala Pro Glu Leu Leu Phe Phe
145                 150                 155                 160

Ala Lys Arg Tyr Lys Ala Ala Phe Thr Glu Cys Cys Gln Ala Ala Asp
                165                 170                 175

Lys Ala Ala Cys Leu Leu Pro Lys Leu Asp Glu Leu Arg Asp Glu Gly
            180                 185                 190

Lys Ala Ser Ser Ala Lys Gln Arg Leu Lys Cys Ala Ser Leu Gln Lys
        195                 200                 205

Phe Gly Glu Arg Ala Phe Lys Ala Trp Ala Val Ala Arg Leu Ser Gln
210                 215                 220

Arg Phe Pro Lys Ala Glu Phe Ala Glu Val Ser Lys Leu Val Thr Asp
225                 230                 235                 240

Leu Thr Lys Val His Thr Glu Cys Cys His Gly Asp Leu Leu Glu Cys
                245                 250                 255

Ala Asp Asp Arg Ala Asp Leu Ala Lys Tyr Ile Cys Glu Asn Gln Asp
            260                 265                 270

Ser Ile Ser Ser Lys Leu Lys Glu Cys Cys Glu Lys Pro Leu Leu Glu
        275                 280                 285

Lys Ser His Cys Ile Ala Glu Val Glu Asn Asp Glu Met Pro Ala Asp
        290                 295                 300

Leu Pro Ser Leu Ala Ala Asp Phe Val Glu Ser Lys Asp Val Cys Lys
305                 310                 315                 320

Asn Tyr Ala Glu Ala Lys Asp Val Phe Leu Gly Met Phe Leu Tyr Glu
                325                 330                 335

Tyr Ala Arg Arg His Pro Asp Tyr Ser Val Val Leu Leu Leu Arg Leu
            340                 345                 350

Ala Lys Thr Tyr Glu Thr Thr Leu Glu Lys Cys Cys Ala Ala Ala Asp
        355                 360                 365

Pro His Glu Cys Tyr Ala Lys Val Phe Asp Glu Phe Lys Pro Leu Val
    370                 375                 380

Glu Glu Pro Gln Asn Leu Ile Lys Gln Asn Cys Glu Leu Phe Glu Gln
385                 390                 395                 400

Leu Gly Glu Tyr Lys Phe Gln Asn Ala Leu Leu Val Arg Tyr Thr Lys
                405                 410                 415
```

```
Lys Val Pro Gln Val Ser Thr Pro Thr Leu Val Glu Val Ser Arg Asn
                420                 425                 430

Leu Gly Lys Val Gly Ser Lys Cys Cys Lys His Pro Glu Ala Lys Arg
            435                 440                 445

Met Pro Cys Ala Glu Asp Tyr Leu Ser Val Val Leu Asn Gln Leu Cys
450                 455                 460

Val Leu His Glu Lys Thr Pro Val Ser Asp Arg Val Thr Lys Cys Cys
465                 470                 475                 480

Thr Glu Ser Leu Val Asn Arg Arg Pro Cys Phe Ser Ala Leu Glu Val
                485                 490                 495

Asp Glu Thr Tyr Val Pro Lys Glu Phe Gln Ala Glu Thr Phe Thr Phe
            500                 505                 510

His Ala Asp Ile Cys Thr Leu Ser Glu Lys Glu Arg Gln Ile Lys Lys
        515                 520                 525

Gln Thr Ala Leu Val Glu Leu Val Lys His Lys Pro Lys Ala Thr Lys
    530                 535                 540

Glu Gln Leu Lys Ala Val Met Asp Asp Phe Ala Ala Phe Val Glu Lys
545                 550                 555                 560

Cys Cys Lys Ala Asp Asp Lys Glu Thr Cys Phe Ala Glu Glu Gly Lys
                565                 570                 575

Lys Leu Val Ala Ala Ser Gln Ala Ala Leu Gly Leu
            580                 585

<210> SEQ ID NO 7
<211> LENGTH: 588
<212> TYPE: PRT
<213> ORGANISM: Artificial Sequence
<220> FEATURE:
<223> OTHER INFORMATION: Synthetic Construct

<400> SEQUENCE: 7

Ala Ala Gln Asp Ala His Lys Ser Glu Val Ala His Arg Phe Lys Asp
1               5                   10                  15

Leu Gly Glu Glu Asn Phe Lys Ala Leu Val Leu Ile Ala Phe Ala Gln
            20                  25                  30

Tyr Leu Gln Gln Ser Pro Phe Glu Asp His Val Lys Leu Val Asn Glu
        35                  40                  45

Val Thr Glu Phe Ala Lys Thr Cys Val Ala Asp Glu Ser Ala Glu Asn
    50                  55                  60

Cys Asp Lys Ser Leu His Thr Leu Phe Gly Asp Lys Leu Cys Thr Val
65                  70                  75                  80

Ala Thr Leu Arg Glu Thr Tyr Gly Glu Met Ala Asp Cys Cys Ala Lys
                85                  90                  95

Gln Glu Pro Glu Arg Asn Glu Cys Phe Leu Gln His Lys Asp Asp Asn
            100                 105                 110

Pro Asn Leu Pro Arg Leu Val Arg Pro Glu Val Asp Val Met Cys Thr
        115                 120                 125

Ala Phe His Asp Asn Glu Glu Thr Phe Leu Lys Lys Tyr Leu Tyr Glu
    130                 135                 140

Ile Ala Arg Arg His Pro Tyr Phe Tyr Ala Pro Glu Leu Leu Phe Phe
145                 150                 155                 160

Ala Lys Arg Tyr Lys Ala Ala Phe Thr Glu Cys Cys Gln Ala Ala Asp
                165                 170                 175

Lys Ala Ala Cys Leu Leu Pro Lys Leu Asp Glu Leu Arg Asp Glu Gly
            180                 185                 190
```

-continued

```
Lys Ala Ser Ser Ala Lys Gln Arg Leu Lys Cys Ala Ser Leu Gln Lys
            195                 200                 205

Phe Gly Glu Arg Ala Phe Lys Ala Trp Ala Val Ala Arg Leu Ser Gln
210                 215                 220

Arg Phe Pro Lys Ala Glu Phe Ala Glu Val Ser Lys Leu Val Thr Asp
225                 230                 235                 240

Leu Thr Lys Val His Thr Glu Cys Cys His Gly Asp Leu Leu Glu Cys
                245                 250                 255

Ala Asp Asp Arg Ala Asp Leu Ala Lys Tyr Ile Cys Glu Asn Gln Asp
            260                 265                 270

Ser Ile Ser Ser Lys Leu Lys Glu Cys Cys Glu Lys Pro Leu Leu Glu
        275                 280                 285

Lys Ser His Cys Ile Ala Glu Val Glu Asn Asp Glu Met Pro Ala Asp
290                 295                 300

Leu Pro Ser Leu Ala Ala Asp Phe Val Glu Ser Lys Asp Val Cys Lys
305                 310                 315                 320

Asn Tyr Ala Glu Ala Lys Asp Val Phe Leu Gly Met Phe Leu Tyr Glu
                325                 330                 335

Tyr Ala Arg Arg His Pro Asp Tyr Ser Val Val Leu Leu Leu Arg Leu
            340                 345                 350

Ala Lys Thr Tyr Glu Thr Thr Leu Glu Lys Cys Cys Ala Ala Ala Asp
        355                 360                 365

Pro His Glu Cys Tyr Ala Lys Val Phe Asp Glu Phe Lys Pro Leu Val
370                 375                 380

Glu Glu Pro Gln Asn Leu Ile Lys Gln Asn Cys Glu Leu Phe Glu Gln
385                 390                 395                 400

Leu Gly Glu Tyr Lys Phe Gln Asn Ala Leu Leu Val Arg Tyr Thr Lys
                405                 410                 415

Lys Val Pro Gln Val Ser Thr Pro Thr Leu Val Glu Val Ser Arg Asn
            420                 425                 430

Leu Gly Lys Val Gly Ser Lys Cys Cys Lys His Pro Glu Ala Lys Arg
        435                 440                 445

Met Pro Cys Ala Glu Asp Tyr Leu Ser Val Val Leu Asn Gln Leu Cys
450                 455                 460

Val Leu His Glu Lys Thr Pro Val Ser Asp Arg Val Thr Lys Cys Cys
465                 470                 475                 480

Thr Glu Ser Leu Val Asn Arg Arg Pro Cys Phe Ser Ala Leu Glu Val
                485                 490                 495

Asp Glu Thr Tyr Val Pro Lys Glu Phe Gln Ala Glu Thr Phe Thr Phe
            500                 505                 510

His Ala Asp Ile Cys Thr Leu Ser Glu Lys Glu Arg Gln Ile Lys Lys
        515                 520                 525

Gln Thr Ala Leu Val Glu Leu Val Lys His Lys Pro Lys Ala Thr Lys
530                 535                 540

Glu Gln Leu Lys Ala Val Met Asp Asp Phe Ala Ala Phe Val Glu Lys
545                 550                 555                 560

Cys Cys Lys Ala Asp Asp Lys Glu Thr Cys Phe Ala Glu Glu Gly Lys
                565                 570                 575

Lys Leu Val Ala Ala Ser Gln Ala Ala Leu Gly Leu
            580                 585

<210> SEQ ID NO 8
<211> LENGTH: 589
<212> TYPE: PRT
```

<213> ORGANISM: Artificial Sequence
<220> FEATURE:
<223> OTHER INFORMATION: Synthetic Construct

<400> SEQUENCE: 8

```
Asp Ala His Lys Ser Glu Val Ala His Arg Phe Lys Asp Leu Gly Glu
1               5                  10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
```

```
                385                 390                 395                 400
Tyr Lys Phe Gln Asn Ala Leu Leu Val Arg Tyr Thr Lys Lys Val Pro
                    405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Gln Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Ala Ala Leu
                580                 585

<210> SEQ ID NO 9
<211> LENGTH: 592
<212> TYPE: PRT
<213> ORGANISM: Artificial Sequence
<220> FEATURE:
<223> OTHER INFORMATION: Synthetic Construct

<400> SEQUENCE: 9

Ala Ala Ser Asp Ala His Lys Ser Glu Val Ala His Arg Phe Lys Asp
1               5                   10                  15

Leu Gly Glu Glu Asn Phe Lys Ala Leu Val Leu Ile Ala Phe Ala Gln
                20                  25                  30

Tyr Leu Gln Gln Ser Pro Phe Glu Asp His Val Lys Leu Val Asn Glu
            35                  40                  45

Val Thr Glu Phe Ala Lys Thr Cys Val Ala Asp Glu Ser Ala Glu Asn
        50                  55                  60

Cys Asp Lys Ser Leu His Thr Leu Phe Gly Asp Lys Leu Cys Thr Val
65                  70                  75                  80

Ala Thr Leu Arg Glu Thr Tyr Gly Glu Met Ala Asp Cys Cys Ala Lys
                85                  90                  95

Gln Glu Pro Glu Arg Asn Glu Cys Phe Leu Gln His Lys Asp Asp Asn
                100                 105                 110

Pro Asn Leu Pro Arg Leu Val Arg Pro Glu Val Asp Val Met Cys Thr
            115                 120                 125

Ala Phe His Asp Asn Glu Glu Thr Phe Leu Lys Lys Tyr Leu Tyr Glu
        130                 135                 140

Ile Ala Arg Arg His Pro Tyr Phe Tyr Ala Pro Glu Leu Leu Phe Phe
145                 150                 155                 160

Ala Lys Arg Tyr Lys Ala Ala Phe Thr Glu Cys Cys Gln Ala Ala Asp
```

-continued

```
            165                 170                 175
Lys Ala Ala Cys Leu Leu Pro Lys Leu Asp Glu Leu Arg Asp Glu Gly
            180                 185                 190
Lys Ala Ser Ser Ala Lys Gln Arg Leu Lys Cys Ala Ser Leu Gln Lys
            195                 200                 205
Phe Gly Glu Arg Ala Phe Lys Ala Trp Ala Val Ala Arg Leu Ser Gln
            210                 215                 220
Arg Phe Pro Lys Ala Glu Phe Ala Glu Val Ser Lys Leu Val Thr Asp
225                 230                 235                 240
Leu Thr Lys Val His Thr Glu Cys Cys His Gly Asp Leu Leu Glu Cys
            245                 250                 255
Ala Asp Asp Arg Ala Asp Leu Ala Lys Tyr Ile Cys Glu Asn Gln Asp
            260                 265                 270
Ser Ile Ser Ser Lys Leu Lys Glu Cys Cys Glu Lys Pro Leu Leu Glu
            275                 280                 285
Lys Ser His Cys Ile Ala Glu Val Glu Asn Asp Glu Met Pro Ala Asp
            290                 295                 300
Leu Pro Ser Leu Ala Ala Asp Phe Val Glu Ser Lys Asp Val Cys Lys
305                 310                 315                 320
Asn Tyr Ala Glu Ala Lys Asp Val Phe Leu Gly Met Phe Leu Tyr Glu
            325                 330                 335
Tyr Ala Arg Arg His Pro Asp Tyr Ser Val Val Leu Leu Leu Arg Leu
            340                 345                 350
Ala Lys Thr Tyr Glu Thr Thr Leu Glu Lys Cys Cys Ala Ala Ala Asp
            355                 360                 365
Pro His Glu Cys Tyr Ala Lys Val Phe Asp Glu Phe Lys Pro Leu Val
            370                 375                 380
Glu Glu Pro Gln Asn Leu Ile Lys Gln Asn Cys Glu Leu Phe Glu Gln
385                 390                 395                 400
Leu Gly Glu Tyr Lys Phe Gln Asn Ala Leu Leu Val Arg Tyr Thr Lys
            405                 410                 415
Lys Val Pro Gln Val Ser Thr Pro Thr Leu Val Glu Val Ser Arg Asn
            420                 425                 430
Leu Gly Lys Val Gly Ser Lys Cys Cys Lys His Pro Glu Ala Lys Arg
            435                 440                 445
Met Pro Cys Ala Glu Asp Tyr Leu Ser Val Val Leu Asn Gln Leu Cys
            450                 455                 460
Val Leu His Glu Lys Thr Pro Val Ser Asp Arg Val Thr Lys Cys Cys
465                 470                 475                 480
Thr Glu Ser Leu Val Asn Arg Arg Pro Cys Phe Ser Ala Leu Glu Val
            485                 490                 495
Asp Glu Thr Tyr Val Pro Lys Glu Phe Gln Ala Glu Thr Phe Thr Phe
            500                 505                 510
His Ala Asp Ile Cys Thr Leu Ser Glu Lys Glu Arg Gln Ile Lys Lys
            515                 520                 525
Gln Thr Ala Leu Val Glu Leu Val Lys His Lys Pro Lys Ala Thr Lys
            530                 535                 540
Glu Gln Leu Lys Ala Val Met Asp Asp Phe Ala Ala Phe Val Glu Lys
545                 550                 555                 560
Cys Cys Lys Ala Asp Asp Lys Glu Thr Cys Phe Ala Glu Glu Gly Lys
            565                 570                 575
Lys Leu Val Ala Ala Ser Gln Ala Ala Leu Gly Leu Ala Ala Ala Leu
            580                 585                 590
```

```
<210> SEQ ID NO 10
<211> LENGTH: 592
<212> TYPE: PRT
<213> ORGANISM: Artificial Sequence
<220> FEATURE:
<223> OTHER INFORMATION: Synthetic Construct

<400> SEQUENCE: 10
```

| Ala | Ala | Gln | Asp | Ala | His | Lys | Ser | Glu | Val | Ala | His | Arg | Phe | Lys | Asp |
|---|---|---|---|---|---|---|---|---|---|---|---|---|---|---|---|
| 1 | | | | 5 | | | | | 10 | | | | | 15 | |

| Leu | Gly | Glu | Glu | Asn | Phe | Lys | Ala | Leu | Val | Leu | Ile | Ala | Phe | Ala | Gln |
|---|---|---|---|---|---|---|---|---|---|---|---|---|---|---|---|
| | | | 20 | | | | | 25 | | | | | 30 | | |

| Tyr | Leu | Gln | Gln | Ser | Pro | Phe | Glu | Asp | His | Val | Lys | Leu | Val | Asn | Glu |
|---|---|---|---|---|---|---|---|---|---|---|---|---|---|---|---|
| | | | 35 | | | | | 40 | | | | | 45 | | |

| Val | Thr | Glu | Phe | Ala | Lys | Thr | Cys | Val | Ala | Asp | Glu | Ser | Ala | Glu | Asn |
|---|---|---|---|---|---|---|---|---|---|---|---|---|---|---|---|
| | 50 | | | | | 55 | | | | | 60 | | | | |

| Cys | Asp | Lys | Ser | Leu | His | Thr | Leu | Phe | Gly | Asp | Lys | Leu | Cys | Thr | Val |
|---|---|---|---|---|---|---|---|---|---|---|---|---|---|---|---|
| 65 | | | | | 70 | | | | | 75 | | | | | 80 |

| Ala | Thr | Leu | Arg | Glu | Thr | Tyr | Gly | Glu | Met | Ala | Asp | Cys | Cys | Ala | Lys |
|---|---|---|---|---|---|---|---|---|---|---|---|---|---|---|---|
| | | | | 85 | | | | | 90 | | | | | 95 | |

| Gln | Glu | Pro | Glu | Arg | Asn | Glu | Cys | Phe | Leu | Gln | His | Lys | Asp | Asp | Asn |
|---|---|---|---|---|---|---|---|---|---|---|---|---|---|---|---|
| | | | 100 | | | | | 105 | | | | | 110 | | |

| Pro | Asn | Leu | Pro | Arg | Leu | Val | Arg | Pro | Glu | Val | Asp | Val | Met | Cys | Thr |
|---|---|---|---|---|---|---|---|---|---|---|---|---|---|---|---|
| | | 115 | | | | | 120 | | | | | 125 | | | |

| Ala | Phe | His | Asp | Asn | Glu | Glu | Thr | Phe | Leu | Lys | Lys | Tyr | Leu | Tyr | Glu |
|---|---|---|---|---|---|---|---|---|---|---|---|---|---|---|---|
| | 130 | | | | | 135 | | | | | 140 | | | | |

| Ile | Ala | Arg | Arg | His | Pro | Tyr | Phe | Tyr | Ala | Pro | Glu | Leu | Leu | Phe | Phe |
|---|---|---|---|---|---|---|---|---|---|---|---|---|---|---|---|
| 145 | | | | | 150 | | | | | 155 | | | | | 160 |

| Ala | Lys | Arg | Tyr | Lys | Ala | Ala | Phe | Thr | Glu | Cys | Cys | Gln | Ala | Ala | Asp |
|---|---|---|---|---|---|---|---|---|---|---|---|---|---|---|---|
| | | | | 165 | | | | | 170 | | | | | 175 | |

| Lys | Ala | Ala | Cys | Leu | Leu | Pro | Lys | Leu | Asp | Glu | Leu | Arg | Asp | Glu | Gly |
|---|---|---|---|---|---|---|---|---|---|---|---|---|---|---|---|
| | | | 180 | | | | | 185 | | | | | 190 | | |

| Lys | Ala | Ser | Ser | Ala | Lys | Gln | Arg | Leu | Lys | Cys | Ala | Ser | Leu | Gln | Lys |
|---|---|---|---|---|---|---|---|---|---|---|---|---|---|---|---|
| | | 195 | | | | | 200 | | | | | 205 | | | |

| Phe | Gly | Glu | Arg | Ala | Phe | Lys | Ala | Trp | Ala | Val | Ala | Arg | Leu | Ser | Gln |
|---|---|---|---|---|---|---|---|---|---|---|---|---|---|---|---|
| | 210 | | | | | 215 | | | | | 220 | | | | |

| Arg | Phe | Pro | Lys | Ala | Glu | Phe | Ala | Glu | Val | Ser | Lys | Leu | Val | Thr | Asp |
|---|---|---|---|---|---|---|---|---|---|---|---|---|---|---|---|
| 225 | | | | | 230 | | | | | 235 | | | | | 240 |

| Leu | Thr | Lys | Val | His | Thr | Glu | Cys | Cys | His | Gly | Asp | Leu | Leu | Glu | Cys |
|---|---|---|---|---|---|---|---|---|---|---|---|---|---|---|---|
| | | | | 245 | | | | | 250 | | | | | 255 | |

| Ala | Asp | Asp | Arg | Ala | Asp | Leu | Ala | Lys | Tyr | Ile | Cys | Glu | Asn | Gln | Asp |
|---|---|---|---|---|---|---|---|---|---|---|---|---|---|---|---|
| | | | 260 | | | | | 265 | | | | | 270 | | |

| Ser | Ile | Ser | Ser | Lys | Leu | Lys | Glu | Cys | Cys | Glu | Lys | Pro | Leu | Leu | Glu |
|---|---|---|---|---|---|---|---|---|---|---|---|---|---|---|---|
| | | 275 | | | | | 280 | | | | | 285 | | | |

| Lys | Ser | His | Cys | Ile | Ala | Glu | Val | Glu | Asn | Asp | Glu | Met | Pro | Ala | Asp |
|---|---|---|---|---|---|---|---|---|---|---|---|---|---|---|---|
| | 290 | | | | | 295 | | | | | 300 | | | | |

| Leu | Pro | Ser | Leu | Ala | Ala | Asp | Phe | Val | Glu | Ser | Lys | Asp | Val | Cys | Lys |
|---|---|---|---|---|---|---|---|---|---|---|---|---|---|---|---|
| 305 | | | | | 310 | | | | | 315 | | | | | 320 |

| Asn | Tyr | Ala | Glu | Ala | Lys | Asp | Val | Phe | Leu | Gly | Met | Phe | Leu | Tyr | Glu |
|---|---|---|---|---|---|---|---|---|---|---|---|---|---|---|---|
| | | | | 325 | | | | | 330 | | | | | 335 | |

| Tyr | Ala | Arg | Arg | His | Pro | Asp | Tyr | Ser | Val | Val | Leu | Leu | Leu | Arg | Leu |
|---|---|---|---|---|---|---|---|---|---|---|---|---|---|---|---|
| | | | 340 | | | | | 345 | | | | | 350 | | |

| Ala | Lys | Thr | Tyr | Glu | Thr | Thr | Leu | Glu | Lys | Cys | Cys | Ala | Ala | Ala | Asp |
|---|---|---|---|---|---|---|---|---|---|---|---|---|---|---|---|
| | | 355 | | | | | 360 | | | | | 365 | | | |

```
Pro His Glu Cys Tyr Ala Lys Val Phe Asp Glu Phe Lys Pro Leu Val
    370                 375                 380

Glu Glu Pro Gln Asn Leu Ile Lys Gln Asn Cys Glu Leu Phe Glu Gln
385                 390                 395                 400

Leu Gly Glu Tyr Lys Phe Gln Asn Ala Leu Leu Val Arg Tyr Thr Lys
                405                 410                 415

Lys Val Pro Gln Val Ser Thr Pro Thr Leu Val Glu Val Ser Arg Asn
                420                 425                 430

Leu Gly Lys Val Gly Ser Lys Cys Cys Lys His Pro Glu Ala Lys Arg
            435                 440                 445

Met Pro Cys Ala Glu Asp Tyr Leu Ser Val Val Leu Asn Gln Leu Cys
    450                 455                 460

Val Leu His Glu Lys Thr Pro Val Ser Asp Arg Val Thr Lys Cys Cys
465                 470                 475                 480

Thr Glu Ser Leu Val Asn Arg Arg Pro Cys Phe Ser Ala Leu Glu Val
                485                 490                 495

Asp Glu Thr Tyr Val Pro Lys Glu Phe Gln Ala Glu Thr Phe Thr Phe
                500                 505                 510

His Ala Asp Ile Cys Thr Leu Ser Glu Lys Glu Arg Gln Ile Lys Lys
            515                 520                 525

Gln Thr Ala Leu Val Glu Leu Val Lys His Lys Pro Lys Ala Thr Lys
    530                 535                 540

Glu Gln Leu Lys Ala Val Met Asp Asp Phe Ala Ala Phe Val Glu Lys
545                 550                 555                 560

Cys Cys Lys Ala Asp Asp Lys Glu Thr Cys Phe Ala Glu Glu Gly Lys
                565                 570                 575

Lys Leu Val Ala Ala Ser Gln Ala Ala Leu Gly Leu Ala Ala Ala Leu
            580                 585                 590

<210> SEQ ID NO 11
<211> LENGTH: 588
<212> TYPE: PRT
<213> ORGANISM: Artificial Sequence
<220> FEATURE:
<223> OTHER INFORMATION: Synthetic Construct

<400> SEQUENCE: 11

Ala Ala Ser Asp Ala His Lys Ser Glu Val Ala His Arg Phe Lys Asp
1               5                  10                  15

Leu Gly Glu Glu Asn Phe Lys Ala Leu Val Leu Ile Ala Phe Ala Gln
                20                  25                  30

Tyr Leu Gln Gln Cys Pro Phe Glu Asp His Val Lys Leu Val Asn Glu
            35                  40                  45

Val Thr Glu Phe Ala Lys Thr Cys Val Ala Asp Glu Ser Ala Glu Asn
    50                  55                  60

Cys Asp Lys Ser Leu His Thr Leu Phe Gly Asp Lys Leu Cys Thr Val
65                  70                  75                  80

Ala Thr Leu Arg Glu Thr Tyr Gly Glu Met Ala Asp Cys Cys Ala Lys
                85                  90                  95

Gln Glu Pro Glu Arg Asn Glu Cys Phe Leu Gln His Lys Asp Asp Asn
            100                 105                 110

Pro Asn Leu Pro Arg Leu Val Arg Pro Glu Val Asp Val Met Cys Thr
    115                 120                 125

Ala Phe His Asp Asn Glu Glu Thr Phe Leu Lys Lys Tyr Leu Tyr Glu
130                 135                 140
```

```
Ile Ala Arg Arg His Pro Tyr Phe Tyr Ala Pro Glu Leu Leu Phe Phe
145                 150                 155                 160

Ala Lys Arg Tyr Lys Ala Ala Phe Thr Glu Cys Cys Gln Ala Ala Asp
            165                 170                 175

Lys Ala Ala Cys Leu Leu Pro Lys Leu Asp Glu Leu Arg Asp Glu Gly
        180                 185                 190

Lys Ala Ser Ser Ala Lys Gln Arg Leu Lys Cys Ala Ser Leu Gln Lys
        195                 200                 205

Phe Gly Glu Arg Ala Phe Lys Ala Trp Ala Val Ala Arg Leu Ser Gln
    210                 215                 220

Arg Phe Pro Lys Ala Glu Phe Ala Glu Val Ser Lys Leu Val Thr Asp
225                 230                 235                 240

Leu Thr Lys Val His Thr Glu Cys Cys His Gly Asp Leu Leu Glu Cys
            245                 250                 255

Ala Asp Asp Arg Ala Asp Leu Ala Lys Tyr Ile Cys Glu Asn Gln Asp
        260                 265                 270

Ser Ile Ser Ser Lys Leu Lys Glu Cys Cys Glu Lys Pro Leu Leu Glu
        275                 280                 285

Lys Ser His Cys Ile Ala Glu Val Glu Asn Asp Glu Met Pro Ala Asp
    290                 295                 300

Leu Pro Ser Leu Ala Ala Asp Phe Val Glu Ser Lys Asp Val Cys Lys
305                 310                 315                 320

Asn Tyr Ala Glu Ala Lys Asp Val Phe Leu Gly Met Phe Leu Tyr Glu
            325                 330                 335

Tyr Ala Arg Arg His Pro Asp Tyr Ser Val Val Leu Leu Leu Arg Leu
        340                 345                 350

Ala Lys Thr Tyr Glu Thr Thr Leu Glu Lys Cys Cys Ala Ala Ala Asp
        355                 360                 365

Pro His Glu Cys Tyr Ala Lys Val Phe Asp Glu Phe Lys Pro Leu Val
    370                 375                 380

Glu Glu Pro Gln Asn Leu Ile Lys Gln Asn Cys Glu Leu Phe Glu Gln
385                 390                 395                 400

Leu Gly Glu Tyr Lys Phe Gln Asn Ala Leu Leu Val Arg Tyr Thr Lys
            405                 410                 415

Lys Val Pro Gln Val Ser Thr Pro Thr Leu Val Glu Val Ser Arg Asn
        420                 425                 430

Leu Gly Lys Val Gly Ser Lys Cys Cys Lys His Pro Glu Ala Lys Arg
        435                 440                 445

Met Pro Cys Ala Glu Asp Tyr Leu Ser Val Val Leu Asn Gln Leu Cys
    450                 455                 460

Val Leu His Glu Lys Thr Pro Val Ser Asp Arg Val Thr Lys Cys Cys
465                 470                 475                 480

Thr Glu Ser Leu Val Asn Arg Arg Pro Cys Phe Ser Ala Leu Glu Val
            485                 490                 495

Asp Glu Thr Tyr Val Pro Lys Glu Phe Asn Ala Glu Thr Phe Thr Phe
        500                 505                 510

His Ala Asp Ile Cys Thr Leu Ser Glu Lys Glu Arg Gln Ile Lys Lys
    515                 520                 525

Gln Thr Ala Leu Val Glu Leu Val Lys His Lys Pro Lys Ala Thr Lys
        530                 535                 540

Glu Gln Leu Lys Ala Val Met Asp Asp Phe Ala Ala Phe Val Glu Lys
545                 550                 555                 560
```

```
Cys Cys Lys Ala Asp Asp Lys Glu Thr Cys Phe Ala Glu Glu Gly Lys
            565                 570                 575
Lys Leu Val Ala Ala Ser Gln Ala Ala Leu Gly Leu
            580                 585
```

<210> SEQ ID NO 12
<211> LENGTH: 588
<212> TYPE: PRT
<213> ORGANISM: Artificial Sequence
<220> FEATURE:
<223> OTHER INFORMATION: Synthetic Construct

<400> SEQUENCE: 12

```
Ala Ala Gln Asp Ala His Lys Ser Glu Val Ala His Arg Phe Lys Asp
1               5                   10                  15
Leu Gly Glu Glu Asn Phe Lys Ala Leu Val Leu Ile Ala Phe Ala Gln
            20                  25                  30
Tyr Leu Gln Gln Cys Pro Phe Glu Asp His Val Lys Leu Val Asn Glu
        35                  40                  45
Val Thr Glu Phe Ala Lys Thr Cys Val Ala Asp Glu Ser Ala Glu Asn
    50                  55                  60
Cys Asp Lys Ser Leu His Thr Leu Phe Gly Asp Lys Leu Cys Thr Val
65                  70                  75                  80
Ala Thr Leu Arg Glu Thr Tyr Gly Glu Met Ala Asp Cys Cys Ala Lys
                85                  90                  95
Gln Glu Pro Glu Arg Asn Glu Cys Phe Leu Gln His Lys Asp Asp Asn
            100                 105                 110
Pro Asn Leu Pro Arg Leu Val Arg Pro Glu Val Asp Val Met Cys Thr
        115                 120                 125
Ala Phe His Asp Asn Glu Glu Thr Phe Leu Lys Lys Tyr Leu Tyr Glu
    130                 135                 140
Ile Ala Arg Arg His Pro Tyr Phe Tyr Ala Pro Glu Leu Leu Phe Phe
145                 150                 155                 160
Ala Lys Arg Tyr Lys Ala Ala Phe Thr Glu Cys Cys Gln Ala Ala Asp
                165                 170                 175
Lys Ala Ala Cys Leu Leu Pro Lys Leu Asp Glu Leu Arg Asp Glu Gly
            180                 185                 190
Lys Ala Ser Ser Ala Lys Gln Arg Leu Lys Cys Ala Ser Leu Gln Lys
        195                 200                 205
Phe Gly Glu Arg Ala Phe Lys Ala Trp Ala Val Ala Arg Leu Ser Gln
    210                 215                 220
Arg Phe Pro Lys Ala Glu Phe Ala Glu Val Ser Lys Leu Val Thr Asp
225                 230                 235                 240
Leu Thr Lys Val His Thr Glu Cys Cys His Gly Asp Leu Leu Glu Cys
                245                 250                 255
Ala Asp Asp Arg Ala Asp Leu Ala Lys Tyr Ile Cys Glu Asn Gln Asp
            260                 265                 270
Ser Ile Ser Ser Lys Leu Lys Glu Cys Cys Glu Lys Pro Leu Leu Glu
        275                 280                 285
Lys Ser His Cys Ile Ala Glu Val Glu Asn Asp Glu Met Pro Ala Asp
    290                 295                 300
Leu Pro Ser Leu Ala Ala Asp Phe Val Glu Ser Lys Asp Val Cys Lys
305                 310                 315                 320
Asn Tyr Ala Glu Ala Lys Asp Val Phe Leu Gly Met Phe Leu Tyr Glu
                325                 330                 335
```

```
Tyr Ala Arg Arg His Pro Asp Tyr Ser Val Val Leu Leu Arg Leu
                340                 345                 350

Ala Lys Thr Tyr Glu Thr Thr Leu Glu Lys Cys Cys Ala Ala Ala Asp
        355                 360                 365

Pro His Glu Cys Tyr Ala Lys Val Phe Asp Glu Phe Lys Pro Leu Val
    370                 375                 380

Glu Glu Pro Gln Asn Leu Ile Lys Gln Asn Cys Glu Leu Phe Glu Gln
385                 390                 395                 400

Leu Gly Glu Tyr Lys Phe Gln Asn Ala Leu Leu Val Arg Tyr Thr Lys
                405                 410                 415

Lys Val Pro Gln Val Ser Thr Pro Thr Leu Val Glu Val Ser Arg Asn
                420                 425                 430

Leu Gly Lys Val Gly Ser Lys Cys Cys Lys His Pro Glu Ala Lys Arg
            435                 440                 445

Met Pro Cys Ala Glu Asp Tyr Leu Ser Val Val Leu Asn Gln Leu Cys
            450                 455                 460

Val Leu His Glu Lys Thr Pro Val Ser Asp Arg Val Thr Lys Cys Cys
465                 470                 475                 480

Thr Glu Ser Leu Val Asn Arg Arg Pro Cys Phe Ser Ala Leu Glu Val
                485                 490                 495

Asp Glu Thr Tyr Val Pro Lys Glu Phe Asn Ala Glu Thr Phe Thr Phe
                500                 505                 510

His Ala Asp Ile Cys Thr Leu Ser Glu Lys Glu Arg Gln Ile Lys Lys
            515                 520                 525

Gln Thr Ala Leu Val Glu Leu Val Lys His Lys Pro Lys Ala Thr Lys
530                 535                 540

Glu Gln Leu Lys Ala Val Met Asp Asp Phe Ala Ala Phe Val Glu Lys
545                 550                 555                 560

Cys Cys Lys Ala Asp Asp Lys Glu Thr Cys Phe Ala Glu Glu Gly Lys
                565                 570                 575

Lys Leu Val Ala Ala Ser Gln Ala Ala Leu Gly Leu
                580                 585

<210> SEQ ID NO 13
<211> LENGTH: 589
<212> TYPE: PRT
<213> ORGANISM: Artificial Sequence
<220> FEATURE:
<223> OTHER INFORMATION: Synthetic Construct

<400> SEQUENCE: 13

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu

```
                530                 535                 540
Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Ala Ala Leu
                580                 585

<210> SEQ ID NO 14
<211> LENGTH: 592
<212> TYPE: PRT
<213> ORGANISM: Artificial Sequence
<220> FEATURE:
<223> OTHER INFORMATION: Synthetic Construct

<400> SEQUENCE: 14

Ala Ala Ser Asp Ala His Lys Ser Glu Val Ala His Arg Phe Lys Asp
1               5                   10                  15

Leu Gly Glu Glu Asn Phe Lys Ala Leu Val Leu Ile Ala Phe Ala Gln
                20                  25                  30

Tyr Leu Gln Gln Cys Pro Phe Glu Asp His Val Lys Leu Val Asn Glu
            35                  40                  45

Val Thr Glu Phe Ala Lys Thr Cys Val Ala Asp Glu Ser Ala Glu Asn
        50                  55                  60

Cys Asp Lys Ser Leu His Thr Leu Phe Gly Asp Lys Leu Cys Thr Val
65                  70                  75                  80

Ala Thr Leu Arg Glu Thr Tyr Gly Glu Met Ala Asp Cys Cys Ala Lys
                85                  90                  95

Gln Glu Pro Glu Arg Asn Glu Cys Phe Leu Gln His Lys Asp Asp Asn
            100                 105                 110

Pro Asn Leu Pro Arg Leu Val Arg Pro Glu Val Asp Val Met Cys Thr
        115                 120                 125

Ala Phe His Asp Asn Glu Glu Thr Phe Leu Lys Lys Tyr Leu Tyr Glu
    130                 135                 140

Ile Ala Arg Arg His Pro Tyr Phe Tyr Ala Pro Glu Leu Leu Phe Phe
145                 150                 155                 160

Ala Lys Arg Tyr Lys Ala Ala Phe Thr Glu Cys Cys Gln Ala Ala Asp
                165                 170                 175

Lys Ala Ala Cys Leu Leu Pro Lys Leu Asp Glu Leu Arg Asp Glu Gly
            180                 185                 190

Lys Ala Ser Ser Ala Lys Gln Arg Leu Lys Cys Ala Ser Leu Gln Lys
        195                 200                 205

Phe Gly Glu Arg Ala Phe Lys Ala Trp Ala Val Ala Arg Leu Ser Gln
    210                 215                 220

Arg Phe Pro Lys Ala Glu Phe Ala Glu Val Ser Lys Leu Val Thr Asp
225                 230                 235                 240

Leu Thr Lys Val His Thr Glu Cys Cys His Gly Asp Leu Leu Glu Cys
                245                 250                 255

Ala Asp Asp Arg Ala Asp Leu Ala Lys Tyr Ile Cys Glu Asn Gln Asp
            260                 265                 270

Ser Ile Ser Ser Lys Leu Lys Glu Cys Cys Glu Lys Pro Leu Leu Glu
        275                 280                 285

Lys Ser His Cys Ile Ala Glu Val Glu Asn Asp Glu Met Pro Ala Asp
    290                 295                 300

Leu Pro Ser Leu Ala Ala Asp Phe Val Glu Ser Lys Asp Val Cys Lys
```

```
            305                 310                 315                 320
Asn Tyr Ala Glu Ala Lys Asp Val Phe Leu Gly Met Phe Leu Tyr Glu
                325                 330                 335

Tyr Ala Arg Arg His Pro Asp Tyr Ser Val Val Leu Leu Arg Leu
            340                 345                 350

Ala Lys Thr Tyr Glu Thr Thr Leu Glu Lys Cys Cys Ala Ala Asp
            355                 360                 365

Pro His Glu Cys Tyr Ala Lys Val Phe Asp Glu Phe Lys Pro Leu Val
370                 375                 380

Glu Glu Pro Gln Asn Leu Ile Lys Gln Asn Cys Glu Leu Phe Glu Gln
385                 390                 395                 400

Leu Gly Glu Tyr Lys Phe Gln Asn Ala Leu Leu Val Arg Tyr Thr Lys
                405                 410                 415

Lys Val Pro Gln Val Ser Thr Pro Thr Leu Val Glu Val Ser Arg Asn
                420                 425                 430

Leu Gly Lys Val Gly Ser Lys Cys Cys Lys His Pro Glu Ala Lys Arg
                435                 440                 445

Met Pro Cys Ala Glu Asp Tyr Leu Ser Val Val Leu Asn Gln Leu Cys
            450                 455                 460

Val Leu His Glu Lys Thr Pro Val Ser Asp Arg Val Thr Lys Cys Cys
465                 470                 475                 480

Thr Glu Ser Leu Val Asn Arg Arg Pro Cys Phe Ser Ala Leu Glu Val
                485                 490                 495

Asp Glu Thr Tyr Val Pro Lys Glu Phe Asn Ala Glu Thr Phe Thr Phe
                500                 505                 510

His Ala Asp Ile Cys Thr Leu Ser Glu Lys Glu Arg Gln Ile Lys Lys
            515                 520                 525

Gln Thr Ala Leu Val Glu Leu Val Lys His Lys Pro Lys Ala Thr Lys
            530                 535                 540

Glu Gln Leu Lys Ala Val Met Asp Asp Phe Ala Ala Phe Val Glu Lys
545                 550                 555                 560

Cys Cys Lys Ala Asp Asp Lys Glu Thr Cys Phe Ala Glu Glu Gly Lys
                565                 570                 575

Lys Leu Val Ala Ala Ser Gln Ala Leu Gly Leu Ala Ala Ala Leu
                580                 585                 590

<210> SEQ ID NO 15
<211> LENGTH: 592
<212> TYPE: PRT
<213> ORGANISM: Artificial Sequence
<220> FEATURE:
<223> OTHER INFORMATION: Synthethic Construct

<400> SEQUENCE: 15

Ala Ala Gln Asp Ala His Lys Ser Glu Val Ala His Arg Phe Lys Asp
1               5                   10                  15

Leu Gly Glu Glu Asn Phe Lys Ala Leu Val Leu Ile Ala Phe Ala Gln
                20                  25                  30

Tyr Leu Gln Gln Cys Pro Phe Glu Asp His Val Lys Leu Val Asn Glu
            35                  40                  45

Val Thr Glu Phe Ala Lys Thr Cys Val Ala Asp Glu Ser Ala Glu Asn
        50                  55                  60

Cys Asp Lys Ser Leu His Thr Leu Phe Gly Asp Lys Leu Cys Thr Val
65                  70                  75                  80

Ala Thr Leu Arg Glu Thr Tyr Gly Glu Met Ala Asp Cys Cys Ala Lys
```

-continued

```
                    85                  90                  95
Gln Glu Pro Glu Arg Asn Glu Cys Phe Leu Gln His Lys Asp Asp Asn
            100                 105                 110

Pro Asn Leu Pro Arg Leu Val Arg Pro Glu Val Asp Val Met Cys Thr
            115                 120                 125

Ala Phe His Asp Asn Glu Glu Thr Phe Leu Lys Lys Tyr Leu Tyr Glu
            130                 135                 140

Ile Ala Arg Arg His Pro Tyr Phe Tyr Ala Pro Glu Leu Leu Phe Phe
145                 150                 155                 160

Ala Lys Arg Tyr Lys Ala Ala Phe Thr Glu Cys Cys Gln Ala Ala Asp
                165                 170                 175

Lys Ala Ala Cys Leu Leu Pro Lys Leu Asp Glu Leu Arg Asp Glu Gly
            180                 185                 190

Lys Ala Ser Ser Ala Lys Gln Arg Leu Lys Cys Ala Ser Leu Gln Lys
            195                 200                 205

Phe Gly Glu Arg Ala Phe Lys Ala Trp Ala Val Ala Arg Leu Ser Gln
            210                 215                 220

Arg Phe Pro Lys Ala Glu Phe Ala Glu Val Ser Lys Leu Val Thr Asp
225                 230                 235                 240

Leu Thr Lys Val His Thr Glu Cys Cys His Gly Asp Leu Leu Glu Cys
                245                 250                 255

Ala Asp Asp Arg Ala Asp Leu Ala Lys Tyr Ile Cys Glu Asn Gln Asp
            260                 265                 270

Ser Ile Ser Ser Lys Leu Lys Glu Cys Cys Glu Lys Pro Leu Leu Glu
            275                 280                 285

Lys Ser His Cys Ile Ala Glu Val Glu Asn Asp Glu Met Pro Ala Asp
            290                 295                 300

Leu Pro Ser Leu Ala Ala Asp Phe Val Glu Ser Lys Asp Val Cys Lys
305                 310                 315                 320

Asn Tyr Ala Glu Ala Lys Asp Val Phe Leu Gly Met Phe Leu Tyr Glu
                325                 330                 335

Tyr Ala Arg Arg His Pro Asp Tyr Ser Val Val Leu Leu Leu Arg Leu
            340                 345                 350

Ala Lys Thr Tyr Glu Thr Thr Leu Glu Lys Cys Cys Ala Ala Ala Asp
            355                 360                 365

Pro His Glu Cys Tyr Ala Lys Val Phe Asp Glu Phe Lys Pro Leu Val
            370                 375                 380

Glu Glu Pro Gln Asn Leu Ile Lys Gln Asn Cys Glu Leu Phe Glu Gln
385                 390                 395                 400

Leu Gly Glu Tyr Lys Phe Gln Asn Ala Leu Leu Val Arg Tyr Thr Lys
                405                 410                 415

Lys Val Pro Gln Val Ser Thr Pro Thr Leu Val Glu Val Ser Arg Asn
            420                 425                 430

Leu Gly Lys Val Gly Ser Lys Cys Cys Lys His Pro Glu Ala Lys Arg
            435                 440                 445

Met Pro Cys Ala Glu Asp Tyr Leu Ser Val Val Leu Asn Gln Leu Cys
            450                 455                 460

Val Leu His Glu Lys Thr Pro Val Ser Asp Arg Val Thr Lys Cys Cys
465                 470                 475                 480

Thr Glu Ser Leu Val Asn Arg Arg Pro Cys Phe Ser Ala Leu Glu Val
                485                 490                 495

Asp Glu Thr Tyr Val Pro Lys Glu Phe Asn Ala Glu Thr Phe Thr Phe
            500                 505                 510
```

His Ala Asp Ile Cys Thr Leu Ser Glu Lys Glu Arg Gln Ile Lys Lys
515                 520                 525

Gln Thr Ala Leu Val Glu Leu Val Lys His Lys Pro Lys Ala Thr Lys
    530                 535                 540

Glu Gln Leu Lys Ala Val Met Asp Asp Phe Ala Ala Phe Val Glu Lys
545                 550                 555                 560

Cys Cys Lys Ala Asp Asp Lys Glu Thr Cys Phe Ala Glu Gly Lys
                565                 570                 575

Lys Leu Val Ala Ala Ser Gln Ala Ala Leu Gly Leu Ala Ala Ala Leu
                580                 585                 590

<210> SEQ ID NO 16
<211> LENGTH: 1095
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
        195                 200                 205

Ala Ser Leu Ile Ile Ser Gly Leu Gln Ala Asp Asp Glu Ala Asp Tyr
    210                 215                 220

Tyr Cys Ser Ser Tyr Gly Ser Ser Thr His Val Ile Phe Gly Gly
225                 230                 235                 240

Gly Thr Lys Val Thr Val Leu Gly Ala Ala Ser Asp Ala His Lys Ser
                245                 250                 255

Glu Val Ala His Arg Phe Lys Asp Leu Gly Glu Glu Asn Phe Lys Ala
            260                 265                 270

Leu Val Leu Ile Ala Phe Ala Gln Tyr Leu Gln Gln Ser Pro Phe Glu
        275                 280                 285

```
Asp His Val Lys Leu Val Asn Glu Val Thr Glu Phe Ala Lys Thr Cys
    290                 295                 300
Val Ala Asp Glu Ser Ala Glu Asn Cys Asp Lys Ser Leu His Thr Leu
305                 310                 315                 320
Phe Gly Asp Lys Leu Cys Thr Val Ala Thr Leu Arg Glu Thr Tyr Gly
                325                 330                 335
Glu Met Ala Asp Cys Cys Ala Lys Gln Glu Pro Glu Arg Asn Glu Cys
            340                 345                 350
Phe Leu Gln His Lys Asp Asp Asn Pro Asn Leu Pro Arg Leu Val Arg
        355                 360                 365
Pro Glu Val Asp Val Met Cys Thr Ala Phe His Asp Asn Glu Glu Thr
    370                 375                 380
Phe Leu Lys Lys Tyr Leu Tyr Glu Ile Ala Arg Arg His Pro Tyr Phe
385                 390                 395                 400
Tyr Ala Pro Glu Leu Leu Phe Phe Ala Lys Arg Tyr Lys Ala Ala Phe
                405                 410                 415
Thr Glu Cys Cys Gln Ala Ala Asp Lys Ala Ala Cys Leu Leu Pro Lys
            420                 425                 430
Leu Asp Glu Leu Arg Asp Glu Gly Lys Ala Ser Ser Ala Lys Gln Arg
        435                 440                 445
Leu Lys Cys Ala Ser Leu Gln Lys Phe Gly Glu Arg Ala Phe Lys Ala
    450                 455                 460
Trp Ala Val Ala Arg Leu Ser Gln Arg Phe Pro Lys Ala Glu Phe Ala
465                 470                 475                 480
Glu Val Ser Lys Leu Val Thr Asp Leu Thr Lys Val His Thr Glu Cys
                485                 490                 495
Cys His Gly Asp Leu Leu Glu Cys Ala Asp Asp Arg Ala Asp Leu Ala
            500                 505                 510
Lys Tyr Ile Cys Glu Asn Gln Asp Ser Ile Ser Ser Lys Leu Lys Glu
        515                 520                 525
Cys Cys Glu Lys Pro Leu Leu Glu Lys Ser His Cys Ile Ala Glu Val
    530                 535                 540
Glu Asn Asp Glu Met Pro Ala Asp Leu Pro Ser Leu Ala Ala Asp Phe
545                 550                 555                 560
Val Glu Ser Lys Asp Val Cys Lys Asn Tyr Ala Glu Ala Lys Asp Val
                565                 570                 575
Phe Leu Gly Met Phe Leu Tyr Glu Tyr Ala Arg Arg His Pro Asp Tyr
            580                 585                 590
Ser Val Val Leu Leu Leu Arg Leu Ala Lys Thr Tyr Glu Thr Thr Leu
        595                 600                 605
Glu Lys Cys Cys Ala Ala Ala Asp Pro His Glu Cys Tyr Ala Lys Val
    610                 615                 620
Phe Asp Glu Phe Lys Pro Leu Val Glu Glu Pro Gln Asn Leu Ile Lys
625                 630                 635                 640
Gln Asn Cys Glu Leu Phe Glu Gln Leu Gly Glu Tyr Lys Phe Gln Asn
                645                 650                 655
Ala Leu Leu Val Arg Tyr Thr Lys Lys Val Pro Gln Val Ser Thr Pro
            660                 665                 670
Thr Leu Val Glu Val Ser Arg Asn Leu Gly Lys Val Gly Ser Lys Cys
        675                 680                 685
Cys Lys His Pro Glu Ala Lys Arg Met Pro Cys Ala Glu Asp Tyr Leu
    690                 695                 700
```

```
Ser Val Val Leu Asn Gln Leu Cys Val Leu His Glu Lys Thr Pro Val
705                 710                 715                 720

Ser Asp Arg Val Thr Lys Cys Cys Thr Glu Ser Leu Val Asn Arg Arg
                725                 730                 735

Pro Cys Phe Ser Ala Leu Glu Val Asp Glu Thr Tyr Val Pro Lys Glu
            740                 745                 750

Phe Gln Ala Glu Thr Phe Thr Phe His Ala Asp Ile Cys Thr Leu Ser
        755                 760                 765

Glu Lys Glu Arg Gln Ile Lys Lys Gln Thr Ala Leu Val Glu Leu Val
770                 775                 780

Lys His Lys Pro Lys Ala Thr Lys Glu Gln Leu Lys Ala Val Met Asp
785                 790                 795                 800

Asp Phe Ala Ala Phe Val Glu Lys Cys Cys Lys Ala Asp Asp Lys Glu
            805                 810                 815

Thr Cys Phe Ala Glu Glu Gly Lys Lys Leu Val Ala Ala Ser Gln Ala
            820                 825                 830

Ala Leu Gly Leu Ala Ala Leu Gln Val Gln Leu Val Gln Ser Gly
            835                 840                 845

Ala Glu Val Lys Lys Pro Gly Glu Ser Leu Lys Ile Ser Cys Lys Gly
850                 855                 860

Ser Gly Tyr Ser Phe Thr Ser Tyr Trp Ile Ala Trp Val Arg Gln Met
865                 870                 875                 880

Pro Gly Lys Gly Leu Glu Tyr Met Gly Leu Ile Tyr Pro Gly Asp Ser
                885                 890                 895

Asp Thr Lys Tyr Ser Pro Ser Phe Gln Gly Gln Val Thr Ile Ser Val
                900                 905                 910

Asp Lys Ser Val Ser Thr Ala Tyr Leu Gln Trp Ser Ser Leu Lys Pro
                915                 920                 925

Ser Asp Ser Ala Val Tyr Phe Cys Ala Arg His Asp Val Gly Tyr Cys
930                 935                 940

Thr Asp Arg Thr Cys Ala Lys Trp Pro Glu Trp Leu Gly Val Trp Gly
945                 950                 955                 960

Gln Gly Thr Leu Val Thr Val Ser Ser Gly Gly Gly Gly Ser Ser Gly
                965                 970                 975

Gly Gly Ser Gly Gly Gly Ser Gln Ser Val Leu Thr Gln Pro Pro
            980                 985                 990

Ser Val Ser Ala Ala Pro Gly Gln Lys Val Thr Ile Ser Cys Ser Gly
            995                 1000                1005

Ser Ser Ser Asn Ile Gly Asn Asn Tyr Val Ser Trp Tyr Gln Gln
    1010                1015                1020

Leu Pro Gly Thr Ala Pro Lys Leu Leu Ile Tyr Asp His Thr Asn
    1025                1030                1035

Arg Pro Ala Gly Val Pro Asp Arg Phe Ser Gly Ser Lys Ser Gly
    1040                1045                1050

Thr Ser Ala Ser Leu Ala Ile Ser Gly Phe Arg Ser Glu Asp Glu
    1055                1060                1065

Ala Asp Tyr Tyr Cys Ala Ser Trp Asp Tyr Thr Leu Ser Gly Trp
    1070                1075                1080

Val Phe Gly Gly Gly Thr Lys Leu Thr Val Leu Gly
    1085                1090                1095

<210> SEQ ID NO 17
<211> LENGTH: 1092
<212> TYPE: PRT
```

-continued

<213> ORGANISM: Artificial Sequence
<220> FEATURE:
<223> OTHER INFORMATION: Synthetic Construct

<400> SEQUENCE: 17

```
Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Ser Phe Asn Thr Tyr
            20                  25                  30

Asp Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Ala Thr Thr Pro Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Val
130                 135                 140

Ser Gly Ala Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
                165                 170                 175

Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Thr Ser Ala Ser
        195                 200                 205

Leu Ala Ile Thr Gly Leu Gln Ala Glu Asp Glu Ala Asp Tyr Tyr Cys
210                 215                 220

Gln Ser Tyr Asp Ser Ser Leu Ser Ala Leu Phe Gly Gly Gly Thr Lys
225                 230                 235                 240

Leu Thr Val Leu Gly Ala Ala Ser Asp Ala His Lys Ser Glu Val Ala
                245                 250                 255

His Arg Phe Lys Asp Leu Gly Glu Glu Asn Phe Lys Ala Leu Val Leu
            260                 265                 270

Ile Ala Phe Ala Gln Tyr Leu Gln Gln Ser Pro Phe Glu Asp His Val
        275                 280                 285

Lys Leu Val Asn Glu Val Thr Glu Phe Ala Lys Thr Cys Val Ala Asp
290                 295                 300

Glu Ser Ala Glu Asn Cys Asp Lys Ser Leu His Thr Leu Phe Gly Asp
305                 310                 315                 320

Lys Leu Cys Thr Val Ala Thr Leu Arg Glu Thr Tyr Gly Glu Met Ala
                325                 330                 335

Asp Cys Cys Ala Lys Gln Glu Pro Glu Arg Asn Glu Cys Phe Leu Gln
            340                 345                 350

His Lys Asp Asp Asn Pro Asn Leu Pro Arg Leu Val Arg Pro Glu Val
        355                 360                 365

Asp Val Met Cys Thr Ala Phe His Asp Asn Glu Glu Thr Phe Leu Lys
370                 375                 380

Lys Tyr Leu Tyr Glu Ile Ala Arg Arg His Pro Tyr Phe Tyr Ala Pro
```

```
           385                 390                 395                 400
Glu Leu Leu Phe Phe Ala Lys Arg Tyr Lys Ala Ala Phe Thr Glu Cys
                    405                 410                 415

Cys Gln Ala Ala Asp Lys Ala Ala Cys Leu Leu Pro Lys Leu Asp Glu
                420                 425                 430

Leu Arg Asp Glu Gly Lys Ala Ser Ala Lys Gln Arg Leu Lys Cys
            435                 440                 445

Ala Ser Leu Gln Lys Phe Gly Glu Arg Ala Phe Lys Ala Trp Ala Val
450                 455                 460

Ala Arg Leu Ser Gln Arg Phe Pro Lys Ala Glu Phe Ala Glu Val Ser
465                 470                 475                 480

Lys Leu Val Thr Asp Leu Thr Lys Val His Thr Glu Cys Cys His Gly
                485                 490                 495

Asp Leu Leu Glu Cys Ala Asp Asp Arg Ala Asp Leu Ala Lys Tyr Ile
                500                 505                 510

Cys Glu Asn Gln Asp Ser Ile Ser Ser Lys Leu Lys Glu Cys Cys Glu
            515                 520                 525

Lys Pro Leu Leu Glu Lys Ser His Cys Ile Ala Glu Val Glu Asn Asp
530                 535                 540

Glu Met Pro Ala Asp Leu Pro Ser Leu Ala Ala Asp Phe Val Glu Ser
545                 550                 555                 560

Lys Asp Val Cys Lys Asn Tyr Ala Glu Ala Lys Asp Val Phe Leu Gly
                565                 570                 575

Met Phe Leu Tyr Glu Tyr Ala Arg Arg His Pro Asp Tyr Ser Val Val
                580                 585                 590

Leu Leu Leu Arg Leu Ala Lys Thr Tyr Glu Thr Thr Leu Glu Lys Cys
            595                 600                 605

Cys Ala Ala Ala Asp Pro His Glu Cys Tyr Ala Lys Val Phe Asp Glu
            610                 615                 620

Phe Lys Pro Leu Val Glu Glu Pro Gln Asn Leu Ile Lys Gln Asn Cys
625                 630                 635                 640

Glu Leu Phe Glu Gln Leu Gly Glu Tyr Lys Phe Gln Asn Ala Leu Leu
                645                 650                 655

Val Arg Tyr Thr Lys Lys Val Pro Gln Val Ser Thr Pro Thr Leu Val
                660                 665                 670

Glu Val Ser Arg Asn Leu Gly Lys Val Gly Ser Lys Cys Cys Lys His
            675                 680                 685

Pro Glu Ala Lys Arg Met Pro Cys Ala Glu Asp Tyr Leu Ser Val Val
        690                 695                 700

Leu Asn Gln Leu Cys Val Leu His Glu Lys Thr Pro Val Ser Asp Arg
705                 710                 715                 720

Val Thr Lys Cys Cys Thr Glu Ser Leu Val Asn Arg Arg Pro Cys Phe
                725                 730                 735

Ser Ala Leu Glu Val Asp Glu Thr Tyr Val Pro Lys Glu Phe Gln Ala
            740                 745                 750

Glu Thr Phe Thr Phe His Ala Asp Ile Cys Thr Leu Ser Glu Lys Glu
            755                 760                 765

Arg Gln Ile Lys Lys Gln Thr Ala Leu Val Glu Leu Val Lys His Lys
        770                 775                 780

Pro Lys Ala Thr Lys Glu Gln Leu Lys Ala Val Met Asp Asp Phe Ala
785                 790                 795                 800

Ala Phe Val Glu Lys Cys Cys Lys Ala Asp Asp Lys Glu Thr Cys Phe
                805                 810                 815
```

Ala Glu Glu Gly Lys Lys Leu Val Ala Ala Ser Gln Ala Ala Leu Gly
            820                 825                 830

Leu Ala Ala Ala Leu Gln Val Gln Leu Val Gln Ser Gly Ala Glu Val
            835                 840                 845

Lys Lys Pro Gly Glu Ser Leu Lys Ile Ser Cys Lys Gly Ser Gly Tyr
850                 855                 860

Ser Phe Thr Ser Tyr Trp Ile Ala Trp Val Arg Gln Met Pro Gly Lys
865                 870                 875                 880

Gly Leu Glu Tyr Met Gly Leu Ile Tyr Pro Gly Asp Ser Asp Thr Lys
                885                 890                 895

Tyr Ser Pro Ser Phe Gln Gly Gln Val Thr Ile Ser Val Asp Lys Ser
            900                 905                 910

Val Ser Thr Ala Tyr Leu Gln Trp Ser Ser Leu Lys Pro Ser Asp Ser
        915                 920                 925

Ala Val Tyr Phe Cys Ala Arg His Asp Val Gly Tyr Cys Thr Asp Arg
    930                 935                 940

Thr Cys Ala Lys Trp Pro Glu Trp Leu Gly Val Trp Gly Gln Gly Thr
945                 950                 955                 960

Leu Val Thr Val Ser Ser Gly Gly Gly Gly Ser Gly Gly Gly Gly Ser
                965                 970                 975

Gly Gly Gly Gly Ser Gln Ser Val Leu Thr Gln Pro Pro Ser Val Ser
            980                 985                 990

Ala Ala Pro Gly Gln Lys Val Thr Ile Ser Cys Ser Gly Ser Ser Ser
            995                 1000                1005

Asn Ile Gly Asn Asn Tyr Val Ser Trp Tyr Gln Gln Leu Pro Gly
        1010                1015                1020

Thr Ala Pro Lys Leu Leu Ile Tyr Asp His Thr Asn Arg Pro Ala
        1025                1030                1035

Gly Val Pro Asp Arg Phe Ser Gly Ser Lys Ser Gly Thr Ser Ala
        1040                1045                1050

Ser Leu Ala Ile Ser Gly Phe Arg Ser Glu Asp Glu Ala Asp Tyr
        1055                1060                1065

Tyr Cys Ala Ser Trp Asp Tyr Thr Leu Ser Gly Trp Val Phe Gly
        1070                1075                1080

Gly Gly Thr Lys Leu Thr Val Leu Gly
        1085                1090

<210> SEQ ID NO 18
<211> LENGTH: 1083
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Ser Phe Asn Thr Tyr
            20                  25                  30

Asp Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Arg Asp Gly Val Ala Thr Thr Pro Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Val
130                 135                 140

Ser Gly Ala Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
                165                 170                 175

Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Thr Ser Ala Ser
        195                 200                 205

Leu Ala Ile Thr Gly Leu Gln Ala Glu Asp Glu Ala Asp Tyr Tyr Cys
    210                 215                 220

Gln Ser Tyr Asp Ser Ser Leu Ser Ala Leu Phe Gly Gly Gly Thr Lys
225                 230                 235                 240

Leu Thr Val Leu Gly Ala Ala Ser Asp Ala His Lys Ser Glu Val Ala
                245                 250                 255

His Arg Phe Lys Asp Leu Gly Glu Glu Asn Phe Lys Ala Leu Val Leu
            260                 265                 270

Ile Ala Phe Ala Gln Tyr Leu Gln Gln Ser Pro Phe Glu Asp His Val
        275                 280                 285

Lys Leu Val Asn Glu Val Thr Glu Phe Ala Lys Thr Cys Val Ala Asp
    290                 295                 300

Glu Ser Ala Glu Asn Cys Asp Lys Ser Leu His Thr Leu Phe Gly Asp
305                 310                 315                 320

Lys Leu Cys Thr Val Ala Thr Leu Arg Glu Thr Tyr Gly Glu Met Ala
                325                 330                 335

Asp Cys Cys Ala Lys Gln Glu Pro Glu Arg Asn Glu Cys Phe Leu Gln
            340                 345                 350

His Lys Asp Asp Asn Pro Asn Leu Pro Arg Leu Val Arg Pro Glu Val
        355                 360                 365

Asp Val Met Cys Thr Ala Phe His Asp Asn Glu Glu Thr Phe Leu Lys
    370                 375                 380

Lys Tyr Leu Tyr Glu Ile Ala Arg Arg His Pro Tyr Phe Tyr Ala Pro
385                 390                 395                 400

Glu Leu Leu Phe Phe Ala Lys Arg Tyr Lys Ala Ala Phe Thr Glu Cys
                405                 410                 415

Cys Gln Ala Ala Asp Lys Ala Ala Cys Leu Leu Pro Lys Leu Asp Glu
            420                 425                 430

Leu Arg Asp Glu Gly Lys Ala Ser Ala Lys Gln Arg Leu Lys Cys
        435                 440                 445

Ala Ser Leu Gln Lys Phe Gly Glu Arg Ala Phe Lys Ala Trp Ala Val
    450                 455                 460

Ala Arg Leu Ser Gln Arg Phe Pro Lys Ala Glu Phe Ala Glu Val Ser
465                 470                 475                 480

Lys Leu Val Thr Asp Leu Thr Lys Val His Thr Glu Cys Cys His Gly
                485                 490                 495
```

```
Asp Leu Leu Glu Cys Ala Asp Asp Arg Ala Asp Leu Ala Lys Tyr Ile
            500                 505                 510

Cys Glu Asn Gln Asp Ser Ile Ser Ser Lys Leu Lys Glu Cys Cys Glu
            515                 520                 525

Lys Pro Leu Leu Glu Lys Ser His Cys Ile Ala Glu Val Glu Asn Asp
        530                 535                 540

Glu Met Pro Ala Asp Leu Pro Ser Leu Ala Ala Asp Phe Val Glu Ser
545                 550                 555                 560

Lys Asp Val Cys Lys Asn Tyr Ala Glu Ala Lys Asp Val Phe Leu Gly
                565                 570                 575

Met Phe Leu Tyr Glu Tyr Ala Arg Arg His Pro Asp Tyr Ser Val Val
            580                 585                 590

Leu Leu Leu Arg Leu Ala Lys Thr Tyr Glu Thr Thr Leu Glu Lys Cys
            595                 600                 605

Cys Ala Ala Ala Asp Pro His Glu Cys Tyr Ala Lys Val Phe Asp Glu
        610                 615                 620

Phe Lys Pro Leu Val Glu Glu Pro Gln Asn Leu Ile Lys Gln Asn Cys
625                 630                 635                 640

Glu Leu Phe Glu Gln Leu Gly Glu Tyr Lys Phe Gln Asn Ala Leu Leu
                645                 650                 655

Val Arg Tyr Thr Lys Lys Val Pro Gln Val Ser Thr Pro Thr Leu Val
            660                 665                 670

Glu Val Ser Arg Asn Leu Gly Lys Val Gly Ser Lys Cys Cys Lys His
            675                 680                 685

Pro Glu Ala Lys Arg Met Pro Cys Ala Glu Asp Tyr Leu Ser Val Val
        690                 695                 700

Leu Asn Gln Leu Cys Val Leu His Glu Lys Thr Pro Val Ser Asp Arg
705                 710                 715                 720

Val Thr Lys Cys Cys Thr Glu Ser Leu Val Asn Arg Arg Pro Cys Phe
                725                 730                 735

Ser Ala Leu Glu Val Asp Glu Thr Tyr Val Pro Lys Glu Phe Gln Ala
            740                 745                 750

Glu Thr Phe Thr Phe His Ala Asp Ile Cys Thr Leu Ser Glu Lys Glu
            755                 760                 765

Arg Gln Ile Lys Lys Gln Thr Ala Leu Val Glu Leu Val Lys His Lys
        770                 775                 780

Pro Lys Ala Thr Lys Glu Gln Leu Lys Ala Val Met Asp Asp Phe Ala
785                 790                 795                 800

Ala Phe Val Glu Lys Cys Cys Lys Ala Asp Asp Lys Glu Thr Cys Phe
                805                 810                 815

Ala Glu Glu Gly Lys Lys Leu Val Ala Ala Ser Gln Ala Ala Leu Gly
            820                 825                 830

Leu Ala Ala Ala Leu Gln Val Gln Leu Val Glu Ser Gly Gly Gly Leu
        835                 840                 845

Val Gln Pro Gly Gly Ser Leu Arg Leu Ser Cys Ala Ala Ser Gly Phe
        850                 855                 860

Thr Phe Arg Ser Tyr Ala Met Ser Trp Val Arg Gln Ala Pro Gly Lys
865                 870                 875                 880

Gly Leu Glu Trp Val Ser Ala Ile Ser Gly Arg Gly Asp Asn Thr Tyr
                885                 890                 895

Tyr Ala Asp Ser Val Lys Gly Arg Phe Thr Ile Ser Arg Asp Asn Ser
            900                 905                 910

Lys Asn Thr Leu Tyr Leu Gln Met Asn Ser Leu Arg Ala Glu Asp Thr
```

```
            915                 920                 925
Ala Val Tyr Tyr Cys Ala Lys Met Thr Ser Asn Ala Val Gly Phe Asp
    930                 935                 940

Tyr Trp Gly Gln Gly Thr Leu Val Thr Val Ser Ser Gly Gly Gly Gly
945                 950                 955                 960

Ser Gly Gly Gly Ser Gly Gly Gly Ser Gly Gln Ser Val Leu Thr
                965                 970                 975

Gln Pro Pro Ser Val Ser Gly Ala Pro Gly Gln Arg Val Thr Ile Ser
                980                 985                 990

Cys Thr Gly Arg His Ser Asn Ile Gly Leu Gly Tyr Gly Val His Trp
                995                 1000                1005

Tyr Gln Gln Leu Pro Gly Thr Ala Pro Lys Leu Leu Ile Tyr Gly
    1010                1015                1020

Asn Thr Asn Arg Pro Ser Gly Val Pro Asp Arg Phe Ser Gly Phe
    1025                1030                1035

Lys Ser Gly Thr Ser Ala Ser Leu Ala Ile Thr Gly Leu Gln Ala
    1040                1045                1050

Glu Asp Glu Ala Asp Tyr Tyr Cys Gln Ser Tyr Asp Arg Arg Thr
    1055                1060                1065

Pro Gly Trp Val Phe Gly Gly Gly Thr Lys Leu Thr Val Leu Gly
    1070                1075                1080

<210> SEQ ID NO 19
<211> LENGTH: 1092
<212> TYPE: PRT
<213> ORGANISM: Artificial Sequence
<220> FEATURE:
<223> OTHER INFORMATION: Synthetic Construct

<400> SEQUENCE: 19

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Ser Phe Asn Thr Tyr
            20                  25                  30

Asp Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Ala Thr Thr Pro Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Val Leu Thr Gln Pro Pro Ser Val
    130                 135                 140

Ser Gly Ala Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
                165                 170                 175

Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Thr Ser Ala Ser
```

```
                 195                 200                 205
Leu Ala Ile Thr Gly Leu Gln Ala Glu Asp Glu Ala Asp Tyr Tyr Cys
210                 215                 220

Gln Ser Tyr Asp Ser Ser Leu Ser Ala Leu Phe Gly Gly Gly Thr Lys
225                 230                 235                 240

Leu Thr Val Leu Gly Ala Ala Ser Asp Ala His Lys Ser Glu Val Ala
                245                 250                 255

His Arg Phe Lys Asp Leu Gly Glu Glu Asn Phe Lys Ala Leu Val Leu
                260                 265                 270

Ile Ala Phe Ala Gln Tyr Leu Gln Gln Ser Pro Phe Glu Asp His Val
                275                 280                 285

Lys Leu Val Asn Glu Val Thr Glu Phe Ala Lys Thr Cys Val Ala Asp
290                 295                 300

Glu Ser Ala Glu Asn Cys Asp Lys Ser Leu His Thr Leu Phe Gly Asp
305                 310                 315                 320

Lys Leu Cys Thr Val Ala Thr Leu Arg Glu Thr Tyr Gly Glu Met Ala
                325                 330                 335

Asp Cys Cys Ala Lys Gln Glu Pro Glu Arg Asn Glu Cys Phe Leu Gln
                340                 345                 350

His Lys Asp Asp Asn Pro Asn Leu Pro Arg Leu Val Arg Pro Glu Val
                355                 360                 365

Asp Val Met Cys Thr Ala Phe His Asp Asn Glu Glu Thr Phe Leu Lys
370                 375                 380

Lys Tyr Leu Tyr Glu Ile Ala Arg Arg His Pro Tyr Phe Tyr Ala Pro
385                 390                 395                 400

Glu Leu Leu Phe Phe Ala Lys Arg Tyr Lys Ala Ala Phe Thr Glu Cys
                405                 410                 415

Cys Gln Ala Ala Asp Lys Ala Ala Cys Leu Leu Pro Lys Leu Asp Glu
                420                 425                 430

Leu Arg Asp Glu Gly Lys Ala Ser Ser Ala Lys Gln Arg Leu Lys Cys
                435                 440                 445

Ala Ser Leu Gln Lys Phe Gly Glu Arg Ala Phe Lys Ala Trp Ala Val
450                 455                 460

Ala Arg Leu Ser Gln Arg Phe Pro Lys Ala Glu Phe Ala Glu Val Ser
465                 470                 475                 480

Lys Leu Val Thr Asp Leu Thr Lys Val His Thr Glu Cys Cys His Gly
                485                 490                 495

Asp Leu Leu Glu Cys Ala Asp Asp Arg Ala Asp Leu Ala Lys Tyr Ile
                500                 505                 510

Cys Glu Asn Gln Asp Ser Ile Ser Ser Lys Leu Lys Glu Cys Cys Glu
                515                 520                 525

Lys Pro Leu Leu Glu Lys Ser His Cys Ile Ala Glu Val Glu Asn Asp
530                 535                 540

Glu Met Pro Ala Asp Leu Pro Ser Leu Ala Ala Asp Phe Val Glu Ser
545                 550                 555                 560

Lys Asp Val Cys Lys Asn Tyr Ala Glu Ala Lys Asp Val Phe Leu Gly
                565                 570                 575

Met Phe Leu Tyr Glu Tyr Ala Arg Arg His Pro Asp Tyr Ser Val Val
                580                 585                 590

Leu Leu Leu Arg Leu Ala Lys Thr Tyr Glu Thr Thr Leu Glu Lys Cys
                595                 600                 605

Cys Ala Ala Ala Asp Pro His Glu Cys Tyr Ala Lys Val Phe Asp Glu
610                 615                 620
```

```
Phe Lys Pro Leu Val Glu Pro Gln Asn Leu Ile Lys Gln Asn Cys
625                 630                 635                 640

Glu Leu Phe Glu Gln Leu Gly Glu Tyr Lys Phe Gln Asn Ala Leu Leu
    645                 650                 655

Val Arg Tyr Thr Lys Lys Val Pro Gln Val Ser Thr Pro Thr Leu Val
            660                 665                 670

Glu Val Ser Arg Asn Leu Gly Lys Val Gly Ser Lys Cys Cys Lys His
        675                 680                 685

Pro Glu Ala Lys Arg Met Pro Cys Ala Glu Asp Tyr Leu Ser Val Val
690                 695                 700

Leu Asn Gln Leu Cys Val Leu His Glu Lys Thr Pro Val Ser Asp Arg
705                 710                 715                 720

Val Thr Lys Cys Cys Thr Glu Ser Leu Val Asn Arg Arg Pro Cys Phe
                725                 730                 735

Ser Ala Leu Glu Val Asp Glu Thr Tyr Val Pro Lys Glu Phe Gln Ala
            740                 745                 750

Glu Thr Phe Thr Phe His Ala Asp Ile Cys Thr Leu Ser Glu Lys Glu
        755                 760                 765

Arg Gln Ile Lys Lys Gln Thr Ala Leu Val Glu Leu Val Lys His Lys
770                 775                 780

Pro Lys Ala Thr Lys Glu Gln Leu Lys Ala Val Met Asp Asp Phe Ala
785                 790                 795                 800

Ala Phe Val Glu Lys Cys Cys Lys Ala Asp Asp Lys Glu Thr Cys Phe
                805                 810                 815

Ala Glu Glu Gly Lys Lys Leu Val Ala Ala Ser Gln Ala Ala Leu Gly
            820                 825                 830

Leu Ala Ala Ala Leu Gln Val Gln Leu Val Gln Ser Gly Ala Glu Val
        835                 840                 845

Lys Lys Pro Gly Glu Ser Leu Lys Ile Ser Cys Lys Gly Ser Gly Tyr
850                 855                 860

Ser Phe Thr Ser Tyr Trp Ile Ala Trp Val Arg Gln Met Pro Gly Lys
865                 870                 875                 880

Gly Leu Glu Tyr Met Gly Leu Ile Tyr Pro Gly Asp Ser Asp Thr Lys
                885                 890                 895

Tyr Ser Pro Ser Phe Gln Gly Gln Val Thr Ile Ser Val Asp Lys Ser
            900                 905                 910

Val Ser Thr Ala Tyr Leu Gln Trp Ser Ser Leu Lys Pro Ser Asp Ser
        915                 920                 925

Ala Val Tyr Phe Cys Ala Arg His Asp Val Gly Tyr Cys Ser Ser Ser
930                 935                 940

Asn Cys Ala Lys Trp Pro Glu Tyr Phe Gln His Trp Gly Gln Gly Thr
945                 950                 955                 960

Leu Val Thr Val Ser Ser Gly Gly Gly Ser Ser Gly Gly Gly Ser
                965                 970                 975

Gly Gly Gly Gly Ser Gln Ser Val Leu Thr Gln Pro Pro Ser Val Ser
            980                 985                 990

Ala Ala Pro Gly Gln Lys Val Thr Ile Ser Cys Ser Gly Ser Ser Ser
        995                 1000                1005

Asn Ile Gly Asn Asn Tyr Val Ser Trp Tyr Gln Gln Leu Pro Gly
        1010                1015                1020

Thr Ala Pro Lys Leu Leu Ile Tyr Asp His Thr Asn Arg Pro Ala
        1025                1030                1035
```

```
Gly Val Pro Asp Arg Phe Ser Gly Ser Lys Ser Gly Thr Ser Ala
    1040                1045                1050

Ser Leu Ala Ile Ser Gly Phe Arg Ser Glu Asp Glu Ala Asp Tyr
    1055                1060                1065

Tyr Cys Ala Ser Trp Asp Tyr Thr Leu Ser Gly Trp Val Phe Gly
    1070                1075                1080

Gly Gly Thr Lys Leu Thr Val Leu Gly
    1085                1090

<210> SEQ ID NO 20
<211> LENGTH: 1096
<212> TYPE: PRT
<213> ORGANISM: Artificial Sequence
<220> FEATURE:
<223> OTHER INFORMATION: Synthetic Construct

<400> SEQUENCE: 20

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Val Tyr Tyr Cys
                85                  90                  95

Ala Arg Asp Leu Gly Ala Lys Gln Trp Leu Glu Gly Phe Asp Tyr Trp
            100                 105                 110

Gly Gln Gly Thr Leu Val Thr Val Ser Ser Ala Ser Thr Gly Gly Gly
        115                 120                 125

Gly Ser Gly Gly Gly Gly Ser Gly Gly Gly Gly Ser Ser Tyr Glu Leu
    130                 135                 140

Thr Gln Asp Pro Ala Val Ser Val Ala Leu Gly Gln Thr Val Arg Ile
145                 150                 155                 160

Thr Cys Gln Gly Asp Ser Leu Arg Ser Tyr Tyr Ala Ser Trp Tyr Gln
                165                 170                 175

Gln Lys Pro Gly Gln Ala Pro Val Leu Val Ile Tyr Gly Lys Asn Asn
            180                 185                 190

Arg Pro Ser Gly Ile Pro Asp Arg Phe Ser Gly Ser Thr Ser Gly Asn
        195                 200                 205

Ser Ala Ser Leu Thr Ile Thr Gly Ala Gln Ala Glu Asp Glu Ala Asp
    210                 215                 220

Tyr Tyr Cys Asn Ser Arg Asp Ser Ser Gly Asn His Trp Val Phe Gly
225                 230                 235                 240

Gly Gly Thr Lys Val Thr Val Leu Gly Ala Ala Ser Asp Ala His Lys
                245                 250                 255

Ser Glu Val Ala His Arg Phe Lys Asp Leu Gly Glu Glu Asn Phe Lys
            260                 265                 270

Ala Leu Val Leu Ile Ala Phe Ala Gln Tyr Leu Gln Gln Ser Pro Phe
        275                 280                 285

Glu Asp His Val Lys Leu Val Asn Glu Val Thr Glu Phe Ala Lys Thr
    290                 295                 300
```

```
Cys Val Ala Asp Glu Ser Ala Glu Asn Cys Asp Lys Ser Leu His Thr
305                 310                 315                 320

Leu Phe Gly Asp Lys Leu Cys Thr Val Ala Thr Leu Arg Glu Thr Tyr
            325                 330                 335

Gly Glu Met Ala Asp Cys Cys Ala Lys Gln Glu Pro Glu Arg Asn Glu
            340                 345                 350

Cys Phe Leu Gln His Lys Asp Asp Asn Pro Asn Leu Pro Arg Leu Val
            355                 360                 365

Arg Pro Glu Val Asp Val Met Cys Thr Ala Phe His Asp Asn Glu Glu
370                 375                 380

Thr Phe Leu Lys Lys Tyr Leu Tyr Glu Ile Ala Arg Arg His Pro Tyr
385                 390                 395                 400

Phe Tyr Ala Pro Glu Leu Leu Phe Phe Ala Lys Arg Tyr Lys Ala Ala
            405                 410                 415

Phe Thr Glu Cys Cys Gln Ala Ala Asp Lys Ala Ala Cys Leu Leu Pro
            420                 425                 430

Lys Leu Asp Glu Leu Arg Asp Glu Gly Lys Ala Ser Ser Ala Lys Gln
            435                 440                 445

Arg Leu Lys Cys Ala Ser Leu Gln Lys Phe Gly Glu Arg Ala Phe Lys
450                 455                 460

Ala Trp Ala Val Ala Arg Leu Ser Gln Arg Phe Pro Lys Ala Glu Phe
465                 470                 475                 480

Ala Glu Val Ser Lys Leu Val Thr Asp Leu Thr Lys Val His Thr Glu
            485                 490                 495

Cys Cys His Gly Asp Leu Leu Glu Cys Ala Asp Asp Arg Ala Asp Leu
            500                 505                 510

Ala Lys Tyr Ile Cys Glu Asn Gln Asp Ser Ile Ser Ser Lys Leu Lys
            515                 520                 525

Glu Cys Cys Glu Lys Pro Leu Leu Glu Lys Ser His Cys Ile Ala Glu
530                 535                 540

Val Glu Asn Asp Glu Met Pro Ala Asp Leu Pro Ser Leu Ala Ala Asp
545                 550                 555                 560

Phe Val Glu Ser Lys Asp Val Cys Lys Asn Tyr Ala Glu Ala Lys Asp
            565                 570                 575

Val Phe Leu Gly Met Phe Leu Tyr Glu Tyr Ala Arg Arg His Pro Asp
            580                 585                 590

Tyr Ser Val Val Leu Leu Leu Arg Leu Ala Lys Thr Tyr Glu Thr Thr
            595                 600                 605

Leu Glu Lys Cys Cys Ala Ala Ala Asp Pro His Glu Cys Tyr Ala Lys
610                 615                 620

Val Phe Asp Glu Phe Lys Pro Leu Val Glu Glu Pro Gln Asn Leu Ile
625                 630                 635                 640

Lys Gln Asn Cys Glu Leu Phe Glu Gln Leu Gly Glu Tyr Lys Phe Gln
            645                 650                 655

Asn Ala Leu Leu Val Arg Tyr Thr Lys Lys Val Pro Gln Val Ser Thr
            660                 665                 670

Pro Thr Leu Val Glu Val Ser Arg Asn Leu Gly Lys Val Gly Ser Lys
            675                 680                 685

Cys Cys Lys His Pro Glu Ala Lys Arg Met Pro Cys Ala Glu Asp Tyr
            690                 695                 700

Leu Ser Val Val Leu Asn Gln Leu Cys Val Leu His Glu Lys Thr Pro
705                 710                 715                 720

Val Ser Asp Arg Val Thr Lys Cys Cys Thr Glu Ser Leu Val Asn Arg
```

```
                725                 730                 735
Arg Pro Cys Phe Ser Ala Leu Glu Val Asp Glu Thr Tyr Val Pro Lys
            740                 745                 750

Glu Phe Gln Ala Glu Thr Phe Thr Phe His Ala Asp Ile Cys Thr Leu
            755                 760                 765

Ser Glu Lys Glu Arg Gln Ile Lys Lys Gln Thr Ala Leu Val Glu Leu
            770                 775                 780

Val Lys His Lys Pro Lys Ala Thr Lys Glu Gln Leu Lys Ala Val Met
785                 790                 795                 800

Asp Asp Phe Ala Ala Phe Val Glu Lys Cys Cys Lys Ala Asp Asp Lys
                805                 810                 815

Glu Thr Cys Phe Ala Glu Glu Gly Lys Lys Leu Val Ala Ala Ser Gln
            820                 825                 830

Ala Ala Leu Gly Leu Ala Ala Leu Gln Val Gln Leu Val Gln Ser
            835                 840                 845

Gly Ala Glu Val Lys Lys Pro Gly Glu Ser Leu Lys Ile Ser Cys Lys
850                 855                 860

Gly Ser Gly Tyr Ser Phe Thr Ser Tyr Trp Ile Ala Trp Val Arg Gln
865                 870                 875                 880

Met Pro Gly Lys Gly Leu Glu Tyr Met Gly Leu Ile Tyr Pro Gly Asp
                885                 890                 895

Ser Asp Thr Lys Tyr Ser Pro Ser Phe Gln Gly Gln Val Thr Ile Ser
                900                 905                 910

Val Asp Lys Ser Val Ser Thr Ala Tyr Leu Gln Trp Ser Ser Leu Lys
                915                 920                 925

Pro Ser Asp Ser Ala Val Tyr Phe Cys Ala Arg His Asp Val Gly Tyr
            930                 935                 940

Cys Thr Asp Arg Thr Cys Ala Lys Trp Pro Glu Trp Leu Gly Val Trp
945                 950                 955                 960

Gly Gln Gly Thr Leu Val Thr Val Ser Ser Gly Gly Gly Gly Ser Ser
                965                 970                 975

Gly Gly Gly Ser Gly Gly Gly Ser Gln Ser Val Leu Thr Gln Pro
            980                 985                 990

Pro Ser Val Ser Ala Ala Pro Gly Gln Lys Val Thr Ile Ser Cys Ser
            995                 1000                1005

Gly Ser Ser Ser Asn Ile Gly Asn Asn Tyr Val Ser Trp Tyr Gln
            1010                1015                1020

Gln Leu Pro Gly Thr Ala Pro Lys Leu Leu Ile Tyr Asp His Thr
            1025                1030                1035

Asn Arg Pro Ala Gly Val Pro Asp Arg Phe Ser Gly Ser Lys Ser
            1040                1045                1050

Gly Thr Ser Ala Ser Leu Ala Ile Ser Gly Phe Arg Ser Glu Asp
            1055                1060                1065

Glu Ala Asp Tyr Tyr Cys Ala Ser Trp Asp Tyr Thr Leu Ser Gly
            1070                1075                1080

Trp Val Phe Gly Gly Gly Thr Lys Leu Thr Val Leu Gly
            1085                1090                1095

<210> SEQ ID NO 21
<211> LENGTH: 1086
<212> TYPE: PRT
<213> ORGANISM: Artificial Sequence
<220> FEATURE:
<223> OTHER INFORMATION: Synthetic Construct
```

```
<400> SEQUENCE: 21

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Val Tyr Tyr Cys
                85                  90                  95

Ala Arg Asp Leu Gly Ala Lys Gln Trp Leu Glu Gly Phe Asp Tyr Trp
            100                 105                 110

Gly Gln Gly Thr Leu Val Thr Val Ser Ser Ala Ser Thr Gly Gly Gly
        115                 120                 125

Gly Ser Gly Gly Gly Gly Ser Gly Gly Gly Gly Ser Ser Tyr Glu Leu
    130                 135                 140

Thr Gln Asp Pro Ala Val Ser Val Ala Leu Gly Gln Thr Val Arg Ile
145                 150                 155                 160

Thr Cys Gln Gly Asp Ser Leu Arg Ser Tyr Tyr Ala Ser Trp Tyr Gln
                165                 170                 175

Gln Lys Pro Gly Gln Ala Pro Val Leu Val Ile Tyr Gly Lys Asn Asn
            180                 185                 190

Arg Pro Ser Gly Ile Pro Asp Arg Phe Ser Gly Ser Thr Ser Gly Asn
        195                 200                 205

Ser Ala Ser Leu Thr Ile Thr Gly Ala Gln Ala Glu Asp Glu Ala Asp
    210                 215                 220

Tyr Tyr Cys Asn Ser Arg Asp Ser Ser Gly Asn His Trp Val Phe Gly
225                 230                 235                 240

Gly Gly Thr Lys Val Thr Val Leu Gly Ala Ala Ser Asp Ala His Lys
                245                 250                 255

Ser Glu Val Ala His Arg Phe Lys Asp Leu Gly Glu Glu Asn Phe Lys
            260                 265                 270

Ala Leu Val Leu Ile Ala Phe Ala Gln Tyr Leu Gln Gln Ser Pro Phe
        275                 280                 285

Glu Asp His Val Lys Leu Val Asn Glu Val Thr Glu Phe Ala Lys Thr
    290                 295                 300

Cys Val Ala Asp Glu Ser Ala Glu Asn Cys Asp Lys Ser Leu His Thr
305                 310                 315                 320

Leu Phe Gly Asp Lys Leu Cys Thr Val Ala Thr Leu Arg Glu Thr Tyr
                325                 330                 335

Gly Glu Met Ala Asp Cys Cys Ala Lys Gln Glu Pro Glu Arg Asn Glu
            340                 345                 350

Cys Phe Leu Gln His Lys Asp Asp Asn Pro Asn Leu Pro Arg Leu Val
        355                 360                 365

Arg Pro Glu Val Asp Val Met Cys Thr Ala Phe His Asp Asn Glu Glu
    370                 375                 380

Thr Phe Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
                405                 410                 415
```

-continued

```
Thr Glu Cys Cys Gln Ala Ala Asp Lys Ala Ala Cys Leu Leu Pro Lys
            420                 425                 430

Leu Asp Glu Leu Arg Asp Glu Gly Lys Ala Ser Ser Ala Lys Gln Arg
            435                 440                 445

Leu Lys Cys Ala Ser Leu Gln Lys Phe Gly Glu Arg Ala Phe Lys Ala
            450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
                485                 490                 495

Cys His Gly Asp Leu Leu Glu Cys Ala Asp Asp Arg Ala Asp Leu Ala
                500                 505                 510

Lys Tyr Ile Cys Glu Asn Gln Asp Ser Ile Ser Ser Lys Leu Lys Glu
            515                 520                 525

Cys Cys Glu Lys Pro Leu Leu Glu Lys Ser His Cys Ile Ala Glu Val
            530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
                565                 570                 575

Phe Leu Gly Met Phe Leu Tyr Glu Tyr Ala Arg Arg His Pro Asp Tyr
                580                 585                 590

Ser Val Val Leu Leu Leu Arg Leu Ala Lys Thr Tyr Glu Thr Thr Leu
            595                 600                 605

Glu Lys Cys Cys Ala Ala Ala Asp Pro His Glu Cys Tyr Ala Lys Val
            610                 615                 620

Phe Asp Glu Phe Lys Pro Leu Val Glu Glu Pro Gln Asn Leu Ile Lys
625                 630                 635                 640

Gln Asn Cys Glu Leu Phe Glu Gln Leu Gly Glu Tyr Lys Phe Gln Asn
                645                 650                 655

Ala Leu Leu Val Arg Tyr Thr Lys Lys Val Pro Gln Val Ser Thr Pro
            660                 665                 670

Thr Leu Val Glu Val Ser Arg Asn Leu Gly Lys Val Gly Ser Lys Cys
            675                 680                 685

Cys Lys His Pro Glu Ala Lys Arg Met Pro Cys Ala Glu Asp Tyr Leu
            690                 695                 700

Ser Val Val Leu Asn Gln Leu Cys Val Leu His Glu Lys Thr Pro Val
705                 710                 715                 720

Ser Asp Arg Val Thr Lys Cys Cys Thr Glu Ser Leu Val Asn Arg Arg
                725                 730                 735

Pro Cys Phe Ser Ala Leu Glu Val Asp Glu Thr Tyr Val Pro Lys Glu
            740                 745                 750

Phe Gln Ala Glu Thr Phe Thr Phe His Ala Asp Ile Cys Thr Leu Ser
            755                 760                 765

Glu Lys Glu Arg Gln Ile Lys Lys Gln Thr Ala Leu Val Glu Leu Val
            770                 775                 780

Lys His Lys Pro Lys Ala Thr Lys Glu Gln Leu Lys Ala Val Met Asp
785                 790                 795                 800

Asp Phe Ala Ala Phe Val Glu Lys Cys Cys Lys Ala Asp Asp Lys Glu
                805                 810                 815

Thr Cys Phe Ala Glu Glu Gly Lys Lys Leu Val Ala Ala Ser Gln Ala
            820                 825                 830
```

```
Ala Leu Gly Leu Ala Ala Leu Gln Val Gln Leu Val Glu Ser Gly
        835                 840                 845

Gly Gly Leu Val Gln Pro Gly Gly Ser Leu Arg Leu Ser Cys Ala Ala
    850                 855                 860

Ser Gly Phe Thr Phe Arg Ser Tyr Ala Met Ser Trp Val Arg Gln Ala
865                 870                 875                 880

Pro Gly Lys Gly Leu Glu Trp Val Ser Ala Ile Ser Gly Arg Gly Asp
                885                 890                 895

Asn Thr Tyr Tyr Ala Asp Ser Val Lys Gly Arg Phe Thr Ile Ser Arg
            900                 905                 910

Asp Asn Ser Lys Asn Thr Leu Tyr Leu Gln Met Asn Ser Leu Arg Ala
        915                 920                 925

Glu Asp Thr Ala Val Tyr Tyr Cys Ala Lys Met Thr Ser Asn Ala Val
    930                 935                 940

Gly Phe Asp Tyr Trp Gly Gln Gly Thr Leu Val Thr Val Ser Ser Gly
945                 950                 955                 960

Gly Gly Gly Ser Gly Gly Gly Ser Gly Gly Gly Ser Gly Gly Gln Ser
                965                 970                 975

Val Leu Thr Gln Pro Pro Ser Val Ser Gly Ala Pro Gly Gln Arg Val
            980                 985                 990

Thr Ile Ser Cys Thr Gly Arg His Ser Asn Ile Gly Leu Gly Tyr Gly
        995                 1000                1005

Val His Trp Tyr Gln Gln Leu  Pro Gly Thr Ala Pro  Lys Leu Leu
    1010                1015                1020

Ile Tyr Gly Asn Thr Asn Arg  Pro Ser Gly Val Pro  Asp Arg Phe
    1025                1030                1035

Ser Gly Phe Lys Ser Gly Thr  Ser Ala Ser Leu Ala  Ile Thr Gly
    1040                1045                1050

Leu Gln Ala Glu Asp Glu Ala  Asp Tyr Tyr Cys Gln  Ser Tyr Asp
    1055                1060                1065

Arg Arg Thr Pro Gly Trp Val  Phe Gly Gly Gly Thr  Lys Leu Thr
    1070                1075                1080

Val Leu Gly
    1085

<210> SEQ ID NO 22
<211> LENGTH: 1096
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Gly Tyr Ser Ser Ser Trp Ser Glu Val Ala Ser Gly Tyr Trp
                100                 105                 110
Gly Gln Gly Thr Leu Val Thr Val Ser Ser Ala Ser Gly Gly Gly Gly
            115                 120                 125
Gly Ser Gly Gly Gly Gly Ser Gly Gly Gly Ser Ala Ile Val Met
        130                 135                 140
Thr Gln Ser Pro Ser Ser Leu Ser Ala Ser Val Gly Asp Arg Val Thr
145                 150                 155                 160
Ile Thr Cys Arg Ala Ser Gln Gly Ile Arg Asn Asp Leu Gly Trp Tyr
                165                 170                 175
Gln Gln Lys Ala Gly Lys Ala Pro Lys Leu Leu Ile Tyr Ala Ala Ser
            180                 185                 190
Ser Leu Gln Ser Gly Val Pro Ser Arg Phe Ser Gly Ser Gly Ser Gly
        195                 200                 205
Thr Asp Phe Thr Leu Thr Ile Ser Ser Leu Gln Pro Asp Asp Phe Ala
210                 215                 220
Thr Tyr Phe Cys Gln Gln Ala His Ser Phe Pro Pro Thr Phe Gly Gly
225                 230                 235                 240
Gly Thr Lys Val Glu Ile Lys Arg Gly Ala Ala Ser Asp Ala His Lys
                245                 250                 255
Ser Glu Val Ala His Arg Phe Lys Asp Leu Gly Glu Glu Asn Phe Lys
            260                 265                 270
Ala Leu Val Leu Ile Ala Phe Ala Gln Tyr Leu Gln Ser Pro Phe
        275                 280                 285
Glu Asp His Val Lys Leu Val Asn Glu Val Thr Glu Phe Ala Lys Thr
290                 295                 300
Cys Val Ala Asp Glu Ser Ala Glu Asn Cys Asp Lys Ser Leu His Thr
305                 310                 315                 320
Leu Phe Gly Asp Lys Leu Cys Thr Val Ala Thr Leu Arg Glu Thr Tyr
                325                 330                 335
Gly Glu Met Ala Asp Cys Cys Ala Lys Gln Glu Pro Glu Arg Asn Glu
            340                 345                 350
Cys Phe Leu Gln His Lys Asp Asp Asn Pro Asn Leu Pro Arg Leu Val
        355                 360                 365
Arg Pro Glu Val Asp Val Met Cys Thr Ala Phe His Asp Asn Glu Glu
370                 375                 380
Thr Phe Leu Lys Lys Tyr Leu Tyr Glu Ile Ala Arg Arg His Pro Tyr
385                 390                 395                 400
Phe Tyr Ala Pro Glu Leu Leu Phe Phe Ala Lys Arg Tyr Lys Ala Ala
                405                 410                 415
Phe Thr Glu Cys Cys Gln Ala Ala Asp Lys Ala Ala Cys Leu Leu Pro
            420                 425                 430
Lys Leu Asp Glu Leu Arg Asp Glu Gly Lys Ala Ser Ser Ala Lys Gln
        435                 440                 445
Arg Leu Lys Cys Ala Ser Leu Gln Lys Phe Gly Glu Arg Ala Phe Lys
450                 455                 460
Ala Trp Ala Val Ala Arg Leu Ser Gln Arg Phe Pro Lys Ala Glu Phe
465                 470                 475                 480
Ala Glu Val Ser Lys Leu Val Thr Asp Leu Thr Lys Val His Thr Glu
                485                 490                 495
Cys Cys His Gly Asp Leu Leu Glu Cys Ala Asp Asp Arg Ala Asp Leu
            500                 505                 510
Ala Lys Tyr Ile Cys Glu Asn Gln Asp Ser Ile Ser Ser Lys Leu Lys
```

```
                515                 520                 525
Glu Cys Cys Glu Lys Pro Leu Leu Glu Lys Ser His Cys Ile Ala Glu
    530                 535                 540

Val Glu Asn Asp Glu Met Pro Ala Asp Leu Pro Ser Leu Ala Ala Asp
545                 550                 555                 560

Phe Val Glu Ser Lys Asp Val Cys Lys Asn Tyr Ala Glu Ala Lys Asp
                565                 570                 575

Val Phe Leu Gly Met Phe Leu Tyr Glu Tyr Ala Arg Arg His Pro Asp
            580                 585                 590

Tyr Ser Val Val Leu Leu Leu Arg Leu Ala Lys Thr Tyr Glu Thr Thr
        595                 600                 605

Leu Glu Lys Cys Cys Ala Ala Ala Asp Pro His Glu Cys Tyr Ala Lys
    610                 615                 620

Val Phe Asp Glu Phe Lys Pro Leu Val Glu Glu Pro Gln Asn Leu Ile
625                 630                 635                 640

Lys Gln Asn Cys Glu Leu Phe Glu Gln Leu Gly Glu Tyr Lys Phe Gln
                645                 650                 655

Asn Ala Leu Leu Val Arg Tyr Thr Lys Lys Val Pro Gln Val Ser Thr
            660                 665                 670

Pro Thr Leu Val Glu Val Ser Arg Asn Leu Gly Lys Val Gly Ser Lys
        675                 680                 685

Cys Cys Lys His Pro Glu Ala Lys Arg Met Pro Cys Ala Glu Asp Tyr
    690                 695                 700

Leu Ser Val Val Leu Asn Gln Leu Cys Val Leu His Glu Lys Thr Pro
705                 710                 715                 720

Val Ser Asp Arg Val Thr Lys Cys Cys Thr Glu Ser Leu Val Asn Arg
                725                 730                 735

Arg Pro Cys Phe Ser Ala Leu Glu Val Asp Glu Thr Tyr Val Pro Lys
            740                 745                 750

Glu Phe Gln Ala Glu Thr Phe Thr Phe His Ala Asp Ile Cys Thr Leu
        755                 760                 765

Ser Glu Lys Glu Arg Gln Ile Lys Lys Gln Thr Ala Leu Val Glu Leu
    770                 775                 780

Val Lys His Lys Pro Lys Ala Thr Lys Glu Gln Leu Lys Ala Val Met
785                 790                 795                 800

Asp Asp Phe Ala Ala Phe Val Glu Lys Cys Cys Lys Ala Asp Asp Lys
                805                 810                 815

Glu Thr Cys Phe Ala Glu Glu Gly Lys Lys Leu Val Ala Ala Ser Gln
            820                 825                 830

Ala Ala Leu Gly Leu Ala Ala Ala Leu Gln Val Gln Leu Val Gln Ser
        835                 840                 845

Gly Ala Glu Val Lys Lys Pro Gly Glu Ser Leu Lys Ile Ser Cys Lys
    850                 855                 860

Gly Ser Gly Tyr Ser Phe Thr Ser Tyr Trp Ile Ala Trp Val Arg Gln
865                 870                 875                 880

Met Pro Gly Lys Gly Leu Glu Tyr Met Gly Leu Ile Tyr Pro Gly Asp
                885                 890                 895

Ser Asp Thr Lys Tyr Ser Pro Ser Phe Gln Gly Gln Val Thr Ile Ser
            900                 905                 910

Val Asp Lys Ser Val Ser Thr Ala Tyr Leu Gln Trp Ser Ser Leu Lys
        915                 920                 925

Pro Ser Asp Ser Ala Val Tyr Phe Cys Ala Arg His Asp Val Gly Tyr
    930                 935                 940
```

```
Cys Thr Asp Arg Thr Cys Ala Lys Trp Pro Glu Trp Leu Val Trp
945                 950                 955                 960

Gly Gln Gly Thr Leu Val Thr Val Ser Ser Gly Gly Gly Ser Ser
                965                 970                 975

Gly Gly Gly Ser Gly Gly Gly Ser Gln Ser Val Leu Thr Gln Pro
            980                 985                 990

Pro Ser Val Ser Ala Ala Pro Gly Gln Lys Val Thr Ile Ser Cys Ser
        995                 1000                1005

Gly Ser Ser Ser Asn Ile Gly Asn Asn Tyr Val Ser Trp Tyr Gln
        1010                1015                1020

Gln Leu Pro Gly Thr Ala Pro Lys Leu Leu Ile Tyr Asp His Thr
        1025                1030                1035

Asn Arg Pro Ala Gly Val Pro Asp Arg Phe Ser Gly Ser Lys Ser
        1040                1045                1050

Gly Thr Ser Ala Ser Leu Ala Ile Ser Gly Phe Arg Ser Glu Asp
        1055                1060                1065

Glu Ala Asp Tyr Tyr Cys Ala Ser Trp Asp Tyr Thr Leu Ser Gly
        1070                1075                1080

Trp Val Phe Gly Gly Gly Thr Lys Leu Thr Val Leu Gly
        1085                1090                1095

<210> SEQ ID NO 23
<211> LENGTH: 1087
<212> TYPE: PRT
<213> ORGANISM: Artificial Sequence
<220> FEATURE:
<223> OTHER INFORMATION: Synthethic Construct

<400> SEQUENCE: 23

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Ser Ser Ser Trp Ser Glu Val Ala Ser Gly Tyr Trp
            100                 105                 110

Gly Gln Gly Thr Leu Val Thr Val Ser Ser Ala Ser Thr Gly Gly Gly
        115                 120                 125

Gly Ser Gly Gly Gly Gly Ser Gly Gly Gly Gly Ser Ala Ile Val Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Gly Ile Arg Asn Asp Leu Gly Trp Tyr
                165                 170                 175

Gln Gln Lys Ala Gly Lys Ala Pro Lys Leu Leu Ile Tyr Ala Ala Ser
            180                 185                 190

Ser Leu Gln Ser Gly Val Pro Ser Arg Phe Ser Gly Ser Gly Ser Gly
        195                 200                 205
```

-continued

```
Thr Asp Phe Thr Leu Thr Ile Ser Ser Leu Gln Pro Asp Phe Ala
    210                 215                 220
Thr Tyr Phe Cys Gln Gln Ala His Ser Phe Pro Pro Thr Phe Gly Gly
225                 230                 235                 240
Gly Thr Lys Val Glu Ile Lys Arg Gly Ala Ser Asp Ala His Lys
                245                 250                 255
Ser Glu Val Ala His Arg Phe Lys Asp Leu Gly Glu Glu Asn Phe Lys
                260                 265                 270
Ala Leu Val Leu Ile Ala Phe Ala Gln Tyr Leu Gln Gln Ser Pro Phe
                275                 280                 285
Glu Asp His Val Lys Leu Val Asn Glu Val Thr Glu Phe Ala Lys Thr
    290                 295                 300
Cys Val Ala Asp Glu Ser Ala Glu Asn Cys Asp Lys Ser Leu His Thr
305                 310                 315                 320
Leu Phe Gly Asp Lys Leu Cys Thr Val Ala Thr Leu Arg Glu Thr Tyr
                325                 330                 335
Gly Glu Met Ala Asp Cys Cys Ala Lys Gln Glu Pro Glu Arg Asn Glu
                340                 345                 350
Cys Phe Leu Gln His Lys Asp Asp Asn Pro Asn Leu Pro Arg Leu Val
    355                 360                 365
Arg Pro Glu Val Asp Val Met Cys Thr Ala Phe His Asp Asn Glu Glu
370                 375                 380
Thr Phe Leu Lys Lys Tyr Leu Tyr Glu Ile Ala Arg Arg His Pro Tyr
385                 390                 395                 400
Phe Tyr Ala Pro Glu Leu Leu Phe Phe Ala Lys Arg Tyr Lys Ala Ala
                405                 410                 415
Phe Thr Glu Cys Cys Gln Ala Ala Asp Lys Ala Ala Cys Leu Leu Pro
                420                 425                 430
Lys Leu Asp Glu Leu Arg Asp Glu Gly Lys Ala Ser Ser Ala Lys Gln
    435                 440                 445
Arg Leu Lys Cys Ala Ser Leu Gln Lys Phe Gly Glu Arg Ala Phe Lys
    450                 455                 460
Ala Trp Ala Val Ala Arg Leu Ser Gln Arg Phe Pro Lys Ala Glu Phe
465                 470                 475                 480
Ala Glu Val Ser Lys Leu Val Thr Asp Leu Thr Lys Val His Thr Glu
                485                 490                 495
Cys Cys His Gly Asp Leu Leu Glu Cys Ala Asp Asp Arg Ala Asp Leu
                500                 505                 510
Ala Lys Tyr Ile Cys Glu Asn Gln Asp Ser Ile Ser Ser Lys Leu Lys
    515                 520                 525
Glu Cys Cys Glu Lys Pro Leu Leu Glu Lys Ser His Cys Ile Ala Glu
530                 535                 540
Val Glu Asn Asp Glu Met Pro Ala Asp Leu Pro Ser Leu Ala Ala Asp
545                 550                 555                 560
Phe Val Glu Ser Lys Asp Val Cys Lys Asn Tyr Ala Glu Ala Lys Asp
                565                 570                 575
Val Phe Leu Gly Met Phe Leu Tyr Glu Tyr Ala Arg Arg His Pro Asp
                580                 585                 590
Tyr Ser Val Val Leu Leu Leu Arg Leu Ala Lys Thr Tyr Glu Thr Thr
    595                 600                 605
Leu Glu Lys Cys Cys Ala Ala Ala Asp Pro His Glu Cys Tyr Ala Lys
    610                 615                 620
```

```
Val Phe Asp Glu Phe Lys Pro Leu Val Glu Glu Pro Gln Asn Leu Ile
625                 630                 635                 640

Lys Gln Asn Cys Glu Leu Phe Glu Gln Leu Gly Glu Tyr Lys Phe Gln
            645                 650                 655

Asn Ala Leu Leu Val Arg Tyr Thr Lys Lys Val Pro Gln Val Ser Thr
            660                 665                 670

Pro Thr Leu Val Glu Val Ser Arg Asn Leu Gly Lys Val Gly Ser Lys
            675                 680                 685

Cys Cys Lys His Pro Glu Ala Lys Arg Met Pro Cys Ala Glu Asp Tyr
690                 695                 700

Leu Ser Val Val Leu Asn Gln Leu Cys Val Leu His Glu Lys Thr Pro
705                 710                 715                 720

Val Ser Asp Arg Val Thr Lys Cys Cys Thr Glu Ser Leu Val Asn Arg
            725                 730                 735

Arg Pro Cys Phe Ser Ala Leu Glu Val Asp Glu Thr Tyr Val Pro Lys
            740                 745                 750

Glu Phe Gln Ala Glu Thr Phe Thr Phe His Ala Asp Ile Cys Thr Leu
            755                 760                 765

Ser Glu Lys Glu Arg Gln Ile Lys Lys Gln Thr Ala Leu Val Glu Leu
770                 775                 780

Val Lys His Lys Pro Lys Ala Thr Lys Glu Gln Leu Lys Ala Val Met
785                 790                 795                 800

Asp Asp Phe Ala Ala Phe Val Glu Lys Cys Cys Lys Ala Asp Asp Lys
            805                 810                 815

Glu Thr Cys Phe Ala Glu Glu Gly Lys Lys Leu Val Ala Ala Ser Gln
            820                 825                 830

Ala Ala Leu Gly Leu Ala Ala Ala Leu Gln Val Gln Leu Val Glu Ser
            835                 840                 845

Gly Gly Gly Leu Val Gln Pro Gly Gly Ser Leu Arg Leu Ser Cys Ala
850                 855                 860

Ala Ser Gly Phe Thr Phe Arg Ser Tyr Ala Met Ser Trp Val Arg Gln
865                 870                 875                 880

Ala Pro Gly Lys Gly Leu Glu Trp Val Ser Ala Ile Ser Gly Arg Gly
            885                 890                 895

Asp Asn Thr Tyr Tyr Ala Asp Ser Val Lys Gly Arg Phe Thr Ile Ser
            900                 905                 910

Arg Asp Asn Ser Lys Asn Thr Leu Tyr Leu Gln Met Asn Ser Leu Arg
            915                 920                 925

Ala Glu Asp Thr Ala Val Tyr Tyr Cys Ala Lys Met Thr Ser Asn Ala
            930                 935                 940

Val Gly Phe Asp Tyr Trp Gly Gln Gly Thr Leu Val Thr Val Ser Ser
945                 950                 955                 960

Gly Gly Gly Gly Ser Gly Gly Gly Ser Gly Gly Gly Gly Ser Gly Gln
            965                 970                 975

Ser Val Leu Thr Gln Pro Pro Ser Val Ser Gly Ala Pro Gly Gln Arg
            980                 985                 990

Val Thr Ile Ser Cys Thr Gly Arg His Ser Asn Ile Gly Leu Gly Tyr
            995                 1000                1005

Gly Val His Trp Tyr Gln Gln Leu Pro Gly Thr Ala Pro Lys Leu
    1010                1015                1020

Leu Ile Tyr Gly Asn Thr Asn Arg Pro Ser Gly Val Pro Asp Arg
    1025                1030                1035

Phe Ser Gly Phe Lys Ser Gly Thr Ser Ala Ser Leu Ala Ile Thr
```

```
                1040                1045                1050

Gly Leu Gln Ala Glu Asp Glu  Ala Asp Tyr Tyr Cys  Gln Ser Tyr
    1055                1060                1065

Asp Arg Arg Thr Pro Gly Trp  Val Phe Gly Gly Gly  Thr Lys Leu
    1070                1075                1080

Thr Val Leu Gly
    1085

<210> SEQ ID NO 24
<211> LENGTH: 1095
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
        195                 200                 205

Ala Ser Leu Ile Ile Ser Gly Leu Gln Ala Asp Asp Glu Ala Asp Tyr
    210                 215                 220

Tyr Cys Ser Ser Tyr Gly Ser Ser Ser Thr His Val Ile Phe Gly Gly
225                 230                 235                 240

Gly Thr Lys Val Thr Val Leu Gly Ala Ala Ser Asp Ala His Lys Ser
                245                 250                 255

Glu Val Ala His Arg Phe Lys Asp Leu Gly Glu Glu Asn Phe Lys Ala
            260                 265                 270

Leu Val Leu Ile Ala Phe Ala Gln Tyr Leu Gln Gln Ser Pro Phe Glu
        275                 280                 285

Asp His Val Lys Leu Val Asn Glu Val Thr Glu Phe Ala Lys Thr Cys
    290                 295                 300

Val Ala Asp Glu Ser Ala Glu Asn Cys Asp Lys Ser Leu His Thr Leu
```

```
              305                 310                 315                 320
        Phe Gly Asp Lys Leu Cys Thr Val Ala Thr Leu Arg Glu Thr Tyr Gly
                        325                 330                 335

Glu Met Ala Asp Cys Cys Ala Lys Gln Glu Pro Glu Arg Asn Glu Cys
                        340                 345                 350

Phe Leu Gln His Lys Asp Asp Asn Pro Asn Leu Pro Arg Leu Val Arg
                        355                 360                 365

Pro Glu Val Asp Val Met Cys Thr Ala Phe His Asp Asn Glu Glu Thr
                    370                 375                 380

Phe Leu Lys Lys Tyr Leu Tyr Glu Ile Ala Arg Arg His Pro Tyr Phe
        385                 390                 395                 400

Tyr Ala Pro Glu Leu Leu Phe Phe Ala Lys Arg Tyr Lys Ala Ala Phe
                        405                 410                 415

Thr Glu Cys Cys Gln Ala Ala Asp Lys Ala Ala Cys Leu Leu Pro Lys
                        420                 425                 430

Leu Asp Glu Leu Arg Asp Glu Gly Lys Ala Ser Ser Ala Lys Gln Arg
                        435                 440                 445

Leu Lys Cys Ala Ser Leu Gln Lys Phe Gly Glu Arg Ala Phe Lys Ala
                    450                 455                 460

Trp Ala Val Ala Arg Leu Ser Gln Arg Phe Pro Lys Ala Glu Phe Ala
        465                 470                 475                 480

Glu Val Ser Lys Leu Val Thr Asp Leu Thr Lys Val His Thr Glu Cys
                        485                 490                 495

Cys His Gly Asp Leu Leu Glu Cys Ala Asp Asp Arg Ala Asp Leu Ala
                        500                 505                 510

Lys Tyr Ile Cys Glu Asn Gln Asp Ser Ile Ser Ser Lys Leu Lys Glu
                        515                 520                 525

Cys Cys Glu Lys Pro Leu Leu Glu Lys Ser His Cys Ile Ala Glu Val
                    530                 535                 540

Glu Asn Asp Glu Met Pro Ala Asp Leu Pro Ser Leu Ala Ala Asp Phe
        545                 550                 555                 560

Val Glu Ser Lys Asp Val Cys Lys Asn Tyr Ala Glu Ala Lys Asp Val
                        565                 570                 575

Phe Leu Gly Met Phe Leu Tyr Glu Tyr Ala Arg Arg His Pro Asp Tyr
                        580                 585                 590

Ser Val Val Leu Leu Leu Arg Leu Ala Lys Thr Tyr Glu Thr Thr Leu
                        595                 600                 605

Glu Lys Cys Cys Ala Ala Ala Asp Pro His Glu Cys Tyr Ala Lys Val
                    610                 615                 620

Phe Asp Glu Phe Lys Pro Leu Val Glu Glu Pro Gln Asn Leu Ile Lys
        625                 630                 635                 640

Gln Asn Cys Glu Leu Phe Glu Gln Leu Gly Glu Tyr Lys Phe Gln Asn
                        645                 650                 655

Ala Leu Leu Val Arg Tyr Thr Lys Lys Val Pro Gln Val Ser Thr Pro
                        660                 665                 670

Thr Leu Val Glu Val Ser Arg Asn Leu Gly Lys Val Gly Ser Lys Cys
                        675                 680                 685

Cys Lys His Pro Glu Ala Lys Arg Met Pro Cys Ala Glu Asp Tyr Leu
                    690                 695                 700

Ser Val Val Leu Asn Gln Leu Cys Val Leu His Glu Lys Thr Pro Val
        705                 710                 715                 720

Ser Asp Arg Val Thr Lys Cys Cys Thr Glu Ser Leu Val Asn Arg Arg
                        725                 730                 735
```

-continued

```
Pro Cys Phe Ser Ala Leu Glu Val Asp Glu Thr Tyr Val Pro Lys Glu
            740                 745                 750

Phe Gln Ala Glu Thr Phe Thr Phe His Ala Asp Ile Cys Thr Leu Ser
            755                 760                 765

Glu Lys Glu Arg Gln Ile Lys Lys Gln Thr Ala Leu Val Glu Leu Val
770                 775                 780

Lys His Lys Pro Lys Ala Thr Lys Glu Gln Leu Lys Ala Val Met Asp
785                 790                 795                 800

Asp Phe Ala Ala Phe Val Glu Lys Cys Cys Lys Ala Asp Asp Lys Glu
                805                 810                 815

Thr Cys Phe Ala Glu Glu Gly Lys Lys Leu Val Ala Ala Ser Gln Ala
                820                 825                 830

Ala Leu Gly Leu Ala Ala Ala Leu Gln Val Gln Leu Val Gln Ser Gly
                835                 840                 845

Ala Glu Val Lys Lys Pro Gly Glu Ser Leu Lys Ile Ser Cys Lys Gly
850                 855                 860

Ser Gly Tyr Ser Phe Thr Ser Tyr Trp Ile Ala Trp Val Arg Gln Met
865                 870                 875                 880

Pro Gly Lys Gly Leu Glu Tyr Met Gly Leu Ile Tyr Pro Gly Asp Ser
                885                 890                 895

Asp Thr Lys Tyr Ser Pro Ser Phe Gln Gly Gln Val Thr Ile Ser Val
                900                 905                 910

Asp Lys Ser Val Ser Thr Ala Tyr Leu Gln Trp Ser Ser Leu Lys Pro
                915                 920                 925

Ser Asp Ser Ala Val Tyr Phe Cys Ala Arg His Asp Val Gly Tyr Cys
                930                 935                 940

Thr Asp Arg Thr Cys Ala Lys Trp Pro Glu Trp Leu Gly Val Trp Gly
945                 950                 955                 960

Gln Gly Thr Leu Val Thr Val Ser Ser Gly Gly Gly Ser Ser Gly
                965                 970                 975

Gly Gly Ser Gly Gly Gly Ser Gln Ser Val Leu Thr Gln Pro Pro
                980                 985                 990

Ser Val Ser Ala Ala Pro Gly Gln Lys Val Thr Ile Ser Cys Ser Gly
                995                 1000                1005

Ser Ser Ser Asn Ile Gly Asn Asn Tyr Val Ser Trp Tyr Gln Gln
            1010                1015                1020

Leu Pro Gly Thr Ala Pro Lys Leu Leu Ile Tyr Asp His Thr Asn
            1025                1030                1035

Arg Pro Ala Gly Val Pro Asp Arg Phe Ser Gly Ser Lys Ser Gly
            1040                1045                1050

Thr Ser Ala Ser Leu Ala Ile Ser Gly Phe Arg Ser Glu Asp Glu
            1055                1060                1065

Ala Asp Tyr Tyr Cys Ala Ser Trp Asp Tyr Thr Leu Ser Gly Trp
            1070                1075                1080

Val Phe Gly Gly Gly Thr Lys Leu Thr Val Leu Gly
            1085                1090                1095

<210> SEQ ID NO 25
<211> LENGTH: 1086
<212> TYPE: PRT
<213> ORGANISM: Artificial Sequence
<220> FEATURE:
<223> OTHER INFORMATION: Synthetic Construct

<400> SEQUENCE: 25
```

-continued

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
            165                 170                 175

His Pro Gly Lys Ala Pro Lys Leu Met Ile Tyr Asp Val Ser Asp Arg
        180                 185                 190

Pro Ser Gly Val Ser Asp Arg Phe Ser Gly Ser Lys Ser Gly Asn Thr
    195                 200                 205

Ala Ser Leu Ile Ile Ser Gly Leu Gln Ala Asp Glu Ala Asp Tyr
210                 215                 220

Tyr Cys Ser Ser Tyr Gly Ser Ser Ser Thr His Val Ile Phe Gly Gly
225                 230                 235                 240

Gly Thr Lys Val Thr Val Leu Gly Ala Ala Ser Asp Ala His Lys Ser
            245                 250                 255

Glu Val Ala His Arg Phe Lys Asp Leu Gly Glu Glu Asn Phe Lys Ala
        260                 265                 270

Leu Val Leu Ile Ala Phe Ala Gln Tyr Leu Gln Gln Ser Pro Phe Glu
    275                 280                 285

Asp His Val Lys Leu Val Asn Glu Val Thr Glu Phe Ala Lys Thr Cys
290                 295                 300

Val Ala Asp Glu Ser Ala Glu Asn Cys Asp Lys Ser Leu His Thr Leu
305                 310                 315                 320

Phe Gly Asp Lys Leu Cys Thr Val Ala Thr Leu Arg Glu Thr Tyr Gly
            325                 330                 335

Glu Met Ala Asp Cys Cys Ala Lys Gln Glu Pro Glu Arg Asn Glu Cys
        340                 345                 350

Phe Leu Gln His Lys Asp Asp Asn Pro Asn Leu Pro Arg Leu Val Arg
    355                 360                 365

Pro Glu Val Asp Val Met Cys Thr Ala Phe His Asp Asn Glu Glu Thr
370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
            405                 410                 415
```

-continued

```
Thr Glu Cys Cys Gln Ala Ala Asp Lys Ala Ala Cys Leu Leu Pro Lys
            420                 425                 430
Leu Asp Glu Leu Arg Asp Glu Gly Lys Ala Ser Ser Ala Lys Gln Arg
        435                 440                 445
Leu Lys Cys Ala Ser Leu Gln Lys Phe Gly Glu Arg Ala Phe Lys Ala
    450                 455                 460
Trp Ala Val Ala Arg Leu Ser Gln Arg Phe Pro Lys Ala Glu Phe Ala
465                 470                 475                 480
Glu Val Ser Lys Leu Val Thr Asp Leu Thr Lys Val His Thr Glu Cys
                485                 490                 495
Cys His Gly Asp Leu Leu Glu Cys Ala Asp Asp Arg Ala Asp Leu Ala
            500                 505                 510
Lys Tyr Ile Cys Glu Asn Gln Asp Ser Ile Ser Ser Lys Leu Lys Glu
        515                 520                 525
Cys Cys Glu Lys Pro Leu Leu Glu Lys Ser His Cys Ile Ala Glu Val
    530                 535                 540
Glu Asn Asp Glu Met Pro Ala Asp Leu Pro Ser Leu Ala Ala Asp Phe
545                 550                 555                 560
Val Glu Ser Lys Asp Val Cys Lys Asn Tyr Ala Glu Ala Lys Asp Val
                565                 570                 575
Phe Leu Gly Met Phe Leu Tyr Glu Tyr Ala Arg Arg His Pro Asp Tyr
            580                 585                 590
Ser Val Val Leu Leu Leu Arg Leu Ala Lys Thr Tyr Glu Thr Thr Leu
        595                 600                 605
Glu Lys Cys Cys Ala Ala Ala Asp Pro His Glu Cys Tyr Ala Lys Val
    610                 615                 620
Phe Asp Glu Phe Lys Pro Leu Val Glu Glu Pro Gln Asn Leu Ile Lys
625                 630                 635                 640
Gln Asn Cys Glu Leu Phe Glu Gln Leu Gly Glu Tyr Lys Phe Gln Asn
                645                 650                 655
Ala Leu Leu Val Arg Tyr Thr Lys Lys Val Pro Gln Val Ser Thr Pro
            660                 665                 670
Thr Leu Val Glu Val Ser Arg Asn Leu Gly Lys Val Gly Ser Lys Cys
        675                 680                 685
Cys Lys His Pro Glu Ala Lys Arg Met Pro Cys Ala Glu Asp Tyr Leu
    690                 695                 700
Ser Val Val Leu Asn Gln Leu Cys Val Leu His Glu Lys Thr Pro Val
705                 710                 715                 720
Ser Asp Arg Val Thr Lys Cys Cys Thr Glu Ser Leu Val Asn Arg Arg
                725                 730                 735
Pro Cys Phe Ser Ala Leu Glu Val Asp Glu Thr Tyr Val Pro Lys Glu
            740                 745                 750
Phe Gln Ala Glu Thr Phe Thr Phe His Ala Asp Ile Cys Thr Leu Ser
        755                 760                 765
Glu Lys Glu Arg Gln Ile Lys Lys Gln Thr Ala Leu Val Glu Leu Val
    770                 775                 780
Lys His Lys Pro Lys Ala Thr Lys Glu Gln Leu Lys Ala Val Met Asp
785                 790                 795                 800
Asp Phe Ala Ala Phe Val Glu Lys Cys Cys Lys Ala Asp Asp Lys Glu
                805                 810                 815
Thr Cys Phe Ala Glu Glu Gly Lys Lys Leu Val Ala Ala Ser Gln Ala
            820                 825                 830
Ala Leu Gly Leu Ala Ala Ala Leu Gln Val Gln Leu Val Glu Ser Gly
```

```
                    835                 840                 845
    Gly Gly Leu Val Gln Pro Gly Gly Ser Leu Arg Leu Ser Cys Ala Ala
        850                 855                 860

Ser Gly Phe Thr Phe Arg Ser Tyr Ala Met Ser Trp Val Arg Gln Ala
    865                 870                 875                 880

Pro Gly Lys Gly Leu Glu Trp Val Ser Ala Ile Ser Gly Arg Gly Asp
                    885                 890                 895

Asn Thr Tyr Tyr Ala Asp Ser Val Lys Gly Arg Phe Thr Ile Ser Arg
                900                 905                 910

Asp Asn Ser Lys Asn Thr Leu Tyr Leu Gln Met Asn Ser Leu Arg Ala
                915                 920                 925

Glu Asp Thr Ala Val Tyr Tyr Cys Ala Lys Met Thr Ser Asn Ala Val
            930                 935                 940

Gly Phe Asp Tyr Trp Gly Gln Gly Thr Leu Val Thr Val Ser Ser Gly
    945                 950                 955                 960

Gly Gly Gly Ser Gly Gly Gly Ser Gly Gly Gly Ser Gly Gln Ser
                    965                 970                 975

Val Leu Thr Gln Pro Pro Ser Val Ser Gly Ala Pro Gly Gln Arg Val
                980                 985                 990

Thr Ile Ser Cys Thr Gly Arg His  Ser Asn Ile Gly Leu  Gly Tyr Gly
                995                1000                1005

Val His  Trp Tyr Gln Gln Leu  Pro Gly Thr Ala Pro  Lys Leu Leu
            1010                1015                1020

Ile Tyr  Gly Asn Thr Asn Arg  Pro Ser Gly Val Pro  Asp Arg Phe
            1025                1030                1035

Ser Gly  Phe Lys Ser Gly Thr  Ser Ala Ser Leu Ala  Ile Thr Gly
            1040                1045                1050

Leu Gln  Ala Glu Asp Glu Ala  Asp Tyr Tyr Cys Gln  Ser Tyr Asp
            1055                1060                1065

Arg Arg  Thr Pro Gly Trp Val  Phe Gly Gly Gly Thr  Lys Leu Thr
            1070                1075                1080

Val Leu  Gly
            1085

<210> SEQ ID NO 26
<211> LENGTH: 248
<212> TYPE: PRT
<213> ORGANISM: Artificial Sequence
<220> FEATURE:
<223> OTHER INFORMATION: Synthetic construct

<400> SEQUENCE: 26

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
```

```
              100                 105                 110
Leu Val Thr Val Ser Ser Ala Ser Thr Gly Gly Gly Ser Gly Gly
            115                 120                 125

Gly Gly Ser Gly Gly Gly Ser Gln Ser Ala Leu Thr Gln Pro Ala
        130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
        195                 200                 205

Ala Ser Leu Ile Ile Ser Gly Leu Gln Ala Asp Asp Glu Ala Asp Tyr
    210                 215                 220

Tyr Cys Ser Ser Tyr Gly Ser Ser Ser Thr His Val Ile Phe Gly Gly
225                 230                 235                 240

Gly Thr Lys Val Thr Val Leu Gly
                245

<210> SEQ ID NO 27
<211> LENGTH: 255
<212> TYPE: PRT
<213> ORGANISM: Artificial Sequence
<220> FEATURE:
<223> OTHER INFORMATION: Synthetic Construct

<400> SEQUENCE: 27

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Thr Asp Arg Thr Cys Ala Lys Trp
            100                 105                 110

Pro Glu Trp Leu Gly Val Trp Gly Gln Gly Thr Leu Val Thr Val Ser
        115                 120                 125

Ser Gly Gly Gly Gly Ser Ser Gly Gly Gly Ser Gly Gly Gly Gly Ser
    130                 135                 140

Gln Ser Val Leu Thr Gln Pro Pro Ser Val Ser Ala Ala Pro Gly Gln
145                 150                 155                 160

Lys Val Thr Ile Ser Cys Ser Gly Ser Ser Ser Asn Ile Gly Asn Asn
                165                 170                 175

Tyr Val Ser Trp Tyr Gln Gln Leu Pro Gly Thr Ala Pro Lys Leu Leu
            180                 185                 190

Ile Tyr Asp His Thr Asn Arg Pro Ala Gly Val Pro Asp Arg Phe Ser
        195                 200                 205

Gly Ser Lys Ser Gly Thr Ser Ala Ser Leu Ala Ile Ser Gly Phe Arg
```

```
                    210                 215                 220
Ser Glu Asp Glu Ala Asp Tyr Tyr Cys Ala Ser Trp Asp Tyr Thr Leu
225                 230                 235                 240

Ser Gly Trp Val Phe Gly Gly Thr Lys Leu Thr Val Leu Gly
                245                 250                 255

<210> SEQ ID NO 28
<211> LENGTH: 245
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Ser Phe Asn Thr Tyr
            20                  25                  30

Asp Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Ala Thr Thr Pro Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Ser Val Leu Thr Gln Pro Pro Ser Val
130                 135                 140

Ser Gly Ala Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
                165                 170                 175

Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Thr Ser Ala Ser
        195                 200                 205

Leu Ala Ile Thr Gly Leu Gln Ala Glu Asp Glu Ala Asp Tyr Tyr Cys
    210                 215                 220

Gln Ser Tyr Asp Ser Ser Leu Ser Ala Leu Phe Gly Gly Gly Thr Lys
225                 230                 235                 240

Leu Thr Val Leu Gly
                245

<210> SEQ ID NO 29
<211> LENGTH: 255
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Asn Cys Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Ser Gly Gly Ser Gly Gly Gly Gly Ser
    130                 135                 140

Gln Ser Val Leu Thr Gln Pro Pro Ser Val Ser Ala Ala Pro Gly Gln
145                 150                 155                 160

Lys Val Thr Ile Ser Cys Ser Gly Ser Ser Asn Ile Gly Asn Asn
            165                 170                 175

Tyr Val Ser Trp Tyr Gln Gln Leu Pro Gly Thr Ala Pro Lys Leu Leu
        180                 185                 190

Ile Tyr Asp His Thr Asn Arg Pro Ala Gly Val Pro Asp Arg Phe Ser
            195                 200                 205

Gly Ser Lys Ser Gly Thr Ser Ala Ser Leu Ala Ile Ser Gly Phe Arg
    210                 215                 220

Ser Glu Asp Glu Ala Asp Tyr Tyr Cys Ala Ser Trp Asp Tyr Thr Leu
225                 230                 235                 240

Ser Gly Trp Val Phe Gly Gly Gly Thr Lys Leu Thr Val Leu Gly
                245                 250                 255

<210> SEQ ID NO 30
<211> LENGTH: 249
<212> TYPE: PRT
<213> ORGANISM: Artificial Sequence
<220> FEATURE:
<223> OTHER INFORMATION: Synthetic Construct

<400> SEQUENCE: 30

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Val Tyr Tyr Cys
                85                  90                  95

Ala Arg Asp Leu Gly Ala Lys Gln Trp Leu Glu Gly Phe Asp Tyr Trp
            100                 105                 110

Gly Gln Gly Thr Leu Val Thr Val Ser Ser Ala Ser Thr Gly Gly Gly
        115                 120                 125
```

```
Gly Ser Gly Gly Gly Gly Ser Gly Gly Gly Ser Ser Tyr Glu Leu
    130                 135                 140

Thr Gln Asp Pro Ala Val Ser Val Ala Leu Gly Gln Thr Val Arg Ile
145                 150                 155                 160

Thr Cys Gln Gly Asp Ser Leu Arg Ser Tyr Tyr Ala Ser Trp Tyr Gln
                165                 170                 175

Gln Lys Pro Gly Gln Ala Pro Val Leu Val Ile Tyr Gly Lys Asn Asn
                180                 185                 190

Arg Pro Ser Gly Ile Pro Asp Arg Phe Ser Gly Ser Thr Ser Gly Asn
                195                 200                 205

Ser Ala Ser Leu Thr Ile Thr Gly Ala Gln Ala Glu Asp Glu Ala Asp
    210                 215                 220

Tyr Tyr Cys Asn Ser Arg Asp Ser Ser Gly Asn His Trp Val Phe Gly
225                 230                 235                 240

Gly Gly Thr Lys Val Thr Val Leu Gly
                245
```

```
<210> SEQ ID NO 31
<211> LENGTH: 249
<212> TYPE: PRT
<213> ORGANISM: Artificial Sequence
<220> FEATURE:
<223> OTHER INFORMATION: Synthetic construct

<400> SEQUENCE: 31

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Ser Ser Ser Trp Ser Glu Val Ala Ser Gly Tyr Trp
                100                 105                 110

Gly Gln Gly Thr Leu Val Thr Val Ser Ser Ala Ser Thr Gly Gly Gly
            115                 120                 125

Gly Ser Gly Gly Gly Gly Ser Gly Gly Gly Ser Ala Ile Val Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Gly Ile Arg Asn Asp Leu Gly Trp Tyr
                165                 170                 175

Gln Gln Lys Ala Gly Lys Ala Pro Lys Leu Leu Ile Tyr Ala Ala Ser
                180                 185                 190

Ser Leu Gln Ser Gly Val Pro Ser Arg Phe Ser Gly Ser Gly Ser Gly
                195                 200                 205

Thr Asp Phe Thr Leu Thr Ile Ser Ser Leu Gln Pro Asp Asp Phe Ala
    210                 215                 220

Thr Tyr Phe Cys Gln Gln Ala His Ser Phe Pro Pro Thr Phe Gly Gly
225                 230                 235                 240
```

```
Gly Thr Lys Val Glu Ile Lys Arg Gly
            245

<210> SEQ ID NO 32
<211> LENGTH: 246
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Thr Ser Asn Ala Val Gly Phe Asp Tyr Trp Gly Gln Gly
            100                 105                 110

Thr Leu Val Thr Val Ser Ser Gly Gly Gly Ser Gly Gly Gly Gly Ser
        115                 120                 125

Gly Gly Gly Gly Ser Gly Gln Ser Val Leu Thr Gln Pro Pro Ser Val
    130                 135                 140

Ser Gly Ala Pro Gly Gln Arg Val Thr Ile Ser Cys Thr Gly Arg His
145                 150                 155                 160

Ser Asn Ile Gly Leu Gly Tyr Gly Val His Trp Tyr Gln Gln Leu Pro
                165                 170                 175

Gly Thr Ala Pro Lys Leu Leu Ile Tyr Gly Asn Thr Asn Arg Pro Ser
            180                 185                 190

Gly Val Pro Asp Arg Phe Ser Gly Phe Lys Ser Gly Thr Ser Ala Ser
        195                 200                 205

Leu Ala Ile Thr Gly Leu Gln Ala Glu Asp Glu Ala Asp Tyr Tyr Cys
    210                 215                 220

Gln Ser Tyr Asp Arg Arg Thr Pro Gly Trp Val Phe Gly Gly Gly Thr
225                 230                 235                 240

Lys Leu Thr Val Leu Gly
            245

<210> SEQ ID NO 33
<211> LENGTH: 10
<212> TYPE: PRT
<213> ORGANISM: Homo sapiens

<400> SEQUENCE: 33

Glu Gln Lys Leu Ile Ser Glu Glu Asp Leu
1               5                   10

<210> SEQ ID NO 34
<211> LENGTH: 9
<212> TYPE: PRT
<213> ORGANISM: Orthomxyoviridue

<400> SEQUENCE: 34
```

Tyr Pro Tyr Asp Val Pro Asp Tyr Ala
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic Construct

<400> SEQUENCE: 35

His His His His His His
1               5

<210> SEQ ID NO 36
<211> LENGTH: 277
<212> TYPE: PRT
<213> ORGANISM: Homo sapiens

<400> SEQUENCE: 36

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Met Ser
            20                  25                  30

Trp Asp Thr Gly Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Asp Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275

<210> SEQ ID NO 37
<211> LENGTH: 479
<212> TYPE: PRT
<213> ORGANISM: Homo sapiens

<400> SEQUENCE: 37

```
Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
            35                  40                  45

Gln Glu Lys Arg Met Leu Glu Glu Ser Asn Leu Ser Phe Leu Lys Glu
        50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Asp Ile Leu Lys Ile Tyr Gln Leu Met Asp His
    290                 295                 300

Ser Asn Met Asp Cys Phe Ile Cys Ile Leu Ser His Gly Asp Lys Gly
305                 310                 315                 320

Gly Ile Ile Tyr Gly Thr Asp Gly Gln Glu Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
    370                 375                 380
```

```
Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Val Ser Asn Lys Asp Lys Asn Met Gly Lys Gln Met Pro
    450                 455                 460

Gln Pro Thr Phe Thr Leu Arg Lys Lys Leu Val Phe Pro Ser Asp
465                 470                 475
```

<210> SEQ ID NO 38
<211> LENGTH: 247
<212> TYPE: PRT
<213> ORGANISM: Homo sapiens

<400> SEQUENCE: 38

```
Met Gln Pro Ile Leu Leu Leu Ala Phe Leu Leu Pro Arg Ala
1               5                   10                  15

Asp Ala Gly Glu Ile Ile Gly Gly His Glu Ala Lys Pro His Ser Arg
            20                  25                  30

Pro Tyr Met Ala Tyr Leu Met Ile Trp Asp Gln Lys Ser Leu Lys Arg
        35                  40                  45

Cys Gly Gly Phe Leu Ile Gln Asp Asp Phe Val Leu Thr Ala Ala His
    50                  55                  60

Cys Trp Gly Ser Ser Ile Asn Val Thr Leu Gly Ala His Asn Ile Lys
65                  70                  75                  80

Glu Gln Glu Pro Thr Gln Gln Phe Ile Pro Val Lys Arg Ala Ile Pro
                85                  90                  95

His Pro Ala Tyr Asn Pro Lys Asn Phe Ser Asn Asp Ile Met Leu Leu
            100                 105                 110

Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220

Met Pro Pro Arg Ala Cys Thr Lys Val Ser Ser Phe Val His Trp Ile
225                 230                 235                 240

Lys Lys Thr Met Lys Arg Tyr
                245
```

<210> SEQ ID NO 39
<211> LENGTH: 105
<212> TYPE: PRT

```
<213> ORGANISM: Homo sapiens

<400> SEQUENCE: 39

Met Gly Asp Val Glu Lys Gly Lys Lys Ile Phe Ile Met Lys Cys Ser
1               5                   10                  15

Gln Cys His Thr Val Glu Lys Gly Gly Lys His Lys Thr Gly Pro Asn
            20                  25                  30

Leu His Gly Leu Phe Gly Arg Lys Thr Gly Gln Ala Pro Gly Tyr Ser
        35                  40                  45

Tyr Thr Ala Ala Asn Lys Asn Lys Gly Ile Ile Trp Gly Glu Asp Thr
    50                  55                  60

Leu Met Glu Tyr Leu Glu Asn Pro Lys Lys Tyr Ile Pro Gly Thr Lys
65                  70                  75                  80

Met Ile Phe Val Gly Ile Lys Lys Lys Glu Glu Arg Ala Asp Leu Ile
                85                  90                  95

Ala Tyr Leu Lys Lys Ala Thr Asn Glu
            100                 105

<210> SEQ ID NO 40
<211> LENGTH: 233
<212> TYPE: PRT
<213> ORGANISM: Homo sapiens

<400> SEQUENCE: 40

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

```
<210> SEQ ID NO 41
<211> LENGTH: 314
<212> TYPE: PRT
<213> ORGANISM: Homo sapiens

<400> SEQUENCE: 41
```

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Val Lys Arg Lys Glu Val Gln Lys
                165                 170                 175

Thr Cys Arg Lys His Arg Lys Glu Asn Gln Gly Ser His Glu Ser Pro
            180                 185                 190

Thr Leu Asn Pro Glu Thr Val Ala Ile Asn Leu Ser Asp Val Asp Leu
        195                 200                 205

Ser Lys Tyr Ile Thr Thr Ile Ala Gly Val Met Thr Leu Ser Gln Val
    210                 215                 220

Lys Gly Phe Val Arg Lys Asn Gly Val Asn Glu Ala Lys Ile Asp Glu
225                 230                 235                 240

Ile Lys Asn Asp Asn Val Gln Asp Thr Ala Glu Gln Lys Val Gln Leu
                245                 250                 255

Leu Arg Asn Trp His Gln Leu His Gly Lys Lys Glu Ala Tyr Asp Thr
            260                 265                 270

Leu Ile Lys Asp Leu Lys Lys Ala Asn Leu Cys Thr Leu Ala Glu Lys
        275                 280                 285

Ile Gln Thr Ile Ile Leu Lys Asp Ile Thr Ser Asp Ser Glu Asn Ser
    290                 295                 300

Asn Phe Arg Asn Glu Ile Gln Ser Leu Val
305                 310

```
<210> SEQ ID NO 42
<211> LENGTH: 168
<212> TYPE: PRT
<213> ORGANISM: Homo sapiens

<400> SEQUENCE: 42
```

Met Phe Gln Ile Pro Glu Phe Glu Pro Ser Gln Glu Asp Ser Ser
1               5                   10                  15

Ser Ala Glu Arg Gly Leu Gly Pro Ser Pro Ala Gly Asp Gly Pro Ser

```
                    20                  25                  30
Gly Ser Gly Lys His His Arg Gln Ala Pro Gly Leu Leu Trp Asp Ala
            35                  40                  45

Ser His Gln Gln Glu Gln Pro Thr Ser Ser His His Gly Gly Ala
    50                  55                  60

Gly Ala Val Glu Ile Arg Ser Arg His Ser Ser Tyr Pro Ala Gly Thr
65                  70                  75                  80

Glu Asp Asp Glu Gly Met Gly Glu Pro Ser Pro Phe Arg Gly Arg
                85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
            115                 120                 125

Leu Pro Arg Pro Lys Ser Ala Gly Thr Ala Thr Gln Met Arg Gln Ser
            130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 43
<211> LENGTH: 279
<212> TYPE: PRT
<213> ORGANISM: Homo sapiens

<400> SEQUENCE: 43

Met Val Asp His Leu Ala Asn Thr Glu Ile Asn Ser Gln Arg Ile Ala
1               5                   10                  15

Ala Val Glu Ser Cys Phe Gly Ala Ser Gly Gln Pro Leu Ala Leu Pro
                20                  25                  30

Gly Arg Val Leu Leu Gly Glu Gly Val Leu Thr Lys Glu Cys Arg Lys
            35                  40                  45

Lys Ala Lys Pro Arg Ile Phe Phe Leu Phe Asn Asp Ile Leu Val Tyr
    50                  55                  60

Gly Ser Ile Val Leu Asn Lys Arg Lys Tyr Arg Ser Gln His Ile Ile
65                  70                  75                  80

Pro Leu Glu Glu Val Thr Leu Glu Leu Leu Pro Glu Thr Leu Gln Ala
                85                  90                  95

Lys Asn Arg Trp Met Ile Lys Thr Ala Lys Lys Ser Phe Val Val Ser
            100                 105                 110

Ala Ala Ser Ala Thr Glu Arg Gln Glu Trp Ile Ser His Ile Glu Glu
            115                 120                 125

Cys Val Arg Arg Gln Leu Lys Ala Thr Gly Arg Pro Pro Ser Thr Glu
            130                 135                 140

His Ala Ala Pro Trp Ile Pro Asp Lys Ala Thr Asp Ile Cys Met Arg
145                 150                 155                 160

Cys Thr Gln Thr Arg Phe Ser Ala Leu Thr Arg Arg His His Cys Arg
                165                 170                 175

Lys Cys Gly Phe Val Val Cys Ala Glu Cys Ser Arg Gln Arg Phe Leu
            180                 185                 190

Leu Pro Arg Leu Ser Pro Lys Pro Val Arg Val Cys Ser Leu Cys Tyr
            195                 200                 205

Arg Glu Leu Ala Ala Gln Gln Arg Gln Glu Glu Ala Glu Glu Gln Gly
            210                 215                 220
```

Ala Gly Ser Pro Arg Gln Pro Ala His Leu Ala Arg Pro Ile Cys Gly
225                 230                 235                 240

Ala Ser Ser Gly Asp Asp Asp Ser Asp Glu Asp Lys Glu Gly Ser
            245                 250                 255

Arg Asp Gly Asp Trp Pro Ser Ser Val Glu Phe Tyr Ala Ser Gly Val
        260                 265                 270

Ala Trp Ser Ala Phe His Ser
                275

<210> SEQ ID NO 44
<211> LENGTH: 850
<212> TYPE: PRT
<213> ORGANISM: Pieris rapae

<400> SEQUENCE: 44

Met Ala Asp Arg Gln Pro Tyr Met Thr Asn Gly Ile Gln Ala Ala Val
1               5                   10                  15

Val Glu Trp Ile Arg Ala Leu Asp Leu Glu Ile Ile Ser Leu Leu Leu
            20                  25                  30

Ser Arg Ala Trp Pro Met Ala Leu Leu Ala Thr Ser Glu Leu Arg Trp
        35                  40                  45

Arg Pro Thr Val Leu Thr Asp Thr Asn Val Val Arg Leu Asp Arg
    50                  55                  60

Arg Gln Arg Leu Val Arg Trp Asp Arg Arg Pro Pro Asn Glu Ile Phe
65              70                  75                  80

Leu Asp Gly Phe Val Pro Ile Val Thr Arg Glu Asn Pro Asp Trp Glu
                85                  90                  95

Glu Thr Asp Leu Tyr Gly Phe Ala Lys Asn Asn His Pro Ser Ile Phe
            100                 105                 110

Val Ser Thr Thr Lys Thr Gln Arg Asn Lys Lys Tyr Val Trp Thr
        115                 120                 125

Pro Arg Asn Ala Asn Arg Gly Ile Val Tyr Gln Tyr Glu Ile Tyr Ala
    130                 135                 140

Pro Gly Gly Val Asp Val Asn Asp Ser Phe Ser Asp Ala Ser Pro Trp
145                 150                 155                 160

Pro Asn Gln Met Glu Val Ala Phe Pro Gly Gly Ile Gln Asn Ile Tyr
                165                 170                 175

Ile Arg Ser Ala Arg Glu Leu His Asn Gly Arg Ile Gln Arg Ile Trp
            180                 185                 190

Ile Asn Pro Asn Phe Leu Asp Pro Gly Asp Leu Glu Pro Ile Val Ser
        195                 200                 205

Ser Ser Arg Thr Pro Gln Val Ile Trp Arg Met Asn His Pro Asp Gly
    210                 215                 220

Gly His Arg Asp Gln Arg Ser Glu Arg Ser Ala Ser Ser Tyr Asp Asp
225                 230                 235                 240

Leu Met Tyr Gly Gly Thr Gly Asn Val Gln Glu Asp Thr Phe Gly Asp
                245                 250                 255

Glu Pro Asn Asn Pro Lys Pro Ile Ala Ala Gly Glu Phe Met Ile Glu
            260                 265                 270

Ser Ile Lys Asp Lys Asn Ser Phe Leu Asp Leu Ser Lys Asn Val Asn
        275                 280                 285

Gly Gly Val Ile His Ser Asn Leu Tyr Ser Gly Gly Asp Asn Gln Ile
    290                 295                 300

Trp Val Phe Ser Tyr Asp Asp Asn Lys Lys Ala Tyr Arg Ile Gln Ser
305                 310                 315                 320

```
Tyr Gln Asn Ser Tyr Leu Tyr Leu Ser Trp Asp Ser Asn Ala Ser Ser
            325                 330                 335

Lys Glu Met Ile Leu Arg Gly Tyr Thr Asn Ser Gly Ser Asn Asn Gln
            340                 345                 350

Tyr Trp Gln Ile Glu Gln Thr Gly Lys Asn Tyr Arg Leu Arg Asn Leu
            355                 360                 365

Leu Asn Leu Asp Met Ile Ile Thr Ala Gln Asp Lys Pro Ser Ala Phe
            370                 375                 380

Gly Gly Lys Glu Val Ile Val Asn Thr Glu Ile Ser Asn Ser Asn Thr
385                 390                 395                 400

Lys Ile Ser Gln Glu Trp Lys Met Ile Pro Phe Asp Phe Arg Pro Ile
            405                 410                 415

Ile Asp Gly Asp Tyr Asn Ile Phe Asn Val Asp Leu Ser Asn Gln Val
            420                 425                 430

Val Asp Phe Ser Asn Gln Pro Asp Leu Leu Val His Gly His Ile Phe
            435                 440                 445

Cys Asp Asn Glu Asn Gln Thr Trp His Phe Thr Tyr Asn Ser Thr Tyr
            450                 455                 460

His Ala Tyr Lys Ile Trp Ser Gly Arg Lys Ser Asn Leu Leu Leu Thr
465                 470                 475                 480

Trp Asp Ser Asn Ala Ala Ser Lys Glu Met Val Val Arg Ala Tyr Thr
            485                 490                 495

Glu Ser Arg Ser Lys Asn Gln Tyr Trp Arg Ile Glu Gln Thr Gly Ser
            500                 505                 510

Lys Ser Tyr Lys Val Arg Asn Leu Glu Asn Ser Ser Met Ile Leu Gly
            515                 520                 525

Leu Thr Arg Val Ser Thr Pro Tyr Gly Gly Leu Asn Leu Met Val Glu
            530                 535                 540

Asp Asp Ser Asp Gly His Ser Asp Leu His Ser Asp Trp Asp Ile Lys
545                 550                 555                 560

Pro Ile Phe Tyr Gln Asp Ile Pro Asp Gly Asp Tyr Asn Ile Phe Asn
            565                 570                 575

Asp Asn Phe Pro Asn Ile Ala Ile Asp Phe Thr Asn Gln Glu Gly Ser
            580                 585                 590

Leu Ile His Gly His Asn Phe Cys Ser Asn Asn Gln Lys Trp Ser
            595                 600                 605

Phe Val Phe Asp Gly Lys Arg Lys Ala Tyr Arg Ile Lys Ser Gly Val
            610                 615                 620

Arg Ser Asn Leu Trp Leu Ser Trp Asp Ser Asn Ala Ser Ser Lys Glu
625                 630                 635                 640

Met Val Leu Arg Ala Tyr Thr Glu Ser Gly Ser Ser Asn Gln Tyr Trp
            645                 650                 655

Arg Leu Asp Glu Ala Asn Asp Gly Ser Tyr Arg Ile Arg Asn Leu Gln
            660                 665                 670

Asp Tyr Tyr Lys Leu Ile Ala Leu Thr Asn Lys Asn Thr Pro Tyr Gly
            675                 680                 685

Gly Lys Glu Leu Ile Val Ser Asp Asn Lys Ser Gly Asn Thr Trp
            690                 695                 700

Tyr Leu Lys Lys Leu Gly Glu Val Pro Leu Pro Asn Arg Lys Phe Arg
705                 710                 715                 720

Ile Ala Thr Lys Leu Asn Tyr Lys Lys Val Ile Asp Ser Ser Thr Ser
            725                 730                 735
```

-continued

Tyr Asn Leu Ile Ile Thr His Asp Leu Asn Phe Ala Ser Ser Ile Trp
            740                 745                 750

Glu Leu Val Tyr Asp Ser Ser Lys Lys Ala Tyr Asn Ile Tyr Ser Ser
        755                 760                 765

Asp Ile Asn Asn Leu Gly Trp Ile Tyr Gln Asn Lys Asn Phe Phe Val
    770                 775                 780

Lys Leu Gly Asn Ile Asp Gly Pro Asp His Gly Asp Leu Arg Tyr Phe
785                 790                 795                 800

Trp Thr Ile Glu Tyr Ser Met Gln Thr Gly Cys Tyr Leu Ile Arg Ser
            805                 810                 815

Leu His Asp Pro Ala Asn Ala Val Gly Tyr Thr Asp Ser Glu Ser Val
        820                 825                 830

Ile Thr Asp Thr Ser Thr Tyr Ser Asp Asn Gln Leu Phe His Phe Ile
            835                 840                 845

Leu Met
    850

<210> SEQ ID NO 45
<211> LENGTH: 281
<212> TYPE: PRT
<213> ORGANISM: Homo sapiens

<400> SEQUENCE: 45

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
            85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
            165                 170                 175

His Glu Lys Gly Phe Tyr Tyr Ile Tyr Ser Gln Thr Tyr Phe Arg Phe
        180                 185                 190

Gln Glu Glu Ile Lys Glu Asn Thr Lys Asn Asp Lys Gln Met Val Gln
    195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

```
Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 46
<211> LENGTH: 192
<212> TYPE: PRT
<213> ORGANISM: Homo sapiens

<400> SEQUENCE: 46

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 47
<211> LENGTH: 238
<212> TYPE: PRT
<213> ORGANISM: Aequorea victoria

<400> SEQUENCE: 47

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110
```

```
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 48
<211> LENGTH: 194
<212> TYPE: PRT
<213> ORGANISM: Aliivibrio fischeri

<400> SEQUENCE: 48

Met Phe Lys Gly Ile Val Glu Gly Ile Gly Ile Ile Glu Lys Ile Asp
1               5                   10                  15

Ile Tyr Thr Asp Leu Asp Lys Tyr Ala Ile Arg Phe Pro Glu Asn Met
            20                  25                  30

Leu Asn Gly Ile Lys Lys Glu Ser Ser Ile Met Phe Asn Gly Cys Phe
        35                  40                  45

Leu Thr Val Thr Ser Val Asn Ser Asn Ile Val Trp Phe Asp Ile Phe
50                  55                  60

Glu Lys Glu Ala Arg Lys Leu Asp Thr Phe Arg Glu Tyr Lys Val Gly
65                  70                  75                  80

Asp Arg Val Asn Leu Gly Thr Phe Pro Lys Phe Gly Ala Ala Ser Gly
                85                  90                  95

Gly His Ile Leu Ser Ala Arg Ile Ser Cys Val Ala Ser Ile Ile Glu
            100                 105                 110

Ile Ile Glu Asn Glu Asp Tyr Gln Gln Met Trp Ile Gln Ile Pro Glu
        115                 120                 125

Asn Phe Thr Glu Phe Leu Ile Asp Lys Asp Tyr Ile Ala Val Asp Gly
    130                 135                 140

Ile Ser Leu Thr Ile Asp Thr Ile Lys Asn Asn Gln Phe Phe Ile Ser
145                 150                 155                 160

Leu Pro Leu Lys Ile Ala Gln Asn Thr Asn Met Lys Trp Arg Lys Lys
                165                 170                 175

Gly Asp Lys Val Asn Val Glu Leu Ser Asn Lys Ile Asn Ala Asn Gln
            180                 185                 190

Cys Trp

<210> SEQ ID NO 49
<211> LENGTH: 225
<212> TYPE: PRT
<213> ORGANISM: Montastraea cavernosa

<400> SEQUENCE: 49
```

```
Met Ser Val Ile Lys Ser Val Met Lys Ile Lys Leu Arg Met Asp Gly
1               5                   10                  15

Ile Val Asn Gly His Lys Phe Met Ile Thr Gly Glu Gly Glu Gly Lys
            20                  25                  30

Pro Phe Glu Gly Thr His Thr Ile Leu Lys Val Lys Glu Gly Gly
        35                  40                  45

Pro Leu Pro Phe Ala Tyr Asp Ile Leu Thr Thr Ala Phe Gln Tyr Gly
50                  55                  60

Asn Arg Val Phe Thr Lys Tyr Pro Lys Asp Ile Pro Asp Tyr Phe Lys
65                  70                  75                  80

Gln Ser Phe Pro Glu Gly Tyr Ser Trp Glu Arg Ser Met Thr Phe Glu
                85                  90                  95

Asp Gln Gly Val Cys Thr Val Thr Ser Asp Ile Lys Leu Glu Gly Asp
            100                 105                 110

Cys Phe Phe Tyr Glu Ile Arg Phe Tyr Gly Val Asn Phe Pro Ser Ser
        115                 120                 125

Gly Pro Val Met Gln Lys Lys Thr Leu Lys Trp Glu Pro Ser Thr Glu
130                 135                 140

Asn Met Tyr Val Arg Asp Gly Val Leu Leu Gly Asp Val Ser Arg Thr
145                 150                 155                 160

Leu Leu Leu Glu Gly Asp Lys His His Arg Cys Asn Phe Arg Ser Thr
                165                 170                 175

Tyr Gly Ala Lys Lys Gly Val Val Leu Pro Glu Tyr His Phe Val Asp
            180                 185                 190

His Arg Ile Glu Ile Leu Ser His Asp Lys Asp Tyr Asn Thr Val Glu
        195                 200                 205

Val Tyr Glu Asn Ala Val Ala Arg Pro Ser Met Leu Pro Val Lys Ala
    210                 215                 220

Lys
225

<210> SEQ ID NO 50
<211> LENGTH: 230
<212> TYPE: PRT
<213> ORGANISM: Discosoma sp.

<400> SEQUENCE: 50

Met Ser Cys Ser Lys Asn Val Ile Lys Glu Phe Met Arg Phe Lys Val
1               5                   10                  15

Arg Met Glu Gly Thr Val Asn Gly His Glu Phe Glu Ile Lys Gly Glu
            20                  25                  30

Gly Glu Gly Arg Pro Tyr Glu Gly His Cys Ser Val Lys Leu Met Val
        35                  40                  45

Thr Lys Gly Gly Pro Leu Pro Phe Ala Phe Asp Ile Leu Ser Pro Gln
50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Ser Gln Asp Ser Ser
            100                 105                 110

Leu Lys Asp Gly Cys Phe Ile Tyr Glu Val Lys Phe Ile Gly Val Asn
        115                 120                 125

Phe Pro Ser Asp Gly Pro Val Met Gln Arg Arg Thr Arg Gly Trp Glu
130                 135                 140
```

```
Ala Ser Ser Glu Arg Leu Tyr Pro Arg Asp Gly Val Leu Lys Gly Asp
145                 150                 155                 160

Ile His Met Ala Leu Arg Leu Glu Gly Gly His Tyr Leu Val Glu
                165                 170                 175

Phe Lys Ser Ile Tyr Met Val Lys Lys Pro Ser Val Gln Leu Pro Gly
            180                 185                 190

Tyr Tyr Tyr Val Asp Ser Lys Leu Asp Met Thr Ser His Asn Glu Asp
                195                 200                 205

Tyr Thr Val Val Glu Gln Tyr Glu Lys Thr Gln Gly Arg His His Pro
210                 215                 220

Phe Ile Lys Pro Leu Gln
225                 230

<210> SEQ ID NO 51
<211> LENGTH: 550
<212> TYPE: PRT
<213> ORGANISM: Photinus pyralis

<400> SEQUENCE: 51

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asn Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Ser Pro Lys Gly Val
        195                 200                 205

Ala Leu Pro His Arg Thr Ala Cys Val Arg Phe Ser His Ala Arg Asp
        210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
```

-continued

```
                275                 280                 285
Pro Thr Leu Phe Ser Phe Phe Ala Lys Ser Thr Leu Ile Asp Lys Tyr
    290                 295                 300
Asp Leu Ser Asn Leu His Glu Ile Ala Ser Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
            355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asp Pro Glu Ala Thr Asn Ala Leu Ile Asp Lys Asp Gly
                405                 410                 415
Trp Leu His Ser Gly Asp Ile Ala Tyr Trp Asp Glu Asp His Phe
            420                 425                 430
Phe Ile Val Asp Arg Leu Lys Ser Leu Ile Lys Tyr Lys Gly Cys Gln
            435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Gly Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
                500                 505                 510
Arg Gly Gly Val Val Phe Val Asp Glu Val Pro Lys Gly Leu Thr Gly
            515                 520                 525
Lys Leu Asp Ala Arg Lys Ile Arg Glu Ile Leu Ile Lys Ala Lys Lys
    530                 535                 540
Gly Gly Lys Ser Lys Leu
545                 550

<210> SEQ ID NO 52
<211> LENGTH: 311
<212> TYPE: PRT
<213> ORGANISM: Renilla reniformis

<400> SEQUENCE: 52

Met Thr Ser Lys Val Tyr Asp Pro Glu Gln Arg Lys Arg Met Ile Thr
1               5                   10                  15
Gly Pro Gln Trp Trp Ala Arg Cys Lys Gln Met Asn Val Leu Asp Ser
            20                  25                  30
Phe Ile Asn Tyr Tyr Asp Ser Glu Lys His Ala Glu Asn Ala Val Ile
        35                  40                  45
Phe Leu His Gly Asn Ala Ala Ser Ser Tyr Leu Trp Arg His Val Val
    50                  55                  60
Pro His Ile Glu Pro Val Ala Arg Cys Ile Ile Pro Asp Leu Ile Gly
65                  70                  75                  80
Met Gly Lys Ser Gly Lys Ser Gly Asn Gly Ser Tyr Arg Leu Leu Asp
                85                  90                  95
```

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
290                 295                 300

Arg Val Leu Lys Asn Glu Gln
305                 310

<210> SEQ ID NO 53
<211> LENGTH: 197
<212> TYPE: PRT
<213> ORGANISM: Artificial Sequence
<220> FEATURE:
<223> OTHER INFORMATION: Synthetic Construct

<400> SEQUENCE: 53

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

```
Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg
        195
```

<210> SEQ ID NO 54
<211> LENGTH: 197
<212> TYPE: PRT
<213> ORGANISM: Homo sapiens

<400> SEQUENCE: 54

```
Gly Lys Ala Ser Ser Ala Lys Gln Arg Leu Lys Cys Ala Ser Leu Gln
1               5                   10                  15

Lys Phe Gly Glu Arg Ala Phe Lys Ala Trp Ala Val Ala Arg Leu Ser
                20                  25                  30

Gln Arg Phe Pro Lys Ala Glu Phe Ala Glu Val Ser Lys Leu Val Thr
            35                  40                  45

Asp Leu Thr Lys Val His Thr Glu Cys Cys His Gly Asp Leu Leu Glu
    50                  55                  60

Cys Ala Asp Asp Arg Ala Asp Leu Ala Lys Tyr Ile Cys Glu Asn Gln
65                  70                  75                  80

Asp Ser Ile Ser Ser Lys Leu Lys Glu Cys Cys Glu Lys Pro Leu Leu
                85                  90                  95

Glu Lys Ser His Cys Ile Ala Glu Val Glu Asn Asp Glu Met Pro Ala
                100                 105                 110

Asp Leu Pro Ser Leu Ala Ala Asp Phe Val Glu Ser Lys Asp Val Cys
            115                 120                 125

Lys Asn Tyr Ala Glu Ala Lys Asp Val Phe Leu Gly Met Phe Leu Tyr
130                 135                 140

Glu Tyr Ala Arg Arg His Pro Asp Tyr Ser Val Val Leu Leu Leu Arg
145                 150                 155                 160

Leu Ala Lys Thr Tyr Glu Thr Thr Leu Glu Lys Cys Cys Ala Ala Ala
                165                 170                 175

Asp Pro His Glu Cys Tyr Ala Lys Val Phe Asp Glu Phe Lys Pro Leu
                180                 185                 190

Val Glu Glu Pro Gln
        195
```

<210> SEQ ID NO 55
<211> LENGTH: 205
<212> TYPE: PRT
<213> ORGANISM: Artificial sequence
<220> FEATURE:
<223> OTHER INFORMATION: Synthetic construct

<400> SEQUENCE: 55

```
Val Glu Glu Pro Gln Asn Leu Ile Lys Gln Asn Cys Glu Leu Phe Glu
1               5                   10                  15

Gln Leu Gly Glu Tyr Lys Phe Gln Asn Ala Leu Leu Val Arg Tyr Thr
                20                  25                  30

Lys Lys Val Pro Gln Val Ser Thr Pro Thr Leu Val Glu Val Ser Arg
            35                  40                  45

Asn Leu Gly Lys Val Gly Ser Lys Cys Cys Lys His Pro Glu Ala Lys
```

```
                    50                  55                  60

Arg Met Pro Cys Ala Glu Asp Tyr Leu Ser Val Val Leu Asn Gln Leu
 65                  70                  75                  80

Cys Val Leu His Glu Lys Thr Pro Val Ser Asp Arg Val Thr Lys Cys
                     85                  90                  95

Cys Thr Glu Ser Leu Val Asn Arg Arg Pro Cys Phe Ser Ala Leu Glu
                100                 105                 110

Val Asp Glu Thr Tyr Val Pro Lys Glu Phe Gln Ala Glu Thr Phe Thr
            115                 120                 125

Phe His Ala Asp Ile Cys Thr Leu Ser Glu Lys Glu Arg Gln Ile Lys
            130                 135                 140

Lys Gln Thr Ala Leu Val Glu Leu Val Lys His Lys Pro Lys Ala Thr
145                 150                 155                 160

Lys Glu Gln Leu Lys Ala Val Met Asp Asp Phe Ala Ala Phe Val Glu
                165                 170                 175

Lys Cys Cys Lys Ala Asp Asp Lys Glu Thr Cys Phe Ala Glu Glu Gly
                180                 185                 190

Lys Lys Leu Val Ala Ala Ser Gln Ala Ala Leu Gly Leu
                195                 200                 205

<210> SEQ ID NO 56
<211> LENGTH: 197
<212> TYPE: PRT
<213> ORGANISM: Homo sapiens

<400> SEQUENCE: 56

Asp Ala His Lys Ser Glu Val Ala His Arg Phe Lys Asp Leu Gly Glu
  1               5                  10                  15

Glu Asn Phe Lys Ala Leu Val Leu Ile Ala Phe Ala Gln Tyr Leu Gln
                 20                  25                  30

Gln Cys Pro Phe Glu Asp His Val Lys Leu Val Asn Glu Val Thr Glu
             35                  40                  45

Phe Ala Lys Thr Cys Val Ala Asp Glu Ser Ala Glu Asn Cys Asp Lys
         50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg
            195

<210> SEQ ID NO 57
<211> LENGTH: 205
```

<212> TYPE: PRT
<213> ORGANISM: Homo sapiens

<400> SEQUENCE: 57

```
Val Glu Glu Pro Gln Asn Leu Ile Lys Gln Asn Cys Glu Leu Phe Glu
1               5                   10                  15

Gln Leu Gly Glu Tyr Lys Phe Gln Asn Ala Leu Leu Val Arg Tyr Thr
            20                  25                  30

Lys Lys Val Pro Gln Val Ser Thr Pro Thr Leu Val Glu Val Ser Arg
        35                  40                  45

Asn Leu Gly Lys Val Gly Ser Lys Cys Cys Lys His Pro Glu Ala Lys
    50                  55                  60

Arg Met Pro Cys Ala Glu Asp Tyr Leu Ser Val Val Leu Asn Gln Leu
65                  70                  75                  80

Cys Val Leu His Glu Lys Thr Pro Val Ser Asp Arg Val Thr Lys Cys
                85                  90                  95

Cys Thr Glu Ser Leu Val Asn Arg Arg Pro Cys Phe Ser Ala Leu Glu
            100                 105                 110

Val Asp Glu Thr Tyr Val Pro Lys Glu Phe Asn Ala Glu Thr Phe Thr
        115                 120                 125

Phe His Ala Asp Ile Cys Thr Leu Ser Glu Lys Glu Arg Gln Ile Lys
    130                 135                 140

Lys Gln Thr Ala Leu Val Glu Leu Val Lys His Lys Pro Lys Ala Thr
145                 150                 155                 160

Lys Glu Gln Leu Lys Ala Val Met Asp Asp Phe Ala Ala Phe Val Glu
                165                 170                 175

Lys Cys Cys Lys Ala Asp Asp Lys Glu Thr Cys Phe Ala Glu Glu Gly
            180                 185                 190

Lys Lys Leu Val Ala Ala Ser Gln Ala Ala Leu Gly Leu
        195                 200                 205
```

<210> SEQ ID NO 58
<211> LENGTH: 609
<212> TYPE: PRT
<213> ORGANISM: Homo sapiens

<400> SEQUENCE: 58

```
Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140
```

```
Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
    370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
        435                 440                 445

Ala Ile Thr Arg Lys Met Ala Ala Thr Ala Thr Cys Cys Gln Leu
450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
    530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
```

```
                  565                 570                 575
Gly Leu Leu Glu Lys Cys Cys Gln Gly Gln Glu Gln Glu Val Cys Phe
                580                 585                 590
Ala Glu Glu Gly Gln Lys Leu Ile Ser Lys Thr Arg Ala Ala Leu Gly
            595                 600                 605
Val

<210> SEQ ID NO 59
<211> LENGTH: 34
<212> TYPE: PRT
<213> ORGANISM: Human

<400> SEQUENCE: 59

Leu Ser Glu Asp Lys Leu Leu Ala Cys Gly Glu Gly Ala Ala Asp Ile
1               5                   10                  15

Ile Ile Gly His Leu Cys Ile Arg His Glu Met Thr Pro Val Asn Pro
            20                  25                  30

Gly Val

<210> SEQ ID NO 60
<211> LENGTH: 8645
<212> TYPE: DNA
<213> ORGANISM: Artificial Sequence
<220> FEATURE:
<223> OTHER INFORMATION: Synthetic Construct

<400> SEQUENCE: 60
```

| | | | | | |
|---|---|---|---|---|---|
| gtgccgacga | tagagcagac | ctcgctaaat | atatctgcga | gaatcaggat | tccattagct | 60 |
| ctaagctgaa | agaatgttgc | gagaagcccc | tcctggaaaa | gagtcattgt | atcgccgagg | 120 |
| tggaaaacga | cgagatgcca | gcagatctgc | catcactcgc | tgccgacttt | gtggaatcca | 180 |
| agatgtctg | caagaattac | gcagaggcta | agacgtgtt | cctggggatg | tttctgtatg | 240 |
| agtacgcccg | gcgtcacccc | gattatagcg | tcgtgctcct | gctccgactg | gcaaagacct | 300 |
| acgaaacaac | tctggagaaa | tgttgcgctg | ccgcagaccc | tcatgaatgt | tatgctaagg | 360 |
| tgttcgatga | gtttaagcca | ctcgtcgaag | agccccagaa | cctgattaaa | cagaattgcg | 420 |
| aactgttcga | gcagctcggt | gaatacaagt | tcagaacgc | cctgctcgtg | cgttatacca | 480 |
| aaaaggtccc | tcaggtgtct | acaccaactc | tggtggaggt | cagtaggaat | ctgggcaaag | 540 |
| tgggatcaaa | gtgttgcaaa | caccccgagg | caaagagaat | gccttgtgct | gaagattacc | 600 |
| tctccgtcgt | gctgaaccag | ctctgcgtgc | tgcatgaaaa | gacccagtc | agcgatcggg | 660 |
| tgacaaaatg | ttgcaccgaa | tctctggtca | atcgccgacc | ctgtttcagt | gccctcgaag | 720 |
| tggacgaaac | ttatgtgcct | aaggagtttc | aggctgaaac | attcacctt | cacgccgata | 780 |
| tctgcactct | gtccgagaaa | gaaaggcaga | ttaagaaaca | gacagcactg | gtcgagctcg | 840 |
| tgaagcataa | accaaaggct | accaaggagc | agctgaaagc | cgtcatggac | gatttcgcag | 900 |
| cttttgtgga | aaagtgttgc | aaagccgacg | ataaggagac | ttgtttcgca | gaagagggga | 960 |
| aaaagctcgt | ggctgccagc | caggcagctc | tgggtctggc | cgcagctctg | caggtgcagc | 1020 |
| tcgtccagag | cggcgctgag | gtgaagaagc | caggcgagtc | cctgaagatc | tcctgtaagg | 1080 |
| gctccggcta | cagcttcacc | tcctactgga | tcgcttgggt | gaggcagatg | ccaggaaagg | 1140 |
| gactggagta | catgggcctg | atctaccctg | gcgactccga | caccaagtac | tccccatcct | 1200 |
| tccagggcca | ggtgaccatc | agcgtggaca | agtccgtgtc | taccgcctac | ctgcaatggg | 1260 |
| cctccctgaa | gccttctgac | tctgccgtgt | acttttgtgc | ccggcacgat | gtgggctact | 1320 |

```
gcaccgaccg gacatgtgcc aagtggcccg agtggctggg agtgtgggga cagggaacac    1380
tggtgacagt gagttctggc ggtggcggct cttccggcgg tggctctggt ggcggcggat    1440
ctcagagcgt gctgacacag ccacctagcg tgtccgctgc ccctggccag aaggtgacaa    1500
tcagctgctc cggcagctct tccaacatcg gcaacaacta cgtgtcttgg tatcagcagc    1560
tgcccggaac agctccaaaa ctgctgatct atgaccacac caatcggcct gccggcgtgc    1620
cagatcggtt ctctggctct aagagcggca cctccgccag cctggctatc tctggcttca    1680
gatctgagga tgaggctgac tactattgtg cctcctggga ctacaccctg tctggctggg    1740
tgttcggcgg tggcaccaag ctgacagtcc tgggatgatg actcgagtct agagggcccg    1800
tttaaacccg ctgatcagcc tcgactgtgc cttctagttg ccagccatct gttgtttgcc    1860
cctcccccgt gccttccttg acctggaag gtgccactcc cactgtcctt tcctaataaa    1920
atgaggaaat tgcatcgcat tgtctgagta ggtgtcattc tattctgggg ggtggggtgg    1980
ggcaggacag caaggggag gattgggaag acaatagcag gcatgctggg gatgcggtgg    2040
gctctatggc ttctgaggcg gaaagaacca gctgggctc taggggtat ccccacgcgc    2100
cctgtagcgg cgcattaagc gcggcgggtg tggtggttac gcgcagcgtg accgctacac    2160
ttgccagcgc cctagcgccc gctcctttcg ctttcttccc ttcctttctc gccacgttcg    2220
ccggctttcc ccgtcaagct ctaaatcggg ggtcccttta gggttccgat ttagtgcttt    2280
acggcacctc gaccccaaaa aacttgatta gggtgatggt tcacgtacct agaagttcct    2340
attccgaagt tcctattctc tagaaagtat aggaacttcc ttggccaaaa agcctgaact    2400
caccgcgacg tctgtcgaga agtttctgat cgaaaagttc gacagcgtct ccgacctgat    2460
gcagctctcg gagggcgaag aatcgcgtgc tttcagcttc gatgtaggag gcgtggata    2520
tgtcctgcgg gtaaatagct gcgccgatgg tttctacaaa gatcgttatg tttatcggca    2580
ctttgcatcg gccgcgctcc cgattccgga agtgcttgac attggggaat tcagcgagag    2640
cctgacctat tgcatctccc gccgtgcaca gggtgtcacg ttgcaagacc tgcctgaaac    2700
cgaactgccc gctgttctgc agccggtcgc ggaggccatg gatgcgatcg ctgcggccga    2760
tcttagccag acgagcgggt tcggcccatt cggaccgcaa ggaatcggtc aatacactac    2820
atggcgtgat ttcatatgcg cgattgctga tccccatgtg tatcactggc aaactgtgat    2880
ggacgacacc gtcagtgcgt ccgtcgcgca ggctctcgat gagctgatgc tttgggccga    2940
ggactgcccc gaagtccggc acctcgtgca cgcggatttc ggctccaaca atgtcctgac    3000
ggacaatggc cgcataacag cggtcattga ctggagcgag gcgatgttcg ggattccca    3060
atacgaggtc gccaacatct tcttctggag gccgtggttg gcttgtatgg agcagcagac    3120
gcgctacttc gagcggaggc atccggagct tgcaggatcg ccgcggctcc gggcgtatat    3180
gctccgcatt ggtcttgacc aactctatca gagcttggtt gacggcaatt tcgatgatgc    3240
agcttgggcg cagggtcgat gcgacgcaat cgtccgatcc ggagccggga ctgtcgggcg    3300
tacacaaatc gcccgcagaa gcgcggccgt ctggaccgat ggctgtgtag aagtactcgc    3360
cgatagtgga aaccgacgcc ccagcactcg tccgagggca aaggaatagc acgtactacg    3420
agatttcgat tccaccgccg ccttctatga aaggttgggc ttcggaatcg ttttccggga    3480
cgccggctgg atgatcctcc agcgcgggga tctcatgctg gagttcttcg cccacccaa    3540
cttgtttatt gcagcttata atggttacaa ataaagcaat agcatcacaa atttcacaaa    3600
taaagcattt ttttcactgc attctagttg tggtttgtcc aaactcatca atgtatctta    3660
```

```
tcatgtctgt ataccgtcga cctctagcta gagcttggcg taatcatggt catagctgtt    3720
tcctgtgtga aattgttatc cgctcacaat tccacacaac atacgagccg gaagcataaa    3780
gtgtaaagcc tggggtgcct aatgagtgag ctaactcaca ttaattgcgt tgcgctcact    3840
gcccgctttc cagtcgggaa acctgtcgtg ccagctgcat taatgaatcg gccaacgcgc    3900
ggggagaggc ggtttgcgta ttgggcgctc ttccgcttcc tcgctcactg actcgctgcg    3960
ctcggtcgtt cggctgcggc gagcggtatc agctcactca aaggcggtaa tacggttatc    4020
cacagaatca ggggataacg caggaaagaa catgtgagca aaaggccagc aaaaggccag    4080
gaaccgtaaa aaggccgcgt tgctggcgtt tttccatagg ctccgccccc ctgacgagca    4140
tcacaaaaat cgacgctcaa gtcagaggtg gcgaaacccg acaggactat aaagatacca    4200
ggcgtttccc cctggaagct ccctcgtgcg ctctcctgtt ccgaccctgc cgcttaccgg    4260
atacctgtcc gcctttctcc cttcgggaag cgtggcgctt tctcatagct cacgctgtag    4320
gtatctcagt tcggtgtagg tcgttcgctc caagctgggc tgtgtgcacg aaccccccgt    4380
tcagcccgac cgctgcgcct tatccggtaa ctatcgtctt gagtccaacc cggtaagaca    4440
cgacttatcg ccactggcag cagccactgg taacaggatt agcagagcga ggtatgtagg    4500
cggtgctaca gagttcttga agtggtggcc taactacggc tacactagaa ggacagtatt    4560
tggtatctgc gctctgctga agccagttac cttcggaaaa agagttggta gctcttgatc    4620
cggcaaacaa accaccgctg gtagcggtgg tttttttgtt tgcaagcagc agattacgcg    4680
cagaaaaaaa ggatctcaag aagatccttt gatcttttct acggggtctg acgctcagtg    4740
gaacgaaaac tcacgttaag ggattttggt catgagatta tcaaaaagga tcttcaccta    4800
gatccttta aattaaaaat gaagttttaa atcaatctaa agtatatatg agtaaacttg    4860
gtctgacagt taccaatgct taatcagtga ggcacctatc tcagcgatct gtctatttcg    4920
ttcatccata gttgcctgac tccccgtcgt gtagataact acgatacggg agggcttacc    4980
atctggcccc agtgctgcaa tgataccgcg agacccacgc tcaccggctc cagatttatc    5040
agcaataaac cagccagccg gaagggccga gcgcagaagt ggtcctgcaa ctttatccgc    5100
ctccatccag tctattaatt gttgccggga agctagagta agtagttcgc cagttaatag    5160
tttgcgcaac gttgttgcca ttgctacagg catcgtggtg tcacgctcgt cgtttggtat    5220
ggcttcattc agctccggtt cccaacgatc aaggcgagtt acatgatccc ccatgttgtg    5280
caaaaaagcg gttagctcct tcggtcctcc gatcgttgtc agaagtaagt tggccgcagt    5340
gttatcactc atggttatgg cagcactgca taattctctt actgtcatgc catccgtaag    5400
atgcttttct gtgactggtg agtactcaac caagtcattc tgagaatagt gtatgcggcg    5460
accgagttgc tcttgcccgg cgtcaatacg ggataatacc gcgccacata gcagaacttt    5520
aaaagtgctc atcattggaa aacgttcttc ggggcgaaaa ctctcaagga tcttaccgct    5580
gttgagatcc agttcgatgt aacccactcg tgcacccaac tgatcttcag catcttttac    5640
tttcaccagc gtttctgggt gagcaaaaac aggaaggcaa aatgccgcaa aaagggaat    5700
aagggcgaca cggaaatgtt gaatactcat actcttcctt tttcaatatt attgaagcat    5760
ttatcagggt tattgtctca tgagcggata catatttgaa tgtatttaga aaataaaca    5820
aataggggtt ccgcgcacat ttccccgaaa agtgccacct gacgtcgacg gatcgggaga    5880
tctcccgatc ccctatggtg cactctcagt acaatctgct ctgatgccgc atagttaagc    5940
cagtatctgc tccctgcttg tgtgttggag gtcgctgagt agtgcgcgag caaaatttaa    6000
gctacaacaa ggcaaggctt gaccgacaat tgcatgaaga atctgcttag ggttaggcgt    6060
```

```
tttgcgctgc ttcgcgatgt acgggccaga tatacgcgtt gacattgatt attgactagt   6120
tattaatagt aatcaattac ggggtcatta gttcatagcc catatatgga gttccgcgtt   6180
acataactta cggtaaatgg cccgcctggc tgaccgccca acgaccccg cccattgacg    6240
tcaataatga cgtatgttcc catagtaacg ccaataggga ctttccattg acgtcaatgg   6300
gtggagtatt tacggtaaac tgcccacttg gcagtacatc aagtgtatca tatgccaagt   6360
acgcccccta ttgacgtcaa tgacggtaaa tggcccgcct ggcattatgc ccagtacatg   6420
accttatggg actttcctac ttggcagtac atctacgtat tagtcatcgc tattaccatg   6480
gtgatgcggt tttggcagta catcaatggg cgtggatagc ggtttgactc acggggattt   6540
ccaagtctcc accccattga cgtcaatggg agtttgtttt ggcaccaaaa tcaacgggac   6600
tttccaaaat gtcgtaacaa ctccgcccca ttgacgcaaa tgggcggtag gcgtgtacgg   6660
tgggaggtct atataagcag agctctctgg ctaactagag aacccactgc ttactggctt   6720
atcgaaatta atacgactca ctatagggag acccaagctt ctagaattcg ctgtctgcga   6780
gggccagctg ttggggtgag tactccctct caaaagcggg catgacttct gcgctaagat   6840
tgtcagtttc caaaaacgag gaggatttga tattcacctg gcccgcggtg atgcctttga   6900
gggtggccgc gtccatctgg tcagaaaaga caatcttttt gttgtcaagc ttgaggtgtg   6960
gcaggcttga gatctggcca tacacttgag tgacaatgac atccactttg cctttctctc   7020
cacaggtgtc cactcccagg tccaactgca gatatccagc acagtggcgg ccgccaccat   7080
gggctggtct ctgatcctgc tgttcctggt ggccgtggcc acgcgtgtgc tgtcccaggt   7140
gcagctgcag gagtctggcg gcggactggt gaagcctggc ggctccctgc ggctgtcctg   7200
cgccgcctcc ggcttcacct tctcctccta ctggatgtcc tgggtgcggc aggcccctgg   7260
caagggcctg gagtgggtgg ccaacatcaa ccggacggc tccgcctcct actacgtgga    7320
ctccgtgaag ggccggttca ccatctcccg ggacgacgcc aagaactccc tgtacctgca   7380
gatgaactcc ctgcgggccg aggacaccgc cgtgtactac tgcgccaggg accggggcgt   7440
gggctacttc gacctgtggg caggggcac cctggtgacc gtgtcctccg ctagtactgg    7500
cggcggagga tctggcggag gagggagcgg gggcggtgga tcccagtccg ccctgaccca   7560
gcctgcctcc gtgtccggct cccctggcca gtccatcacc atcagctgca ccggcacctc   7620
ctccgacgtg ggcggctaca acttcgtgtc ctggtatcag cagcaccccg gcaaggcccc   7680
taagctgatg atctacgacg tgtccgaccg gccttccggc gtgtccgaca ggttctccgg   7740
ctccaagtcc ggcaacaccg cctccctgat catcagcggc ctgcaggcag acgacgaggc   7800
cgactactac tgctcctcct acggctcctc ctccacccac gtgatctttg gcggcggaac   7860
aaaggtgacc gtgctgggcg ccgcctccga cgctcacaag agcgaagtgg cacataggtt   7920
caaagatctg ggcgaagaga actttaaggc cctcgtcctg atcgctttcg cacagtacct   7980
ccagcagtct ccctttgaag atcacgtgaa actggtcaat gaggtgaccg aatttgccaa   8040
gacatgcgtg gctgatgaga gtgcagaaaa ctgtgacaaa tcactgcata ctctctttgg   8100
agataagctg tgcaccgtcg ccacactcag agagacttat ggggaaatgg ctgactgttg   8160
cgcaaaacag gagcctgaac ggaatgagtg tttcctccag cacaaggatg acaacccaaa   8220
tctgccccgc ctcgtgcgac tgaggtcga tgtgatgtgc accgcctttc atgacaacga   8280
agagacattc tgaagaaat acctgtatga aattgctcgt aggcacccat acttttatgc   8340
ccccgagctc ctgttctttg caaagagata caaagctgcc ttcactgaat gttgccaggc   8400
```

```
agctgataag gccgcatgtc tcctgcctaa actggacgag ctccgggatg aaggtaaggc      8460
ttccagcgcc aaacagcgcc tgaagtgcgc ttctctccag aagtttggcg agcgagcatt      8520
caaagcctgg gctgtggccc gtctcagtca gaggtttcca aaggcagaat ttgctgaggt      8580
ctcaaaactg gtgaccgacc tcacaaaggt ccatactgag tgttgccacg agatctgct       8640 ggaat                                                                   8645

<210> SEQ ID NO 61
<211> LENGTH: 34
<212> TYPE: DNA
<213> ORGANISM: Artificial Sequence
<220> FEATURE:
<223> OTHER INFORMATION: Synthetic Construct

<400> SEQUENCE: 61
gtacttttgt gcccgggccg atgtgggcta ctgc                                  34

<210> SEQ ID NO 62
<211> LENGTH: 34
<212> TYPE: DNA
<213> ORGANISM: Artificial Sequence
<220> FEATURE:
<223> OTHER INFORMATION: Synthetic Construct

<400> SEQUENCE: 62
gcagtagccc acatcggccc gggcacaaaa gtac                                  34

<210> SEQ ID NO 63
<211> LENGTH: 34
<212> TYPE: DNA
<213> ORGANISM: Artificial Sequence
<220> FEATURE:
<223> OTHER INFORMATION: Synthetic Construct

<400> SEQUENCE: 63
gacatgtgcc aaggcccccg cgtggctggg agtg                                  34

<210> SEQ ID NO 64
<211> LENGTH: 34
<212> TYPE: DNA
<213> ORGANISM: Artificial Sequence
<220> FEATURE:
<223> OTHER INFORMATION: Synthetic Construct

<400> SEQUENCE: 64
cactcccagc cacgcggggg ccttggcaca tgtc                                  34

<210> SEQ ID NO 65
<211> LENGTH: 101
<212> TYPE: DNA
<213> ORGANISM: Artificial Sequence
<220> FEATURE:
<223> OTHER INFORMATION: Synthetic Construct

<400> SEQUENCE: 65
acagtggcgg ccgccaccat gggctggtct ctgatcctgc tgttcctggt ggccgtggcc      60
acgcgtgtgc tgtcccaggt gcagctcgtc cagagcggcg c                         101

<210> SEQ ID NO 66
<211> LENGTH: 40
<212> TYPE: DNA
<213> ORGANISM: Artificial Sequence
<220> FEATURE:
<223> OTHER INFORMATION: Synthetic Construct
```

<400> SEQUENCE: 66
ggaggcggcg cccaggactg tcagcttggt gccaccgccg    40

<210> SEQ ID NO 67
<211> LENGTH: 1102
<212> TYPE: PRT
<213> ORGANISM: Artificial Sequence
<220> FEATURE:
<223> OTHER INFORMATION: Synthetic Construct

<400> SEQUENCE: 67

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg Ala Asp Val Gly Tyr Cys Thr Asp Arg Thr Cys Ala Lys Ala
            100                 105                 110

Pro Ala Trp Leu Gly Val Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gln Ser Val Leu Thr Gln Pro Pro Ser Val Ser Ala Ala Pro Gly Gln
145                 150                 155                 160

Lys Val Thr Ile Ser Cys Ser Gly Ser Ser Ser Asn Ile Gly Asn Asn
                165                 170                 175

Tyr Val Ser Trp Tyr Gln Gln Leu Pro Gly Thr Ala Pro Lys Leu Leu
            180                 185                 190

Ile Tyr Asp His Thr Asn Arg Pro Ala Gly Val Pro Asp Arg Phe Ser
        195                 200                 205

Gly Ser Lys Ser Gly Thr Ser Ala Ser Leu Ala Ile Ser Gly Phe Arg
    210                 215                 220

Ser Glu Asp Glu Ala Asp Tyr Tyr Cys Ala Ser Trp Asp Tyr Thr Leu
225                 230                 235                 240

Ser Gly Trp Val Phe Gly Gly Gly Thr Lys Leu Thr Val Leu Gly Ala
                245                 250                 255

Ala Ser Asp Ala His Lys Ser Glu Val Ala His Arg Phe Lys Asp Leu
            260                 265                 270

Gly Glu Glu Asn Phe Lys Ala Leu Val Leu Ile Ala Phe Ala Gln Tyr
        275                 280                 285

Leu Gln Gln Ser Pro Phe Glu Asp His Val Lys Leu Val Asn Glu Val
    290                 295                 300

Thr Glu Phe Ala Lys Thr Cys Val Ala Asp Glu Ser Ala Glu Asn Cys
305                 310                 315                 320

Asp Lys Ser Leu His Thr Leu Phe Gly Asp Lys Leu Cys Thr Val Ala
                325                 330                 335

Thr Leu Arg Glu Thr Tyr Gly Glu Met Ala Asp Cys Cys Ala Lys Gln
```

```
            340                 345                 350
Glu Pro Glu Arg Asn Glu Cys Phe Leu Gln His Lys Asp Asp Asn Pro
            355                 360                 365

Asn Leu Pro Arg Leu Val Arg Pro Glu Val Asp Val Met Cys Thr Ala
            370                 375             380

Phe His Asp Asn Glu Glu Thr Phe Leu Lys Lys Tyr Leu Tyr Glu Ile
385                     390                 395                 400

Ala Arg Arg His Pro Tyr Phe Tyr Ala Pro Glu Leu Leu Phe Phe Ala
                405                 410                 415

Lys Arg Tyr Lys Ala Ala Phe Thr Glu Cys Cys Gln Ala Ala Asp Lys
            420                 425                 430

Ala Ala Cys Leu Leu Pro Lys Leu Asp Glu Leu Arg Asp Glu Gly Lys
            435                 440                 445

Ala Ser Ser Ala Lys Gln Arg Leu Lys Cys Ala Ser Leu Gln Lys Phe
            450                 455                 460

Gly Glu Arg Ala Phe Lys Ala Trp Ala Val Ala Arg Leu Ser Gln Arg
465                 470                 475                 480

Phe Pro Lys Ala Glu Phe Ala Glu Val Ser Lys Leu Val Thr Asp Leu
                485                 490                 495

Thr Lys Val His Thr Glu Cys Cys His Gly Asp Leu Leu Glu Cys Ala
            500                 505                 510

Asp Asp Arg Ala Asp Leu Ala Lys Tyr Ile Cys Glu Asn Gln Asp Ser
            515                 520                 525

Ile Ser Ser Lys Leu Lys Glu Cys Cys Glu Lys Pro Leu Leu Glu Lys
            530                 535                 540

Ser His Cys Ile Ala Glu Val Glu Asn Asp Glu Met Pro Ala Asp Leu
545                 550                 555                 560

Pro Ser Leu Ala Ala Asp Phe Val Glu Ser Lys Asp Val Cys Lys Asn
                565                 570                 575

Tyr Ala Glu Ala Lys Asp Val Phe Leu Gly Met Phe Leu Tyr Glu Tyr
            580                 585                 590

Ala Arg Arg His Pro Asp Tyr Ser Val Val Leu Leu Leu Arg Leu Ala
            595                 600                 605

Lys Thr Tyr Glu Thr Thr Leu Glu Lys Cys Cys Ala Ala Ala Asp Pro
            610                 615                 620

His Glu Cys Tyr Ala Lys Val Phe Asp Glu Phe Lys Pro Leu Val Glu
625                 630                 635                 640

Glu Pro Gln Asn Leu Ile Lys Gln Asn Cys Glu Leu Phe Glu Gln Leu
                645                 650                 655

Gly Glu Tyr Lys Phe Gln Asn Ala Leu Leu Val Arg Tyr Thr Lys Lys
            660                 665                 670

Val Pro Gln Val Ser Thr Pro Thr Leu Val Glu Val Ser Arg Asn Leu
            675                 680                 685

Gly Lys Val Gly Ser Lys Cys Cys Lys His Pro Glu Ala Lys Arg Met
            690                 695                 700

Pro Cys Ala Glu Asp Tyr Leu Ser Val Val Leu Asn Gln Leu Cys Val
705                 710                 715                 720

Leu His Glu Lys Thr Pro Val Ser Asp Arg Val Thr Lys Cys Cys Thr
                725                 730                 735

Glu Ser Leu Val Asn Arg Arg Pro Cys Phe Ser Ala Leu Glu Val Asp
            740                 745                 750

Glu Thr Tyr Val Pro Lys Glu Phe Gln Ala Glu Thr Phe Thr Phe His
            755                 760                 765
```

Ala Asp Ile Cys Thr Leu Ser Glu Lys Glu Arg Gln Ile Lys Lys Gln
770                 775                 780

Thr Ala Leu Val Glu Leu Val Lys His Lys Pro Lys Ala Thr Lys Glu
785                 790                 795                 800

Gln Leu Lys Ala Val Met Asp Asp Phe Ala Ala Phe Val Glu Lys Cys
                805                 810                 815

Cys Lys Ala Asp Asp Lys Glu Thr Cys Phe Ala Glu Glu Gly Lys Lys
                820                 825                 830

Leu Val Ala Ala Ser Gln Ala Ala Leu Gly Leu Ala Ala Ala Leu Gln
            835                 840                 845

Val Gln Leu Val Gln Ser Ala Glu Val Lys Lys Pro Gly Glu Ser
        850                 855                 860

Leu Lys Ile Ser Cys Lys Gly Ser Gly Tyr Ser Phe Thr Ser Tyr Trp
865                 870                 875                 880

Ile Ala Trp Val Arg Gln Met Pro Gly Lys Gly Leu Glu Tyr Met Gly
                885                 890                 895

Leu Ile Tyr Pro Gly Asp Ser Asp Thr Lys Tyr Ser Pro Ser Phe Gln
                900                 905                 910

Gly Gln Val Thr Ile Ser Val Asp Lys Ser Val Ser Thr Ala Tyr Leu
        915                 920                 925

Gln Trp Ser Ser Leu Lys Pro Ser Asp Ser Ala Val Tyr Phe Cys Ala
930                 935                 940

Arg His Asp Val Gly Tyr Cys Thr Asp Arg Thr Cys Ala Lys Trp Pro
945                 950                 955                 960

Glu Trp Leu Gly Val Trp Gly Gln Gly Thr Leu Val Thr Val Ser Ser
                965                 970                 975

Gly Gly Gly Gly Ser Ser Gly Gly Ser Gly Gly Gly Gly Ser Gln
            980                 985                 990

Ser Val Leu Thr Gln Pro Pro Ser Val Ser Ala Ala Pro Gly Gln Lys
        995                 1000                1005

Val Thr Ile Ser Cys Ser Gly Ser Ser Ser Asn Ile Gly Asn Asn
        1010                1015                1020

Tyr Val Ser Trp Tyr Gln Gln Leu Pro Gly Thr Ala Pro Lys Leu
        1025                1030                1035

Leu Ile Tyr Asp His Thr Asn Arg Pro Ala Gly Val Pro Asp Arg
        1040                1045                1050

Phe Ser Gly Ser Lys Ser Gly Thr Ser Ala Ser Leu Ala Ile Ser
        1055                1060                1065

Gly Phe Arg Ser Glu Asp Glu Ala Asp Tyr Tyr Cys Ala Ser Trp
        1070                1075                1080

Asp Tyr Thr Leu Ser Gly Trp Val Phe Gly Gly Gly Thr Lys Leu
        1085                1090                1095

Thr Val Leu Gly
    1100

<210> SEQ ID NO 68
<211> LENGTH: 1095
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Gln Glu Ser Gly Gly Gly Leu Val Lys Pro Gly Gly
1               5                   10                  15

```
Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Asn Arg Asp Gly Ser Ala Ser Tyr Tyr Val Asp Ser Val
 50                  55                  60

Lys Gly Arg Phe Thr Ile Ser Arg Asp Asp Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Val Gly Tyr Phe Asp Leu Trp Gly Arg Gly Thr
                100                 105                 110

Leu Val Thr Val Ser Ser Ala Ser Thr Gly Gly Gly Ser Gly Gly
            115                 120                 125

Gly Gly Ser Gly Gly Gly Ser Gln Ser Ala Leu Thr Gln Pro Ala
 130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
            195                 200                 205

Ala Ser Leu Ile Ile Ser Gly Leu Gln Ala Asp Asp Glu Ala Asp Tyr
            210                 215                 220

Tyr Cys Ser Ser Tyr Gly Ser Ser Ser Thr His Val Ile Phe Gly Gly
225                 230                 235                 240

Gly Thr Lys Val Thr Val Leu Gly Ala Ala Ser Asp Ala His Lys Ser
                245                 250                 255

Glu Val Ala His Arg Phe Lys Asp Leu Gly Glu Glu Asn Phe Lys Ala
                260                 265                 270

Leu Val Leu Ile Ala Phe Ala Gln Tyr Leu Gln Gln Ser Pro Phe Glu
            275                 280                 285

Asp His Val Lys Leu Val Asn Glu Val Thr Glu Phe Ala Lys Thr Cys
            290                 295                 300

Val Ala Asp Glu Ser Ala Glu Asn Cys Asp Lys Ser Leu His Thr Leu
305                 310                 315                 320

Phe Gly Asp Lys Leu Cys Thr Val Ala Thr Leu Arg Glu Thr Tyr Gly
                325                 330                 335

Glu Met Ala Asp Cys Cys Ala Lys Gln Glu Pro Glu Arg Asn Glu Cys
            340                 345                 350

Phe Leu Gln His Lys Asp Asp Asn Pro Asn Leu Pro Arg Leu Val Arg
            355                 360                 365

Pro Glu Val Asp Val Met Cys Thr Ala Phe His Asp Asn Glu Glu Thr
            370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
                405                 410                 415

Thr Glu Cys Cys Gln Ala Ala Asp Lys Ala Ala Cys Leu Leu Pro Lys
            420                 425                 430
```

```
Leu Asp Glu Leu Arg Asp Glu Gly Lys Ala Ser Ser Ala Lys Gln Arg
            435                 440                 445

Leu Lys Cys Ala Ser Leu Gln Lys Phe Gly Glu Arg Ala Phe Lys Ala
            450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
            485                 490                 495

Cys His Gly Asp Leu Leu Glu Cys Ala Asp Asp Arg Ala Asp Leu Ala
            500                 505                 510

Lys Tyr Ile Cys Glu Asn Gln Asp Ser Ile Ser Ser Lys Leu Lys Glu
            515                 520                 525

Cys Cys Glu Lys Pro Leu Leu Glu Lys Ser His Cys Ile Ala Glu Val
            530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
            565                 570                 575

Phe Leu Gly Met Phe Leu Tyr Glu Tyr Ala Arg Arg His Pro Asp Tyr
            580                 585                 590

Ser Val Val Leu Leu Leu Arg Leu Ala Lys Thr Tyr Glu Thr Thr Leu
            595                 600                 605

Glu Lys Cys Cys Ala Ala Ala Asp Pro His Glu Cys Tyr Ala Lys Val
            610                 615                 620

Phe Asp Glu Phe Lys Pro Leu Val Glu Glu Pro Gln Asn Leu Ile Lys
625                 630                 635                 640

Gln Asn Cys Glu Leu Phe Glu Gln Leu Gly Glu Tyr Lys Phe Gln Asn
            645                 650                 655

Ala Leu Leu Val Arg Tyr Thr Lys Lys Val Pro Gln Val Ser Thr Pro
            660                 665                 670

Thr Leu Val Glu Val Ser Arg Asn Leu Gly Lys Val Gly Ser Lys Cys
            675                 680                 685

Cys Lys His Pro Glu Ala Lys Arg Met Pro Cys Ala Glu Asp Tyr Leu
            690                 695                 700

Ser Val Val Leu Asn Gln Leu Cys Val Leu His Glu Lys Thr Pro Val
705                 710                 715                 720

Ser Asp Arg Val Thr Lys Cys Cys Thr Glu Ser Leu Val Asn Arg Arg
            725                 730                 735

Pro Cys Phe Ser Ala Leu Glu Val Asp Glu Thr Tyr Val Pro Lys Glu
            740                 745                 750

Phe Gln Ala Glu Thr Phe Thr Phe His Ala Asp Ile Cys Thr Leu Ser
            755                 760                 765

Glu Lys Glu Arg Gln Ile Lys Lys Gln Thr Ala Leu Val Glu Leu Val
            770                 775                 780

Lys His Lys Pro Lys Ala Thr Lys Glu Gln Leu Lys Ala Val Met Asp
785                 790                 795                 800

Asp Phe Ala Ala Phe Val Glu Lys Cys Cys Lys Ala Asp Asp Lys Glu
            805                 810                 815

Thr Cys Phe Ala Glu Glu Gly Lys Lys Leu Val Ala Ala Ser Gln Ala
            820                 825                 830

Ala Leu Gly Leu Ala Ala Ala Leu Gln Val Gln Leu Val Gln Ser Gly
            835                 840                 845
```

```
-continued

Ala Glu Val Lys Lys Pro Gly Glu Ser Leu Lys Ile Ser Cys Lys Gly
    850                 855                 860

Ser Gly Tyr Ser Phe Thr Ser Tyr Trp Ile Ala Trp Val Arg Gln Met
865                 870                 875                 880

Pro Gly Lys Gly Leu Glu Tyr Met Gly Leu Ile Tyr Pro Gly Asp Ser
                885                 890                 895

Asp Thr Lys Tyr Ser Pro Ser Phe Gln Gly Gln Val Thr Ile Ser Val
            900                 905                 910

Asp Lys Ser Val Ser Thr Ala Tyr Leu Gln Trp Ser Ser Leu Lys Pro
        915                 920                 925

Ser Asp Ser Ala Val Tyr Phe Cys Ala Arg Ala Asp Val Gly Tyr Cys
    930                 935                 940

Thr Asp Arg Thr Cys Ala Lys Ala Pro Ala Trp Leu Gly Val Trp Gly
945                 950                 955                 960

Gln Gly Thr Leu Val Thr Val Ser Ser Gly Gly Gly Ser Ser Gly
                965                 970                 975

Gly Gly Ser Gly Gly Gly Ser Gln Ser Val Leu Thr Gln Pro Pro
            980                 985                 990

Ser Val Ser Ala Ala Pro Gly Gln  Lys Val Thr Ile Ser  Cys Ser Gly
            995                 1000                1005

Ser Ser  Ser Asn Ile Gly Asn  Asn Tyr Val Ser Trp  Tyr Gln Gln
    1010                1015                1020

Leu Pro  Gly Thr Ala Pro Lys  Leu Leu Ile Tyr Asp  His Thr Asn
    1025                1030                1035

Arg Pro  Ala Gly Val Pro Asp  Arg Phe Ser Gly Ser  Lys Ser Gly
    1040                1045                1050

Thr Ser  Ala Ser Leu Ala Ile  Ser Gly Phe Arg Ser  Glu Asp Glu
    1055                1060                1065

Ala Asp Tyr Tyr Cys Ala Ser  Trp Asp Tyr Thr Leu  Ser Gly Trp
    1070                1075                1080

Val Phe Gly Gly Gly Thr Lys  Leu Thr Val Leu Gly
    1085                1090                1095
```

What is claimed is:

1. A human serum albumin (HSA) linker conjugate that is:
   a) HSA linker conjugate B2B3-1 having or comprising an amino acid sequence that is SEQ ID NO:16; or
   b) HSA linker conjugate B2B3-2 having or comprising an amino acid sequence that is SEQ ID NO:17; or
   c) HSA linker conjugate B2B3-3 having or comprising an amino acid sequence that is SEQ ID NO:18; or
   d) HSA linker conjugate B2B3-4 having or comprising an amino acid sequence that is SEQ ID NO:19; or
   e) HSA linker conjugate B2B3-5 having or comprising an amino acid sequence that is SEQ ID NO:20; or
   f) HSA linker conjugate B2B3-6 having or comprising an amino acid sequence that is SEQ ID NO:21; or
   g) HSA linker conjugate B2B3-7 having or comprising an amino acid sequence that is SEQ ID NO:22; or
   h) HSA linker conjugate B2B3-8 having or comprising an amino acid sequence that is SEQ ID NO:23; or
   i) HSA linker conjugate B2B3-10 having or comprising an amino acid sequence that is SEQ ID NO:25.

2. The HSA linker conjugate of claim 1 admixed with a pharmaceutically acceptable carrier, excipient, or diluent.

3. A composition comprising the HSA linker conjugate of claim 1 in combination with one or more therapeutic agents selected from the group consisting of cyclophosphamide, camptothecin, homocamptothecin, colchicine, combretastatin, rhizoxin, dolistatin, ansamitocin p3, maytansinoid, auristatin, caleachimicin, methotrexate, 5-fluorouracil (5-FU), doxorubicin, paclitaxel, docetaxel, cisplatin, carboplatin, tamoxifen, raloxifene, letrozole, epirubicin, bevacizumab, pertuzumab, trastuzumab, and derivatives thereof.

4. The composition of claim 3 wherein the therapeutic agent is trastuzumab.

5. The composition of claim 3 wherein the therapeutic agent is trastuzumab and the HSA linker conjugate is HSA linker conjugate B2B3-1 having or comprising an amino acid sequence that is SEQ ID NO:16.

6. The composition of claim 5 wherein, when tested in a nude mouse human xenograft model using human breast tumor cells at a first dosage of the therapeutic agent and a second dosage of the HSA linker conjugate, the combination provides greater efficacy than is provided by the first dosage of the therapeutic agent alone or the second dosage of the HSA linker conjugate alone in the same model.

7. The composition of claim 6 in a dosage form that can be administered to a subject to provide at least 3 mg/kg of B2B3-1 and at least 0.1 mg/kg trastuzumab.

8. The composition of claim 3, wherein the therapeutic agent is paclitaxel or docetaxel.

9. The composition of claim 3 wherein the therapeutic agent is a letrozole.

10. The HSA linker conjugate of claim 1, wherein said HSA linker conjugate binds ErbB3 with a $K_d$ of about 16 nM and ErbB2 with a $K_d$ of about 0.3 nM.

11. A method of treating a subject, said subject being in need of treatment for a tumor, said treating comprising administering to the subject an effective amount of the HSA linker conjugate of claim 1.

12. A method of treating a subject, said subject being in need of treatment for a tumor, said treating comprising administering to the subject an effective amount of the composition of claim 3.

13. An HSA linker conjugate comprising:
i) a human serum albumin (HSA) linker comprising an amino acid sequence set forth in any one of SEQ ID NOs:6-15; and
ii) first and second binding moieties selected from the group consisting of antibodies, single-chain Fv molecules, bispecific single chain Fv ((scFv')$_2$) molecules, domain antibodies, diabodies, triabodies, hormones, Fab fragments, F(ab')$_2$ molecules, tandem scFv (taFv) fragments, receptors, ligands, aptamers, and biologically-active fragments thereof, wherein said first binding moiety is bonded to the amino terminus of said HSA linker and said second binding moiety is bonded to the carboxy terminus of said HSA linker.

14. A HSA linker conjugate comprising the amino acid sequence of SEQ ID NO:16.

15. The HSA linker conjugate of claim 14 consisting of the amino acid sequence of SEQ ID NO:16.

16. A composition comprising the HSA linker conjugate of claim 14 in combination with one or more therapeutic agents selected from the group consisting of cyclophosphamide, camptothecin, homocamptothecin, colchicine, combretastatin, rhizoxin, dolistatin, ansamitocin p3, maytansinoid, auristatin, caleachimicin, methotrexate, 5-fluorouracil (5-FU), doxorubicin, paclitaxel, docetaxel, cisplatin, carboplatin, tamoxifen, raloxifene, letrozole, epirubicin, bevacizumab, pertuzumab, trastuzumab, and derivatives thereof.

17. The composition of claim 16, wherein the HSA linker conjugate consists of the amino acid sequence of SEQ ID NO: 16.

18. The composition of claim 16, wherein the therapeutic agent is trastuzumab.

19. The composition of claim 18, wherein the HSA linker conjugate consists of the amino acid sequence of SEQ ID NO: 16.

20. The method of claim 11, wherein said HSA linker conjugate consists of the amino acid sequence of SEQ ID NO: 16.

21. The method of claim 12, wherein said HSA linker conjugate consists of the amino acid sequence of SEQ ID NO: 16.

* * * * *